(12) United States Patent
Huang

(10) Patent No.: US 12,290,521 B2
(45) Date of Patent: *May 6, 2025

(54) METHODS AND MATERIALS FOR IDENTIFYING AND TREATING BET INHIBITOR-RESISTANT CANCERS

(71) Applicant: Mayo Foundation for Medical Education and Research, Rochester, MN (US)

(72) Inventor: Haojie Huang, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 871 days.

This patent is subject to a terminal disclaimer.

(21) Appl. No.: 17/263,010

(22) PCT Filed: Jul. 25, 2019

(86) PCT No.: PCT/US2019/043471
§ 371 (c)(1),
(2) Date: Jan. 25, 2021

(87) PCT Pub. No.: WO2020/023768
PCT Pub. Date: Jan. 30, 2020

(65) Prior Publication Data
US 2022/0016130 A1   Jan. 20, 2022

Related U.S. Application Data

(60) Provisional application No. 62/703,367, filed on Jul. 25, 2018.

(51) Int. Cl.
*A61K 31/551* (2006.01)
*A61K 45/06* (2006.01)
*A61P 35/00* (2006.01)

(52) U.S. Cl.
CPC ............ *A61K 31/551* (2013.01); *A61K 45/06* (2013.01); *A61P 35/00* (2018.01)

(58) Field of Classification Search
CPC ........ A61P 35/00; A61K 31/551; A61K 45/06
See application file for complete search history.

(56) References Cited

U.S. PATENT DOCUMENTS

| | | | | |
|---|---|---|---|---|
| 11,391,740 B2* | 7/2022 | Huang | ............ | G01N 33/57434 |
| 11,712,439 B2* | 8/2023 | Huang | ............... | C12Q 1/6886 |
| | | | | 514/220 |
| 2015/0320754 A1 | 11/2015 | Kutok et al. | | |
| 2016/0279141 A1 | 9/2016 | Bradner et al. | | |
| 2017/0304315 A1 | 10/2017 | Haudenschild et al. | | |
| 2021/0361653 A1 | 11/2021 | Huang et al. | | |

FOREIGN PATENT DOCUMENTS

| | | | |
|---|---|---|---|
| CN | 107299133 | 10/2017 | |
| WO | WO 2012/115789 | 8/2012 | |
| WO | WO 2015/160986 | 10/2015 | |
| WO | WO 2016/044694 | 3/2016 | |
| WO | WO-2016044694 A1 * | 3/2016 | ........... A61K 31/421 |
| WO | WO 2016/201370 | 12/2016 | |
| WO | WO-2016201370 A1 * | 12/2016 | ......... A61K 31/4162 |
| WO | WO 2017/027571 | 2/2017 | |
| WO | WO 2018/087401 | 5/2018 | |

OTHER PUBLICATIONS

Fujisawa, T., Filippakopoulos, P. Functions of bromodomain-containing proteins and their roles in homeostasis and cancer. Nat Rev Mol Cell Biol 18, 246-262 (2017). https://doi.org/10.1038/nrm.2016.143 (Year: 2017).*
GenBank Accession No. NG_041815.1, "*Homo sapiens* speckle type BTB/POZ protein (SPOP), RefSeqGene on chromosome 17," dated Feb. 13, 2016, 22 pages.
Chandarlapaty et al. AKT inhibition Relieves Feedback Suppression of Receptor Tyrosine Kinase Expression and Activity. Cancer Cell, 19, 58-71, 2011 (Year: 2011).
Stratikopoulos et al. Kinase inhibitors Together Clamp Inhibition of PI3K Signaling and Overcome Resistance to Therapy. Cancer Cell. 27, 837-851. 2015 (Year: 2015).
Abeshouse et al., "The molecular taxonomy of primary prostate cancer," Cell, Nov. 2015, 163(4):1011-25.
An et al., "Destruction of Full-Length Androgen Receptor by Wild-Type SPOP, but Not Prostate-Cancer-Associated Mutants," Cell Rep, 2014, 6(4):657-669.
An et al., "Truncated ERG Oncoproteins from TMPRSS2-ERG Fusions Are Resistant to SPOP-Mediated Proteasome Degradation," Mol. Cell, 2015, 59(6):904-916.
Asangani et al., "Therapeutic targeting of BET bromodomain proteins in castration-resistant prostate cancer," Nature, 2014, 510(7504):278-282.
Baker et al., "BET Inhibitors Induce Apoptosis Through a MYC Independent Mechanism and Synergise with CDK Inhibitors to Kill Osteosarcoma Cells," Scientific Reports, 2015, 5(10120):1-14.
Barbieri et al., "Exome sequencing identifies recurrent SPOP, FOXA1 and MED12 mutations in prostate cancer," Nat. Genet., 2012, 44(6):685-689.
Beaver et al., "FDA approval: palbociclib for the treatment of postmenopausal patients with estrogen receptor-positive, HER2-negative metastatic breast cancer," Clinical Cancer Research, Nov. 2015, 21(21):4760-6.

(Continued)

*Primary Examiner* — Jennifer A Berrios
*Assistant Examiner* — Richard Grant Peckham
(74) *Attorney, Agent, or Firm* — Fish & Richardson P.C.

(57) ABSTRACT

Methods and materials involved in identifying and treating mammals having a cancer resistant to BET inhibitors are provided. For example, methods and materials for administering (a) one or more AKT inhibitors and/or one or more CDK inhibitors and/or one or more CBP/p300 inhibitors in combination with (b) one or more BET inhibitors to mammals identified as having a cancer resistant to treatment with one or more BET inhibitors in the absence of AKT, CDK, and CBP/p300 inhibitors are provided.

6 Claims, 136 Drawing Sheets
Specification includes a Sequence Listing.

(56) References Cited

OTHER PUBLICATIONS

Blattner et al., "SPOP Mutation Drives Prostate Tumorigenesis In Vivo through Coordinate Regulation of PI3K/mTOR and AR Signaling," Cancer Cell, 2017, 31(3):436-451.
Blattner et al., "SPOP Mutations in Prostate Cancer across Demographically Diverse Patient Cohorts 1,2," Neoplasia, 2014, 16(1):14-20.
Blee et al., "BET bromodomain-mediated interaction between ERG and BRD4 promotes prostate cancer cell invasion," Oncotarget, 2016, 7(25):38319-38332.
Bookstein et al., "Suppression of tumorigenicity of human prostate carcinoma cells by replacing a mutated RB gene," Science, Feb. 1990, 247(4943):712-5.
Borbely et al., "Induction of USP17 by combining BET and HDAC inhibitors in breast cancer cells," Oncotarget, Oct. 2015, 6(32):33623-33635.
Boyer et al., "Core transcriptional regulatory circuitry in human embryonic stem cells," Cell, 2005, 122(6):947-956.
Cancer Genome Atlas Research Network, "The Molecular Taxonomy of Primary Prostate Cancer," Cell, Nov. 2015, 163(4):1011-25.
Chan et al., "Targeting chromatin binding regulation of constitutively active AR variants to overcome prostate cancer resistance to endocrine-based therapies," Nucleic Acids Res, 2015, 43(12):5880-5897.
Dai X, Gan W, Li X, Wang S, Zhang W, Huang L, Liu S, Zhong Q, Guo J, Zhang J, Chen T. Prostate cancer-associated SPOP mutations confer resistance to BET inhibitors through stabilization of BRD4. Nature medicine. Sep. 2017;23(9):1063-1071.
Dali-Youcef et al., "Gene Expression Mapping of Histone Deacetylases and Co-factors, and Correlation with Survival Time and 1 H-HRMAS Metabolomic Profile in Human Gliomas," Scientific reports, Mar. 2015, 5:9087.
Dawson et al., "Inhibition of BET recruitment to chromatin as an effective treatment for MLL-fusion leukaemia," Nature, 2011, 478(7370):529-533.
Delmore et al., "BET Bromodomain Inhibition as a Therapeutic Strategy to Target c-Myc," Cell, 2011, 146(6):904-917.
Deng et al., "Deubiquitination and activation of AMPK by USP10," Molecular cell, Feb. 2016, 61(4):614-24.
Drost et al., "Organoid culture systems for prostate epithelial and cancer tissue," Nat. Protoc., 2016, 11(2):347-358.
Esen et al., "WNT-LRP5 signaling induces Warburg effect through mTORC2 activation during osteoblast differentiation," Cell Metab, 2013, 17(5):745-755.
Filippakopoulos et al., "Selective inhibition of BET bromodomains," Nature, 2010, 468(7327):1067-1073.
Finn et al., "Palbociclib and letrozole in advanced breast cancer," New England Journal of Medicine, Nov. 2016, 375(20):1925-36.
Fischer et al., "Isolation and characterization of a novel class II histone deacetylase, HDAC10," Journal of Biological Chemistry, Feb. 2002, 277(8):6656-66.
Fong et al., "BET inhibitor resistance emerges from leukaemia stem cells," Nature, 2015, 525(7570):538-542.
Fu et al., "Inhibition of BET Bromodomains as a Therapeutic Strategy for Cancer Drug Discovery," Oncotarget, 2015, 6(8):5501-5516.
GenBank Accession No. AAB87862.1, "BRDT [*Homo sapiens*]," dated Dec. 1, 1997, 2 pages.
GenBank Accession No. CAA04199.1, "SPOP [*Homo sapiens*]," dated Oct. 7, 2008, 2 pages.
GenBank Accession No. NP_001106653.1, "bromodomain-containing protein 2 isoform 1 [*Homo sapiens*]," dated Dec. 23, 2018, 4 pages.
GenBank Accession No. NP_031397.1, "bromodomain-containing protein 3 [*Homo sapiens*]," dated Mar. 9, 2016, 4 pages.
GenBank Accession No. NP_490597.1, "bromodomain-containing protein 4 isoform long [*Homo sapiens*]," dated Feb. 3, 2019, 4 pages.

Geng et al., "Prostate cancer-associated mutations in speckle-type POZ protein (SPOP) regulate steroid receptor coactivator 3 protein turnover," Proc. Natl. Acad. Sci. USA, 2013, 110(17):6997-7002.
GEO Accession No. GSE44931, "Selective Inhibition of Tumor Oncogenes by Disruption of Super-Enhancers," dated Mar. 7, 2013, 2 pages.
GEO Accession No. GSE51633, "Brd4 and JMJD6-associated Anti-pause Enhancers in Regulation of Transcriptional Pause Release," dated Jan. 14, 2014, 2 pages.
GEO Accession No. GSE66122, "BET Bromodomain Inhibition Suppresses the Function of Hematopoietic Transcription Factors in Acute Myeloid Leukemia [ChIP-Seq]," dated May 1, 2015, 2 pages.
GEO Accession No. GSE88872, "SPOP mutation confers intrinsic BET inhibitor resistance in prostate cancer," dated Jul. 21, 2017, 2 pages.
Grasso et al., "The mutational landscape of lethal castration-resistant prostate cancer," Nature, Jul. 2012, 487(7406):239-43.
Groner et al., "TRIM24 Is an Oncogenic Transcriptional Activator in Prostate Cancer," Cancer Cell, 2016, 29(6):846-858.
Hagen et al., "AM-MLV reverse transcriptase with reduced RNaseH activity allows greater sensitivity of gene expression detection in formalin fixed and paraffin embedded prostate cancer samples," Exp. Mol. Pathol., 2013, 95(1):98-104.
Hayward et al., "Establishment and characterization of an immortalized but non-transformed human prostate epithelial cell line: BPH-1," In Vitro Cell Dev. Biol. Anim., 1995, 31(1):14-24.
Janouskova et al., "Opposing effects of cancer-type-specific SPOP mutants on BET protein degradation and sensitivity to BET inhibitors," Nature medicine, Sep. 2017, 23(9):1046.
Janouskova et al., "Opposing therapeutic efficacy of BET inhibitors is determined by cancer type-specific SPOP mutants," European Journal of Cancer, Dec. 2016, 69:S2.
Jin et al., "Fructose-1, 6-bisphosphatase inhibits ERK activation and bypasses gemcitabine resistance in pancreatic cancer by blocking IQGAP1-MAPK interaction," Cancer research, Aug. 2017, 77(16):4328-41.
Kurimchak et al., "Resistance to BET bromodomain inhibitors is mediated by kinome reprogramming in ovarian cancer," Cell reports, Aug. 2016, 16(5):1273-86.
Lasserre et al., "Raft nanodomains contribute to Akt/PKB plasma membrane recruitment and activation," Nat Chem Biol., 2008, 4(9):538-547.
LeRoy et al., "The double bromodomain proteins Brd2 and Brd3 couple histone acetylation to transcription," Mol. Cell, Apr. 11, 2008, 30(1):51-60.
Li et al., Fructose-1, 6-bisphosphatase opposes renal carcinoma progression, Nature, Sep. 2014, 513(7517):251-5.
Liu et al., "Brd4 and JMJD6-associated anti-pause enhancers in regulation of transcriptional pause release," Cell, 2013, 155(7):1581-1595.
Liu et al., "CDK4/6-dependent activation of DUB3 regulates cancer metastasis through SNAIL1," Nature communications, Jan. 2017, 8(1):13923.
Loven et al., "Selective inhibition of tumor oncogenes by disruption of super-enhancers," Cell, 2013, 153(2):320-334.
Lu et al., "Hijacking the E3 Ubiquitin Ligase Cereblon to Efficiently Target BRD4," Chem. Biol., 2015, 22(6):755-763.
Mertz et al., "Targeting MYC dependence in cancer by inhibiting BET bromodomains," Proc. Natl. Acad. Sci. USA, 2011, 108(40):16669-16674.
Mittempergher et al., "Gene expression profiles from formalin fixed paraffin embedded breast cancer tissue are largely comparable to fresh frozen matched tissue," PLoS One, 2011, 6(2):e17163, 15 pages.
Mortazavi et al., "Mapping and quantifying mammalian transcriptomes by RNA-Seq," Nature Methods, 2008, 5(7):621-628.
Nicodeme et al., "Suppression of inflammation by a synthetic histone mimic," Nature, 2010, 468(7327):1119-1123.
O'Leary et al., "Treating cancer with selective CDK4/6 inhibitors," Nature reviews Clinical oncology, Jul. 2016, 13(7):417-30.
Patel et al., "BET bromodomain inhibition triggers apoptosis of NF1-associated malignant peripheral nerve sheath tumors through Bim induction," Cell Rep., 2014, 6(1):81-92.

(56) References Cited

OTHER PUBLICATIONS

PCT International Preliminary Report on Patentability in International Appln. No. PCT/US2019/043471, dated Jan. 26, 2021, 8 pages.
PCT International Search Report and Written Opinion in International Appln. No. PCT/US2019/043471, dated Oct. 28, 2019, 11 pages.
Rathert et al., "Transcriptional plasticity promotes primary and acquired resistance to BET inhibition," Nature, 2015, 525(7570):543-547.
Renwick et al., "Multicolor microRNA FISH effectively differentiates tumor types," J. Clin. Invest., 2013, 123(6):2694-2702.
Robinson et al., "A scaling normalization method for differential expression analysis of RNA-seq data," Genome Biol., 2010, 11(3):R25, 9 pages.
Robinson et al., "Integrative clinical genomics of advanced prostate cancer," Cell, May 2015, 161(5):1215-28.
Roe et al., "BET Bromodomain Inhibition Suppresses the Function of Hematopoietic Transcription Factors in Acute Myeloid Leukemia," Mol. Cell, 2015, 58(6):1028-1039.
Saci et al., "Rac1 regulates the activity of mTORC1 and mTORC2 and controls cellular size," Mol Cell, 2011, 42(1):50-61.
Saura et al., "A First-in-Human Phase I Study of the ATP-Competitive AKT Inhibitor Ipatasertib Demonstrates Robust and Safe Targeting of AKT in Patients with Solid Tumors," Cancer Discov., 2017, 7(1):102-113.
Shi et al., "Disrupting the interaction of BRD4 with diacetylated Twist suppresses tumorigenesis in basal-like breast cancer," Cancer cell, Feb. 2014, 10;25(2):210-25.
Shu et al., "Response and resistance to BET bromodomain inhibitors in triple negative breast cancer," Nature, 2016, 529(7586):413-417.
Stanlie et al., "Chromatin reader Brd4 functions in Ig class switching as a repair complex adaptor of nonhomologous end-joining," Mol. Cell., Jul. 2014, 55(1):97-110.
Stratikopoulos et al., "Kinase and BET Inhibitors Together Clamp Inhibition of PI3K Signaling and Overcome Resistance to Therapy," Cancer Cell, 2015, 27(6):837-851.
The Cancer Genome Atlas Research Network, "The Molecular Taxonomy of Primary Prostate Cancer," Cell, 2015, 163(4):1011-1025.
Theurillat et al., "Ubiquitylome analysis identifies dysregulation of effector substrates in SPOP-mutant prostate cancer," Science, 2014, 346(6205):85-89.
Trapnell et al., "TopHat: discovering splice junctions with RNA-Seq," Bioinformatics, 2009, 25(9):1105-1111.
Turnbull et al., "Molecular basis of USP7 inhibition by selective small-molecule inhibitors," Nature, Oct. 2017, 550(7677):481-486.
Urbanucci et al., "Androgen receptor deregulation drives bromodomain-mediated chromatin alterations in prostate cancer," Cell reports, Jun. 2017, 19(10):2045-59.
Urbanucci et al., "Bromodomain-containing proteins in prostate cancer," Mol. Cell. Endocrinology, Feb. 15, 2018, 462(Pt A):31-40.
Wang et al., "BRCA1 is a negative modulator of the PRC2 complex," Embo. J., 2013, 32(11):1584-1597.
Wang et al., "Reprogramming transcription by distinct classes of enhancers functionally defined by eRNA," Nature, 2011, 474(7351):390-394.
Wang et al., "RSeQC: quality control of RNA-seq experiments," Bioinformatics, 2012, 28(16):2184-2185.
Wikipedia.org [online], "Biosynthesis," last updated Jul. 5, 2021, retrieved on Jul. 26, 2021, retrieved from URL<https://en.wikipedia.org/wiki/Biosynthesis>, 21 pages.
Wu et al., "Dub3 inhibition suppresses breast cancer invasion and metastasis by promoting Snail1 degradation," Nature communications, Feb. 2017, 8(1):14228.
Wu et al., "The Deubiquitinase USP28 Stabilizes LSD1 and Confers Stem-Cell-like Traits to Breast Cancer Cells," Cell Reports, Oct. 2013, 5(1):224-236.
Yuan et al., "USP10 Regulates p53 Localization and Stability by Deubiquitinating p53," Cell, Feb. 2010, 140(3):384-396.
Yue et al., "Cholesteryl ester accumulation induced by PTEN loss and PI3K/AKT activation underlies human prostate cancer aggressiveness," Cell Metab, 2014, 19(3):393-406.
Zhang et al., "Intrinsic BET inhibitor resistance in SPOP-mutated prostate cancer is mediated by BET protein stabilization and AKT-mTORC1 activation," Nature medicine, Sep. 2017, 23(9):1055-1062.
Zhang et al., "Model-based analysis of ChIP-Seq (MACS)," Genome Biol., 2008, 9(9):R137, 9 pages.
Zhang et al., "USP49 deubiquitinates histone H2B and regulates cotranscriptional pre-mRNA splicing," Genes Development, Jul. 2013, 27(14):1581-1595.
Zhao et al., "Activation of P-TEFb by Androgen Receptor-Regulated Enhancer RNAs in Castration-Resistant Prostate Cancer," Cell Rep., 2016, 15(3):599-610.
Zhao et al., "CrossMap: a versatile tool for coordinate conversion between genome assemblies," Bioinformatics, 2014, 30(7):1006-1007.
Zhuang et al., "Cholesterol targeting alters lipid raft composition and cell survival in prostate cancer cells and xenografts," J. Clin, Invest., 2005, 115(4):959-968.
Zhuang et al., "Cholesterol-rich lipid rafts mediate akt-regulated survival in prostate cancer cells," Cancer Res, 2002, 62(8):2227-2231.
Zhuang et al., "Structures of SPOP-substrate complexes: insights into molecular architectures of BTB-Cul3 ubiquitin ligases," Mol. Cell, 2009, 36(1):39-50.
Zuber et al., "RNAi screen identifies Brd4 as a therapeutic target in acute myeloid leukaemia," Nature, 2011, 478(7370):524-528.
U.S. Appl. No. 16/637,674, filed Feb. 7, 2020, Haojie Huang, Pending.
Bradley. Nature Reviews Cancer. 17, 574 2017. (Year: 2017).

\* cited by examiner

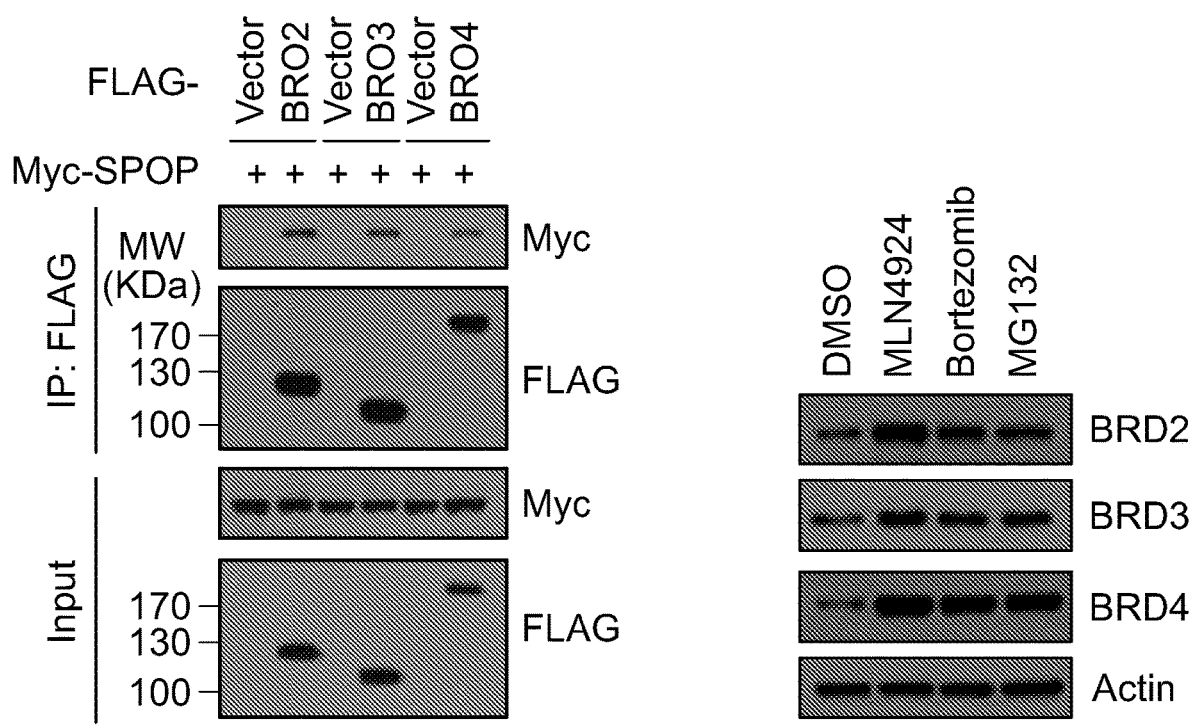
FIG. 2A
FIG. 2B
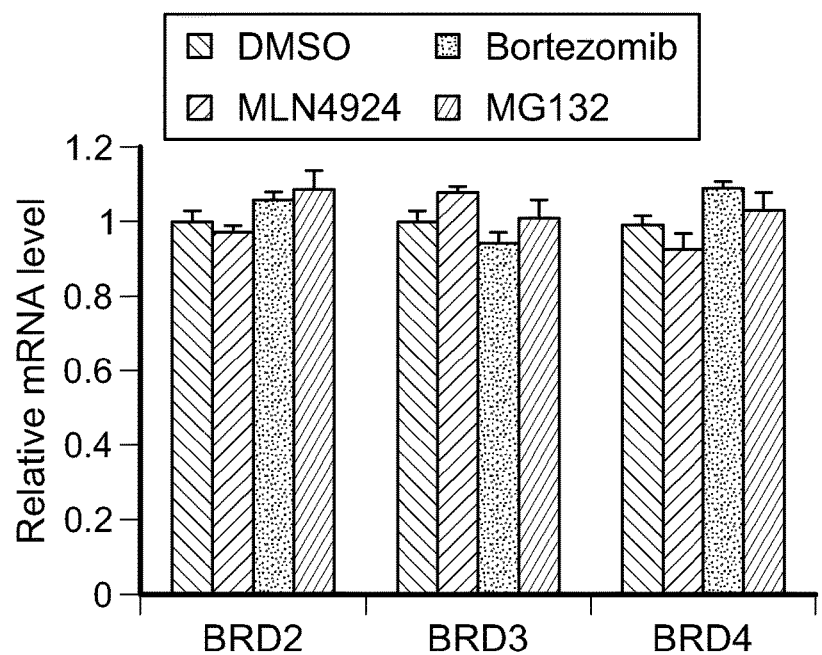
FIG. 2C

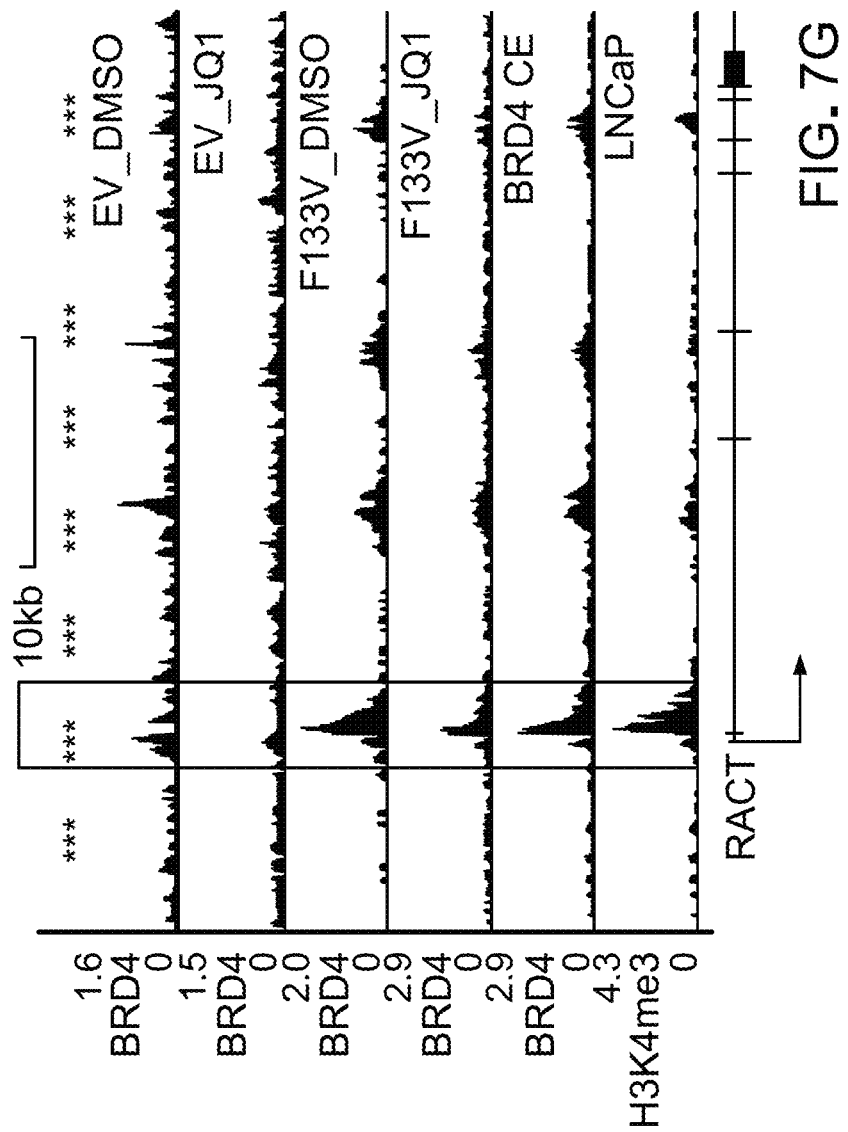

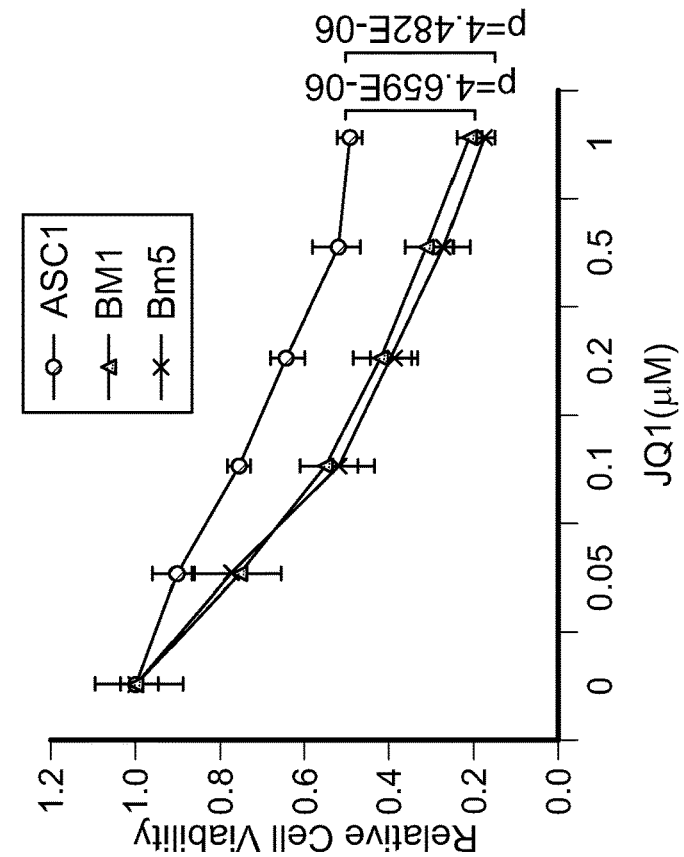
FIG. 9E
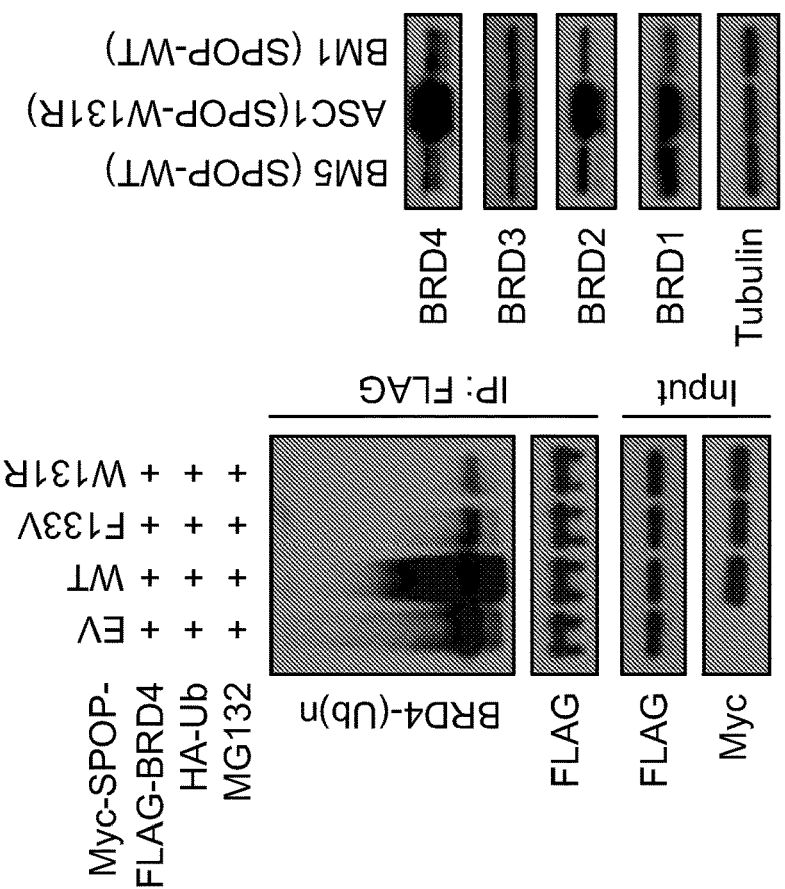
FIG. 9D
FIG. 9C

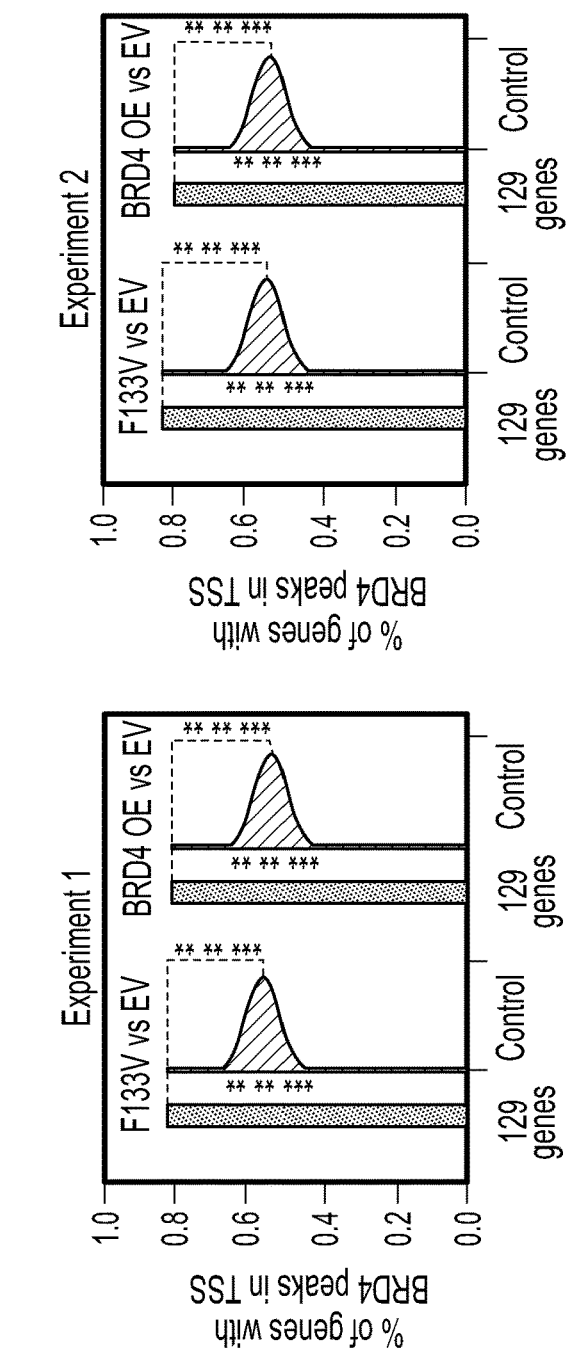
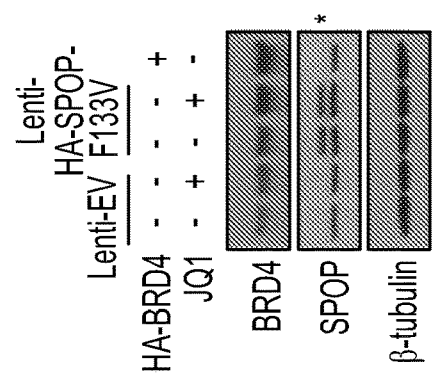
FIG. 12B
FIG. 12A

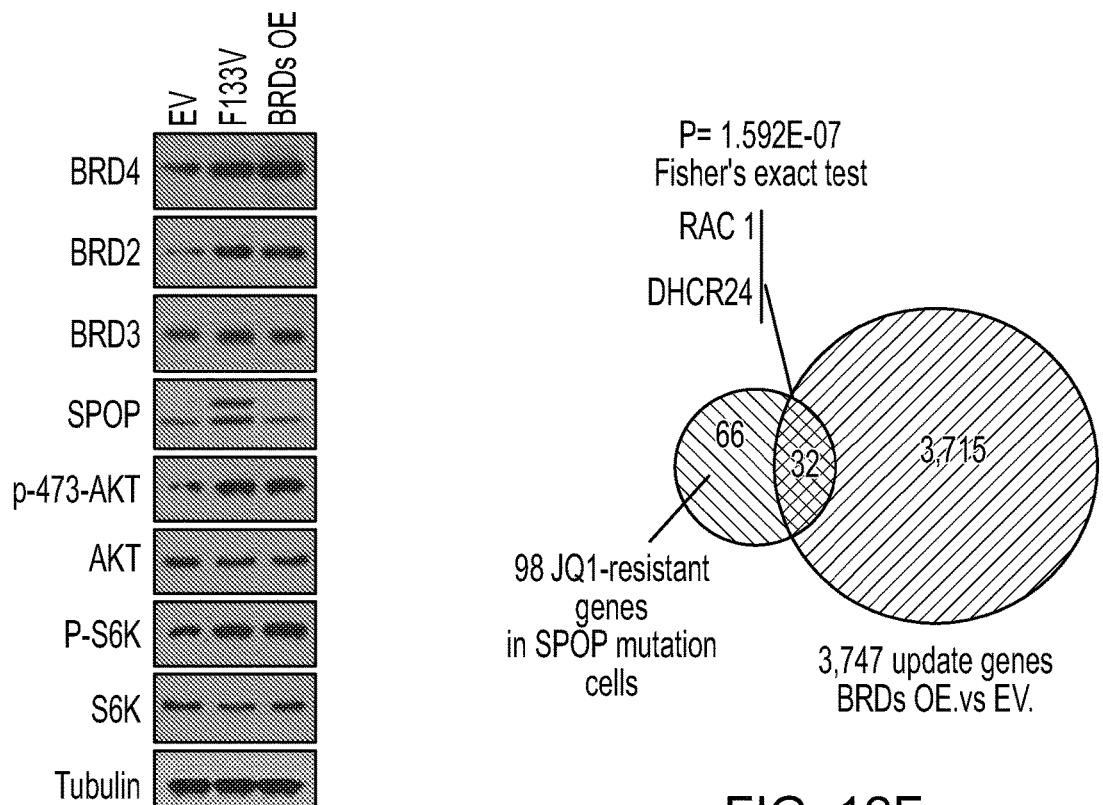
FIG. 12E
FIG. 12F
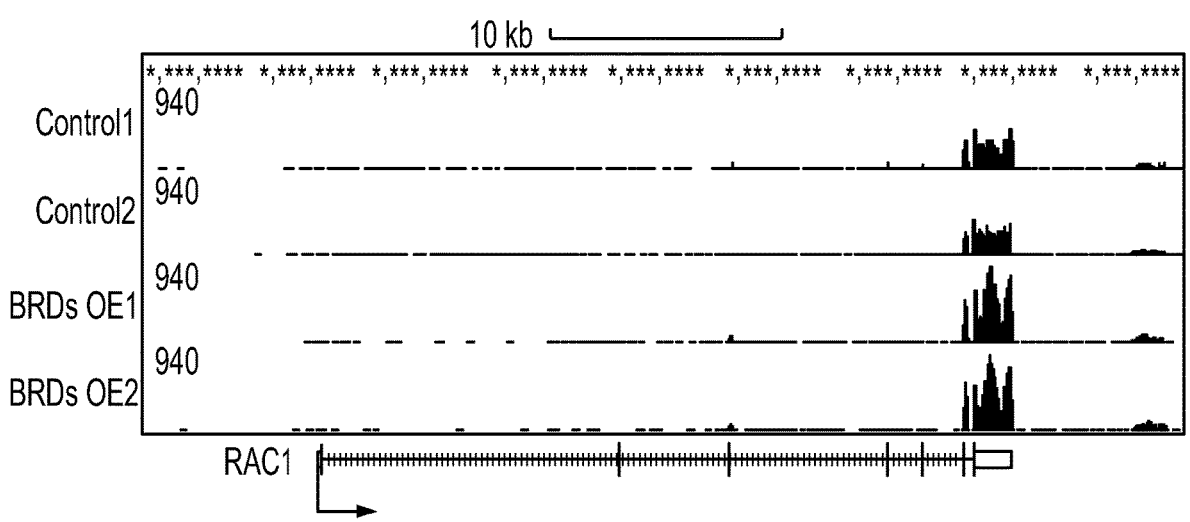
FIG. 12G

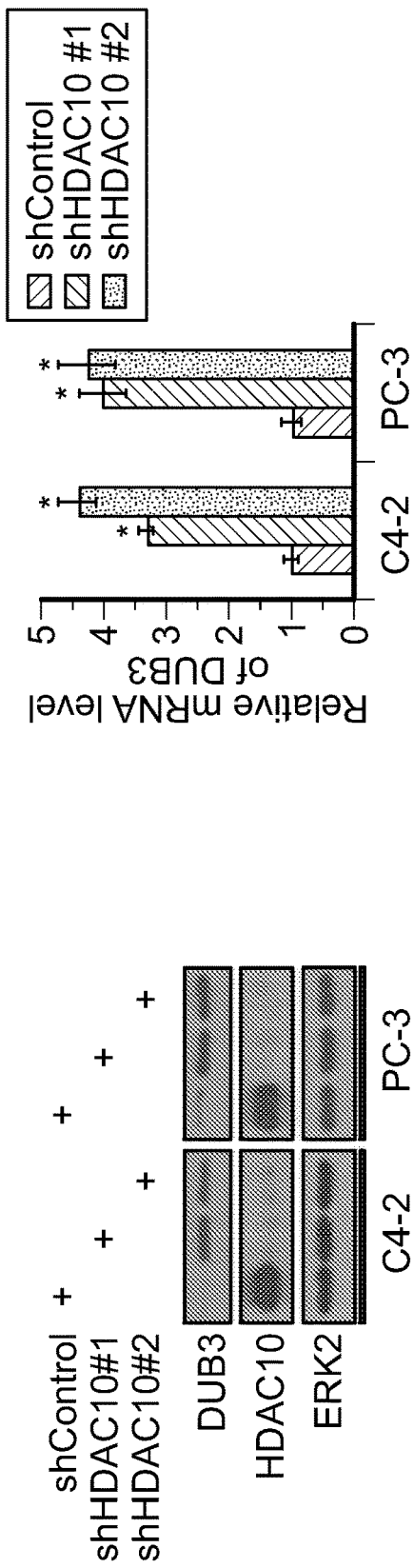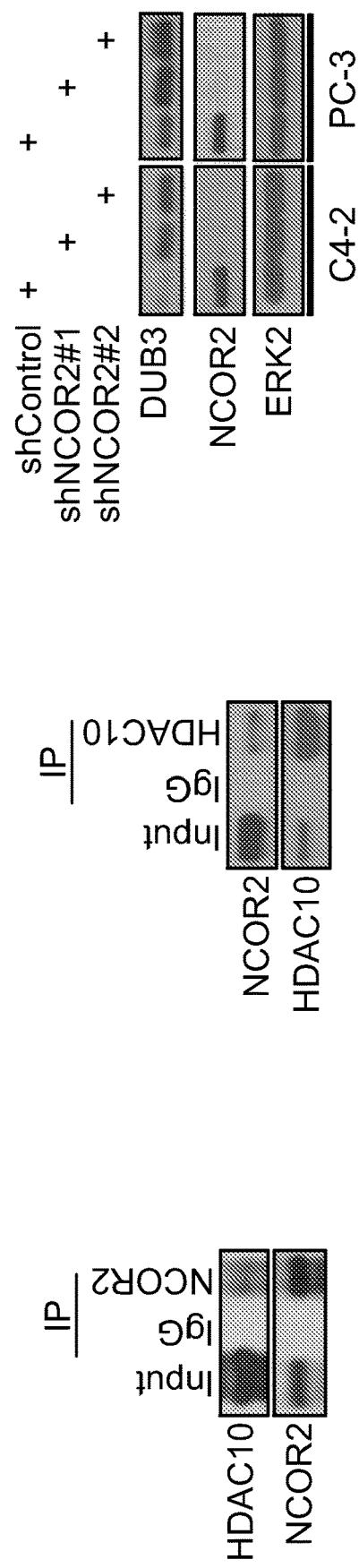
FIG. 15D
FIG. 15E
FIG. 15F
FIG. 15G
FIG. 15H

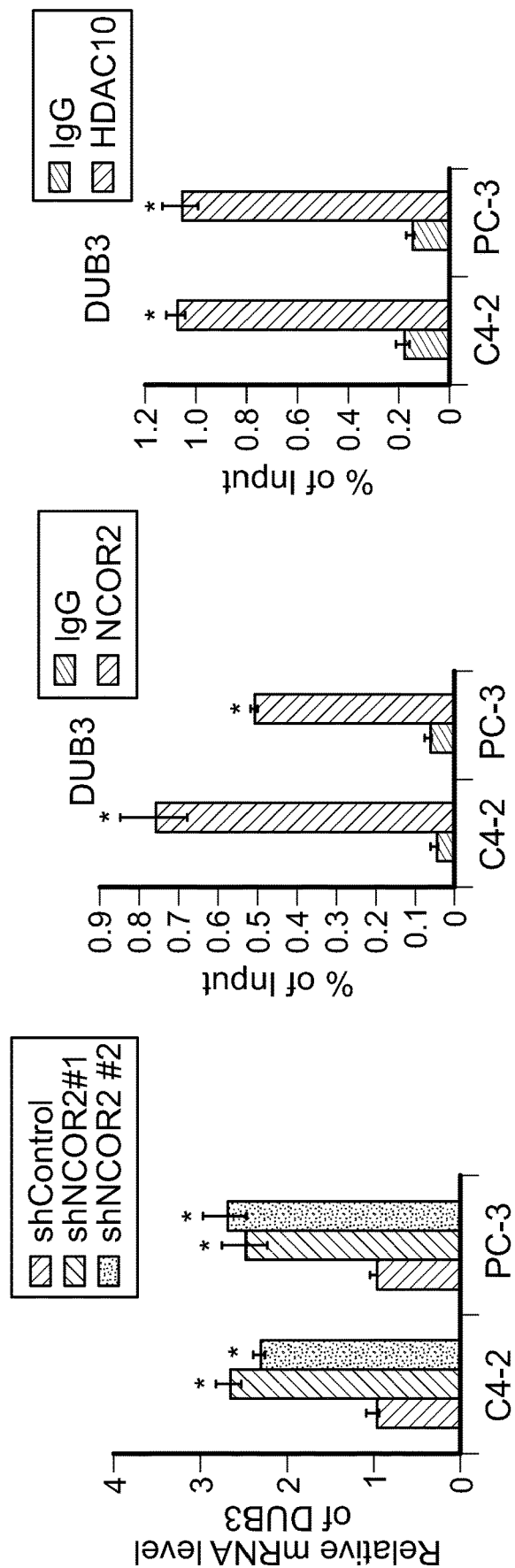

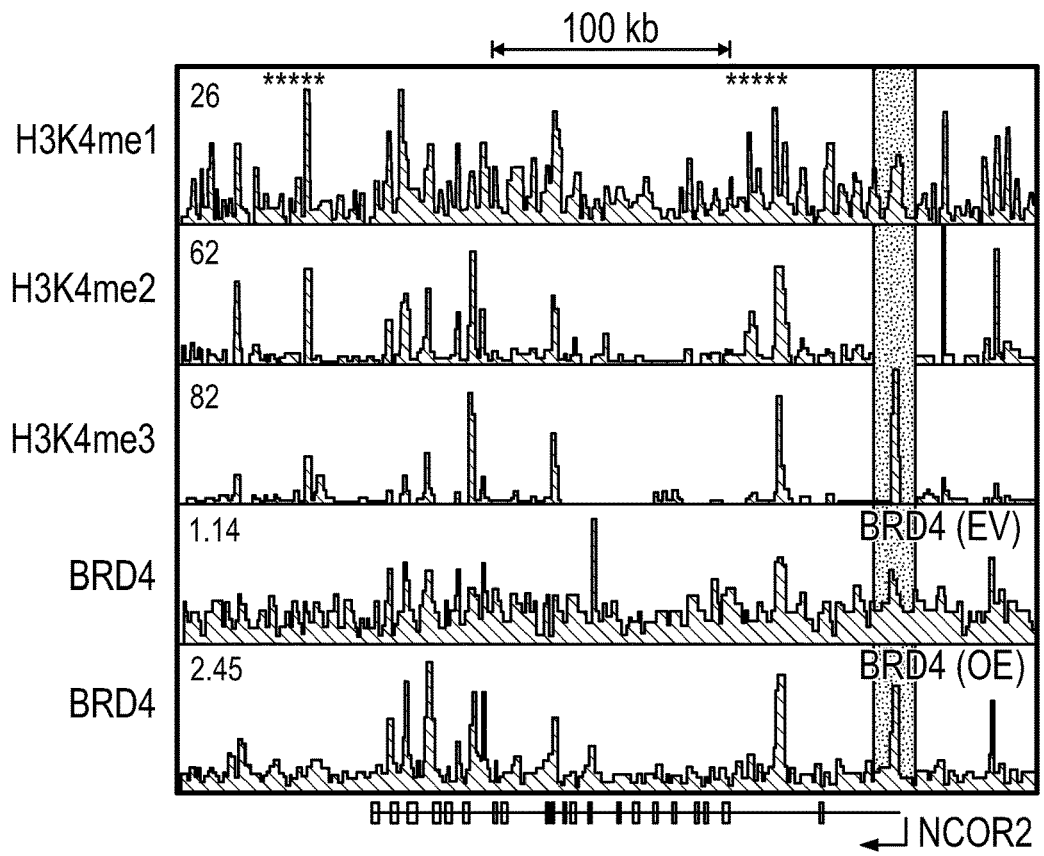
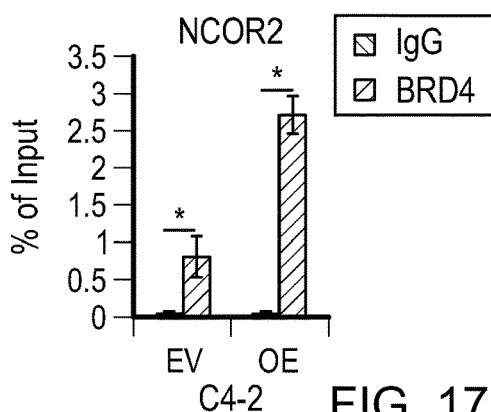
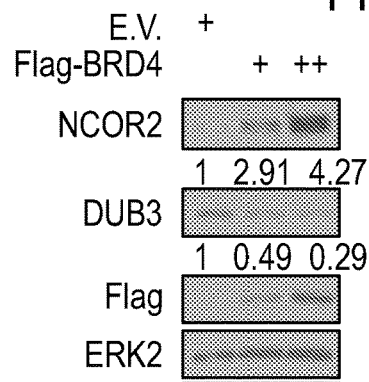
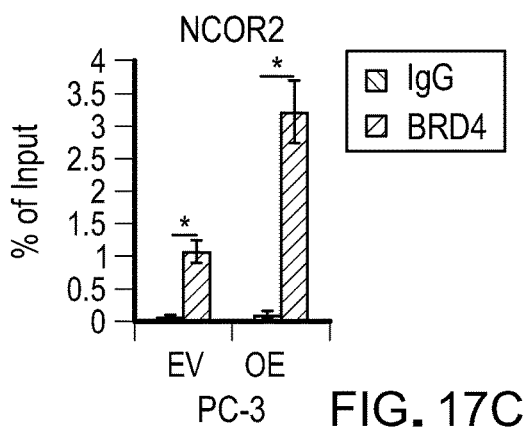
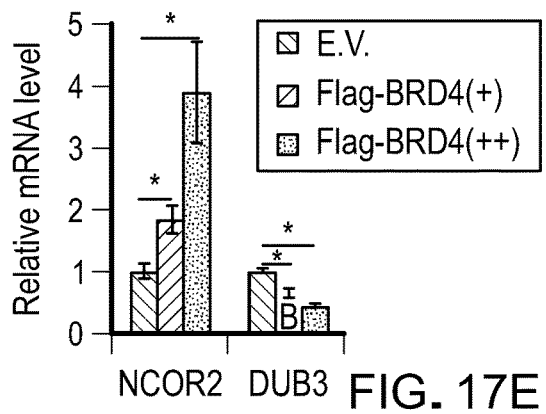
FIG. 17A
FIG. 17B
FIG. 17C
FIG. 17D
FIG. 17E

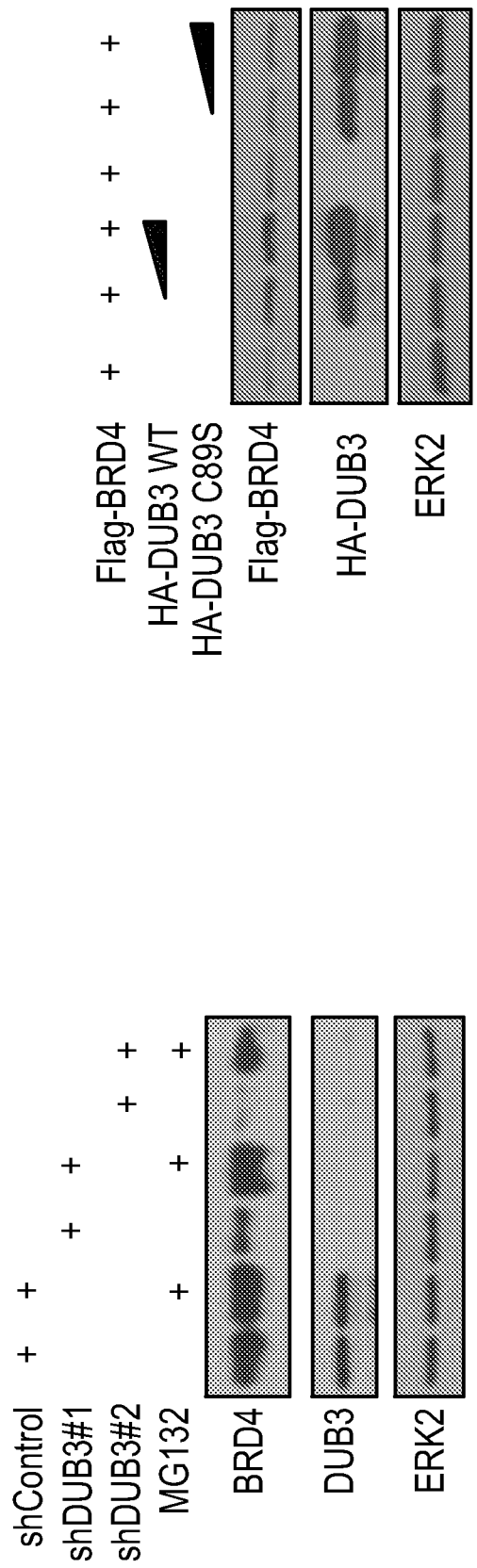

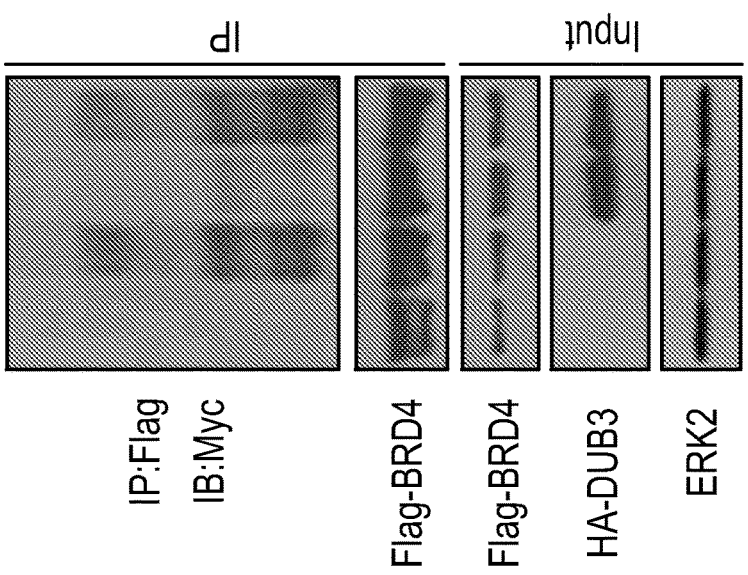
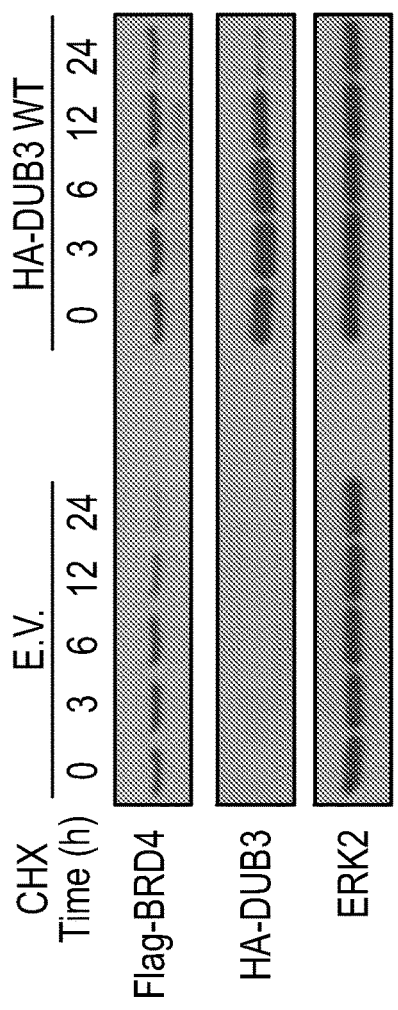
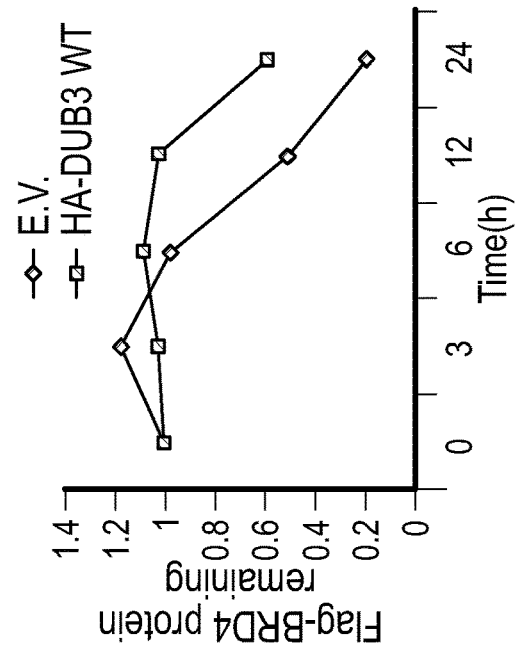
FIG. 18H
FIG. 18G

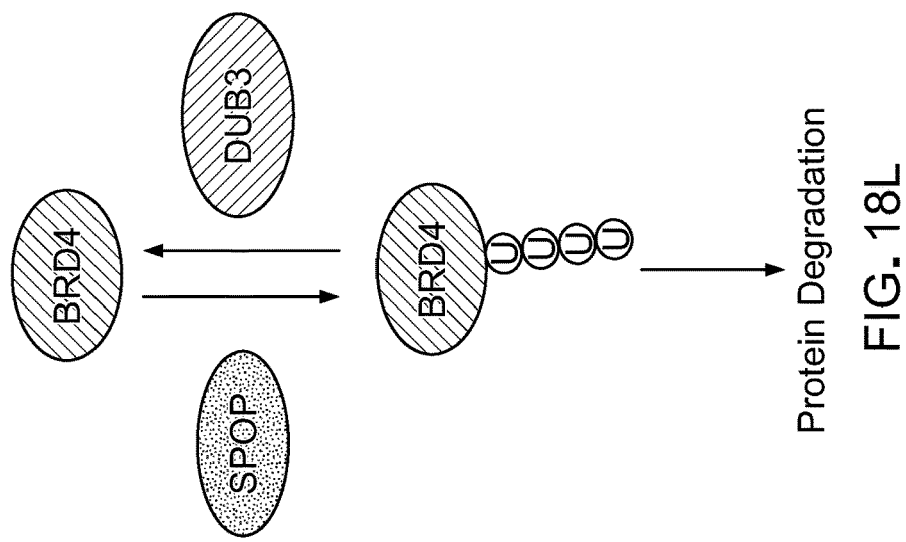
FIG. 18L
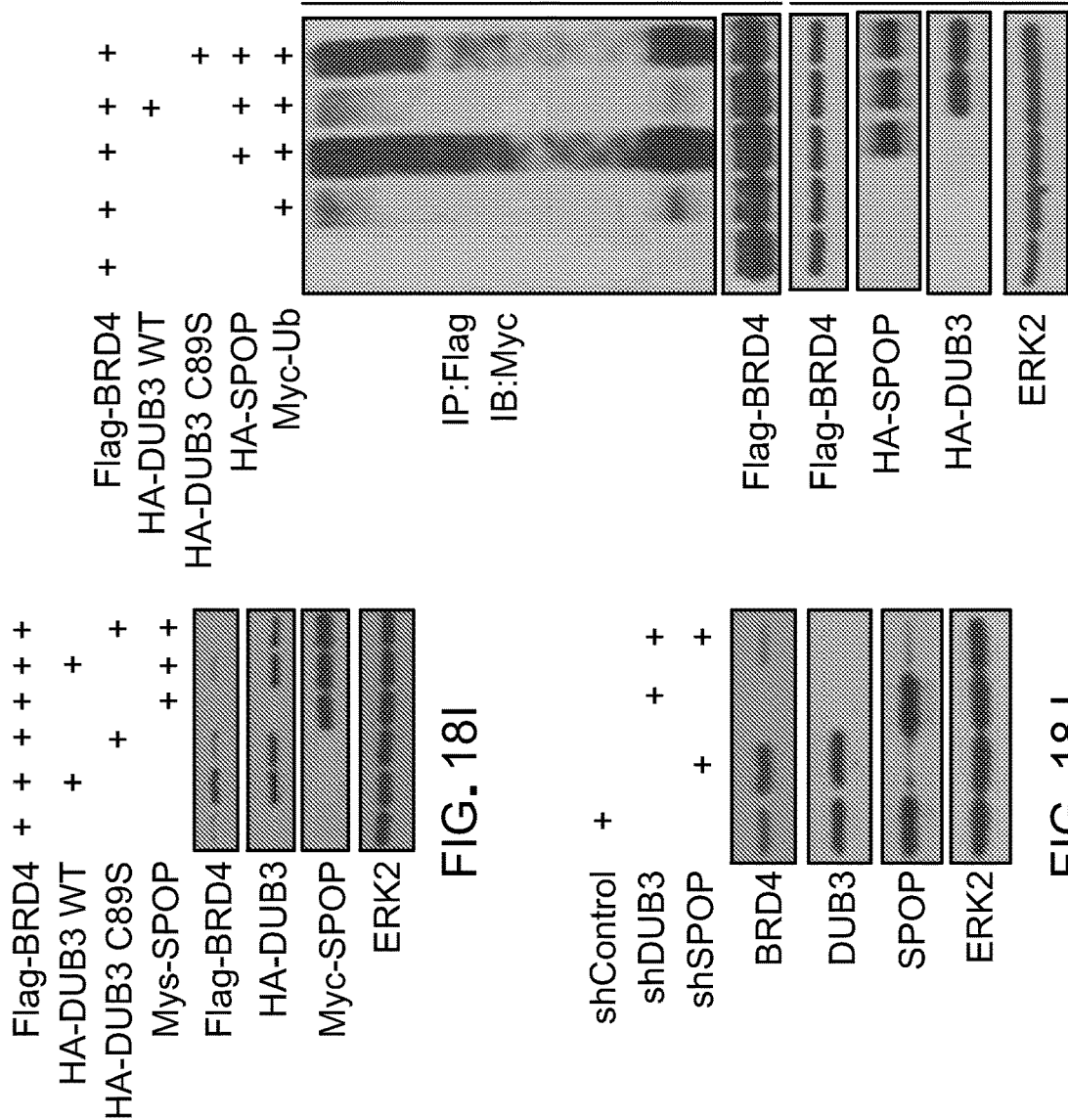
FIG. 18K
FIG. 18I
FIG. 18J

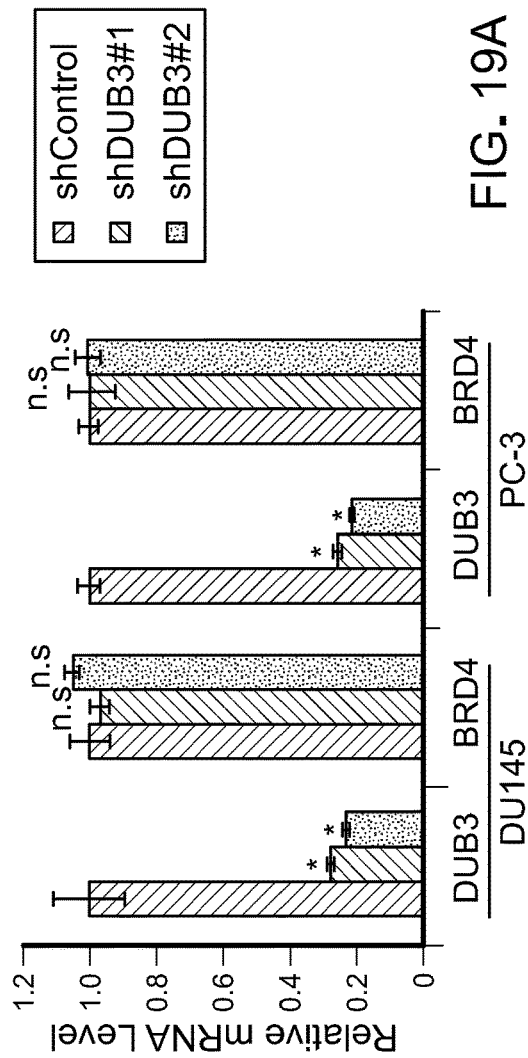
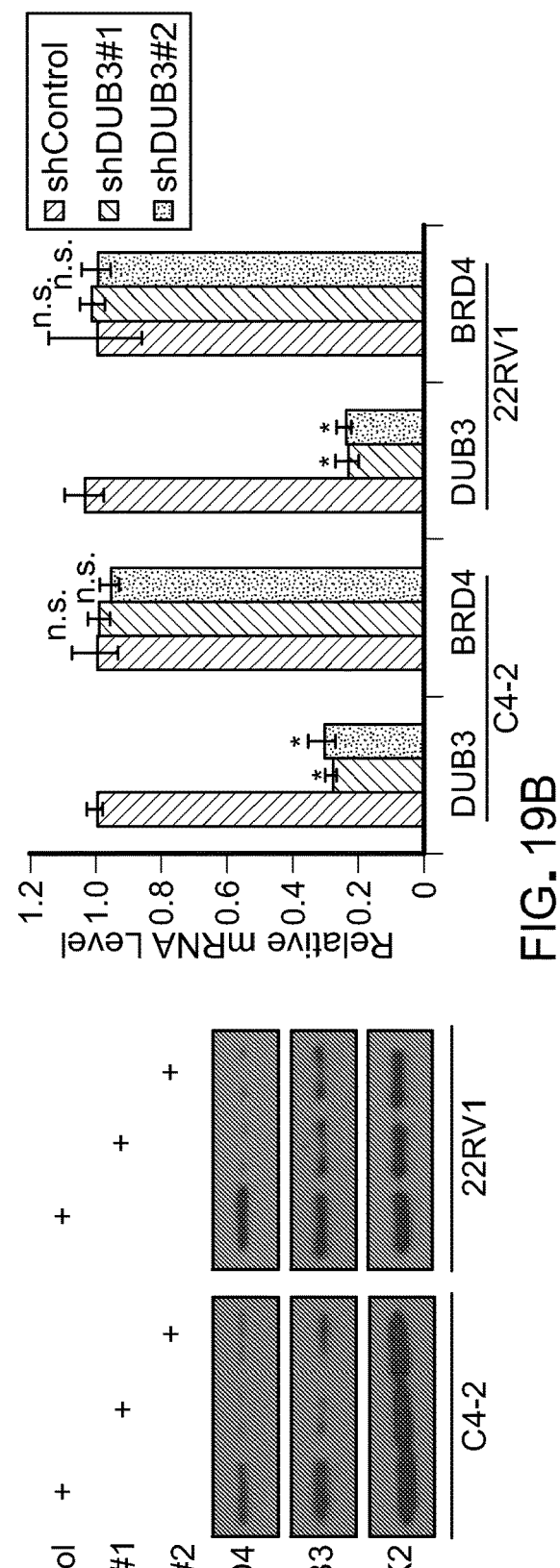
FIG. 19A
FIG. 19B

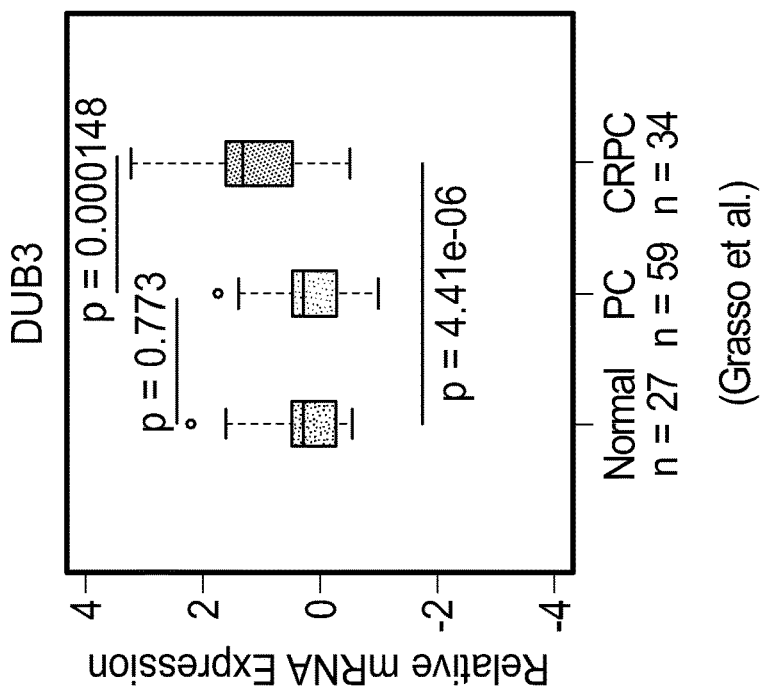
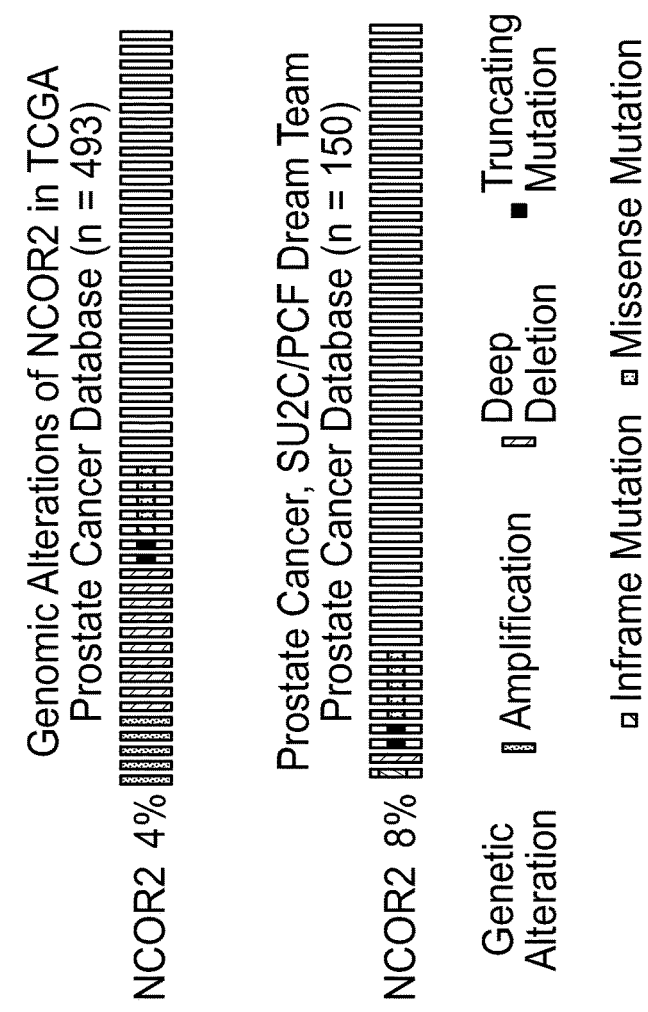
FIG. 23B
FIG. 23A

FIG. 25A
FIG. 25B
FIG. 25C
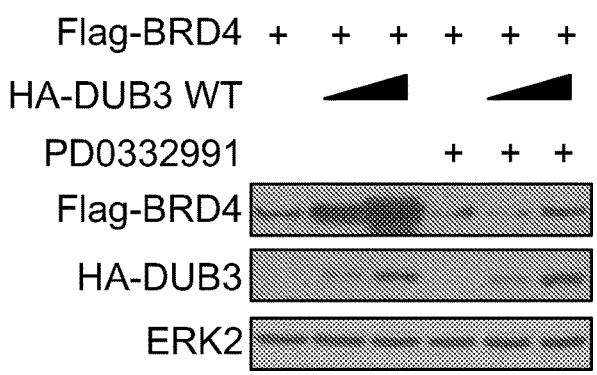
FIG. 25D
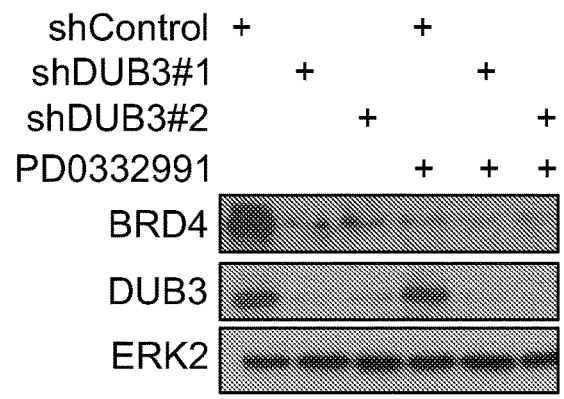
FIG. 25E

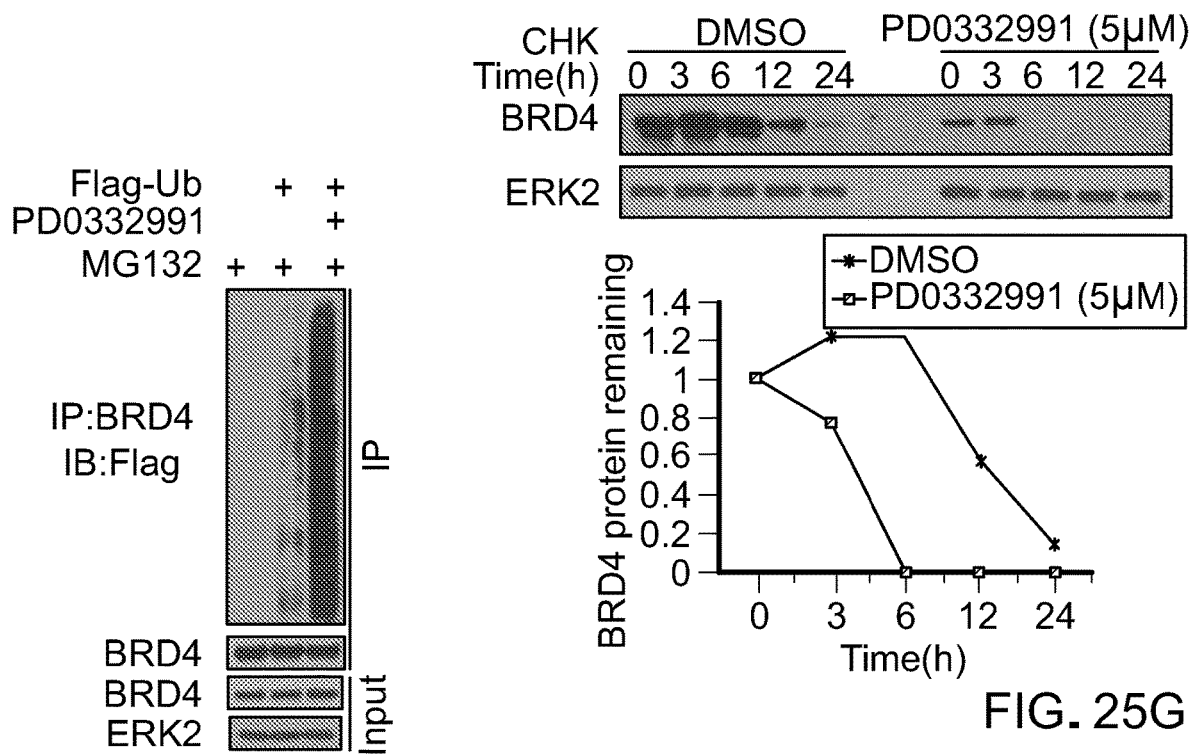
FIG. 25F
FIG. 25G
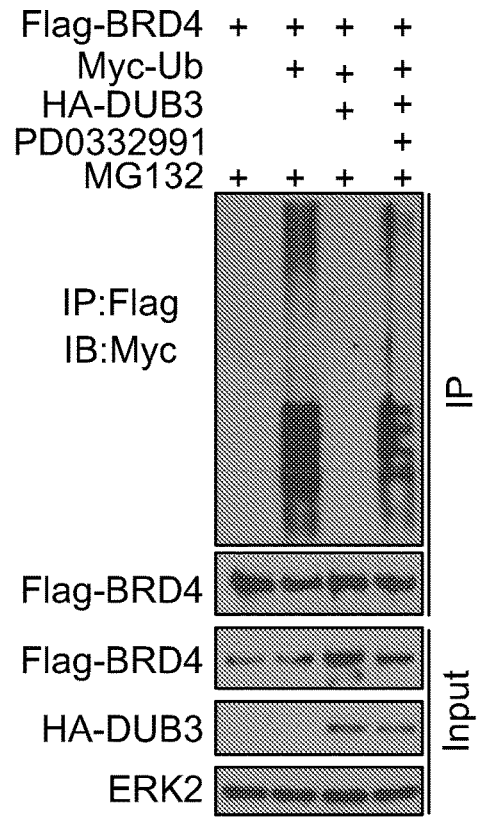
FIG. 25H

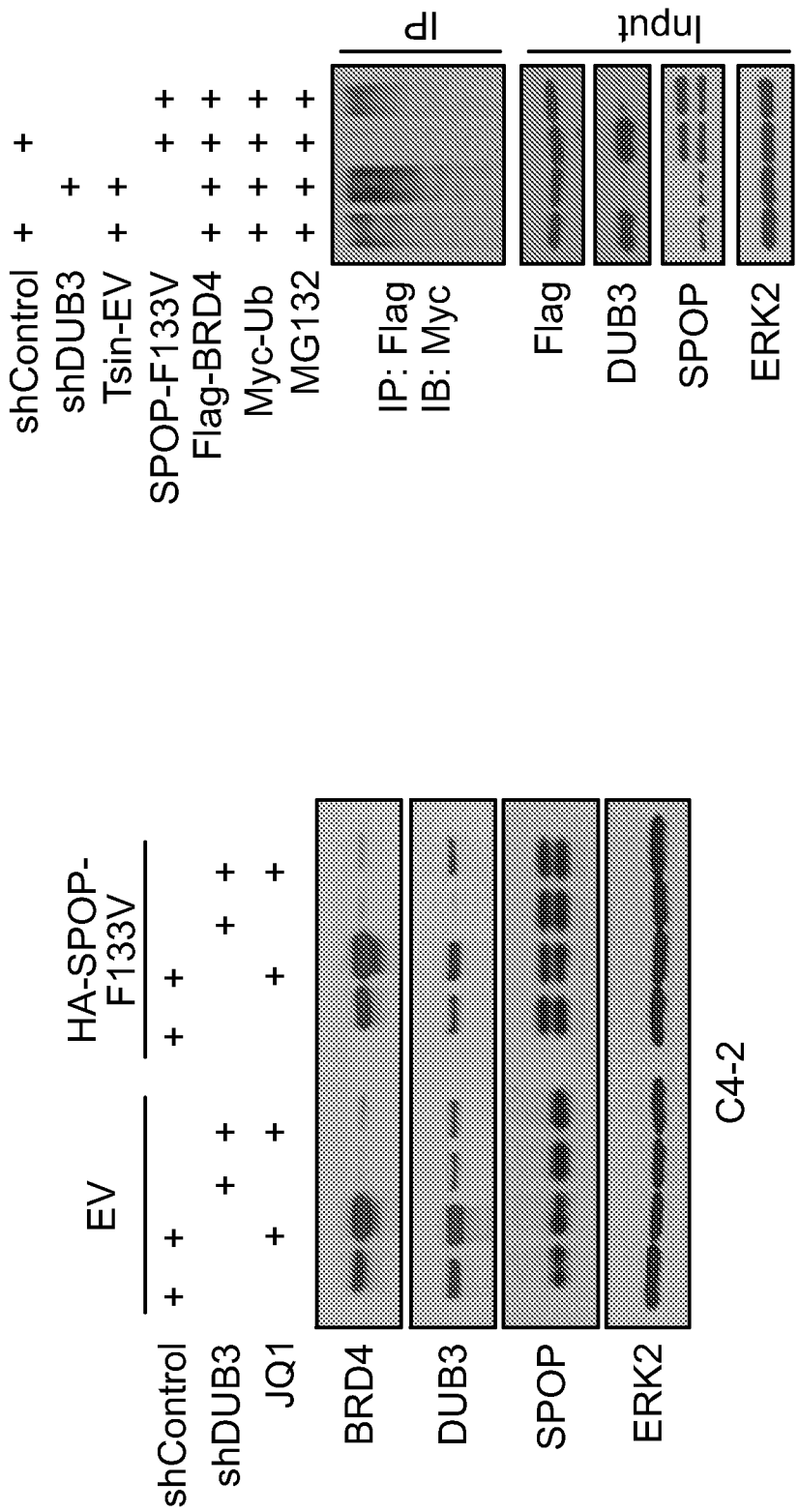

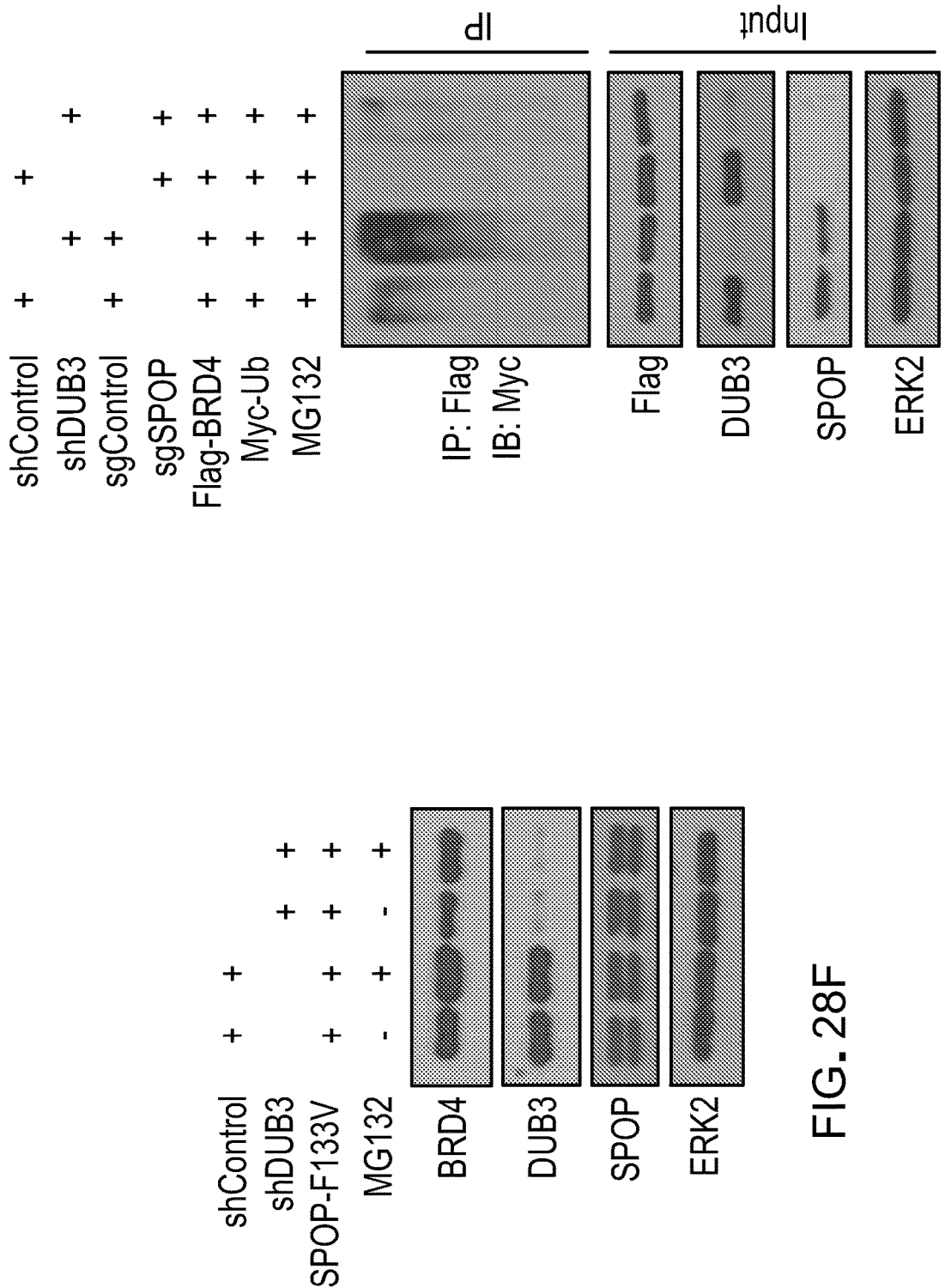

SEQUENCE LISTING

```
<160> NUMBER OF SEQ ID NOS: 116

<210> SEQ ID NO 1
<211> LENGTH: 25
<212> TYPE: DNA
<213> ORGANISM: Homo sapiens

<400> SEQUENCE: 1
acccatagct ttggtttctt ctccc                                        25

<210> SEQ ID NO 2
<211> LENGTH: 25
<212> TYPE: DNA
<213> ORGANISM: Homo sapiens

<400> SEQUENCE: 2
tatctgtttt ggacaggtgt ttgcg                                        25

<210> SEQ ID NO 3
<211> LENGTH: 22
<212> TYPE: DNA
<213> ORGANISM: Homo sapiens

<400> SEQUENCE: 3
actcatcaga tctgggaact gc                                           22

<210> SEQ ID NO 4
<211> LENGTH: 21
```

-continued

```
<212> TYPE: DNA
<213> ORGANISM: Homo sapiens

<400> SEQUENCE: 4
agttgtggct ttgatctggt t                                    21

<210> SEQ ID NO 5
<211> LENGTH: 19
<212> TYPE: RNA
<213> ORGANISM: Homo sapiens

<400> SEQUENCE: 5
ggaugaugua aaugagcaa                                       19

<210> SEQ ID NO 6
<211> LENGTH: 19
<212> TYPE: DNA
<213> ORGANISM: Homo sapiens

<400> SEQUENCE: 6
ggacagcgac tctgaatct                                       19

<210> SEQ ID NO 7
<211> LENGTH: 19
<212> TYPE: RNA
<213> ORGANISM: Homo sapiens

<400> SEQUENCE: 7 gaaccuccccu gauuacuau                                      19

<210> SEQ ID NO 8
<211> LENGTH: 19
<212> TYPE: RNA
<213> ORGANISM: Homo sapiens

<400> SEQUENCE: 8
agcugaaccu cccugauua                                       19

<210> SEQ ID NO 9
<211> LENGTH: 19
<212> TYPE: RNA
<213> ORGANISM: artificial
<220> FEATURE:
<223> OTHER INFORMATION: non-specific control siRNA

<400> SEQUENCE: 9
acagacuucg gaguaccug                                       19

<210> SEQ ID NO 10
<211> LENGTH: 21
<212> TYPE: DNA
<213> ORGANISM: Homo sapiens

<400> SEQUENCE: 10
ctacgtaaga aaccccggaa g                                    21

<210> SEQ ID NO 11
<211> LENGTH: 21
<212> TYPE: DNA
<213> ORGANISM: Homo sapiens

<400> SEQUENCE: 11 gcttttctc caaagccagt t                                     21
```

```
<210> SEQ ID NO 12
<211> LENGTH: 20
<212> TYPE: DNA
<213> ORGANISM: Homo sapiens

<400> SEQUENCE: 12
cctcagggag atgctatcca                                                    20

<210> SEQ ID NO 13
<211> LENGTH: 20
<212> TYPE: DNA
<213> ORGANISM: Homo sapiens

<400> SEQUENCE: 13
atgtcgtggt agtcgtgcag                                                    20

<210> SEQ ID NO 14
<211> LENGTH: 20
<212> TYPE: DNA
<213> ORGANISM: Homo sapiens

<400> SEQUENCE: 14
agcagcaaca gcaatgtgag                                                    20

<210> SEQ ID NO 15
<211> LENGTH: 20
<212> TYPE: DNA
<213> ORGANISM: Homo sapiens

<400> SEQUENCE: 15
gcttgcactt gtcctcttcc                                                    20

<210> SEQ ID NO 16
<211> LENGTH: 20
<212> TYPE: DNA
<213> ORGANISM: Homo sapiens

<400> SEQUENCE: 16
tggctaagga gattggtgct                                                    20

<210> SEQ ID NO 17
<211> LENGTH: 20
<212> TYPE: DNA
<213> ORGANISM: Homo sapiens

<400> SEQUENCE: 17
gcaaagcgta caaaggttcc                                                    20

<210> SEQ ID NO 18
<211> LENGTH: 20
<212> TYPE: DNA
<213> ORGANISM: Homo sapiens

<400> SEQUENCE: 18
actatgttgc tgggctggtc                                                    20

<210> SEQ ID NO 19
<211> LENGTH: 20
<212> TYPE: DNA
<213> ORGANISM: Homo sapiens

<400> SEQUENCE: 19
acctgctcca aacctcttga                                                    20
```

<210> SEQ ID NO 20
<211> LENGTH: 20
<212> TYPE: DNA
<213> ORGANISM: Homo sapiens

<400> SEQUENCE: 20
caaaggaaat gaggcagagc                                            20

<210> SEQ ID NO 21
<211> LENGTH: 20
<212> TYPE: DNA
<213> ORGANISM: Homo sapiens

<400> SEQUENCE: 21
tgtggtacaa ggagccatca                                            20

<210> SEQ ID NO 22
<211> LENGTH: 20
<212> TYPE: DNA
<213> ORGANISM: Homo sapiens

<400> SEQUENCE: 22
tgacatctgc catgaccact                                            20

<210> SEQ ID NO 23
<211> LENGTH: 20
<212> TYPE: DNA
<213> ORGANISM: Homo sapiens

<400> SEQUENCE: 23
acaggtcctt ctggtggttg                                            20

<210> SEQ ID NO 24
<211> LENGTH: 20
<212> TYPE: DNA
<213> ORGANISM: Homo sapiens

<400> SEQUENCE: 24
aggacagcaa ccagttccac                                            20

<210> SEQ ID NO 25
<211> LENGTH: 20
<212> TYPE: DNA
<213> ORGANISM: Homo sapiens

<400> SEQUENCE: 25
cacacagcag ccacaaactc                                            20

<210> SEQ ID NO 26
<211> LENGTH: 21
<212> TYPE: DNA
<213> ORGANISM: Homo sapiens

<400> SEQUENCE: 26
ggcagcattg aaccagagga g                                          21

<210> SEQ ID NO 27
<211> LENGTH: 22
<212> TYPE: DNA
<213> ORGANISM: Homo sapiens

<400> SEQUENCE: 27

```
gcatgaactt ggtcaccttc tg                                                22

<210> SEQ ID NO 28
<211> LENGTH: 19
<212> TYPE: DNA
<213> ORGANISM: Homo sapiens

<400> SEQUENCE: 28
cctgcaagga catgggtat                                                    19

<210> SEQ ID NO 29
<211> LENGTH: 20
<212> TYPE: DNA
<213> ORGANISM: Homo sapiens

<400> SEQUENCE: 29
cggcacttgt gttcagtttc                                                   20

<210> SEQ ID NO 30
<211> LENGTH: 18
<212> TYPE: DNA
<213> ORGANISM: Homo sapiens

<400> SEQUENCE: 30
ggattctctg ctctcctc                                                     18

<210> SEQ ID NO 31
<211> LENGTH: 19
<212> TYPE: DNA
<213> ORGANISM: Homo sapiens

<400> SEQUENCE: 31
cttgttcctc ctcagagtc                                                    19

<210> SEQ ID NO 32
<211> LENGTH: 20
<212> TYPE: DNA
<213> ORGANISM: Homo sapiens

<400> SEQUENCE: 32
gacgcttcta ccagctcacc                                                   20

<210> SEQ ID NO 33
<211> LENGTH: 20
<212> TYPE: DNA
<213> ORGANISM: Homo sapiens

<400> SEQUENCE: 33
gcttcactgg gtgtggaaat                                                   20

<210> SEQ ID NO 34
<211> LENGTH: 20
<212> TYPE: DNA
<213> ORGANISM: Homo sapiens

<400> SEQUENCE: 34
tgcaccacca actgcttagc                                                   20

<210> SEQ ID NO 35
<211> LENGTH: 21
<212> TYPE: DNA
<213> ORGANISM: Homo sapiens

<400> SEQUENCE: 35
```

```
ggcatggact gtggtcatga g                                              21

<210> SEQ ID NO 36
<211> LENGTH: 20
<212> TYPE: DNA
<213> ORGANISM: Homo sapiens

<400> SEQUENCE: 36
ccaaagtgtt gggattacgg                                                20

<210> SEQ ID NO 37
<211> LENGTH: 20
<212> TYPE: DNA
<213> ORGANISM: Homo sapiens

<400> SEQUENCE: 37
cggagtttct ctggacttcg                                                20

<210> SEQ ID NO 38
<211> LENGTH: 20
<212> TYPE: DNA
<213> ORGANISM: Homo sapiens

<400> SEQUENCE: 38
acatcacatg aaggccgttt                                                20

<210> SEQ ID NO 39
<211> LENGTH: 20
<212> TYPE: DNA
<213> ORGANISM: Homo sapiens

<400> SEQUENCE: 39
gaccttccac caaccaccta                                                20

<210> SEQ ID NO 40
<211> LENGTH: 20
<212> TYPE: DNA
<213> ORGANISM: Homo sapiens

<400> SEQUENCE: 40
ccctgagtca gtcacccttt                                                20

<210> SEQ ID NO 41
<211> LENGTH: 20
<212> TYPE: DNA
<213> ORGANISM: Homo sapiens

<400> SEQUENCE: 41
acaatggagc tcaccactcc                                                20

<210> SEQ ID NO 42
<211> LENGTH: 20
<212> TYPE: DNA
<213> ORGANISM: Homo sapiens

<400> SEQUENCE: 42
gcacattgat ggagcgtatg                                                20

<210> SEQ ID NO 43
<211> LENGTH: 20
<212> TYPE: DNA
<213> ORGANISM: Homo sapiens
```

```
<400> SEQUENCE: 43
taataagcag gccacccaga                                               20

<210> SEQ ID NO 44
<211> LENGTH: 20
<212> TYPE: DNA
<213> ORGANISM: Homo sapiens

<400> SEQUENCE: 44
cgcattacct ctcagccaat                                               20

<210> SEQ ID NO 45
<211> LENGTH: 19
<212> TYPE: DNA
<213> ORGANISM: Homo sapiens

<400> SEQUENCE: 45
agacaggtag cccccacag                                                19

<210> SEQ ID NO 46
<211> LENGTH: 17
<212> TYPE: DNA
<213> ORGANISM: Homo sapiens

<400> SEQUENCE: 46
ccctcccctt ccacagc                                                  17

<210> SEQ ID NO 47
<211> LENGTH: 26
<212> TYPE: DNA
<213> ORGANISM: Homo sapiens

<400> SEQUENCE: 47
gccctataaa accttcattc cccagg                                        26

<210> SEQ ID NO 48
<211> LENGTH: 18
<212> TYPE: DNA
<213> ORGANISM: Homo sapiens

<400> SEQUENCE: 48
cgccccagag tcccttat                                                 18

<210> SEQ ID NO 49
<211> LENGTH: 20
<212> TYPE: DNA
<213> ORGANISM: Homo sapiens

<400> SEQUENCE: 49
taatctcagg aggcggtgtc                                               20

<210> SEQ ID NO 50
<211> LENGTH: 20
<212> TYPE: DNA
<213> ORGANISM: Homo sapiens

<400> SEQUENCE: 50
agggatcgcg ctgagtataa                                               20

<210> SEQ ID NO 51
<211> LENGTH: 20
<212> TYPE: DNA
<213> ORGANISM: Homo sapiens
```

```
<400> SEQUENCE: 51
tgcctctcgc tggaattact                                               20

<210> SEQ ID NO 52
<211> LENGTH: 20
<212> TYPE: DNA
<213> ORGANISM: Homo sapiens

<400> SEQUENCE: 52
gcaggagcta ttcaggaagc                                               20

<210> SEQ ID NO 53
<211> LENGTH: 20
<212> TYPE: DNA
<213> ORGANISM: Homo sapiens

<400> SEQUENCE: 53
aggtggagag caaatgcaac                                               20

<210> SEQ ID NO 54
<211> LENGTH: 18
<212> TYPE: DNA
<213> ORGANISM: Artificial Sequence
<220> FEATURE:
<223> OTHER INFORMATION: Synthetic oligonucleotides

<400> SEQUENCE: 54
agactgggga gtcaagaa                                                 18

<210> SEQ ID NO 55
<211> LENGTH: 18
<212> TYPE: DNA
<213> ORGANISM: Artificial Sequence
<220> FEATURE:
<223> OTHER INFORMATION: Synthetic oligonucleotides

<400> SEQUENCE: 55
tcgggcaaaa tgcaaatt                                                 18

<210> SEQ ID NO 56
<211> LENGTH: 18
<212> TYPE: DNA
<213> ORGANISM: Artificial Sequence
<220> FEATURE:
<223> OTHER INFORMATION: Synthetic oligonucleotides

<400> SEQUENCE: 56
tcgggcaaaa tccaaatt                                                 18

<210> SEQ ID NO 57
<211> LENGTH: 20
<212> TYPE: DNA
<213> ORGANISM: Homo sapiens

<400> SEQUENCE: 57
acccagaaga ctgtggatgg                                               20

<210> SEQ ID NO 58
<211> LENGTH: 20
<212> TYPE: DNA
<213> ORGANISM: Homo sapiens

<400> SEQUENCE: 58
```
ttcagctcag ggatgacctt                                           20

<210> SEQ ID NO 59
<211> LENGTH: 20
<212> TYPE: DNA
<213> ORGANISM: Homo sapiens

<400> SEQUENCE: 59
gacctctatg ccaacacagt                                           20

<210> SEQ ID NO 60
<211> LENGTH: 20
<212> TYPE: DNA
<213> ORGANISM: Homo sapiens

<400> SEQUENCE: 60
agtacttgcg ctcaggagga                                           20

<210> SEQ ID NO 61
<211> LENGTH: 20
<212> TYPE: DNA
<213> ORGANISM: Homo sapiens

<400> SEQUENCE: 61
ggaagaggac aagtgcaagc                                           20

<210> SEQ ID NO 62
<211> LENGTH: 20
<212> TYPE: DNA
<213> ORGANISM: Homo sapiens

<400> SEQUENCE: 62
gcttcagggt ctcaaagtcg                                           20

<210> SEQ ID NO 63
<211> LENGTH: 19
<212> TYPE: DNA
<213> ORGANISM: Homo sapiens

<400> SEQUENCE: 63
gtgtacccgc tgctgtacc                                            19

<210> SEQ ID NO 64
<211> LENGTH: 20
<212> TYPE: DNA
<213> ORGANISM: Homo sapiens

<400> SEQUENCE: 64
ctggtgttgc ctggagactt                                           20

<210> SEQ ID NO 65
<211> LENGTH: 19
<212> TYPE: DNA
<213> ORGANISM: Homo sapiens

<400> SEQUENCE: 65 cccctctgg ctccttaaa                                             19

<210> SEQ ID NO 66
<211> LENGTH: 20
<212> TYPE: DNA
<213> ORGANISM: Homo sapiens

<400> SEQUENCE: 66
aggagaagag ggagggggaag                                              20

<210> SEQ ID NO 67
<211> LENGTH: 20
<212> TYPE: DNA
<213> ORGANISM: Homo sapiens

<400> SEQUENCE: 67
ggccacacag ttgccttatt                                               20

<210> SEQ ID NO 68
<211> LENGTH: 20
<212> TYPE: DNA
<213> ORGANISM: Homo sapiens

<400> SEQUENCE: 68
atgacggtag ctgccaaaag                                               20

<210> SEQ ID NO 69
<211> LENGTH: 20
<212> TYPE: DNA
<213> ORGANISM: artificial
<220> FEATURE:
<223> OTHER INFORMATION: synthetic oligonucleotide

<400> SEQUENCE: 69
ctgcccattg cctaaagaag                                               20

<210> SEQ ID NO 70
<211> LENGTH: 18
<212> TYPE: DNA
<213> ORGANISM: artificial
<220> FEATURE:
<223> OTHER INFORMATION: synthetic oligonucleotide

<400> SEQUENCE: 70
tgggaagctg tggctgac                                                 18

<210> SEQ ID NO 71
<211> LENGTH: 20
<212> TYPE: DNA
<213> ORGANISM: artificial
<220> FEATURE:
<223> OTHER INFORMATION: synthetic oligonucleotide

<400> SEQUENCE: 71
gaccttctgg aggaagtggc                                               20

<210> SEQ ID NO 72
<211> LENGTH: 20
<212> TYPE: DNA
<213> ORGANISM: artificial
<220> FEATURE:
<223> OTHER INFORMATION: synthetic oligonucleotide

<400> SEQUENCE: 72
atcgtaactc atgggcctgc                                               20

<210> SEQ ID NO 73
<211> LENGTH: 21
<212> TYPE: DNA
<213> ORGANISM: artificial
<220> FEATURE:
<223> OTHER INFORMATION: synthetic oligonucleotide

<400> SEQUENCE: 73
tcaaattgaa cctgccggat t                                              21

<210> SEQ ID NO 74
<211> LENGTH: 21
<212> TYPE: DNA
<213> ORGANISM: artificial
<220> FEATURE:
<223> OTHER INFORMATION: synthetic oligonucleotide

<400> SEQUENCE: 74
tgcatacatt cgcttgcact c                                              21

<210> SEQ ID NO 75
<211> LENGTH: 20
<212> TYPE: DNA
<213> ORGANISM: artificial
<220> FEATURE:
<223> OTHER INFORMATION: synthetic oligonucleotide

<400> SEQUENCE: 75
acctccaacc ctaacaagcc                                                20

<210> SEQ ID NO 76
<211> LENGTH: 22
<212> TYPE: DNA
<213> ORGANISM: artificial
<220> FEATURE:
<223> OTHER INFORMATION: synthetic oligonucleotide

<400> SEQUENCE: 76
tttccatagt gtcttgagca cc                                             22

<210> SEQ ID NO 77
<211> LENGTH: 22
<212> TYPE: DNA
<213> ORGANISM: artificial
<220> FEATURE:
<223> OTHER INFORMATION: synthetic oligonucleotide

<400> SEQUENCE: 77
acccgttgaa ccccattcgt ga                                             22

<210> SEQ ID NO 78
<211> LENGTH: 23
<212> TYPE: DNA
<213> ORGANISM: artificial
<220> FEATURE:
<223> OTHER INFORMATION: synthetic oligonucleotide

<400> SEQUENCE: 78
gcctcactaa accatccaat cgg                                            23

<210> SEQ ID NO 79
<211> LENGTH: 20
<212> TYPE: DNA
<213> ORGANISM: artificial
<220> FEATURE:
<223> OTHER INFORMATION: synthetic oligonucleotide

<400> SEQUENCE: 79
ggtgagtgct ggcctccagg                                                20

<210> SEQ ID NO 80
<211> LENGTH: 20

```
<212> TYPE: DNA
<213> ORGANISM: artificial
<220> FEATURE:
<223> OTHER INFORMATION: synthetic oligonucleotide

<400> SEQUENCE: 80
gcgctaacgc ctgcctagtg                                              20

<210> SEQ ID NO 81
<211> LENGTH: 23
<212> TYPE: DNA
<213> ORGANISM: artificial
<220> FEATURE:
<223> OTHER INFORMATION: synthetic oligonucleotide

<400> SEQUENCE: 81
ctcagccttt gtctctgatg aag                                          23

<210> SEQ ID NO 82
<211> LENGTH: 22
<212> TYPE: DNA
<213> ORGANISM: artificial
<220> FEATURE:
<223> OTHER INFORMATION: synthetic oligonucleotide

<400> SEQUENCE: 82
tcagatccag gcttgcttac tg                                           22

<210> SEQ ID NO 83
<211> LENGTH: 22
<212> TYPE: DNA
<213> ORGANISM: artificial
<220> FEATURE:
<223> OTHER INFORMATION: synthetic oligonucleotide

<400> SEQUENCE: 83
gtctccctgc accactaact ag                                           22

<210> SEQ ID NO 84
<211> LENGTH: 20
<212> TYPE: DNA
<213> ORGANISM: artificial
<220> FEATURE:
<223> OTHER INFORMATION: synthetic oligonucleotide

<400> SEQUENCE: 84
gcaaacattg aaaagagcct                                              20

<210> SEQ ID NO 85
<211> LENGTH: 23
<212> TYPE: DNA
<213> ORGANISM: artificial
<220> FEATURE:
<223> OTHER INFORMATION: synthetic oligonucleotide

<400> SEQUENCE: 85
caaaggtgag caacctaggc tta                                          23

<210> SEQ ID NO 86
<211> LENGTH: 21
<212> TYPE: DNA
<213> ORGANISM: artificial
<220> FEATURE:
<223> OTHER INFORMATION: synthetic oligonucleotide

<400> SEQUENCE: 86
```
atgttcctcc agagtaggtc t 21

<210> SEQ ID NO 87
<211> LENGTH: 22
<212> TYPE: DNA
<213> ORGANISM: artificial
<220> FEATURE:
<223> OTHER INFORMATION: synthetic oligonucleotide

<400> SEQUENCE: 87
ggcttacagg ataccccaa ct 22

<210> SEQ ID NO 88
<211> LENGTH: 19
<212> TYPE: DNA
<213> ORGANISM: artificial
<220> FEATURE:
<223> OTHER INFORMATION: synthetic oligonucleotide

<400> SEQUENCE: 88
gggctatcac acctcgccc 19

<210> SEQ ID NO 89
<211> LENGTH: 58
<212> TYPE: DNA
<213> ORGANISM: artificial
<220> FEATURE:
<223> OTHER INFORMATION: synthetic oligonucleotide

<400> SEQUENCE: 89
ccggcaaggt agtgaaattc tcctactcga gtaggagaat ttcactacct tgtttttt 58

<210> SEQ ID NO 90
<211> LENGTH: 58
<212> TYPE: DNA
<213> ORGANISM: artificial
<220> FEATURE:
<223> OTHER INFORMATION: synthetic oligonucleotide

<400> SEQUENCE: 90
ccggcacaag gctatcttag cagctctcga gagctgctaa gatagccttg tgtttttt 58

<210> SEQ ID NO 91
<211> LENGTH: 57
<212> TYPE: DNA
<213> ORGANISM: artificial
<220> FEATURE:
<223> OTHER INFORMATION: synthetic oligonucleotide

<400> SEQUENCE: 91
ccggcagtga cagttcgact gatgactcga gtcatcagtc gaactgtcac tgttttt 57

<210> SEQ ID NO 92
<211> LENGTH: 57
<212> TYPE: DNA
<213> ORGANISM: artificial
<220> FEATURE:
<223> OTHER INFORMATION: synthetic oligonucleotide

<400> SEQUENCE: 92
ccggcctgga gatgacatag tcttactcga gtaagactat gtcatctcca ggttttt 57

<210> SEQ ID NO 93
<211> LENGTH: 57
<212> TYPE: DNA
<213> ORGANISM: artificial

```
<220> FEATURE:
<223> OTHER INFORMATION: synthetic oligonucleotide

<400> SEQUENCE: 93
ccggcccaag aggaagttga attatctcga gataattcaa cttcctcttg ggttttt        57

<210> SEQ ID NO 94
<211> LENGTH: 57
<212> TYPE: DNA
<213> ORGANISM: artificial
<220> FEATURE:
<223> OTHER INFORMATION: synthetic oligonucleotide

<400> SEQUENCE: 94
ccgggctgat gttctcgaat tgctactcga gtagcaattc gagaacatca gcttttt        57

<210> SEQ ID NO 95
<211> LENGTH: 57
<212> TYPE: DNA
<213> ORGANISM: artificial
<220> FEATURE:
<223> OTHER INFORMATION: synthetic oligonucleotide

<400> SEQUENCE: 95
ccggcccttt gctgtgacac ttcttctcga gaagaagtgt cacagcaaag ggttttt        57

<210> SEQ ID NO 96
<211> LENGTH: 57
<212> TYPE: DNA
<213> ORGANISM: artificial
<220> FEATURE:
<223> OTHER INFORMATION: synthetic oligonucleotide

<400> SEQUENCE: 96
ccggccctgc ctacaggtta tgattctcga gaatcataac ctgtaggcag ggttttt        57

<210> SEQ ID NO 97
<211> LENGTH: 57
<212> TYPE: DNA
<213> ORGANISM: artificial
<220> FEATURE:
<223> OTHER INFORMATION: synthetic oligonucleotide

<400> SEQUENCE: 97
ccgggcggag acagaccaac tagaactcga gttctagttg gtctgtctcc gcttttt        57

<210> SEQ ID NO 98
<211> LENGTH: 57
<212> TYPE: DNA
<213> ORGANISM: artificial
<220> FEATURE:
<223> OTHER INFORMATION: synthetic oligonucleotide

<400> SEQUENCE: 98
ccggtctgct ttgcagaccg agattctcga gaatctcggt ctgcaaagca gatttttt       57

<210> SEQ ID NO 99
<211> LENGTH: 58
<212> TYPE: DNA
<213> ORGANISM: artificial
<220> FEATURE:
<223> OTHER INFORMATION: synthetic oligonucleotide

<400> SEQUENCE: 99
ccggcggacc ttatggctac agtaactcga gttactgtag ccataaggtc cgttttttg      58
```

```
<210> SEQ ID NO 100
<211> LENGTH: 58
<212> TYPE: DNA
<213> ORGANISM: artificial
<220> FEATURE:
<223> OTHER INFORMATION: synthetic oligonucleotide

<400> SEQUENCE: 100
ccggcgcaaa cctcagcaac ttcaactcga gttgaagttg ctgaggtttg cgtttttg        58

<210> SEQ ID NO 101
<211> LENGTH: 57
<212> TYPE: DNA
<213> ORGANISM: artificial
<220> FEATURE:
<223> OTHER INFORMATION: synthetic oligonucleotide

<400> SEQUENCE: 101
ccggcctgct aatcaagtca cacatctcga gatgtgtgac ttgattagca ggttttt         57

<210> SEQ ID NO 102
<211> LENGTH: 57
<212> TYPE: DNA
<213> ORGANISM: artificial
<220> FEATURE:
<223> OTHER INFORMATION: synthetic oligonucleotide

<400> SEQUENCE: 102
ccggcgcgac tactacaact ttccactcga gtggaaagtt gtagtagtcg cgttttt         57

<210> SEQ ID NO 103
<211> LENGTH: 57
<212> TYPE: DNA
<213> ORGANISM: artificial
<220> FEATURE:
<223> OTHER INFORMATION: synthetic oligonucleotide

<400> SEQUENCE: 103
ccggccatac atttaattgc cgtatctcga gatacggcaa ttaaatgtat ggttttt         57

<210> SEQ ID NO 104
<211> LENGTH: 57
<212> TYPE: DNA
<213> ORGANISM: artificial
<220> FEATURE:
<223> OTHER INFORMATION: synthetic oligonucleotide

<400> SEQUENCE: 104
ccgggcagtc tattcgtcct ccatactcga gtatggagga cgaatagact gctttttt       57

<210> SEQ ID NO 105
<211> LENGTH: 57
<212> TYPE: DNA
<213> ORGANISM: artificial
<220> FEATURE:
<223> OTHER INFORMATION: synthetic oligonucleotide

<400> SEQUENCE: 105
ccgggccagt gctaacttgg aagaactcga gttcttccaa gttagcactg gctttttt       57

<210> SEQ ID NO 106
<211> LENGTH: 57
<212> TYPE: DNA
<213> ORGANISM: artificial
<220> FEATURE:
<223> OTHER INFORMATION: synthetic oligonucleotide
```

```
<400> SEQUENCE: 106
ccggtgaaat tgagaggata catttctcga gaaatgtatc ctctcaattt cattttt         57

<210> SEQ ID NO 107
<211> LENGTH: 57
<212> TYPE: DNA
<213> ORGANISM: artificial
<220> FEATURE:
<223> OTHER INFORMATION: synthetic oligonucleotide

<400> SEQUENCE: 107
ccggccctac tgtctttgac aattactcga gtaattgtca aagacagtag ggttttt         57

<210> SEQ ID NO 108
<211> LENGTH: 58
<212> TYPE: DNA
<213> ORGANISM: artificial
<220> FEATURE:
<223> OTHER INFORMATION: synthetic oligonucleotide

<400> SEQUENCE: 108
ccgggctaag gagattggtg ctgtactcga gtacagcacc aatctcctta gcttttg         58

<210> SEQ ID NO 109
<211> LENGTH: 58
<212> TYPE: DNA
<213> ORGANISM: artificial
<220> FEATURE:
<223> OTHER INFORMATION: synthetic oligonucleotide

<400> SEQUENCE: 109
ccggtatgcc cagttctctg agaaactcga gtttctcaga gaactgggca tatttttg         58

<210> SEQ ID NO 110
<211> LENGTH: 58
<212> TYPE: DNA
<213> ORGANISM: artificial
<220> FEATURE:
<223> OTHER INFORMATION: synthetic oligonucleotide

<400> SEQUENCE: 110
ccggtctgca ccaggaccag ttaaactcga gtttaactgg tcctggtgca gattttttg      58

<210> SEQ ID NO 111
<211> LENGTH: 58
<212> TYPE: DNA
<213> ORGANISM: artificial
<220> FEATURE:
<223> OTHER INFORMATION: synthetic oligonucleotide

<400> SEQUENCE: 111
ccggacttgc tacaagtatc tcaatctcga gattgagata cttgtagcaa gtttttg        58

<210> SEQ ID NO 112
<211> LENGTH: 58
<212> TYPE: DNA
<213> ORGANISM: artificial
<220> FEATURE:
<223> OTHER INFORMATION: synthetic oligonucleotide

<400> SEQUENCE: 112
ccggcaacga tctcccttga gtttactcga gtaaactcaa gggagatcgt tgttttg         58

<210> SEQ ID NO 113
```

```
<211> LENGTH: 62
<212> TYPE: DNA
<213> ORGANISM: artificial
<220> FEATURE:
<223> OTHER INFORMATION: synthetic oligonucleotide

<400> SEQUENCE: 113
gtaccggact tcaagctgtt cttcaatgct cgagcattga agaacagctt gaagtttttt        60
tg                                                                       62

<210> SEQ ID NO 114
<211> LENGTH: 58
<212> TYPE: DNA
<213> ORGANISM: artificial
<220> FEATURE:
<223> OTHER INFORMATION: synthetic oligonucleotide

<400> SEQUENCE: 114
ccggggccca agactccacc tataactcga gttataggtg gagtcttggc ccttttg          58

<210> SEQ ID NO 115
<211> LENGTH: 58
<212> TYPE: DNA
<213> ORGANISM: artificial
<220> FEATURE:
<223> OTHER INFORMATION: synthetic oligonucleotide

<400> SEQUENCE: 115
ccggccaaca catctgcact gcttactcga gtaagcagtg cagatgtgtt ggttttg          58

<210> SEQ ID NO 116
<211> LENGTH: 58
<212> TYPE: DNA
<213> ORGANISM: artificial
<220> FEATURE:
<223> OTHER INFORMATION: synthetic oligonucleotide

<400> SEQUENCE: 116
ccgggctctc gcttatcttc gatatctcga gatatcgaag ataagcgaga gctttttg         58
```

METHODS AND MATERIALS FOR IDENTIFYING AND TREATING BET INHIBITOR-RESISTANT CANCERS

CROSS-REFERENCE TO RELATED APPLICATIONS

This application is a National Stage application under 35 U.S.C. § 371 of International Application No. PCT/US2019/043471, having an International Filing Date of Jul. 25, 2019, which claims priority to U.S. Application Ser. No. 62/703,367, filed on Jul. 25, 2018. The disclosure of the prior application is considered part of the disclosure of this application, and is incorporated in its entirety into this application.

STATEMENT AS TO FEDERALLY SPONSORED RESEARCH

This invention was made with government support under CA134514 and CA193239 awarded by National Institutes of Health. The government has certain rights in the invention.

SEQUENCE LISTING

This application contains a Sequence Listing that has been submitted electronically as an ASCII text file named "07039-1826US1_SubstituteSL_ST25.txt." The ASCII text file, created on Jun. 18, 2024, is 19,839 bytes in size. The material in the ASCII text file is hereby incorporated by reference in its entirety.

BACKGROUND

1. Technical Field

This document relates to methods and materials involved in identifying and treating mammals having a cancer resistant to BET inhibitors (bromodomain and extra-terminal domain (BET) protein inhibitors). For example, this document provides methods and materials for administering (a) one or more AKT inhibitors (also known as Protein Kinase B (PKB) inhibitors), one or more CDK inhibitors (cyclin-dependent kinase (CDK) inhibitor), and/or one or more CBP/p300 inhibitors in combination with (b) one or more BET inhibitors to mammals identified as having a cancer resistant to treatment with one or more BET inhibitors alone.

2. Background Information

BET inhibitors are anti-cancer agents currently in clinical trials. These agents can bind to the bromodomains of BET proteins such as BRD2, BRD3, and BRD4, and interfere with protein-protein interactions between the BET proteins and acetylated histones and transcription factors.

SUMMARY

This document provides methods and materials involved in identifying mammals having a cancer with at least some resistance to treatment with a BET inhibitor. For example, this document provides methods and materials for detecting the presence of cancer cells having a mutant SPOP polypeptide (the E3 ubiquitin ligase substrate-binding adaptor speckle-type POZ polypeptide) and/or an elevated level of BET polypeptide (e.g., BRD2, BRD3, and/or BRD4 polypeptide) expression to identify that cancer as being at least partially resistance to treatment with a BET inhibitor. As described herein, cancers (e.g., prostate cancers) having a mutant SPOP polypeptide or an elevated level of BET polypeptide expression can exhibit a resistance to BET inhibitors. Identifying cancers (e.g., prostate cancers) as being at least partially resistant to BET inhibitor treatment as described herein can allow clinicians to proceed with proper treatment options for cancer patients.

This document also provides methods and materials involved in treating mammals identified as having a cancer with at least some resistance to treatment with a BET inhibitor. For example, this document provides methods and materials for administering (a) one or more AKT inhibitors, one or more CDK inhibitors, and/or one or more CBP/p300 inhibitors in combination with (b) one or more BET inhibitors to mammals identified as having a cancer resistant to treatment with one or more BET inhibitors alone. AKT (also known as PKB) is a serine/threonine-specific protein kinase. As described herein, mammals having a cancer at least partially resistant to BET inhibitor treatment can be administered one or more AKT inhibitors and/or one or more CDK inhibitors and/or one or more CBP/p300 inhibitors to reduce the level of BET inhibitor resistance of the cancer, thereby making the cancer more susceptible to treatment with one or more BET inhibitors. Having the ability to use one or more AKT inhibitors and/or one or more CDK inhibitors and/or one or more CBP/p300 inhibitors to reduce the level of BET inhibitor resistance of a cancer can allow clinicians and patients to proceed with treatment options that include the effective use of one or more BET inhibitors when such BET inhibitors would have been less effective in the absence of AKT inhibitor, CDK inhibitor, and CBP/p300 inhibitor treatment.

In general, one aspect of this document features a method for increasing the susceptibility of a cancer to treatment with a BET inhibitor. The method comprises, or consists essentially of, (a) identifying a mammal as having a cancer at least partially resistant to BET inhibitor treatment, and (b) administering a CDK inhibitor or a CBP/p300 inhibitor to the mammal, thereby increasing the susceptibility of the cancer to the treatment with the BET inhibitor. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The method can comprise administering the CDK inhibitor to the mammal. The CDK inhibitor can be a CDK4 inhibitor, a CDK6 inhibitor, or a CDK4/6 inhibitor. The CDK inhibitor can be Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516. The method can comprise administering the CBP/p300 inhibitor to the mammal. The CBP/p300 inhibitor can be CPI-637, SGC-CBP30, PF-CBP1 HCl, I-CBP 112, or C646. The method can comprise administering the CDK inhibitor and the CBP/p300 inhibitor to the mammal. The method can comprise administering an AKT inhibitor to the mammal. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO: 55) for detecting a F102C mutant SPOP polypeptide, or 5'-TCGGGCAAAATCCAAATT-3' (SEQ ID NO: 56) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO:55) for detecting a F102C mutant SPOP polypeptide, or 5'-TCGGGCAAAATCC-AAATT-3' (SEQ ID NO: 56) for detecting a F102S mutant SPOP polypeptide.

In another aspect, this document features a method for increasing the susceptibility of a cancer to treatment with a BET inhibitor. The method comprises, or consists essentially of, administering a CDK inhibitor or a CBP/p300 inhibitor to a mammal identified as having a cancer at least partially resistant to BET inhibitor treatment. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208.

The method can comprise administering the CDK inhibitor to the mammal. The CDK inhibitor can be a CDK4 inhibitor, a CDK6 inhibitor, or a CDK4/6 inhibitor. The CDK inhibitor can be Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516. The method can comprise administering the CBP/p300 inhibitor to the mammal. The CBP/p300 inhibitor can be CPI-637, SGC-CBP30, PF-CBP1 HCl, I-CBP 112, or C646. The method can comprise administering the CDK inhibitor and the CBP/p300 inhibitor to the mammal. The method can comprise administering an AKT inhibitor to the mammal. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The mammal identified as having a cancer at least partially resistant to BET inhibitor treatment can be a mammal identified using an identifying method of either of the following two paragraphs.

In some cases, the identifying method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO:55) for detecting a F102C mutant SPOP polypeptide, or 5'-TCGGGCAAAATCCAAATT-3' (SEQ ID NO: 56) for detecting a F102S mutant SPOP polypeptide.

In some cases, the identifying method can comprise, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO: 55) for detecting a F102C mutant SPOP polypeptide, or 5'-TCGGGCAAAATCC-AAATT-3' (SEQ ID NO:56) for detecting a F102S mutant SPOP polypeptide.

In another aspect, this document features a method for treating cancer. The method comprises, or consists essentially of, (a) identifying a mammal as having a cancer at least partially resistant to BET inhibitor treatment, (b) administering a CDK inhibitor or a CBP/p300 inhibitor to the mammal to increase the susceptibility of the cancer to a BET inhibitor, and (c) administering a BET inhibitor to the mammal. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The method can comprise administering the CDK inhibitor to the mammal. The CDK inhibitor can be a CDK4 inhibitor, a CDK6 inhibitor, or a CDK4/6 inhibitor. The CDK inhibitor can be Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516. The method can comprise administering the CBP/p300 inhibitor to the mammal. The CBP/p300 inhibitor can be CPI-637, SGC-CBP30, PF-CBP1 HCl, I-CBP 112, or C646. The method can comprise administering the CDK inhibitor and the CBP/p300 inhibitor to the mammal. The method can comprise administering an AKT inhibitor to the mammal. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO: 55) for detecting a F102C mutant SPOP polypeptide, or 5'-TCGGGCAAAATCCAAATT-3' (SEQ ID NO:56) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO:55) for detecting a F102C mutant SPOP polypeptide, or 5'-TCGGGCAAAATCC-AAATT-3' (SEQ ID NO: 56) for detecting a F102S mutant SPOP polypeptide.

In another aspect, this document features a method for treating cancer. The method comprises, or consists essentially of, (a) administering a CDK inhibitor or a CBP/p300 inhibitor to a mammal identified as having a cancer at least partially resistant to BET inhibitor treatment to increase the susceptibility of the cancer to a BET inhibitor, and (b) administering a BET inhibitor to the mammal to reduce the number of cancer cells within the mammal. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The method can comprise administering the CDK inhibitor to the mammal. The CDK inhibitor can be a CDK4 inhibitor, a CDK6 inhibitor, or a CDK4/6 inhibitor. The CDK inhibitor can be Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516. The method can comprise administering the CBP/p300 inhibitor to the mammal. The CBP/p300 inhibitor can be CPI-637, SGC-CBP30, PF-CBP1 HCl, I-CBP 112, or C646. The method can comprise administering the CDK inhibitor and the CBP/p300 inhibitor to the mammal. The method can comprise administering an AKT inhibitor to the mammal. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The mammal identified as having a cancer at least partially resistant to BET inhibitor treatment can be a mammal identified using an identifying method of either of the following two paragraphs.

The identifying method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3'(SEQ ID NO:55) for detecting a F102C mutant SPOP polypeptide, or 5'-TCGGGCAAAATCCAAATT-3'(SEQ ID NO:56) for detecting a F102S mutant SPOP polypeptide.

In some cases, the identifying method can comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3'(SEQ ID NO:55) for detecting a F102C mutant SPOP polypeptide, or 5'-TCGGGCAAAATCC-AAATT-3' (SEQ ID NO:56) for detecting a F102S mutant SPOP polypeptide.

In another aspect, this document features a method for treating cancer. The method comprises, or consists essentially of, administering (a) a CDK inhibitor or a CBP/p300 inhibitor and (b) a BET inhibitor to a mammal identified as having a cancer at least partially resistant to BET inhibitor treatment. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The method can comprise administering the CDK inhibitor to the mammal. The CDK inhibitor can be a CDK4 inhibitor, a CDK6 inhibitor, or a CDK4/6 inhibitor. The CDK inhibitor can be Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516. The method can comprise administering the CBP/p300 inhibitor to the mammal. The CBP/p300 inhibitor can be CPI-637, SGC-CBP30, PF-CBP1 HCl, I-CBP 112, or C646. The method can comprise administering the CDK inhibitor and the CBP/p300 inhibitor to the mammal. The method can comprise administering an AKT inhibitor to the mammal. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The mammal identified as having a cancer at least partially resistant to BET inhibitor treatment can be a mammal identified using an identifying method of either of the following two paragraphs.

In some cases, the identifying method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO:55) for detecting a F102C mutant SPOP polypeptide, or 5'-TCGGGCAAAATCCAAATT-3' (SEQ ID NO: 56) for detecting a F102S mutant SPOP polypeptide.

In some cases, the identifying method can comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:54) for detecting a F133V mutant SPOP polypeptide, 5'-TCGGGCAAAATGCAAATT-3' (SEQ ID NO: 55) for detecting a F102C mutant SPOP polypeptide, or 5'-TCGGGCAAAATCC-AAATT-3' (SEQ ID NO:56) for detecting a F102S mutant SPOP polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A, Diagram showing portions of BRD2/3/4 proteins identified by yeast two-hybrid screen in a human fetal brain cDNA library using the full-length SPOP as bait. The region between two dashed red lines is the minimal interaction region shared by positive clones, and the bolded red vertical line represents the substrate-binding consensus (SBC) motif. BD1, bromodomain 1; BD2, bromodomain 2; ET, extraterminal domain; CTM, C-terminal motif. FIG. 1B, Western blot of co-IP samples of IgG or anti-BRD2/3/4 antibodies from cell lysate of LNCaP cells treated with 20 µM MG132 for 8 hours. FIG. 1C, Western blot of whole cell lysate (WCL) of 293T cells transfected with indicated plasmids and treated with or without 20 µM MG132 for 8 hours. Actin was used as a loading control. FIG. 1D, Western blot of WCL of different cell lines transfected with indicated siRNAs. FIG. 1E, Western blot of the products of in vivo ubiquitination assay performed using cell lysate of 293T cells transfected with indicated plasmids and treated with 20 µM MG132 for 8 hours. FIG. 1F, Western blot of the products of in vitro ubiquitination assay performed by incubating the reconstituted SPOP-CUL3-RBX1 E3 ligase complex with E1, E2, Ub, and His-BRD4-N(amino acids 1-500) at 30° C. for 2 hours.

FIGS. 2A-2I. SPOP promotes BRD2/3/4 protein degradation and ubiquitination. FIG. 2A, Western blot of whole cell lysate (WCL) and co-IP samples of anti-FLAG antibody from 293T cells transfected with indicated plasmids and treated with 20 µM MG132 for 8 hours. FIG. 2B, Western blot of WCL of LNCaP cells treated with DMSO, MLN4924 (200 nM), Bortezmib (200 nM) or MG132 (20 µM) for 8 hours. Actin was used as a loading control. FIG. 2C, RT-qPCR assessment of BRD2/3/4 mRNA expression in LNCaP cells treated as in (FIG. 2B). The level of GAPDH mRNA was used for normalization. Data are shown as means±SD (n=3 technical replicates), and similar results were obtained from two independent experiments. FIG. 2D and FIG. 2E, Western blot of WCL of LNCaP cells transfected with control siRNA (siC) or a pool of SPOP specific siRNAs for 48 hours and then treated with 50 µg/mL cycloheximide (CHX) and harvested at different time points (FIG. 2D). At each time point, the intensity of each BET protein was normalized to the intensity of actin and then to the value at 0 hours (FIG. 2E). Similar results were obtained from two independent experiments. FIG. 2F, RT-qPCR measurement of SPOP and BRD2/3/4 mRNA expression in LNCaP cells at 48 hours after being transfected with control and SPOP-specific siRNAs. Data are shown as means=SD (n=3 technical replicates), and similar results were obtained from two independent experiments. FIG. 2G, Western blot of WCL of 293T cells transfected with indicated plasmids. FIG. 2H, Western blot of the products of in vivo ubiquitination assay performed by using cell lysate from 293T cells transfected with indicated plasmids and treated with 20 μM of MG132 for 8 hours. K48O, K48-only ub, K63O, K63-only ub. FIG. 2I, Western blot of the products of in vivo ubiquitination assay performed by using anti-Ub or Ub-linkage specific (K48, K63) antibodies.

FIG. 3A, Amino acid (aa) sequencing alignment of a putative SBC motif in BRD2/3/4. MacroH2A and DEK, positive controls. Φ represents a nonpolar residue, and π represents a polar residue. S, serine; T, threonine. FIG. 3B, Diagram showing the wild-type BRD2/3/4 and SBC motif-deleted mutants. FIG. 3C, Western blot of WCL and co-IP samples of anti-FLAG antibody from 293T cells transfected with indicated plasmids and treated with 20 μM MG132 for 8 hours. FIG. 3D, Western blot of WCL of 293T cells transfected with indicated plasmids. e and f, Western blot of WCL of 293T cells transfected with indicated plasmids and treated with 50 μg/mL cycloheximide (CHX) and harvested at different time points (FIG. 3E). At each time point, the intensity of BET protein was normalized to the intensity of actin and then to the value at 0 hours (FIG. 3F). FIG. 3G, Western blot of the products of in vivo ubiquitination assay from 293T cells transfected with indicated plasmids and treated with 20 μM MG132 for 8 hours.

FIG. 4A, Western blot of WCL and co-IP samples of anti-FLAG antibody from 293T cells transfected with indicated Myc- or FLAG-tagged plasmids and treated with 20 μM MG132 for 8 hours. FIG. 4B, Western blot of the products of in vivo ubiquitination assay from 293T cells transfected with indicated Myc- or FLAG-tagged plasmids and treated with 20 μM MG132 for 8 hours. FIG. 4C, Western blot of indicated proteins in WCL of C4-2 cells infected with lentivirus expressing empty vector (EV), wild-type (WT) or mutated SPOP. FIG. 4D and FIG. 4E, Representative images of BRD2/3/4 IHC in SPOP-WT and -mutated (MUT) prostate cancer tissues (FIG. 4D). The quantitative data of BRD2/3/4 staining are shown in (FIG. 4E). Statistical significance was determined by Wilcoxon rank sum test.

FIG. 5A, Western blot of WCL and co-IP samples of anti-FLAG antibody from 293T cells transfected with indicated plasmids and treated with 20 μM MG132 for 8 hours. exp., exposure. FIG. 5B, Western blot of the products of in vivo ubiquitination assay of 293T cells transfected with indicated plasmids and treated with 20 μM MG132 for 8 hours. FIG. 5C, RT-qPCR assessment of BRD2/3/4 mRNA expression in SPOP-WT and SPOP-MUT prostate tumors from 99 patients of Shanghai Changhai Hospital (Shanghai, China). BRD2/3/4 mRNA expression level in each tumor specimen was normalized by the expression level of 18S rRNA (internal control) and exhibited as a value of log 10. P values were determined by Mann-Whitney test (two-sided). FIG. 5D, Comparing BRD2/3/4 mRNA expression between SPOP-WT and SPOP-MUT patient tumors using The Cancer Genome Atlas (TCGA) RNA-seq data. Y-axis indicates the mean-centered gene expression level precalculated from pan-cancer analysis (downloaded from UCSC Cancer browser: genomecancer.ucsc.edu/). P values were determined by non-parametric Wilcoxon rank sum test (two sided).

FIG. 6A, Western blot of WCL from C4-2 cells infected with lentivirus expressing control shRNA (shC) or SPOP-specific shRNA #2 or #4 and treated with or without JQ1 (1 μM) for 24 hours. β-tubulin was used as a loading control. FIG. 6B and FIG. 6E, C4-2 cells infected with lentivirus expressing empty vector (EV) or SPOP F133V mutant in combination with control shRNA (shC), or BRD2/3/4 specific shRNAs. Cells were used for western blot analysis of indicated proteins in whole-cell lysate (FIG. 6D) or for analysis of cell growth measured by cell proliferation assay (left panel) and trypan blue assay (right panel) at indicated time points (FIG. 6E). β-tubulin was used as a loading control. Data are shown as means±SD (n=6). Statistical significance was determined by two-tailed Student's t-test for cells treated with JQ1 at day 4. FIG. 6F and FIG. 6G, 22Rv1 cells infected with lentivirus expressing empty vector (EV) or SPOP F133V mutant in combination with control shRNA (shC), or BRD2/3/4 specific shRNAs. Cells were used for western blot analysis of indicated proteins in whole-cell lysate (FIG. 6F) or for analysis of cell growth measured by cell proliferation assay (left panel) and trypan blue assay (right panel) at indicated time points (FIG. 6G). β-tubulin was used as a loading control. Data are shown as means±SD (n=6). Statistical significance was determined by two-tailed Student's t-test for cells treated with JQ1 at day 4. FIG. 6Q, 22Rv1 cells was infected with lentivirus as in (FIG. 6M) and then treated with or without i-BET (0.5 μM) every other day. Cell growth was measured by trypan blue assay at indicated time points. Data are shown as means±SD (n=6 biological replicates).

FIGS. 7A-7I. Mechanism of BET inhibitor resistance in SPOP-mutated prostate cancer cells. FIG. 7A, Western blot of indicated proteins including p-AKT (Ser473) and p-S6K (Thr389) in C4-2 cells infected with lentivirus expressing empty vector (EV) or SPOP-F133V mutant in combination with control shRNA (shC) or BRD2/3/4-specific shRNAs. Cells were treated with or without JQ1 (1 μM) for 24 hours before being harvested. Asterisk indicates exogenous SPOP-F133V mutant. FIG. 7B, C4-2 cells infected with lentivirus as in (FIG. 7A) were implanted subcutaneously in mice (n=6/group). When tumors reached a size of approximately 100 mm³, xenografted mice were treated with vehicle or JQ1 (50 mg/kg) 5 days a week. Tumors were measured by caliper twice a week. Data are shown as means±SD. Statistical significance was determined by two-tailed Student's t-test for tumors at day 21 of drug treatment. FIG. 7C, Image of tumors isolated from each group of mice at day 21 of drug treatment as shown in (FIG. 7B). FIG. 7D, Heat map of RNA-seq data shows expression of a cluster of genes (n=1,017) in C4-2 cells infected with lentivirus expressing EV or F133V and treated with or without JQ1 (1 μM) for 24 hours. FIG. 7E, Heat map showing expression of 129 genes associated with JQ1 resistance was upregulated in SPOP-mutated (MUT) prostate tumors compared to SPOP-WT tumors in the TCGA cohort. FIG. 7F, Venn diagram shows that JQ1-resistant genes upregulated in SPOP-mutated prostate tumors significantly overlapped with the common BRD4 target genes of SPOP F133V and HA-BRD4 overexpressed (OE) in C4-2 cells (P=9.407e-12, Permutation test). FIG. 7G, UCSC genome browser screen shots showing BRD4 ChIP-seq signal profiles in the RAC1 gene locus in C4-2 cells expressing EV, F133V, or HA-BRD4 treated with DMSO or JQ1 (1 μM) for 24 hours. H3K4me3 ChIP-seq was acquired from LNCaP cells as reported elsewhere (Wang et al., Nature, 474:390-394 (2011)). FIG. 7H, C4-2 cells infected with lentivirus as in (FIG. 7A) were implanted subcutaneously in mice (n=6/group). When tumors reached a size of approximately 100 mm³, xenografted mice were treated with vehicle, JQ1 (50 mg/kg) or GDC-0068 (100 mg/kg) individually or in combination 5 days a week. Tumors were measured by caliper twice a week. Data are shown as means±SD. Statistical significance was determined by two-tailed Student's t-test for tumors at day 21 of drug treatment. FIG. 7I, Image of tumors isolated from each group of mice at day 21 of drug treatment as shown in (FIG. 7H).

FIG. 8A, C4-2 cells were infected with lentivirus expressing empty vector (EV) or SPOP-F133V mutant in combination with control shRNA (shC) or BRD2/3/4-specific shRNAs as in FIG. 7A and treated with vehicle (DMSO) or JQ1 (0.25 μM) every other day. Cell growth was measured by cell proliferation assay at indicated time points. Data are shown as means±SD (n=6 biological replicates). FIG. 8B, Left, representative IHC images of BRD2/3/4 in xenograft tumors isolated from each groups of mice at day 21 of drug treatment as shown in FIG. 7C. The inset in each panel shows a high magnification image of the representative (framed) area. Scale bar, 50 μm. Scale bar in inset, 20 μm. Right, the quantitative data of BRD2/3/4 IHC staining indicate the percentage of the cells with different intensity of staining (weak, intermediate and strong) in each high-power field image. Similar results were obtained from three independent xenograft tumors in each group (n=3 xenograft tissues/group). Dash lines in green indicate the base-line level of strong staining of BRD2/3/4 proteins in control (EV-shC) C4-2 cells without JQ1 treatment. FIG. 8C, Left, representative IHC images of Ki-67 in xenograft tumors isolated from each groups of mice at day 21 of drug treatment as shown in FIG. 7C. The inset in each panel shows a high magnification image of the representative (framed) area. Scale bar, 50 μm. Scale bar in inset, 20 μm. Right, the quantitative data of Ki-67 IHC staining indicate the percentage of Ki-67-positive cells among population in each high-power field image. Data are shown as means±SD (n=3 xenograft tissues/group). FIG. 8D, Western blot of WCL from xenograft tumors in four groups as shown in FIG. 7C. Equal amount of tissues from 3 tumors per group were combined and lysed together prior to analysis. Asterisk indicates the exogenous HA-SPOP-F133V. FIG. 8E, Western blot of WCL of C4-2 cells infected with lentivirus expressing empty vector (EV) or SPOPF133V mutant in combination with control shRNA (shC), ERG-, DEK-, or SRC-3-specific shRNAs and treated with vehicle (DMSO) or JQ1 (1 μM) for 24 hours before being harvested. FIG. 8F, C4-2 cells were infected with lentivirus as in (FIG. 8E) and treated with vehicle (DMSO) or JQ1 (0.25 μM) every other day, and cell growth was measured by cell proliferation assay at indicated time points. Data are shown as means±SD (n=6 biological replicates).

FIGS. 9A-9G. SPOP mutated organoids are resistant to JQ1. FIG. 9A, Western blot of WCL and co-IP samples of anti-FLAG antibody from 293T cells transfected with indicated plasmids and treated with 20 μM MG132 for 8 hours. FIG. 9B, Western blot of indicated proteins in WCL of 293T cells transfected with indicated plasmids. FIG. 9C, Western blot of the products of in vivo ubiquitination assay from 293T cells transfected with indicated plasmids and treated with 20 μM MG132 for 8 hours. FIG. 9D, Western blot of the expression of BRD2, BRD3, BRD4, and SPOP in three patient-derived organoid cell lines. β-tubulin was used as a loading control. ASC1, SPOP-W131R mutation cells; BMI and BM5, SPOP wild-type cells. FIG. 9E, Cell viability of organoids were measured by cell proliferation assay by treating with different concentration of JQ1 for 24 hours. FIG. 9F, Representative pictures of 3D cultured organoids treated with 0.2 μM JQ1 at day 7. Scale bars, 100 μm. FIG. 9G, The quantitative data of the size of organoids shown in (FIG. 9F). n=50.

4, and the half-life of BRD2/3/4 proteins. FIG. 10A, Western blot of WCL of C4-2 cells treated with vehicle (DMSO) or different doses of JQ1 or i-BET for 24 hours. Actin was used as a loading control. FIG. 10B, RT-qPCR assessment of BRD2/3/4 mRNA expression in C4-2 cells treated as in (FIG. 10A). The expression level of BRD2/3/4 mRNA was first normalized to the level of GAPDH mRNA (internal control) and then further normalized to the value in cells treated with vehicle. Data are shown as means±SD (n=3 technical replicates), and similar results were obtained from two independent experiments. FIG. 10C, Western blot of WCL of 293T cells transfected with indicated plasmids and treated with or without JQ1 (1 µM) or i-BET (1 µM) for 24 hours. Western blot signal intensity of FLAG-tagged BET proteins was first normalized to actin level (loading control), and the value was further normalized to the one in cells transfected with wild-type BRD2/3/4 without JQ1 treatment. FIG. 10D, Western blot of WCL of 293T cells co-transfected with SPOP and BRD4 and treated with or without JQ1 (1 µM) or i-BET (1 µM) for 24 hours. Western blot signal intensity of FLAG-tagged BET proteins was first normalized to actin level (loading control), and the value was further normalized to the one in cells transfected with empty vector without JQ1 treatment. FIG. 10E, Western blot of WCL and co-IP samples of anti-FLAG antibody from 293T cells transfected with indicated plasmids and treated with or without JQ1 (1 µM) for 24 hours. Western blot signal intensity of immunoprecipitated Myc-tagged SPOP proteins was first normalized to Myc-SPOP input level, and the value was further normalized to the one in cells without JQ1 treatment. FIG. 10F, Western blot of the products of in vivo ubiquitination assay in 293T cells transfected with indicated plasmids and treated with or without JQ1 (1 µM) for 24 hours. Cells were treated with MG132 (20 µM) 8 hours before being harvested. FIG. 10G and FIG. 10H, C4-2 cells infected with lentivirus expressing empty vector (EV) and SPOP F133V were treated with or without JQ1 (1 µM) for 24 hours. Cells were then treated with 50 µg/mL cycloheximide (CHX) and harvested at different time points for western blot (FIG. 10G). At each time point, the intensity of BET protein was normalized to the intensity of actin (loading control) and further normalized to the value at 0 hours (FIG. 10H). Similar results were obtained from two independent experiments.

FIG. 11A, Heat map of RNA-seq data showing a group of genes (n=5,079) whose expression was inhibited by JQ1 (1 µM, 24-hour treatment) in C4-2 cells infected with lentivirus expressing empty vector (EV) or SPOPF133V mutant. Representative genes in the MYC (purple) and AR (red) signaling pathways are highlighted. Rep, replicates. FIG. 11B-, Western blot of WCL of C4-2 cells infected with lentivirus as in (FIG. 11A) and treated with or without JQ1 (1 µM) for 24 hours before being harvested. β-tubulin was used as a loading control. Asterisk indicates the exogenous HA-SPOP-F133V. FIG. 11C, UCSC genome browser screen shots showing signal profiles of BRD4 ChIP-seq in C4-2 cells infected with lentivirus expressing empty vector (EV) or SPOP-F133V or transfected with HA tagged BRD4 and ChIP-seq signaling profiles of H3K4me1 and H3K4me3 (histone markER for enhancer and promoter, respectively) in LNCaP cells (Wang et al., Nature, 474:390-394 (2011)). The promoter and enhancer regions are highlighted in yellow. FIG. 11D, ChIP-qPCR analysis of BRD4 binding at the MYC enhancer and the AR promoter in C4-2 cells infected with indicated lentivirus and treated with JQ1 as in FIG. 11B. All data are shown as mean values±SD (n=3 technical replicates), and similar results were obtained from two independent experiments. FIG. 11E, RT-qPCR analysis of mRNA expression of the AR target genes PSA, TMPRSS2, and KLK2 in C4-2 cells infected with indicated lentivirus and treated with or without JQ1 as in (FIG. 11B). Data are shown as mean values±SD (n=3 technical replicates), and similar results were obtained from two independent experiments. FIG. 11F, ChIP-qPCR analysis of AR binding at the promoter of PSA, TMPRSS2, and KLK2 genes in C4-2 infected with indicated lentivirus and treated with or without JQ1 as in (FIG. 11B). Data are shown as mean values±SD (n=3 technical replicates), and similar results were obtained in two independent experiments. FIG. 11G, Western blot of WCL of C4-2 infected with lentivirus expressing empty vector (EV) or SPOPF133V in combination with control shRNA (shC) or AR-specific shRNAs and treated with or without JQ1 (1 µM) for 24 hours before being harvested. FIG. 11H, C4-2 cells were infected with lentivirus as in (FIG. 11G) and treated with vehicle (DMSO) or JQ1 (0.25 µM) every other day. Cell growth was measured by cell proliferation assay at different time points. Data are shown as mean values±SD (n=6 biological replicates).

FIGS. 12A-12P. RAC1 is a BRD4 binding target and upregulation of RAC1 contributes to JQ1-resistance in SPOP-mutated prostate cancer cells. FIG. 12A, Western blot of WCL of C4-2 cells infected with lentivirus expressing empty vector (EV) or SPOPF133V mutant or transfected with HA-BRD4 and treated with vehicle (DMSO) or 1 µM JQ1 for 24 hours before being harvested. Asterisk indicates the exogenous HA-SPOP-F133V. FIG. 12B, BRD4 binding corrects with 129 JQ1-resistant genes whose expression was upregulated in SPOP-mutated tumors. The red bar represents the percentage of 129 genes having BRD4 binding sites within 1 kb of the transcription start sites (TSS). The blue bell shape curve represents the background distribution as control, where 10,000 permutation tests were performed by randomly choosing 129 genes from refGenes and calculating the percentage of random genes with BRD4 binding in TSS. The enrichment of BRD4 binding at 129 upregulated genes over whole genome background is statistically significant. EV, empty vector. OE, overexpression. FIG. 12E, Western blot analysis of indicated proteins in whole-cell lysate of C4-2 cells infected with empty vector (EV) or SPOP F133V or BRD2/3/4 expressed vectors for 48 hours before being harvested. FIG. 12F, Venn diagram shows that JQ1-resistant genes upregulated in SPOP-mutated prostate tumors significantly overlapped with the genes upregulated by BRD2/3/4 over-expression (OE) in C4-2 cells (P<0.001, Permutation test). FIG. 12G, UCSC genome browser screen shots showing signal profiles of RNA-seq in the gene region of the RAC1 gene in C4-2 cells transfected with empty vector (control) and BRD2/3/4 overexpressed (OE). FIG. 12K and FIG. 12L, RT-qPCR (FIG. 12K) and western blot (FIG. 12L) analysis of RAC1 expression in C4-2 cells infected with lentivirus as indicated. The expression level of RAC1 mRNA was first normalized to the level of GAPDH mRNA (internal control) and then further normalized to the value in control (EV-shC) C4-2 cells. Data are shown as mean values±SD (n=3 technical replicates), and similar results were obtained from two independent experiments. Comparing to the data in control (EV-shC) C4-2 cells. FIG. 12P, C4-2 cells were infected with lentivirus as in (FIG. 12O) and treated with JQ1 (0.25 µM) every other day. Cell growth was measured by cell proliferation assay. Data are shown as means±SD (n=6 biological replicates).

FIG. 13A, A scheme shows the cholesterol biosynthesis pathway, which is modified from the website (en.wikipedia.org/wiki/Biosynthesis). The genes whose expression was affected by JQ1 and SPOP-F133V in C4-2 cells are highlighted by red boxes. FIG. 13P, Western blot analysis of indicated proteins in whole cell lysate of C4-2 cells infected with empty vector (EV) or SPOP F133V expressed vectors and with or without knockdown of BRD4, FOS/JUN, or SRC3 for 48 hours before being harvested.

FIG. 14A, Western blot analysis of expression of receptor tyrosine kinases (RTKs) including HER3, INSR, and IGF1R in C4-2 cells infected with lentivirus expressing empty vector (EV) or SPOP F133V mutant. Cells were treated with vehicle (DMSO) or 1 µM JQ1 for 24 hours before being harvested. β-tubulin was used as a loading control. FIG. 14B-14G, C4-2 cells were infected with lentivirus expressing empty vector (EV) or SPOP F133V mutant in combination with control shRNA (shC) or shRNAs specific for HER3 (FIG. 14B), IGF1R (FIG. 14C), INSR (FIG. 14D), AKT (FIG. 14E), mTOR (FIG. 14F), or Raptor (FIG. 14G). Cells were treated with vehicle (DMSO) or JQ1 (1 µM) for 24 hours before being harvested for Western blot (all the left panels). β-tubulin was used as a loading control. For cell proliferation assay (the right panels), cells were treated with vehicle (DMSO) or JQ1 (0.25 µM) every other day, and cell growth was measured at indicated time points. Data are shown as means+SD (n=6). Statistical significance was determined by two-tailed Student's t-test for cells treated with JQ1 at day 4. FIG. 14H, C4-2 cells were infected with lentivirus expressing empty vector (EV) or SPOP F133V mutant and treated with vehicle (DMSO) or JQ1 (0.25 µM, 5 days for proliferation; or 1 µM, 24 hours for WB) and/or the AKT inhibitor MK2206 (1 µM, 5 days for proliferation; or 5 µM, 24 hours for WB). Western blot analysis of indicated proteins was performed (left panel), and cell growth was measured by cell proliferation assay at different time points (right panel). Data are shown as means±SD (n=6). Statistical significance was determined by two-tailed Student's t-test at day 5. FIG. 14I, C4-2 cells were infected with lentivirus expressing empty vector (EV) or SPOP F133V mutant and treated with vehicle (DMSO) or JQ1 (0.25 µM, 5 days for proliferation; or 1 µM, 24 hours for WB) and/or the AKT inhibitor GDC-0068 (0.2 µM, 5 days for proliferation; or 1 µM, 24 hours for WB). Western blot analysis of indicated proteins was performed (left panel), and cell growth was measured by cell proliferation assay at different time points (right panel). Data are shown as means±SD (n=6). Statistical significance was determined by two-tailed Student's t-test at day 5. FIG. 14J, A model proposed according to the results provided herein. Left, wild-type SPOP inhibits the activity of BET proteins BRD2, BRD3, and BRD4 by binding to and targeting these proteins for ubiquitination and proteasomal degradation, thereby sensitizing prostate cancer cells to JQ1 treatment (left panel). Middle, prostate cancer-associated SPOP mutations impair SPOP mediated degradation of BET proteins and other target proteins including AR, SRC-3, and ERG. The results provided herein demonstrate that activities of AR and ERG can be inhibited by JQ1 even in SPOP mutated cells which could be due to JQ1-sensitive, acetylation (red dot)-dependent interaction of AR and ERG with BET proteins. In contrast, the results provided herein also demonstrate that deregulation of BET proteins due to SPOP mutation leads to upregulation of RAC1 and cholesterol biosynthesis genes (Chol. Syn. Genes), both of which are needed for aberrant activation of the AKTmTORC1 pathway and thereby contribute to JQ1-resistance in SPOP-mutated prostate cancer cells. Right, treatment of SPOP mutated cancer cells (e.g., SPOP mutated prostate cancer cells) and xenografts with AKT inhibitors completely overcomes SPOP mutation-conferred BET inhibitor resistance in cancer cells (e.g., SPOP mutated prostate cancer cells).

(FIG. 15A, FIG. 15B), C4-2 cells were treated with or without TSA (1 µM) for 24 hours for Western blot (FIG. 15A) and RT-qPCR (FIG. 15B). ERK2, a loading control. *P<0.05. (FIG. 15D, FIG. 15E), C4-2 and PC-3 cells were infected with lentivirus expressing indicated shRNAs for 48 hours for Western blot (FIG. 15D) and RT-qPCR (FIG. 15E). Data are shown as mean±SD (n=3). *P<0.05. (FIG. 15F, FIG. 15G), Western blot analysis of reciprocal co-immunoprecipitation of endogenous proteins in C4-2 cells. (FIG. 15H, FIG. 15I), C4-2 and PC-3 cells were infected with lentivirus expressing indicated shRNAs for 48 hours for Western blot (FIG. 15H) and RT-qPCR (FIG. 15I). Data are shown as mean±SD (n=3). *P<0.05. (FIG. 15J, FIG. 15K), ChIP-qPCR analysis of NCOR2 (FIG. 15J) and HDAC10 (FIG. 15K) binding at the DUB3 gene promotor in C4-2 and PC-3 cells. Data are shown as mean±SD (n=3). *P<0.05. (FIG. 15O), a hypothetical model depicting transcription repression of DUB3 by NCOR2 and HDAC10.

(FIG. 16A, FIG. 16B) UCSC Genome Browser screenshots showing BRD4 ChIP-seq signal profiles in the USP17L2 (DUB3) or HDAC10 gene loci in C4-2 cells transfected with empty vector or HA-BRD4 for 24 hours. H3K4me1, H3K4me2, and H3K4me3 ChIP-seq data were acquired from LNCaP cells.

FIGS. 17A-17N. BRD4 represses DUB3 expression via transcriptionally activating NCOR2. (FIG. 17A), UCSC Genome Browser screenshots for BRD4 ChIP-seq profiles in the DUB3 gene locus in C4-2 cells reported in Example 1 and elsewhere (Zhang et al. Nat. Med., 23:1055-1062 (2017)). H3K4me1, H3K4me2, and H3K4me3 ChIP-seq data were reported elsewhere (Wang et al., Nature, 474:390-394 (2011)). (FIG. 17B, FIG. 17C), ChIP-qPCR analysis of BRD4 binding at the DUB3 gene promotor in C4-2 (FIG. 17B) and PC-3 cells (FIG. 17C). Data are shown as mean±SD (n=3). *P<0.001. (FIG. 17D, FIG. 17E), C4-2 cells were transfected with indicated plasmids for 24 hours for Western blot (FIG. 17D) and RT-qPCR (FIG. 17E). Data are shown as mean±SD (n=3). *P<0.05. (FIG. 17N), a hypothetical model depicting that BRD4 represses DUB3 expression via transcriptionally activating NCOR2.

FIGS. 18A-18L. DUB3 deubiquitinates and antagonizes SPOP-mediated ubiquitination of BRD4. (FIG. 18A), Western blot analysis in PC-3 cells 24 hours after transfected with indicated plasmids. (FIG. 18B), Western blot analysis in PC-3 and DU145 cells 48 hours after infected with indicated shRNAs. (FIG. 18C), PC-3 cells were infected with indicated shRNAs for 48 hours for Western blot. Cells were treated with MG132 for 8 h before harvested. (FIG. 18D), Western blot analysis in PC-3 cells 24 hours after transfected with indicated plasmids. (FIG. 18E), PC-3 cells were infected with indicated shRNA for 48 hours followed by treatment with 50 μg/μL cycloheximide (CHX) for Western blot. At each time point, the intensity of BRD4 was normalized to the intensity of ERK2 (loading control) first and then to the value at the 0-hour time point. (FIG. 18F), Western blot analysis in PC-3 cells transfected with indicated shRNAs for 48 hours for Western blot. Cells were treated with MG132 for 8 hours before harvested. (FIG. 18G), PC-3 cells were transfected with indicated plasmids for 24 hours followed by treatment of 50 μg/μL CHX for Western blot. Protein bands were quantified as in (FIG. 18E). (FIG. 18H), Western blot analysis in PC-3 cells transfected with the indicated plasmids for 24 hours. Cells were treated with MG132 for 8 hours before harvested. (FIG. 18I), Western blot analysis in PC-3 cells 24 hours after transfected with the indicated plasmids. (FIG. 18J), Western blot analysis in PC-3 cells 48 hours post infected with indicated shRNAs. (FIG. 18K), Western blot analysis in PC-3 cells transfected with the indicated plasmids for 24 hours. Cells were treated with MG132 for 8 hours before harvested. (FIG. 18L), a hypothetical model depicting that DUB3 deubiquitinates and antagonizes SPOP-mediated ubiquitination of BRD4.

FIGS. 19A-19D. The effect of DUB3 knockdown on expression of BRD4 protein and mRNA in prostate, breast and pancreatic cancer cell lines. (FIG. 19A) DU145 and PC-3 cells were infected with lentivirus expressing control or DUB3-specific shRNAs. After 48 hours, cells were harvested for RT-qPCR analysis. *P<0.01, n.s., not significant. (FIG. 19B-19D) C4-2 and 22RV1 prostate cancer cell lines (FIG. 19B), MiaPaCa-2 and Panc-1 pancreatic cancer cell lines (FIG. 19C), and MDA-MB-231, MDA-MB-436 and MCF-7 breast cancer cell lines were infected with lentivirus expressing control or DUB3-specific shRNAs. After 48 hours, cells were subjected to Western blot (left panel) and RT-qPCR (right panel) analysis. *P<0.01, n.s., not significant.

(FIG. 20A) Western blot analysis of co-immunoprecipitated proteins from 293T cells transfected with different Flag-tagged USPs (DUB3 and other DUBs) and HA-BRD4. (FIG. 20B) Western blot analysis of indicated proteins in DU145 cells 48 hours after infected with lentivirus expressing control or USP-specific shRNAs.

(FIG. 21A, FIG. 21B), Western blot analysis of co-immunoprecipitated proteins from 293T cells transfected with Flag-BRD4 and HA-DUB3. (FIG. 21C, FIG. 21D), Western blot analysis of co-immunoprecipitated endogenous BRD2/3/4 and DUB3 proteins in PC-3 cells. (FIG. 21E), schematic diagram depicting a set of GST-DUB3 recombinant protein constructs. (FIG. 21F), Western blot analysis of Flag-BRD4 proteins in PC-3 cells pulled down by GST or GST-DUB3 recombinant proteins. Arrows indicate the protein bands at the expected molecular weight. (FIG. 21G), schematic diagram depicting a set of Flag-tagged BRD4 expression constructs. (FIG. 21H), Western blot analysis of DUB3 proteins in PC-3 cells immunoprecipitated by Flag-BRD4. (FIG. 21I), Western blot analysis of proteins immunoprecipitated by ectopically expressed Flag-BRD4 or Flag-BRD4 AC™ in 293T cells. (FIG. 21J), Western blot analysis in PC-3 cells transfected with indicated plasmids.

(FIG. 22A) Schematic diagram depicting the domain structure of BRD2, BRD3 and BRD4 proteins. (FIG. 22B, FIG. 22C) Western blot analysis of indicated proteins in whole cell lysate of 293T cells at 24 hours after transfected with indicated constructs. (FIG. 22D) PC-3 cells were infected with lentivirus expressing control or DUB3-specific shRNAs. After 48 hours, cells were harvested for Western blot analysis.

FIGS. 23A-23C. Genetic alteration of NCOR2 genes in TCGA prostate cancer specimens, DUB3 mRNA expression in CRPC patient samples and RT-qPCR evaluation of NCOR2 and DUB3 shRNA knockdown efficiency. (FIG. 23A) Genomic alterations of the NCOR2 gene in TCGA prostate cancer database (n=493) and SU2C/PCF dream team metastatic prostate cancer database (n=150). (FIG. 23B) Analysis of DUB3 mRNA in a cohort of patient samples including normal, primary prostate cancer and castration-resistant prostate cancer (CRPC) specimens as described elsewhere (Grasso et al., Nature, 487:239-243 (2012)). (FIG. 23C) PC-3 cells were infected with lentivirus expressing control shRNA, NCOR2-specific, and/or DUB3-specific shRNAs. After 48 hours, cells were harvested for RT-qPCR analysis. All data are shown as mean values±SD (n=3). *P<0.05.

(FIG. 24A), a hypothetical model depicting that loss of NCOR2 correlates with increased expression of DUB3 and BRD4. (FIG. 24N), PC-3 cells were infected as in (FIG. 24L) and harvested for RT-qPCR. Data are shown as mean±SD (n=3). n.s., not significant.

FIGS. 25A-25M. CDK4/6 inhibitor suppresses the deubiquitinase activity of DUB3 and promotes BRD4 degradation in prostate cancer cells. (FIG. 25A), DU145 cells were infected with indicated shRNA for 48 hours for Western blot analysis. (FIG. 25B), Western blot analysis in DU145 cells treated with 2 μM of PD0332991. (FIG. 25C), Western blot analysis in DU145 cells treated with indicated inhibitors for 24 hours. (FIG. 25D), DU145 cells were transfected with indicated plasmids for 24 hours followed by treatment with 2 μM of PD0332991 for another 24 hours before Western blot. (FIG. 25E), DU145 cells were infected with indicated shRNAs for 24 hours and then treated with 2 µM of PD0332991 for another 24 hours before Western blot. (FIG. 25F), DU145 cells were transfected indicated plasmids and treated with 2 µM of PD0332991 for 24 hours. Cells were treated with MG132 for 8 h before analysis. (FIG. 25G), DU145 cells were treated with 5 µM of PD0332991 for 24 hours followed by treatment with 50 µg/µL CHX. Protein bands were quantified as in FIG. 18E. (FIG. 25H), DU145 cells were transfected indicated plasmids and treated with 2 µM of PD0332991 for 24 hours. Cells were treated with MG132 for 8 hours before analysis. (FIG. 25I), DU145 cells were infected with indicated shRNAs for 24 hours followed by transfection of indicated constructs for another 24 hours before analysis. (FIG. 25J), DU145 cells were transfected indicated plasmids for 24 hours and treated with MG132 for 8 hours before harvested for immunoprecipitation and western blot analysis. (FIG. 25K, FIG. 25L), DU145 cells were transfected with indicated plasmids for 24 hours followed by treatment of 50 µg/µL CHX for Western blot. Protein bands were quantified as in (FIG. 25G). (FIG. 25M), a hypothetical model depicting that CDK4/6 inhibitor suppresses the deubiquitinase activity of DUB3 and enhances BRD4 degradation.

(FIG. 26A) Western blot analysis of indicated proteins in PC-3 cells infected with lentivirus expressing control or DUB3-specific shRNA for 24 hours and then co-transfected with plasmids for wild-type (WT) and mutants of HA-DUB3 for 24 hours. (FIG. 26B) Western blot analysis of indicated proteins in PC-3 cells infected with lentivirus expressing control or DUB3-specific shRNAs for 24 hours and then co-transfected with the indicated plasmids for 24 hours. Cells were treated with MG132 for 8 hours before harvested. (FIG. 26C) DU145 cells were infected with lentivirus expressing control or DUB3-specific shRNAs. After 48 hours puromycin selection, cells were treated with I-BET (5 µM), PD0332991 (5 µM) or both followed by MTS assay. All data are shown as mean values±SD (n=6). *P<0.001, n.s., not significant. (FIG. 26D, FIG. 26E) DU145 cells were infected with lentivirus expressing indicated shRNAs and/or plasmids. After 48 hours puromycin selection, cells were treated with JQ1 (2 µM), PD0332991 (5 µM) or both followed by MTS assay (FIG. 26D) and Western blot (FIG. 26E). The quantitative data are shown as mean values±SD (n=6). *P<0.001, n.s., not significant. (FIG. 26F, FIG. 26G) DU145 cells were infected with lentivirus expressing indicated shRNAs and/or plasmids. After 48 hours puromycin selection, cells were treated with I-BET (5 µM), PD0332991 (5 µM) or both followed by MTS assay (FIG. 26F) and Western blot (FIG. 26G). All data are shown as mean values±SD (n=6). *P<0.05, ***P<0.001, n.s., not significant. (FIG. 26H) DU145 cells were infected with lentivirus expressing control, DUB3 expressing vector and/or control or BRD4-specific shRNAs. After 48 hours puromycin selection, cells were plated for clonogenic survival assay. Cells were treated with a series of JQ1 concentrations for 3 days and harvested at day 10. Colonies with more than 50 cells were counted. $IC_{50}$ is shown as a dotted line in the middle of the graph. Specifically, $IC_{50}$ of EV=0.421 µM; $IC_{50}$ of DUB3 OE=0.576 µM; $IC_{50}$ of BRD4 KD=0.278 µM; $IC_{50}$ of DUB3 OE BRD4 KD=0.297 µM. OE, overexpression. KD, shRNA-mediated knockdown. (FIG. 26I) DU145 cells were infected with lentivirus as in (FIG. 26H) for 48 hours and then treated with 0.5 µM of JQ1 for 3 days and harvested at day 10. Colonies were photographed and quantified. Data represent means±SEM (n=3); P values were determined by the unpaired two-tailed Student's t-test. *P<0.05, **P<0.01.

(FIG. 27A), DU145 cells were treated with JQ1 for 24 hours followed by treatment of 50 µg/µL CHX for Western blot. Protein bands were quantified as in FIG. 18E. (FIG. 27B), DU145 cells were infected with indicated shRNAs for 24 hours and treated with 2 µM of JQ1 for another 24 hours before Western blot. (FIG. 27C), Western blot analysis in DU145 cells 24 hours after treated with indicated chemicals. (FIG. 27D), DU145 cells were transfected indicated plasmids for 48 hours and treated with MG132 for 8 hours before analysis. (FIG. 27E), DU145 cells were treated with indicated chemicals for 24 hours and treated with MG132 for 8 hours before analysis. (FIG. 27F), DU145 cells were infected with indicated shRNAs for 48 hours and treated with JQ1 (2 µM), PD0332991 (5 µM) or both before MTS assay. Data are shown as mean±SD (n=6).*** P<0.001, n.s., not significant. (FIG. 27G, FIG. 27H), DU145 cells were infected with lentivirus as in (FIG. 27F) and injected s.c. into the right flank of NSG mice and treated with JQ1, PD0332991 or both. Tumor growth was measured every other day for 21 days. Tumors in each group at day 21 were harvested, photographed and shown in (FIG. 27G). Data in (FIG. 27H) are shown as mean±SD (n=6). *P<0.05 comparing size of tumors in different groups at day 21. (FIG. 27I), a hypothetical model depicting that DUB3 inhibition by CDK4/6 inhibitor sensitizes prostate cancer cells to BET-inhibitor.

FIGS. 28A-28H. Examination of the effect of DUB3 on BRD4 protein level and sensitivity to JQ1 in SPOP mutated prostate cancer cells. (FIG. 28A, FIG. 28B) DU145 cells were infected with lentivirus expressing control, SPOP F133V mutant overexpressing vector and/or control or DUB3-specific shRNAs. After 48 hours puromycin selection, cells were treated with JQ1 (2 µM) followed by MTS assay (FIG. 28A) and Western blot (FIG. 28B). All data are shown as mean values±SD (n=6). *P<0.05, ***P<0.001, n.s., not significant. (FIG. 28C, FIG. 28D) C4-2 cells were infected with lentivirus expressing control, SPOP F133V mutant overexpressing vector and/or control or DUB3-specific shRNAs. After 48 hours puromycin selection, cells were treated with JQ1 (2 µM) followed by MTS assay (FIG. 28C) and Western blot (FIG. 28D). All data are shown as mean values±SD (n=6). *P<0.05, ***P<0.001, n.s., not significant. (FIG. 28E) Western blot analysis of indicated proteins in DU145 cells infected with lentivirus expressing control or DUB3-specific shRNA for 24 hours and then co-transfected with the indicated constructs for 24 hours. Cells were treated with MG132 for 8 hours before harvested. (FIG. 28F) Western blot analysis of indicated proteins in DU145 cells infected with lentivirus expressing control or DUB3-specific shRNA for 24 hours and then co-transfected with HA-SPOP-F133V mutant for 24 hours. Cells were treated with or without MG132 for 8 hours before harvested. (FIG. 28G) Western blot analysis of indicated proteins in control or SPOP-specific sgRNA mediated CRISPR/Cas9 knockout PC-3 cells infected with lentivirus expressing indicated shRNAs and/or expression vector. After 48 hours, cells were treated with MG132 for 8 hours before harvested. (FIG. 28H) Western blot analysis of indicated proteins in control or SPOP-specific sgRNA mediated CRISPR/Cas9 knockout PC-3 cells infected with lentivirus expressing indicated shRNAs and/or expression vector. After 48 hours, cells were treated with or without MG132 for 8 hours before harvested.

DETAILED DESCRIPTION

Figure 1A:
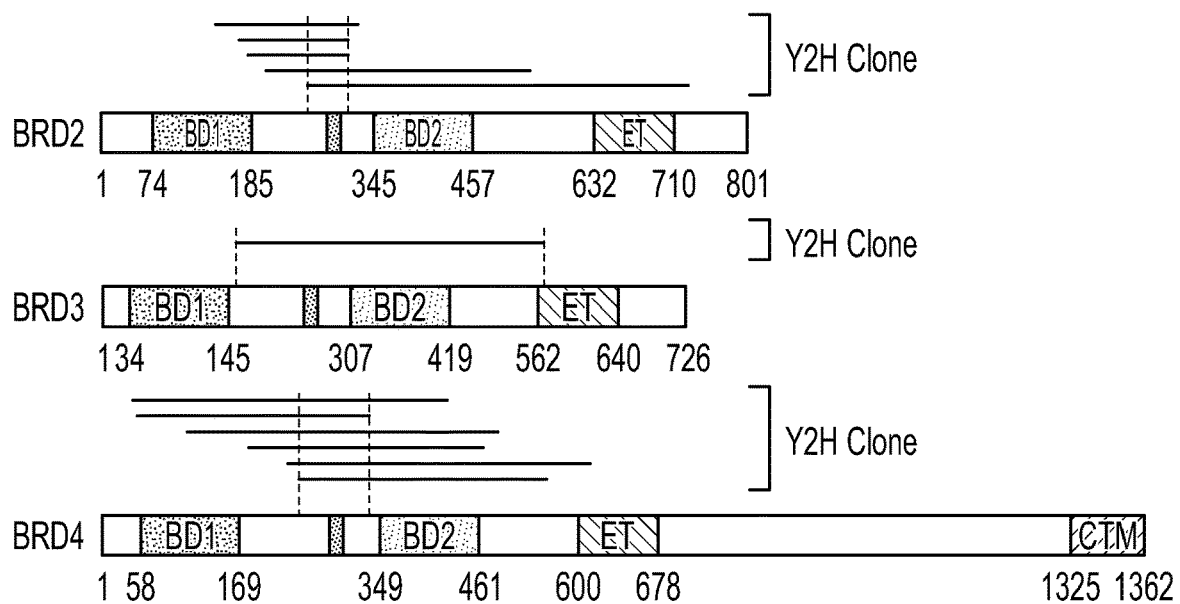
FIGS. 1A-1F. SPOP interacts with and promotes BRD2/3/4 protein ubiquitination and degradation.

This document provides methods and materials for identifying and/or treating cancers having at least a partial resistance to treatment with a BET inhibitor. For example, this document provides methods and materials for identifying a mammal (e.g., a human) as having a cancer at least partially resistant to BET inhibitor treatment. Any appropriate mammal can be identified as having a cancer at least partially resistant to BET inhibitor treatment. For example, humans and other primates such as monkeys can be identified as having a cancer at least partially resistant to BET inhibitor treatment. In some cases, dogs, cats, horses, cows, pigs, sheep, mice, or rats can be identified as having a cancer at least partially resistant to BET inhibitor treatment as described herein.

Any appropriate cancer can be assessed as described herein to determine whether it is at least partially resistant to BET inhibitor treatment. For example, prostate cancer, lung adenocarcinoma cancer, small cell lung cancer, colorectal adenocarcinoma cancer, acral melanoma cancer, or oral squamous cell carcinoma cancer can be assessed as described herein to determine whether it is at least partially resistant to BET inhibitor treatment.

As described herein, a mammal (e.g., a human) can be identified as having a cancer at least partially resistant to BET inhibitor treatment by detecting cancer cells having a mutated SPOP polypeptide. Examples of mutated SPOP polypeptides that can be detected and used to classify a mammal (e.g., a human) as having cancer at least partially resistant to BET inhibitor treatment include, without limitation, SPOP polypeptides having one or more amino acid mutations present within the MATH domain of the SPOP polypeptide. A wild-type human SPOP polypeptide can have the amino acid sequence as set forth in GenBank Accession No. CAA04199 (see also, 2695708), and the MATH domain of a human SPOP polypeptide can extend from amino acid residue 28 to amino acid residue 166. Examples of human SPOP polypeptides having one or more amino acid mutations present within the MATH domain that can be used to identify a mammal (e.g., a human) as having cancer at least partially resistant to BET inhibitor treatment as described herein include, without limitation, F133V SPOP polypeptides, F133L SPOP polypeptides, F102C SPOP polypeptides, Y87C SPOP polypeptides, Y87N SPOP polypeptides, S119N SPOP polypeptides, F125V SPOP polypeptides, K129E SPOP polypeptides, W131C SPOP polypeptides, W131G SPOP polypeptides, K134N SPOP polypeptides, and Q165P SPOP polypeptides.

Any appropriate method can be used to determine if a mammal (e.g., a human) has cancer cells containing a mutated SPOP polypeptide. For example, a cancer cell biopsy sample obtained from a mammal (e.g., a human) having cancer can be assessed for the presence of nucleic acid encoding a mutant SPOP polypeptide using nucleic acid sequencing techniques, nucleic acid hybridization techniques, and/or mutation-specific polymerase chain reaction (PCR). In some cases, nucleic acid probes specific for particular nucleic acid mutations can be used to detect the presence of nucleic acid encoding a mutant SPOP polypeptide, thereby identifying the mammal as having cancer cells with a mutant SPOP polypeptide. In some cases, immunological techniques such as cell staining techniques, Western blot analyses, and/or ELIZAs can be used to detect the presence of cancer cells having a mutant SPOP polypeptide. For example, antibodies specific for a mutant version of an SPOP polypeptide with no binding to wild-type SPOP polypeptides can be used in an immunological assay to detect the presence of cancer cells having a mutant SPOP polypeptide.

Also as described herein, a mammal (e.g., a human) can be identified as having a cancer at least partially resistant to BET inhibitor treatment by detecting cancer cells having an elevated level of BET polypeptide expression. Examples of BET polypeptides that can be assessed for having an elevated level and used to classify a mammal (e.g., a human) as having cancer at least partially resistant to BET inhibitor treatment include, without limitation, BRD2, BRD3, BRD4, and BRDT (a testis-specific BET polypeptide that also contains the conserved SBC (amino acids ADTTT) motif). A human BRD2 polypeptide can have the amino acid sequence as set forth in GenBank Accession No. NP_001106653. A human BRD3 polypeptide can have the amino acid sequence as set forth in GenBank Accession No. NP_031397. A human BRD4 polypeptide can have the amino acid sequence as set forth in GenBank Accession No. NP_490597. A human BRDT polypeptide can have the amino acid sequence as set forth in GenBank Accession No. AAB87862. The term "elevated level" as used herein with respect to a BET polypeptide expression level refers to a level of polypeptide expression by cancer cells (e.g., prostate cancer cells) that is greater (e.g., at least 5, 10, 25, 35, 45, 50, 55, 65, 75, 80, 90, or 100 percent greater) than the median expression level of that polypeptide in adjacent non-malignant (e.g., "normal") tissue or cells of the same organ or type known not to have a mutant SPOP polypeptide from the same mammal.

Any appropriate method can be used to identify cancer cells as having an elevated level of one or more BET polypeptides. For example, polypeptide-based assays such as antibody staining techniques, ELISAs, or antibody array hybridization assays using antibodies can be performed to detect the presence of cancer cells expressing an elevated level of one or more BET polypeptides.

Once a mammal (e.g., a human) is identified as having cancer cells with a mutant SPOP polypeptide as described herein and/or an elevated level of one or more BET polypeptides as described herein, the mammal can be classified as having cancer that is at least partially resistant to BET inhibitor treatment. For example, a human identified as having cancer cells with a mutant SPOP polypeptide (e.g., a F133V SPOP polypeptide) can be classified as having cancer that is at least partially resistant to BET inhibitor treatment.

As described herein, this document also provides methods and materials for increasing the susceptibility of a cancer to treatment with a BET inhibitor. For example, a mammal (e.g., a human) identified as having cancer that is at least partially resistant to BET inhibitor treatment can be administered one or more AKT inhibitors and/or one or more CDK inhibitors and/or one or more CBP/p300 inhibitors to increase the susceptibility of that cancer to treatment with a BET inhibitor.

Any appropriate mammal identified as having a cancer at least partially resistant to BET inhibitor treatment can be administered one or more AKT inhibitors and/or one of more CDK inhibitors and/or one or more CBP/p300 inhibitors to increase the susceptibility of that cancer to treatment with a BET inhibitor. For example, humans and other primates such as monkeys identified as having a cancer at least partially resistant to BET inhibitor treatment can be administered one or more AKT inhibitors and/or one of more CDK inhibitors and/or one or more CBP/p300 inhibitors to increase the susceptibility of that cancer to treatment with a BET inhibitor. In some cases, dogs, cats, horses, cows, pigs, sheep, mice, or rats identified as having a cancer at least partially resistant to BET inhibitor treatment as described herein can be administered one or more AKT inhibitors and/or one of more CDK inhibitors and/or one or more CBP/p300 inhibitors to increase the susceptibility of that cancer to treatment with a BET inhibitor. In addition, any appropriate cancer identified as being at least partially resistant to BET inhibitor treatment as described herein can be exposed to one or more AKT inhibitors and/or one of more CDK inhibitors and/or one or more CBP/p300 inhibitors to increase the susceptibility of that cancer to treatment with a BET inhibitor. For example, prostate cancer, lung adenocarcinoma cancer, small cell lung cancer, colorectal adenocarcinoma cancer, acral melanoma cancer, or oral squamous cell carcinoma cancer identified as being at least partially resistant to BET inhibitor treatment can be exposed to one or more AKT inhibitors and/or one of more CDK inhibitors and/or one or more CBP/p300 inhibitors to increase the susceptibility of that cancer to treatment with a BET inhibitor.

Any appropriate AKT inhibitor or combination of AKT inhibitors can be administered to a mammal identified as having a cancer at least partially resistant to BET inhibitor treatment to increase the susceptibility of that cancer to treatment with a BET inhibitor. For example, one or more AKT inhibitors can be administered, in the absence of any CDK inhibitors and any CBP/p300 inhibitors, to a mammal identified as having a cancer at least partially resistant to BET inhibitor treatment to increase the susceptibility of that cancer to treatment with a BET inhibitor. In some cases, an AKT inhibitor can be administered, as the sole active ingredient, to a mammal identified as having a cancer at least partially resistant to BET inhibitor treatment to increase the susceptibility of that cancer to treatment with a BET inhibitor. In some cases, a combination of AKT inhibitors can be administered, as the sole active ingredients, to a mammal identified as having a cancer at least partially resistant to BET inhibitor treatment to increase the susceptibility of that cancer to treatment with a BET inhibitor. Examples of AKT inhibitors that can be used as described herein to increase the susceptibility of that cancer to treatment with a BET inhibitor include, without limitation, MK-2206 2HCl (available commercially from Selleck Chemicals, Houston, TX; Catalog #S1078), Perifosine (KRX-0401; available commercially from Selleck Chemicals, Houston, TX; Catalog #S1037), GSK690693 (available commercially from Selleck Chemicals, Houston, TX; Catalog #S1113), Ipatasertib (GDC-0068; available commercially from Selleck Chemicals, Houston, TX; Catalog #S2808), AZD5363 (available commercially from Selleck Chemicals, Houston, TX; Catalog #S8019), Miransertib HCl (ARQ 092 HCl; available commercially from Selleck Chemicals, Houston, TX; Catalog #S8339), Deguelin (available commercially from Selleck Chemicals, Houston, TX; Catalog #S8132), PF-04691502 (available commercially from Selleck Chemicals, Houston, TX; Catalog #S2743), AT7867 (available commercially from Selleck Chemicals, Houston, TX; Catalog #S1558), Triciribine (available commercially from Selleck Chemicals, Houston, TX; Catalog #S1117), CCT128930 (available commercially from Selleck Chemicals, Houston, TX; Catalog #S2635), A-674563 (available commercially from Selleck Chemicals, Houston, TX; Catalog #S2670), PHT-427 (available commercially from Selleck Chemicals, Houston, TX; Catalog #S1556), Miltefosine (available commercially from Selleck Chemicals, Houston, TX; Catalog #S3056), Honokiol (available commercially from Selleck Chemicals, Houston, TX; Catalog #S2310), TIC10 Analogue (available commercially from Selleck Chemicals, Houston, TX; Catalog #S7127), Uprosertib (GSK2141795; available commercially from Selleck Chemicals, Houston, TX; Catalog #S7492), TIC10 (available commercially from Selleck Chemicals, Houston, TX; Catalog #S7963), Akti-1/2 (available commercially from Selleck Chemicals, Houston, TX; Catalog #S7776), Afuresertib (GSK2110183; available commercially from Selleck Chemicals, Houston, TX; Catalog #S7521), AT13148 (available commercially from Selleck Chemicals, Houston, TX; Catalog #S7563), and SC79 (available commercially from Selleck Chemicals, Houston, TX; Catalog #S7863). In some cases, two or more (e.g., two, three, four, five, six, or more) AKT inhibitors can be administered to a mammal identified as having a cancer at least partially resistant to BET inhibitor treatment to increase the susceptibility of that cancer to treatment with a BET inhibitor. For example, two different AKT inhibitors can be administered to a human identified as having cancer (e.g., prostate cancer) at least partially resistant to BET inhibitor treatment to increase the susceptibility of that cancer to treatment with a BET inhibitor.

Any appropriate CDK inhibitor or combination of CDK inhibitors can be administered to a mammal identified as having a cancer at least partially resistant to BET inhibitor treatment to increase the susceptibility of that cancer to treatment with a BET inhibitor. For example, one or more CDK inhibitors can be administered, in the absence of any AKT inhibitors and any CBP/p300 inhibitors, to a mammal identified as having a cancer at least partially resistant to BET inhibitor treatment to increase the susceptibility of that cancer to treatment with a BET inhibitor. In some cases, a CDK inhibitor can be administered, as the sole active ingredient, to a mammal identified as having a cancer at least partially resistant to BET inhibitor treatment to increase the susceptibility of that cancer to treatment with a BET inhibitor. In some cases, a combination of CDK inhibitors can be administered, as the sole active ingredients, to a mammal identified as having a cancer at least partially resistant to BET inhibitor treatment to increase the susceptibility of that cancer to treatment with a BET inhibitor. In some cases, a CDK inhibitor such as a CDK4 inhibitor, a CDK6 inhibitor, or a CDK4/6 inhibitor can be administered to a mammal identified as having a cancer at least partially resistant to BET inhibitor treatment to increase the susceptibility of that cancer to treatment with a BET inhibitor. Examples of CDK inhibitors that can be used as described herein to increase the susceptibility of that cancer to treatment with a BET inhibitor include, without limitation, Palbociclib (6-acetyl-8-cyclopentyl-5-methyl-2-[(5-piperazin-1-ylpyridin-2-yl) amino]pyrido[2,3-d]pyrimidin-7-one), Palbociclib HCl (PD-0332991; available commercially from Selleck Chemicals, Houston, TX; Catalog #S1116), Palbociclib Isethionate (PD0332991; available commercially from Selleck Chemicals, Houston, TX; Catalog #S1579), Abemaciclib (LY2835219; N-[5-[(4-ethylpiperazin-1-yl)methyl]pyridin-2-yl]-5-fluoro-4-(7-fluoro-2-methyl-3-propan-2-ylbenzimidazol-5-yl)pyrimidin-2-amine; available commercially from Selleck Chemicals, Houston, TX; Catalog #7158), Ribociclib (LEE011; 7-cyclopentyl-N,N-dimethyl-2-[(5-piperazin-1-ylpyridin-2-yl) amino]pyrrolo[2,3-d]pyrimidine-6-carboxamide; available commercially from Selleck Chemicals, Houston, TX; Catalog #7440), Flavopiridol (Alvocidib; available commercially from Selleck Chemicals, Houston, TX; Catalog #S1230), AT7519 (available commercially from Selleck Chemicals, Houston, TX; Catalog #S1524), Flavopiridol HCl (available commercially from Selleck Chemicals, Houston, TX; Catalog #S2679), JNJ-7706621 (available commercially from Selleck Chemicals, Houston, TX; Catalog #S1249), PHA-793887 (available commercially from Selleck Chemicals, Houston, TX; Catalog #S1487), BMS-265246 (available commercially from Selleck Chemicals, Houston, TX; Catalog #S2014), Milciclib (PHA-848125 (available commercially from Selleck Chemicals, Houston, TX; Catalog #S2751), R547 (available commercially from Selleck Chemicals, Houston, TX; Catalog #S2688), P276-00 (available commercially from Selleck Chemicals, Houston, TX; Catalog #S8058), ON123300 (available commercially from Selleck Chemicals, Houston, TX; Catalog #S8161), AT7519 HCL (available commercially from Selleck Chemicals, Houston, TX; Catalog #S7808), Purvalanol A (available commercially from Selleck Chemicals, Houston, TX; Catalog #S7793), and SU9516 (available commercially from Selleck Chemicals, Houston, TX; Catalog #S7636). In some cases, two or more (e.g., two, three, four, five, six, or more) CDK inhibitors can be administered to a mammal identified as having a cancer at least partially resistant to BET inhibitor treatment to increase the susceptibility of that cancer to treatment with a BET inhibitor. For example, two different CDK inhibitors can be administered to a human identified as having cancer (e.g., prostate cancer) at least partially resistant to BET inhibitor treatment to increase the susceptibility of that cancer to treatment with a BET inhibitor.

Any appropriate CBP/p300 inhibitor or combination of CBP/p300 inhibitors can be administered to a mammal identified as having a cancer at least partially resistant to BET inhibitor treatment to increase the susceptibility of that cancer to treatment with a BET inhibitor. For example, one or more CBP/p300 inhibitors can be administered, in the absence of any AKT inhibitors and any CDK inhibitors, to a mammal identified as having a cancer at least partially resistant to BET inhibitor treatment to increase the susceptibility of that cancer to treatment with a BET inhibitor. In some cases, a CBP/p300 inhibitor can be administered, as the sole active ingredient, to a mammal identified as having a cancer at least partially resistant to BET inhibitor treatment to increase the susceptibility of that cancer to treatment with a BET inhibitor. In some cases, a combination of CBP/p300 inhibitors can be administered, as the sole active ingredients, to a mammal identified as having a cancer at least partially resistant to BET inhibitor treatment to increase the susceptibility of that cancer to treatment with a BET inhibitor. Examples of CBP/p300 inhibitors that can be used as described herein to increase the susceptibility of that cancer to treatment with a BET inhibitor include, without limitation, CPI-637 (available commercially from Selleck Chemicals, Houston, TX; Catalog #S8190), SGC-CBP30 (available commercially from Selleck Chemicals, Houston, TX; Catalog #S7256), PF-CBP1 HCl (available commercially from Selleck Chemicals, Houston, TX; Catalog #S8180), I-CBP 112 (available commercially from Tocris, Minneapolis, MN, Catalog #4891), and C646 (available commercially from Sigma-Aldrich, St. Louis, MO; Catalog #SML0002). In some cases, two or more (e.g., two, three, four, five, six, or more) CBP/p300 inhibitors can be administered to a mammal identified as having a cancer at least partially resistant to BET inhibitor treatment to increase the susceptibility of that cancer to treatment with a BET inhibitor. For example, two different CBP/p300 inhibitors can be administered to a human identified as having cancer (e.g., prostate cancer) at least partially resistant to BET inhibitor treatment to increase the susceptibility of that cancer to treatment with a BET inhibitor.

In some cases, one or more (e.g., one, two, three, four, five, six, or more) AKT inhibitors can be administered in combination with one or more (e.g., one, two, three, four, five, six, or more) CDK inhibitors to a mammal identified as having a cancer at least partially resistant to BET inhibitor treatment to increase the susceptibility of that cancer to treatment with a BET inhibitor. For example, an AKT inhibitor such as Ipatasertib and a CDK inhibitor such as Palbociclib can be administered to a human identified as having cancer (e.g., prostate cancer) at least partially resistant to BET inhibitor treatment to increase the susceptibility of that cancer to treatment with a BET inhibitor.

In some cases, one or more (e.g., one, two, three, four, five, six, or more) AKT inhibitors can be administered in combination with one or more (e.g., one, two, three, four, five, six, or more) CBP/p300 inhibitors to a mammal identified as having a cancer at least partially resistant to BET inhibitor treatment to increase the susceptibility of that cancer to treatment with a BET inhibitor. For example, an AKT inhibitor such as Ipatasertib and a CBP/p300 inhibitor such as CPI-637 can be administered to a human identified as having cancer (e.g., prostate cancer) at least partially resistant to BET inhibitor treatment to increase the susceptibility of that cancer to treatment with a BET inhibitor.

In some cases, one or more (e.g., one, two, three, four, five, six, or more) CBP/p300 inhibitors can be administered in combination with one or more (e.g., one, two, three, four, five, six, or more) CDK inhibitors to a mammal identified as having a cancer at least partially resistant to BET inhibitor treatment to increase the susceptibility of that cancer to treatment with a BET inhibitor. For example, a CBP/p300 inhibitor such as CPI-637 and a CDK inhibitor such as Palbociclib can be administered to a human identified as having cancer (e.g., prostate cancer) at least partially resistant to BET inhibitor treatment to increase the susceptibility of that cancer to treatment with a BET inhibitor.

In some cases, one or more (e.g., one, two, three, four, five, six, or more) AKT inhibitors can be administered in combination with one or more (e.g., one, two, three, four, five, six, or more) CDK inhibitors and one or more (e.g., one, two, three, four, five, six, or more) CBP/p300 inhibitors to a mammal identified as having a cancer at least partially resistant to BET inhibitor treatment to increase the susceptibility of that cancer to treatment with a BET inhibitor. For example, an AKT inhibitor such as Ipatasertib, a CBP/p300 inhibitor such as CPI-637, and a CDK inhibitor such as Palbociclib can be administered to a human identified as having cancer (e.g., prostate cancer) at least partially resistant to BET inhibitor treatment to increase the susceptibility of that cancer to treatment with a BET inhibitor.

When using one or more AKT inhibitors and/or one or more CDK inhibitors and/or one or more CBP/p300 inhibitors to increase the susceptibility of cancer to treatment with a BET inhibitor as described herein, the AKT inhibitor(s) and/or CKD inhibitor(s) and/or CBP/p300 inhibitor(s) can increase that cancer's susceptibility to any appropriate BET inhibitor. Examples of such BET inhibitors include, without limitation, JQ1 (available commercially from Selleck Chemicals, Houston, TX; Catalog #S7110), I-BET 151 (GSK1210151A) (available commercially from Selleck Chemicals, Houston, TX; Catalog #S2780), I-BET 762 (GSK525762) (available commercially from Selleck Chemicals, Houston, TX; Catalog #S7189), OTX-015 (available commercially from Selleck Chemicals, Houston, TX; Catalog #S7360), TEN-010 (available commercially from APExBIO, Houston, TX; Catalog #A3692), CPI-203 (available commercially from Selleck Chemicals, Houston, TX; Catalog #S7304), CPI-0610 (available commercially from Selleck Chemicals, Houston, TX; Catalog #S7853), olinone, and RVX-208 (available commercially from Selleck Chemicals, Houston, TX; Catalog #S7295).

In some cases, one or more AKT inhibitors and/or one or more CDK inhibitors and/or one or more CBP/p300 inhibitors can be administered to a mammal once or multiple times over a period of time ranging from days to months. In some cases, one or more AKT inhibitors and/or one or more CDK inhibitors and/or one or more CBP/p300 inhibitors can be formulated into a pharmaceutically acceptable composition for administration to a mammal having cancer at least partially resistant to BET inhibitor treatment to increase the susceptibility of that cancer to treatment with a BET inhibitor. For example, a therapeutically effective amount of an AKT inhibitor (e.g., GDC-0068) or a CDK inhibitor (e.g., Palbociclib) or a CBP/p300 inhibitor (e.g., CPI-637) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more AKT inhibitors and/or one or more CDK inhibitors and/or one or more CBP/p300 inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more AKT inhibitors and/or one or more CDK inhibitors and/or one or more CBP/p300 inhibitors can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments, and the judgment of the treating physician.

An effective amount of a composition containing one or more AKT inhibitors and/or one or more CDK inhibitors and/or one or more CBP/p300 inhibitors can be any amount that increases a cancer's susceptibility to a BET inhibitor without producing significant toxicity to the mammal. For example, an effective amount of an AKT inhibitor such as GDC-0068 can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of an AKT inhibitor can be administered to an average sized human (e.g., about 75-85 kg human) per administration (e.g., per daily or weekly administration) for about two to about twelve weeks. In some cases, an effective amount of a CDK inhibitor such as Palbociclib can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of a CDK inhibitor can be administered to an average sized human (e.g., about 75-85 kg human) per administration (e.g., per daily or weekly administration) for about two to about twelve weeks. In some cases, an effective amount of a CDK inhibitor such as Palbociclib can be from about 100 mg to about 150 mg (e.g., about 125 mg) daily for about 21 days of a 28-day cycle.

In some cases, an effective amount of a CBP/p300 inhibitor such as CPI-637 can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of a CDK inhibitor can be administered to an average sized human (e.g., about 75-85 kg human) per administration (e.g., per daily or weekly administration) for about two to about twelve weeks. In some cases, an AKT inhibitor and/or a CDK inhibitor and/or a CBP/p300 inhibitor can be administered daily within one of these dose ranges for 21 days followed by a seven-day rest period.

If a particular mammal fails to respond to a particular amount, then the amount of an AKT inhibitor and/or a CDK inhibitor and/or a CBP/p300 inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an AKT inhibitor and/or a CDK inhibitor and/or a CBP/p300 inhibitor can be any amount that increases a cancer's susceptibility to a BET inhibitor without producing significant toxicity to the mammal. For example, the frequency of administration of an AKT inhibitor and/or a CDK inhibitor and/or a CBP/p300 inhibitor can be from about once a day to about once a month (e.g., from about once a week to about once every other week). The frequency of administration of an AKT inhibitor and/or a CDK inhibitor and/or a CBP/p300 inhibitor can remain constant or can be variable during the duration of treatment. A course of treatment with a composition containing an AKT inhibitor and/or a CDK inhibitor and/or a CBP/p300 inhibitor can include rest periods. For example, a composition containing one or more AKT inhibitors and/or one or more CDK inhibitors and/or one or more CBP/p300 inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more AKT inhibitors and/or one or more CDK inhibitors and/or one or more CBP/p300 inhibitors can be any duration that increases a cancer's susceptibility to a BET inhibitor without producing significant toxicity to the mammal. In some cases, the effective duration can vary from several days to several months. In general, the effective duration for increasing a cancer's susceptibility to a BET inhibitor can range in duration from about six weeks to about six months. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to the condition being treated (e.g., cancer) can be monitored. Any appropriate method can be used to determine whether or not a cancer's susceptibility to a BET inhibitor is being increased. For example, cancer cell survival can be assessed following administration of a BET inhibitor to determine if the AKT inhibitor treatment and/or the CDK inhibitor treatment and/or the CBP/p300 inhibitor treatment increased the cancer's susceptibility to that BET inhibitor.

After administering one or more AKT inhibitors and/or one or more CDK inhibitors and/or one or more CBP/p300 inhibitors to a mammal to increase a cancer's susceptibility to a BET inhibitor, one or more BET inhibitors can be administered to the mammal to reduce the number of cancer cells within the mammal. For example, a human identified as having a cancer that is at least partially resistant to BET inhibitor treatment and administered one or more AKT inhibitors and/or one or more CDK inhibitors and/or one or more CBP/p300 inhibitors to increase that cancer's susceptibility to a BET inhibitor can be administered one or more BET inhibitors to reduce the number of cancer cells within the human.

In some cases, the one or more AKT inhibitors and/or one or more CDK inhibitors and/or one or more CBP/p300 inhibitors can be administered before, after, or together with the administration of one or more BET inhibitors. For example, one or more CDK inhibitors and one or more BET inhibitors can be administered daily for a period of time. In some cases, one or more AKT inhibitors (and/or one or more CDK inhibitors and/or one or more CBP/p300 inhibitors) and one or more BET inhibitors can be formulated into a single composition that can be administered to a mammal identified as having a cancer that is at least partially resistant to BET inhibitor treatment.

As described herein, this document also provides methods and materials for treating cancer that is at least partially resistant to BET inhibitor treatment. For example, a mammal (e.g., a human) identified as having cancer (e.g., a mammal identified as having a cancer that is at least partially resistant to BET inhibitor treatment) can be administered one or more AKT inhibitors and/or one or more CDK inhibitors and/or one or more CBP/p300 inhibitors to increase the susceptibility of that cancer to treatment with a BET inhibitor and can be administered one or more BET inhibitors to reduce the number of cancer cells within the mammal. Any appropriate mammal identified as having a cancer at least partially resistant to BET inhibitor treatment can be administered one or more AKT inhibitors and/or one or more CDK inhibitors and/or one or more CBP/p300 inhibitors to increase the susceptibility of that cancer to treatment with a BET inhibitor and one or more BET inhibitors to reduce the number of cancer cells within the mammal. For example, humans and other primates such as monkeys identified as having a cancer at least partially resistant to BET inhibitor treatment can be administered one or more AKT inhibitors and/or one or more CDK inhibitors and/or one or more CBP/p300 inhibitors to increase the susceptibility of that cancer to treatment with a BET inhibitor and one or more BET inhibitors to reduce the number of cancer cells within the mammal. In some cases, dogs, cats, horses, cows, pigs, sheep, mice, or rats identified as having a cancer at least partially resistant to BET inhibitor treatment as described herein can be administered one or more AKT inhibitors and/or one or more CDK inhibitors and/or one or more CBP/p300 inhibitors to increase the susceptibility of that cancer to treatment with a BET inhibitor and one or more BET inhibitors to reduce the number of cancer cells within the mammal. In addition, any appropriate cancer identified as being at least partially resistant to BET inhibitor treatment as described herein can be exposed to one or more AKT inhibitors and/or one or more CDK inhibitors and/or one or more CBP/p300 inhibitors to increase the susceptibility of that cancer to treatment with a BET inhibitor and one or more BET inhibitors to reduce the number of cancer cells within the mammal. For example, prostate cancer, lung adenocarcinoma cancer, small cell lung cancer, colorectal adenocarcinoma cancer, acral melanoma cancer, or oral squamous cell carcinoma cancer identified as being at least partially resistant to BET inhibitor treatment can be exposed to one or more AKT inhibitors and/or one or more CDK inhibitors and/or one or more CBP/p300 inhibitors to increase the susceptibility of that cancer to treatment with a BET inhibitor and one or more BET inhibitors to reduce the number of cancer cells within the mammal.

In some cases, (a) one or more AKT inhibitors and/or one or more CDK inhibitors and/or one or more CBP/p300 inhibitors and (b) one or more BET inhibitors can be administered to a mammal once or multiple times over a period of time ranging from days to months. In some cases, (a) one or more AKT inhibitors and/or one or more CDK inhibitors and/or one or more CBP/p300 inhibitors and (b) one or more BET inhibitors can be formulated into a pharmaceutically acceptable composition for administration to a mammal having cancer at least partially resistant to BET inhibitor treatment to increase the susceptibility of that cancer to treatment with a BET inhibitor and to reduce the number of cancer cells within the mammal. For example, a therapeutically effective amount of a CDK inhibitor (e.g., Palbociclib) and a therapeutically effective amount of a BET inhibitor (e.g., JQ1) can be formulated together with one or more pharmaceutically acceptable carriers (additives) and/or diluents. In some cases, a therapeutically effective amount of a CBP/p300 inhibitor (e.g., CPI-637) and a therapeutically effective amount of a BET inhibitor (e.g., JQ1) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more BET inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more BET inhibitors can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments, and the judgment of the treating physician.

An effective amount of a composition containing one or more BET inhibitors can be any amount that reduces the number of cancer cells within a mammal without producing significant toxicity to the mammal. For example, an effective amount of a BET inhibitor such as JQ1 can be from about 0.25 mg/kg to about 50 mg/kg (from about 0.25 mg/kg to about 40 mg/kg, from about 0.25 mg/kg to about 30 mg/kg, from about 0.25 mg/kg to about 25 mg/kg, from about 0.25 mg/kg to about 20 mg/kg, from about 0.25 mg/kg to about 15 mg/kg, from about 0.25 mg/kg to about 10 mg/kg, from about 0.25 mg/kg to about 5 mg/kg, from about 0.5 mg/kg to about 25 mg/kg, from about 1 mg/kg to about 25 mg/kg, from about 2 mg/kg to about 25 mg/kg, from about 5 mg/kg to about 25 mg/kg, from about 0.5 mg/kg to about 5 mg/kg, or from about 0.75 mg/kg to about 3 mg/kg). In some cases, from about 10 mg to about 100 mg (e.g., from about 15 mg to about 100 mg, from about 20 mg to about 100 mg, from about 25 mg to about 100 mg, from about 50 mg to about 100 mg, from about 10 mg to about 90 mg, from about 10 mg to about 80 mg, from about 50 mg to about 90 mg, or from about 60 mg to about 80 mg) of a BET inhibitor can be administered to an average sized human (e.g., about 75-85 kg human) per administration (e.g., per daily or weekly administration) for about two to about twelve weeks. If a particular mammal fails to respond to a particular amount, then the amount of a BET inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of a BET inhibitor can be any amount that reduces the number of cancer cells within a mammal without producing significant toxicity to the mammal. For example, the frequency of administration of a BET inhibitor can be from about once a day to about once a month. The frequency of administration of a BET inhibitor can remain constant or can be variable during the duration of treatment. A course of treatment with a composition containing a BET inhibitor can include rest periods. For example, a composition containing one or more BET inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more BET inhibitors can be any duration that reduces the number of cancer cells within a mammal without producing significant toxicity to the mammal. In some cases, the effective duration can vary from several days to several months. In general, the effective duration for reducing the number of cancer cells within a mammal can range in duration from about six weeks to about six months. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and/or the severity of one or more symptoms related to the condition being treated (e.g., cancer) can be monitored. Any appropriate method can be used to determine whether or not the number of cancer cells within a mammal is being reduced. For example, cancer imaging techniques and/or patient symptom assessments can be performed to determine if the BET inhibitor is reducing the number of cancer cells within a mammal (e.g., a human).

In some cases, a phosphoinositide 3-kinase (PI3K) inhibitor can be used in addition to or in place of an AKT inhibitor for any of the methods or materials described herein. For example, a PI3K inhibitor can be used in place of an AKT inhibitor to increase the susceptibility of a cancer to BET inhibitor treatment as described herein. An example of a PI3K inhibitor that can be used as described herein includes, without limitation, LY294002 (available commercially from Selleck Chemicals, Houston, TX; Catalog #S1105).

The invention will be further described in the following examples, which do not limit the scope of the invention described in the claims.

EXAMPLES

Example 1—Intrinsic Bet Inhibitor Resistance in Spop-Mutated Prostate Cancer is Mediated by BET Protein Stabilization and AKT-mTORC1 Activation Antibodies and Chemicals The following antibodies were used: SPOP (ab137537; Abcam), SPOP (16750-1-AP; Proteintech), BRD2 (A302-583A; Bethyl), BRD2 (ab139690; Abcam), BRD3 (A302-368A; Bethyl), BRD4 (ab128874; Abcam), BRD4 (A301-985A; Bethyl), Myc (9E10; Sigma-Aldrich), Myc (SC-40; Santa Cruz Biotechnology), FLAG (M2; Sigma), HA (MM5-101R; Convance), Actin (AC-74; Sigma-Aldrich), DEK (13962S; Cell Signaling Technology), ERG (SC-352; Santa Cruz Biotechnology), AR (SC-816; Santa Cruz Biotechnology), SRC-3 (611104; BD), phospho-AKT-S473 (9471; Cell Signaling Technology), phospho-AKT-T308 (9275S; Cell Signaling Technology), AKT (9272; Cell Signaling Technology), phospho-S6K-T389 (9205; Cell Signaling Technology), S6K (9202; Cell Signaling Technology), β-tubulin (T4026; Sigma-Aldrich), RAC1 (23A8; BD), FDFT1 (ab195046; Abcam), DHCR24 (ab137845; Abcam), DHCR7 (ab103296; Abcam), MVD (ab12906; Abcam), HER3 (12708S; Cell Signaling Technology), INSR (ab131238; Abcam), IGF1R (SC-9038; Santa Cruz Biotechnology), mTOR (2972, Cell Signaling Technology), and Raptor (24C12, Cell Signaling Technology). MG132 and cycloheximide were purchased from Sigma-Aldrich, while MLN4924, Bortezomib, and MK2206 were purchased from Selleckchem. JQ1 was obtained from Dr. James Bradner and purchased from Sigma-Aldrich. i-BET762 (i-BET) was obtained from MedchemExpress, and GDC-0068 was obtained from Calbiochem.

Plasmids and Mutagenesis

Expression vectors for SPOP-WT or mutants were described elsewhere (An et al., *Cell Rep.*, 6:657-669 (2014)). FLAG-BRD2 and BRD3 constructs were obtained from Dr. S. J. Flint (Princeton University). FLAG-BRD4 constructs were obtained from Dr. Tasuku Honjo (Kyoto University). FLAG-BRD2/3/4 mutants were generated by KOD Plus Mutagenesis Kit (TOYOBO) following the manufacturer's instructions. LenticrisprV2 plasmid (#52961) was purchased from Addgene (USA).

Cell Culture, Transfection, and Lentivirus Infection

LNCaP, 22Rv1, and 293T cells were obtained from the American Type Culture Collection (ATCC). C4-2 cells were purchased from Uro Corporation (Oklahoma City, OK). BPH-1 cells were obtained from Dr. Simon Hayward (Hayward et al., *In Vitro Cell Dev. Biol. Anim.*, 31:14-24 (1995)). 293T cells were maintained in DMEM medium with 10% FBS, while LNCaP, C4-2, 22Rv1, and BPH-1 cells were maintained in RPMI medium with 10% FBS. Cells were transiently transfected using Lipofectamine RNAi MAX (for siRNA transfection) or 3000 (for plasmids transfection) (Thermo Fisher Scientific) according to manufacturer's instructions. pTsin-HA-SPOP-F133V mutant expression or pLKO-based gene knocking down lentivirus vectors or lenticrisprV2-BRD4 and packing constructs were transfected into 293T cells. Virus supernatant was collected 48 hours after transfection. C4-2 and 22Rv1 cells were infected with viral supernatant in the presence of polybrene (8 µg/mL) and were then selected in growth media containing 1.5 µg/mL puromycin. Sequences of gene-specific shRNAs are listed in Table 1. All the cell lines used were tested and authenticated by karyotyping, and prostate cancer cell lines also were authenticated by examining AR expression and SPOP mutation status. Plasmocin (InvivoGen) was added to cell culture media to prevent *mycoplasma* contamination. *Mycoplasma* contamination was tested regularly using Lookout *Mycoplasma* PCR Detection Kit from Sigma-Aldrich.

TABLE 1

Primers used for RT-qPCR in cultured cell lines, FFPE prostate cancer tissues, ChIP and sequences of shRNAs Primers for RT-PCR with cell line samples

| Gene name | F: 5'-3' | SEQ ID NO | R: 5'-3' | SEQ ID NO |
|---|---|---|---|---|
| BRD2 | CTACGTAAGAAACCCCGGAAG | 10 | GCTTTTTCTCCAAAGCCAGTT | 11 |
| BRD3 | CCTCAGGGAGATGCTATCCA | 12 | ATGTCGTGGTAGTCGTGCAG | 13 |

TABLE 1-continued

| Gene name | F: 5'-3' | SEQ ID NO | R: 5'-3' | SEQ ID NO |
|---|---|---|---|---|
| BRD4 | AGCAGCAACAGCAATGTGAG | 14 | GCTTGCACTTGTCCTCTTCC | 15 |
| FDFT1 | ACTATGTTGCTGGGCTGGTC | 18 | ACCTGCTCCAAACCTCTTGA | 19 |
| DHCR24 | CAAAGGAAATGAGGCAGAGC | 20 | TGTGGTACAAGGAGCCATCA | 21 |
| DHCR7 | TFACATCTGCCATGACCACT | 22 | ACAGGTCCTTCTGGTGGTTG | 23 |
| MVD | AGGACAGCAACCAGTTCCAC | 24 | CACACAGCAGCCACAAACTC | 25 |
| RAC1 | TGGCTAAGGAGATTGGTGCT | 16 | GCAAAGCGTACAAAGGTTCC | 17 |
| PSA | GGCAGCATTGAACCAGAGGAG | 26 | GCATGAACTTGGTCACCTTCTG | 27 |
| TMPRSS2 | CCTGCAAGGACATGGGTAT | 28 | CGGCACTTGTGTTCAGTTTC | 29 |
| KLK2 | CTGCCCATTGCCTAAAGAAG | 69 | TGGGAAGCTGTGGCTGAC | 70 |
| MYC | GGATTCTCTGCTCTCCTC | 30 | CTTGTTCCTCCTCAGAGTC | 31 |
| AR | GCAGGAGCTATTCAGGAAGC | 52 | AGGTGGAGAGCAAATGCAAC | 53 |
| GAPDH | TGCACCACCAACTGCTTAGC | 34 | GGCATGGACTGTGGTCATGAG | 35 |

Primers for RT-PCR with FFPE patient tumor samples

| Gene name | F: 5'-3' | SEQ ID NO | R: 5'-3' | SEQ ID NO |
|---|---|---|---|---|
| BRD2 | GACCTTCTGGAGGAAGTGGC | 71 | ATCGTAACTCATGGGCCTGC | 72 |
| BRD3 | TCAAATTGAACCTGCCGGATT | 73 | TGCATACATTCGCTTGCACTC | 74 |
| BRD4 | ACCTCCAACCCTAACAAGCC | 75 | TTTCCATAGTGTCTTGAGCACC | 76 |
| 18s RNA | ACCCGTTGAACCCCATTCGTGA | 77 | GCCTCACTAAACCATCCAATCGG | 78 |

Primers for ChIP-αPCR

| Gene name | F: 5'-3' | SEQ ID NO | R: 5'-3' | SEQ ID NO |
|---|---|---|---|---|
| RAC1 promoter | CCAAAGTGTTGGGATTACGG | 36 | CGGAGTTTCTCTGGACTTCG | 37 |
| FDFT1 promoter | ACATCACATGAAGGCCGTTT | 38 | GACCTTCCACCAACCACCTA | 39 |
| DHCR24 promoter | CCCTGAGTCAGTCACCCTTT | 40 | ACAATGGAGCTCACCACTCC | 41 |
| DHCR7 promoter | GCACATTGATGGAGCGTATG | 42 | TAATAAGCAGGCCACCCAGA | 43 |
| MVD promoter | CGCATTACCTCTCAGCCAAT | 44 | AGACAGGTAGCCCCCACAG | 45 |
| AR promoter | GGTGAGTGCTGGCCTCCAGG | 79 | GCGCTAACGCCTGCCTAGTG | 80 |
| PSA enhancer | CTCAGCCTTTGTCTCTGATGAAG | 81 | TCAGATCCAGGCTTGCTTACTG | 82 |
| TMPRSS2 enhancer | GTCTCCCTGCACCACTAACTAG | 83 | GCAAACATTGAAAAGAGCCT | 84 |
| KLK2 enhancer | CAAAGGTGAGCAACCTAGGCTTA | 85 | ATGTTCCTCCAGAGTAGGTCT | 86 |
| MYC enhancer | GGCTTACAGGATACCCCCAACT | 87 | GGGCTATCACACCTCGCCC | 88 |

Sequences of shRNAs

| Gene name | Sequence | SEQ ID NO |
|---|---|---|
| shSPOP#2 | CCGGCAAGGTAGTGAAATTCTCCTACTCGAGTAGGAGAATTTCACTACCTTGTTTTTT | 89 |
| shSPOP#4 | CCGGCACAAGGCTATCTTAGCAGCTCTCGAGAGCTGCTAAGATAGCCTTGTGTTTTT | 90 |
| shBRD4#1 | CCGGCAGTGACAGTTCGACTGATGACTCGAGTCATCAGTCGAACTGTCACTGTTTTT | 91 |
| shBRD4#2 | CCGGCCTGGAGATGACATAGTCTTACTCGAGTAAGACTATGTCATCTCCAGGTTTTT | 92 |
| shBRD3#1 | CCGGCCCAAGAGGAAGTTGAATTATCTCGAGATAATTCAACTTCCTCTTGGGTTTTT | 93 |

TABLE 1-continued

| | | |
|---|---|---|
| shBRD3#2 | CCGGGCTGATGTTCTCGAATTGCTACTCGAGTAGCAATTCGAGAACATCAGCTTTTT | 94 |
| shBRD2#1 | CCGGCCCTTTGCTGTGACACTTCTTCTCGAGAAGAAGTGTCACAGCAAAGGGTTTTT | 95 |
| shBRD2#2 | CCGGCCCTGCCTACAGGTTATGATTCTCGAGAATCATAACCTGTAGGCAGGGTTTTT | 96 |
| shFOS#1 | CCGGGCGGAGACAGACCAACTAGAACTCGAGTTCTAGTTGGTCTGTCTCCGCTTTTT | 97 |
| shFOS#2 | CCGGTCTGCTTTGCAGACCGAGATTCTCGAGAATCTCGGTCTGCAAAGCAGATTTTT | 98 |
| shJUN#1 | CCGGCGGACCTTATGGCTACAGTAACTCGAGTTACTGTAGCCATAAGGTCCGTTTTTG | 99 |
| shJUN#2 | CCGGCGCAAACCTCAGCAACTTCAACTCGAGTTGAAGTTGCTGAGGTTTGCGTTTTTG | 100 |
| shAR#1 | CCGGCCTGCTAATCAAGTCACACATCTCGAGATGTGTGACTTGATTAGCAGGTTTTT | 101 |
| shAR#2 | CCGGCGCGACTACTACAACTTTCCACTCGAGTGGAAAGTTGTAGTAGTCGCGTTTTT | 102 |
| shSRC-3#1 | CCGGCCATACATTTAATTGCCGTATCTCGAGATACGGCAATTAAATGTATGGTTTTT | 103 |
| shSRC-3#2 | CCGGGCAGTCTATTCGTCCTCCATACTCGAGTATGGAGGACGAATAGACTGCTTTTT | 104 |
| shDEK#1 | CCGGGCCAGTGCTAACTTGGAAGAACTCGAGTTCTTCCAAGTTAGCACTGGCTTTTT | 105 |
| shDEK#2 | CCGGTGAAATTGAGAGGATACATTTCTCGAGAAATGTATCCTCTCAATTTCATTTTT | 106 |
| shRAC1#1 | CCGGCCCTACTGTCTTTGACAATTACTCGAGTAATTGTCAAAGACAGTAGGGTTTTT | 107 |
| shRAC1#2 | CCGGGCTAAGGAGATTGGTGCTGTACTCGAGTACAGCACCAATCTCCTTAGCTTTTT | 108 |
| shMVD#1 | CCGGTATGCCCAGTTCTCTGAGAAACTCGAGTTTCTCAGAGAACTGGGCATATTTTG | 109 |
| shMVD#2 | CCGGTCTGCACCAGGACCAGTTAAACTCGAGTTTAACTGGTCCTGGTGCAGATTTTG | 110 |
| shFDFT1#1 | CCGGACTTGCTACAAGTATCTCAATCTCGAGATTGAGATACTTGTAGCAAGTTTTTG | 111 |
| shFDFT1#2 | CCGGCAACGATCTCCCTTGAGTTTACTCGAGTAAACTCAAGGGAGATCGTTGTTTTG | 112 |
| shDHCR7#1 | GTACCGGACTTCAAGCTGTTCTTCAATGCTCGAGCATTGAAGAACAGCTTGAAGTTTTTTG | 113 |
| shDHCR7#2 | CCGGGGGCCAAGACTCCACCTATAACTCGAGTTATAGGTGGAGTCTTGGCCCTTTTG | 114 |
| shDHCR24#1 | CCGGCCAACACATCTGCACTGCTTACTCGAGTAAGCAGTGCAGATGTGTTGGTTTTG | 115 |
| shDHCR24#2 | CCGGGCTCTCGCTTATCTTCGATATCTCGAGATATCGAAGATAAGCGAGAGCTTTTG | 116 |

Organoid Cultures and Cell Viability Assay

Organoid cells were obtained from Dr. Yu Chen from MSKCC and cultured according to the methodology as described elsewhere (Drost et al., Nat. Protoc., 11:347-358 (2016)). In brief, organoid cells were imbedded in 40 μL Matrigel each drop and cultured in FBS free DMEM/F12 medium supplied with several growth factors. Cell viability assays were conducted by plating 2,000 organoid cells per well of a collagen coated 96-well cell culture plate in 100 mL media with vehicle (DMSO) control or JQ1 (0.05~1 μM). Viable cells were counted by using a CellTiter-Glo (Promega) Luminescent Cell Viability Assay Kit.

Prostate Cancer Patient Samples

Treatment-naive prostate cancer and matched benign tissues were collected from a radical prostatectomy series. Haematoxylin and eosin (H&E) slides of frozen and formalin-fixed paraffin-embedded (FFPE) human tumor tissues and matched benign tissues were examined by a general pathologists and a genitourinary pathologist to confirm histological diagnosis, Gleason score, and high-density cancer foci (>80%) of the selected tumor tissue. The frozen blocks for DNA/RNA extraction were examined by the pathologists, followed by consecutive ten 10-μm sections of each tumor. These qualified samples were then used for DNA/RNA isolation. FFPE tissues were used for immunohistochemistry (IHC).

Detection of SPOP Mutation Prostate Cancer Patient Specimens by Whole-Genome and Sanger Sequencing For whole genome sequencing, DNA was extracted by phenol-chloroform and purified by the ethanol precipitation method from 32 paired tumor and benign frozen patient samples. DNA samples were fragmented in fragmentation buffer using Covaris Ultrasonicator system. The fragmented DNA with average length of 500 bp was subjected to DNA library construction. Libraries were constructed according to Illumina's protocol with DNA samples. High-throughput short-gun sequencing was performed on the IlluminaHiSeq 2000 platform. For DNA sequencing, pair-end reads with length of 90 bp were generated. Raw reads of DNA sequencing were filtered using an in-house pipeline. Clean DNA reads were processed with SAMTools to remove the PCR duplicates and aligned to the human reference genome hg19 with Burrows-Wheeler Aligner (http://bio-bwa.sourceforge.net/). The whole genome sequencing data were deposited in The European Genome-phenome Archive with the accession #EGAS00001000888.

For Sanger sequencing, DNA was extracted from all 99 cases of FFPE prostate cancer tissues using a QIAamp DNA FFPE Tissue kit. PCR was performed, and PCR products were purified using a GeneJET Extraction kit according to manufacturer's instruction and used for Sanger sequencing. The primers used for DNA amplification were: Amp-Exon6-

Forward 5'-ACCCATAGCTTTGGT-TTCTTCTCCC-3' (SEQ ID NO:1); Amp-Exon6-Reverse 5'-TATCTGTTT TGGACAGGTGTTTGCG-3' (SEQ ID NO:2); Amp-Exon7-Forward 5'-ACTCA-TCAGATCTGGGAACTGC-3' (SEQ ID NO:3); Amp-Exon7-Reverse 5'-AGTTG-TGGCTTTGATCTGGTT-3' (SEQ ID NO:4). Amp-Exon6-Reverse and Amp-Exon7-Forward were also used for Sanger sequencing.

Yeast Two-Hybrid Screen

Yeast two-hybrid screen was performed with the full-length SPOP cloned in-frame with the GAL4 DNA binding domain in vector PGBKT7 (Clontech). The yeast cells were transformed with PGBKT7-SPOP and the human fetal brain cDNA library. A total of $2 \times 10^7$ independent clones were screened by growth in deficient medium and X-gal staining. The positive clones were subsequently retested in fresh yeast cells, and the identities of prey were determined with interaction sequence tags (ISTs) obtained by DNA sequencing. The reading frame was verified.

RNA Interference

Non-specific control siRNA and gene-specific siRNAs for human SPOP and BRD4 were purchased from Thermo Fisher Scientific Dharmacon. siRNA transfection of cells was performed following the manufacturer's instructions. The sequences of siRNA oligos were: siSPOP #1 5'-GGAUGAUGUAAAUGAGCAA-3' (SEQ ID NO: 5); siSPOP #2 5'-GGACAGCGACTCTGAATCT-3' (SEQ ID NO:6); siBRD4 #1 5'-GAACCUCCCUGAUUACUAU-3' (SEQ ID NO:7); siBRD4 #2 5'-AGCUGAACCUCC-CUGAUUA-3' (SEQ ID NO:8); and non-specific control siRNA (siC) 5'-ACAGACUUCGGAGUACCUG-3' (SEQ ID NO:9).

Co-Immunoprecipitation (Co-IP)

To immunoprecipitate the ectopically expressed FLAG-tagged proteins, transfected cells were lysed 24 hours post-transfection in BC100 buffer. The whole-cell lysates were immunoprecipitated with the monoclonal anti-FLAG antibody-conjugated M2 agarose beads (Sigma-Aldrich) at 4° C. overnight. After three washes with lysis buffer, followed by two washes with BC100 buffer, the bound proteins were eluted using FLAG-Peptide (Sigma-Aldrich) prepared in BC100 for 3 hours at 4° C. The eluted protein sample was resolved by SDS-PAGE. To immunoprecipitate the endogenous proteins, cells were lysed with 1× cell lysis buffer (Cell Signaling Technology), and the lysate was centrifuged. The supernatant was precleared with protein A/G beads (Sigma-Aldrich) and incubated with the indicated antibody and protein A/G beads at 4° C. overnight. Beads were washed five times with lysis buffer and resuspended in sample buffer and analyzed by SDS-PAGE.

Western Blot

Cell lysates or immunoprecipitates were subjected to SDS-PAGE, and proteins were transferred to nitrocellulose membranes (GE Healthcare Sciences). The membranes were blocked in Tris-buffered saline (TBS, pH 7.4) containing 5% non-fat milk and 0.1% Tween-20, washed twice in TBS containing 0.1% Tween-20, and incubated with primary antibody overnight at 4° C., followed by secondary antibody for 1 hour at room temperature. The proteins of interest were visualized using ECL chemiluminescence system (Santa Cruz Biotechnology). Densitometry analysis of protein bands was analyzed on the Gel-Pro Analyzer software.

In Vitro Ubiquitination Assay

An in vitro ubiquitination assay was carried out using a protocol as described elsewhere (An et al., *Molecular Cell*, 59:904-916 (2015)). Briefly, 2 µg APP-BP1/Uba3, 2 µg His-UBE2M enzymes, and 5 µg NEDD8 were incubated at 30° C. for 2 hours in the presence of ATP. The thioester loaded His-UBE2M-NEDD8 was further incubated with 3 µg His-DCNL2, 6 µg CUL3/RBX1 at 4° C. for 2 hours to obtain the NEDDylated CUL3/RBX1. The NEDDylated CUL3/RBX1, 5 µg GST-SPOP, 5 µg Ub, 500 ng E1, 750 ng E2 (UbcH5a and UbcH5b), and 5 µg His-BRD4-N (amino acids 1-500) were incubated with 0.6 µL 100 mM ATP, 1.5 µL 20 µM ubiquitin aldehyde, 3 µL 10× ubiquitin reaction buffer (500 mM Tris-HCl (pH7.5), 50 mM KCl, 50 mM NaF, 50 mM $MgCl_2$ and 5 mM DTT), 3 µL 10× energy regeneration mix (200 mM creatine phosphate and 2 µg/µL creatine phosphokinase), 3 µL 10× protease inhibitor cocktail at 30° C. for 2 hours, followed by western blot analysis. The Ub, E1, E2, and CUL3/RBX1 were purchased from UBIQUIGENT.

In Vivo Ubiquitination Assay

For the in vivo ubiquitination assay, C4-2 cells were transfected with plasmids for HA-Ub, FLAG-BRD4, and other indicated proteins. Cells were treated with 20 µM MG132 for 8 hours before being harvested and lysed with lysis buffer (50 mM Tris-HCl, pH 7.5, 150 mM NaCl, 1% NP40, 0.5% sodium deoxycholate, 1× protease inhibitor cocktail (PIC)). The lysate was subjected to co-immunoprecipitation using anti-FLAG-conjugated agarose beads as described in the Co-IP assay.

Quantitative RT-PCR

Total RNA was isolated from transiently transfected cells using the Trizol reagent (Thermo Fisher Scientific), and cDNA was reverse-transcribed using the Superscript RT kit (TOYOBO, Japan) according to the manufacturer's instructions. PCR amplification was performed using the SYBR Green PCR master mix Kit (TOYOBO, Japan). All quantization was normalized to the level of endogenous control GAPDH. The primer sequences for the SYBR green qPCR used were as follows: BRD2-F: 5'-CTACGTAAGAAACCCCGGAAG-3' (SEQ ID NO:10); BRD2-R: 5'-GCTTTTTCTCCAAAGCCAGTT-3' (SEQ ID NO:11); BRD3-F: 5'-CCTCAGGGAGATGCTATCCA-3' (SEQ ID NO:12); BRD3-R: 5'-ATGTCGTGG-TAGTCGTGCAG-3' (SEQ ID NO:13); BRD4-F: 5'-AGCAGCAACAGCAATGT-GAG-3' (SEQ ID NO:14); BRD4-F: 5'-GCTTGCACTTGTCCTCTTCC-3' (SEQ ID NO: 15); RAC1-F: 5'-TGGCTAAGGAGATTGGTGCT-3' (SEQ ID NO:16); RAC1-R: 5'-GCAAAGCGTA-CAAAGGTTCC-3' (SEQ ID NO:17); FDFT1-F: 5'-ACTAT-GTTGCTGGGCTGGTC-3' (SEQ ID NO:18); FDFT1-R: 5'-ACCTGCTCCA-AACCTCTTGA-3' (SEQ ID NO:19); DHCR24-F: 5'-CAAAGGAAATGAGGCA-GAGC-3' (SEQ ID NO:20); DHCR24-R: 5'-TGTGGTACAAGGAGC-CATCA-3'(SEQ ID NO:21); DHCR7-F: 5'-TGA-CATCTGCCATGACCACT-3' (SEQ ID NO: 22); DHCR7-R: 5'-ACAGGTCCTTCTGGTGGTTG-3' (SEQ ID NO:23); MVD-F: 5'-AGGACAGCAACCAGTTCCAC-3' (SEQ ID NO:24); MVD-R: 5'-CACAC-AGCAGCCACAAACTC-3' (SEQ ID NO:25); PSA-F: 5'-GGCAGCATTGAAC-CAGAGGAG-3' (SEQ ID NO:26); PSA-R: 5'-GCAT-GAACTTGGTCACCTTCTG-3' (SEQ ID NO:27); TMPRSS2-F: 5'-CCTGCAAGGACATGGGTAT-3' (SEQ ID NO: 28); TMPRSS2-R: 5'-CGGCACTTGTGTTCAGTTTC-3' (SEQ ID NO:29); MYC-F: 5'-GGATTCTCTGCTCTCCTC-3' (SEQ ID NO:30); MYC-R: 5'-CTTGT-TCCTCCTCAGAGTC-3' (SEQ ID NO:31); AR-F: 5'-GACGCTTCTACCAGC-TCACC-3' (SEQ ID NO:32); AR-R: 5'-GCTT-CACTGGGTGTGGAAAT-3' (SEQ ID NO: 33); GAPDH- F: 5'-TGCACCACCAACTGCTTAGC-3' (SEQ ID NO:34); and GAPDH-R: 5'-GGCATGGACTGTGGTCATGAG-3' (SEQ ID NO:35).

Cell Proliferation Assay

CellTiter 96® AQueous One Solution Cell Proliferation Assay (MTS) (Promega) was used to measure cell growth according to the manufacturer's instructions. Briefly, cells were plated in 96-well plates at a density of 2,000 cells per well. At the indicated times, 20 µL of Cell Titer 96R Aqueous One Solution Reagent was added to medium. After incubating for 1 hour at 37° C. in the cell incubator, cell growth was measured in a microplate reader at 490 nm.

Trypan Blue Assay

Trypan blue assay was performed to measure cell growth according to the manufacturer's instructions. Briefly, cells were plated in 6-well plates at a density of about $5 \times 10^4$ to about $1 \times 10^5$ cells per well. At the indicated time points, cells were trypsinized and suspended in 1 mL 1×PBS. 100 µL cells and 100 µL trypan blue solution (Sigma-Aldrich) were mixed, and the number of viable cells was measured using the Bio-Rad automated cell counter.

Immunohistochemistry (IHC)

FFPE tumor samples from patients or C4-2 xenograft tumors were deparaffinized, rehydrated, and subjected to heat-mediated antigen retrieval. UltraSensitive™ S-P (Rabbit) IHC Kit (KIT-9706, Fuzhou Maixin Biotech) was used by following the manufacturer's instructions with minor modification as described elsewhere (Patel et al., Cell Rep., 6:81-92 (2014)). Briefly, the sections were incubated with 3% $H_2O_2$ for 15 minutes at room temperature to quench endogenous peroxidase activity. After antigen retrieval using unmasking solution (Vector Labs), slides were blocked with normal goat serum for 1 hour and then incubated with primary antibody at 4° C. overnight. IHC analysis of tumor samples was performed using primary antibodies against BRD2 (dilution 1:250; Abcam; catalog number: ab139690), BRD3 (dilution 1:200; Bethyl; catalog number: A302-368A), and BRD4 (dilution 1:500; Bethyl; catalog number: A301-985A100). The sections were then washed 3 times in 1×PBS and treated for 30 minutes with biotinylated goat-anti-rabbit IgG secondary antibodies (Fuzhou Maixin Biotech). After washing three times in 1×PBS, sections were incubated with streptavidin-conjugated HRP (Fuzhou Maixin Biotech). After washing three times in 1×PBS for 5 minutes each, specific detection was developed with 3'3-diaminobenzidine (DAB-2031, Fuzhou Maixin Biotech). Images were taken by using an Olympus camera and matched software. The IHC staining was scored by two independent pathologists based on the 'most common' criteria.

RNA Extraction from FFPE Patient Tissues and RT-qPCR

These experiments were performed using a method described elsewhere (Renwick et al., J. Clin. Invest., 123: 2694-2702 (2013); An et al., Mol. Cell, 59:904-916 (2015); and Zhao et al. Cell Rep., 15:599-610 (2016)). Briefly, a 4-µm pre-cut H&E stained section was obtained and reviewed by a pathologist. Only blocks with >80% tumor cells were used. Total RNA was isolated from FFPE tissue sections from the same cohorts of patients using the RNeasy FFPE Kit (Qiagen, Catalog no. 73504) using the method as described elsewhere (Mittempergher et al., PLOS One, 6: e17163 (2011)). The NanoDrop 2000 spectrophotometer (Thermo Fisher Scientific) was used to assess the RNA yield and quality. The cDNA was synthesized using Prime-Script™ RT reagent Kit (Perfect Real Time) according to the manufacturer's instructions (TaKaRa, Catalog no. RR037A) with minor modifications. qPCR was performed using SYBR® Premix Ex Taq™ II (Tli RNaseH Plus) (TaKaRa, Catalog no. RR820A) on a StepOnePlus Real-Time PCR system (Thermo Fisher Scientific) according to TaKaRa's recommended cycling conditions (95° C. for 30 seconds, followed by 40 cycles of 95° C. for 5 seconds, 60° C. for 30 seconds and a melt curve analysis). 18S RNA served as internal reference as described elsewhere (Hagen et al., Exp. Mol. Pathol., 95:98-104 (2013)). The primers used in RT-qPCR were listed in Table 1. All the samples were run in triplicate on the same plate, and the expression level of BRD2/3/4 mRNA was automatically calculated by the StepOnePlus Real-Time PCR system (Thermo Fisher Scientific). The comparison of the expression level of BRD2/3/4 mRNA was performed with Mann-Whitney test by the MedCalc statistical software Version 10.4.7.0 (MedCalc Software bvba, Mariakerke, Belgium). Two-sided P<0.05 was considered statistically significant.

RNA-Seq and Data Analysis

C4-2 cells infected with lentivirus expressing empty vector (EV), HA-SPOP-F133V, or BRD2/3/4 were treated with or without JQ1 (1 µM) for 24 hours. Total RNAs were isolated from cells using the methods as described elsewhere (Wang et al., Embo J., 32:1584-1597 (2013)). Briefly, RNA was isolated using RNeasy Plus Mini Kit (Qiagen). High quality (Agilent Bioanalyzer RIN>7.0) total RNAs were employed for the preparation of sequencing libraries using Illumina TruSeq Stranded Total RNA/Ribo-Zero Sample Prep Kit. A total of 500-1,000 ng of riboRNA-depleted total RNA was fragmented by RNase III treatment at 37° C. for 10-18 minutes, and RNase III was inactivated at 65° C. for 10 minutes. Size selection (50 to 150 bp fragments) was performed using the FlashPAGE denaturing PAGE-fractionator (Thermo Fisher Scientific) prior to ethanol precipitation overnight. The resulting RNA was directionally ligated, reverse-transcribed, and RNase H treated.

Samples with biological triplicates were sequenced using the Illumina HiSeq2000 platform. Pre-analysis quality control was performed using FastQC (bioinformatics.babraham.ac.uk/projects/fastqc/) and RSeQC software (Wang et al., Bioinformatics, 28:2184-2185 (2012)) to ensure that raw data were in excellent condition and suitable for downstream analyses. Pair-end raw reads were aligned to the human reference genome (GRch37/hg19) using Tophat (Trapnell et al., Bioinformatics, 25:1105-1111 (2009)). Genome-wide coverage signals were represented in BigWig format to facilitate convenient visualization using the UCSC genome browser. Gene expression was measured using RPKM (Reads Per Kilo-base exon per Million mapped reads) as described elsewhere (Mortazavi et al., Nature Methods, 5:621-628 (2008)). EdgeR (Robinson et al., Genome Biol., 11: R25 (2010)) was used to identify genes that were differentially expressed between EV-expressing and SPOP-F133V-expressing C4-2 cells treated with or without JQ1. Raw and processed data were deposited into NCBI Gene Expression Omnibus with accession number GSE88872.

Chromatin Immunoprecipitation (ChIP) Sequencing (ChIP-Seq) and Data Analysis, and ChIP-qPCR ChIP was performed as described elsewhere (Boyer et al., Cell, 122:947-956 (2005)). ChIP-seq libraries were prepared using the methods as described elsewhere (Boyer et al., Cell, 122:947-956 (2005)), and high throughput sequencing was performed using the Illumina HiSeq2000 platforms. The data were analyzed using the following pipeline: ChIP-seq raw reads were aligned to the human reference genome (GRCh37/hg19) using Bowtie2 (2.2.9), and reads mapped to one or two locations were kept for further analysis. Peak calling was performed by MACS2 (2.1.1) with p-value threshold of 1e-5. BigWig files were generated for visualization with the UCSC genome browser or IGV. GREAT (bejerano.stanford.edu/great/public/html/) was used to assign peaks to their potential target genes (a peak-gene association was determined if the peak fell into 2 kb region centering on the transcription start site of the gene). The common BRD4 target genes induced by SPOP F133V and HA-BRD4 expression were determined independently in each of two biological repeat experiments. Raw and processed data were deposited into NCBI Gene Expression Omnibus with accession number GSE88872.

For ChIP-qPCR experiments, DNAs pulled down by antibodies or non-specific IgG were amplified by real-time PCR. The ChIP primers used were: RAC1 ChIP-F: 5'-CCAAAGTGTTGGGATTACGG-3' (SEQ ID NO:36); RAC1 ChIP-R: 5'-CGGAGTTTCTCTGGACTTCG-3' (SEQ ID NO:37); FDFT1 ChIP-F: 5'-ACA-TCACAT-GAAGGCCGTTT-3' (SEQ ID NO:38); FDFT1 ChIP-R: 5'-GACCTTCC-ACCAACCACCTA-3' (SEQ ID NO:39); DHCR24 ChIP-F: 5'-CCCTGAGTCAGT-CACCCTTT-3' (SEQ ID NO:40); DHCR24 ChIP-R: 5'-ACAATGGAGCT-CACCA-CTCC-3' (SEQ ID NO:41); DHCR7 ChIP-F: 5'-GCACATTGATGGAGCGTATG-3' (SEQ ID NO: 42); DHCR7 ChIP-R: 5'-TAATAAGCAGGCCACCCAGA-3' (SEQ ID NO: 43); MVD ChIP-F: 5'-CGCAT-TACCTCTCAGCCAAT-3' (SEQ ID NO:44); MVD ChIP-R: 5'-AGACAGGTAGCCCCCACAG-3' (SEQ ID NO:45); PSA promoter ChIP-F: 5'-CCCTCCCCTTCCACAGC-3' (SEQ ID NO:46); PSA promoter ChIP-R: 5'-GCCC-TATAAAACCTTCATTCCCCAGG-3' (SEQ ID NO:47); TMPRSS2 ChIP-F: 5'-CGCCCCAGAGTCCCTTAT-3' (SEQ ID NO:48); TMPRSS2 ChIP-R: 5'-TAATCTCAG-GAGGCGGTGTC-3' (SEQ ID NO:49); MYC ChIP-F: 5'-AGGGATCGCGCTGAGTATAA-3' (SEQ ID NO:50); MYC ChIP-R: 5'-TGCCT-CTCGCTGGAATTACT-3' (SEQ ID NO:51); AR ChIP-F: 5'-GCAGGAGCTATTC-AG-GAAGC-3' (SEQ ID NO:52); and AR ChIP-R: 5'-AGGTG-GAGAGCAAATGC-AAC-3' (SEQ ID NO:53). Detailed information regarding PCR primers at the enhancer and promoters of all analyzed genes are also summarized in Table 1.

Meta-Analysis of BRD4 and Histone Mark ChIP-Seq Data

BRD4 ChIP-seq data in HEK293T and HeLa cells (accession number GSE51633; Liu et al., Cell, 155:1581-1595 (2013)), H2171 and U87 cells (accession number GSE44931; Loven et al., Cell, 153:320-334 (2013)), and mouse acute myeloid leukemia (AML) cells (accession number GSE66122; Roe et al., Mol. Cell., 58:1028-1039 (2015)) as well as H3K4me1 and H3K4me3 ChIP-seq data in LNCaP cells (Wang et al., Nature, 474:390-394 (2011)) were downloaded from NCBI Gene Expression Omnibus. If the original alignments were based on hg18/GRCh36, they were converted into hg19/GRCh37 based-alignments using CrossMap (Zhao et al., Bioinformatics, 30:1006-1007 (2014)). Peak calling was performed using MACS2 (v2.0.10; Zhang et al., Genome Biol., 9: R137 (2008)).

Analysis of JQ1-Resistant Gene Expression in the TCGA Dataset and Pathway Analysis Primary tumor samples from the prostate cancer cohort in TCGA were classified into SPOP-MUT (with mutation, N=48) and SPOP-WT (without mutation, N=449) groups according to the mutation status of SPOP. Differential expression between the above two groups for the JQ1-resistant genes (n=1,017) were investigated by Mann-Whitney test with the significance threshold of P-value<0.001. A total of 129 genes were identified as up-regulated in SPOP-MUT samples. A heat-map was generated using the z-score transformed expression of each gene across all samples. Pathway analyses were performed using Ingenuity IPA.

Cholesterol Analysis

The cells were washed with PBS with twice and lysed in the buffer (10 mM Tris-HCl (pH7.6), 500 mM NaCl, 1% Triton X-100, 10 mM β-methylphenethylamine, 2 mM $Na_3VO_4$, and 1 mM PMSF) for 30 minutes on ice. The lysates were extracted in the chloroform/methanol/HCl as described elsewhere (Zhuang et al., J. Clin. Invest., 115:959-968 (2005)). The cholesterol concentration was measured using the Infinity reagent (Thermo Fisher Scientific).

Generation and Treatment of Prostate Cancer Xenografts in Mice 6-week-old NOD-SCID IL-2-receptor gamma null (NSG) mice were generated and randomly divided into different experimental groups as indicated. All mice were housed in standard conditions with a 12-hour light/dark cycle and access to food and water ad libitum. For BRD2/3/4 knock-down studies, C4-2 cells ($5\times10^6$), infected with lentivirus expressing empty vector (EV) or HA-SPOP-F133V mutant in combination with control shRNA or BRD2/3/4-specific shRNA, were mixed with Matrigel (in 100 µL 1×PBS plus 100 µL Matrigel (BD Biosciences)) and injected s.c. into the right flank of mice. After xenografts reached the size of about 100 $mm^3$, vehicle (10% beta cyclodextrin) or JQ1 (Sigma-Aldrich) at 50 mg/kg body weight was administered by i.p. injection 5 days a week. For studies with tumors treated with JQ1 and AKT inhibitor GDC-0068, C4-2 cells ($5\times10^6$) infected with lentivirus expressing empty vector (EV) or HA-SPOP-F133V mutant were mixed with Matrigel (in 100 µL 1×PBS plus 100 µL Matrigel (BD Biosciences)) and injected s.c. into the right flank of mice. After xenografts reached the size of about 100 $mm^3$, vehicle (10% beta cyclodextrin), JQ1 (50 mg/kg), or GDC-0068 (100 mg/kg) were administrated individually or in combination 5 days a week. Growth in tumor volume was measured in a blinded fashion using digital caliper, and tumor volumes were estimated using the formula $(L \times W2)/2$, where L is length of tumor and W is width. The volumes of tumors were compared, and P values were determined by a two-tailed Student's t test. Upon the completion of treatment, tumor grafts were harvested. Tumor tissues were divided, and a portion was subjected to FFPE. the rest was frozen for protein and RNA extraction.

Statistical Analysis

All data were shown as mean values±SD for experiments performed with at least three replicates. The difference between two groups was analyzed using paired Student's t-test unless otherwise specified. A P value less than 0.05 was considered statistically significant.

Results

Ubiquitously-expressed BET proteins including BRD2, BRD3 and BRD4 function as factors for transcriptional activation of distinct sets of cancer-related genes through context-specific interaction with acetylated histones and/or transcription factors (Filippakopoulos et al., Nature, 468: 1067-1073 (2010); and Nicodeme et al., Nature, 468:1119-1123 (2010)). Several small molecule inhibitors specifically targeting the bromodomains of BET proteins have been developed and display promising anti-cancer activity via selective blockage of expression of cancer promoters such as MYC in multiple myeloma and androgen receptor (AR) in prostate cancer (Filippakopoulos et al., Nature, 468:1067-1073 (2010); Nicodeme et al., Nature, 468:1119-1123 (2010); Delmore et al., Cell, 146:904-917 (2011); Dawson et al., Nature, 478:529-533 (2011); Zuber et al., Nature, 478: 524-528 (2011); and Asangani et al., Nature, 510:278-282

(2014)). While BET inhibitors are undergoing clinical trials for treatment of various cancer types, several mechanisms of drug resistance have been documented (Fong et al., *Nature*, 525:538-542 (2015); Rathert et al., *Nature*, 525:543-547 (2015); and Shu et al., *Nature*, 529:413-417 (2016)). At present, there are no genetic alterations that can be exploited as a biomarker to guide targeted use of these drugs.

SPOP is the substrate recognition subunit of the CULLIN3-RBX1 E3 ubiquitin ligase (CRL) complex. SPOP binding triggers the ubiquitination and proteasomal degradation of target proteins mediated by RBX1-dependent recruitment of E2 ubiquitin-conjugating enzyme into the CRL complex. Cancer whole genome- and exome-sequencing studies revealed that SPOP is the most frequently mutated gene in primary prostate cancer (Barbieri et al., *Nat. Genet.*, 44:685-689 (2012); and The Molecular Taxonomy of Primary Prostate Cancer, *Cell*, 163:1011-1025 (2015)). Notably, SPOP mutations detected in prostate cancer occur in the structurally defined substrate-binding motif termed MATH domain (meprin and TRAF homology domain; Barbieri et al., *Nat. Genet.*, 44:685-689 (2012); Theurillat et al., *Science*, 346:85-89 (2014); Geng et al., *Proc. Natl. Acad. Sci. USA*, 110:6997-7002 (2013); and An et al., *Mol. Cell*, 59:904-916 (2015)), possibly suggesting that the pathophysiology of SPOP mutations is likely mediated by impaired ubiquitination of substrates.

Figure 1B:
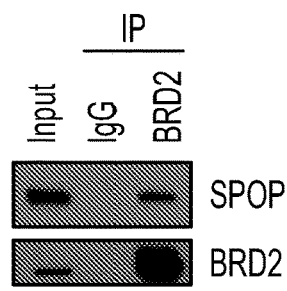
Figure 1B:
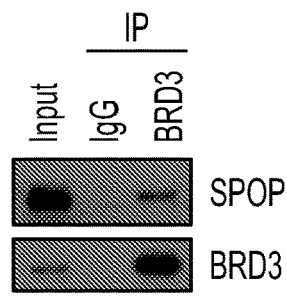
Figure 1B:
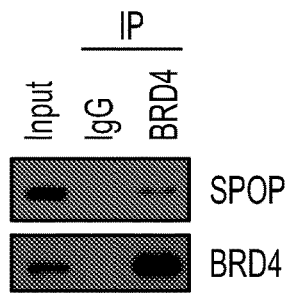

To identify new degradation substrates of SPOP, yeast two-hybrid screens using the full-length SPOP as bait were performed. A total of 246 positive clones were obtained, including known SPOP substrates DEK and SRC-3 (Table 2). Gene Ontology analysis showed that SPOP bound to a number of proteins involved in regulation of various signaling pathways, but the top hit was BET proteins (FIG. 1*a* and Table 3). Co-immunoprecipitation (co-IP) assays confirmed that ectopically expressed and endogenous SPOP and BRD2/3/4 proteins interacted with each other in 293T and LNCaP prostate cancer cells (FIGS. 1*b* and 2*a*). Thus, SPOP interacts with BET proteins in physiological conditions.

TABLE 2

Table 2. SPOP interacted proteins identified by yeast two hybrid screen

| Positive No. | clone name* | Full name |
|---|---|---|
| 2 | BRD2 | bromodomain containing 2 |
| 1 | CHD3 | chromodomain helicase DNA binding protein 3 |
| 3 | CAPRIN1 | cell cycle associated protein 1 |
| 4 | ZMYND8 | zinc finger MYND-type containing 8 |
| 5 | | SET domain containing 2 |
| 6 | BRD4 | bromodomain containing 4 |
| 7 | | GLI family zinc finger 3 |
| 8 | | death domain associated protein |
| 9 | | H2A histone family member Y |
| 10 | SRRM1 | serine and arginine repetitive matrix 1 |
| 11 | INF2 | inverted formin, FH2 and WH2 domain containing |
| 12 | UBE2I | ubiquitin conjugating enzyme E2 I |
| 13 | RANBP9 | RAN binding protein 9 |
| 14 | ZCCHC12 | zinc finger CCHC-type containing 12 |
| 15 | SPOP | speckle type BTB/POZ protein |
| 16 | NUDCD3 | NudC domain containing 3 |
| 17 | GCC2 | GRIP and coiled-coil domain containing 2 |
| 18 | PIAS3 | protein inhibitor of activated STAT 3 |
| 19 | RBFOX2 | RNA binding protein, fox-1 homolog 2 |
| 20 | CBX4 | chromobox 4 |
| 21 | AMOTL2 | angiomotin like 2 |
| 22 | FAF1 | Fas associated factor 1 |
| 23 | BRD3 | bromodomain containing 3 |
| 24 | | GLI family zinc finger 2 |
| 25 | RBPJ | recombination signal binding protein for immunoglobulin kappa J region |
| 26 | GCC2 | TOP1 binding arginine/serine rich protein |
| 27 | CHAF1A | chromatin assembly factor 1 subunit A |
| 28 | | DEK proto-oncogene |
| 29 | PIAS1 | protein inhibitor of activated STAT 1 |
| 30 | TCOF1 | treacle ribosome biogenesis factor 1 |
| 31 | SUMO1 | small ubiquitin-like modifier 1 |
| 32 | RPRD2 | regulation of nuclear pre-mRNA domain containing 2 |
| 33 | MRE11A | MRE11 homolog A, double strand break repair nuclease |
| 34 | LRCH4 | leucine rich repeats and calponin homology domain containing 4 |
| 35 | KPNA5 | karyopherin subunit alpha 5 |
| 36 | | nuclear receptor coactivator 3 |
| 37 | HMGCS1 | 3-hydroxy-3-methylglutaryl-CoA synthase 1 |
| 38 | GMEB1 | glucocorticoid modulatory element binding protein 1 |
| 39 | DHX15 | DEAH-box helicase 15 |
| 40 | CTDSPL2 | CTD small phosphatase-like protein 2 |
| 41 | CACUL1 | CDK2 associated cullin domain 1 |

*Highlighted in red are the known substrates of SPOP

TABLE 3

Table 3. Gene Ontology (GO) analysis of SPOP binding partners indetified via yeast-two-hybrid screen

| p-value | q-value | pathway | source |
|---|---|---|---|
| 4.87E−07 | 3.21E−05 | Chemical Compounds to monitor Proteins | Wikipathways |
| 1.66E−06 | 5.30E−05 | regulation of transcriptional activity by pml | BioCarta |
| 2.41E−06 | 5.30E−05 | Androgen receptor signaling pathway | Wikipathways |
| 4.35E−06 | 6.87E−05 | TGF-Ncore | Signalink |
| 5.65E−06 | 6.87E−05 | Hedgehog signaling events mediated by Gli proteins | PID |
| 6.25E−06 | 6.87E−05 | Sumoylation by RanBP2 regulates transcriptional repression | PID |
| 1.48E−05 | 0.000139607 | Coregulation or Androgen receptor activity | PID |
| 3.19E−05 | 0.000234127 | SUMOylation of DNA damage response and repair proteins | Reactome |
| 3.19E−05 | 0.000234127 | SUMO E3 ligases SUMOylate target proteins | Reactome |
| 4.13E−05 | 0.000272801 | SUMOylation | Reactome |
| 8.99E−05 | 0.000458494 | GLI proteins bind promoters of Hh responsive genes to promote transcription | Reactome |
| 8.99E−05 | 0.000458494 | SUMO is transferred from E1 to E2 (UBE2I, UBC9) | Reactome |
| 8.99E−05 | 0.000458494 | basic mechanisms of sumoylation | BioCarta |
| 0.000111453 | 0.000525423 | Hedgehog on state | Reactome |

TABLE 3-continued

Table 3. Gene Ontology (GO) analysis of SPOP binding partners indetified via yeast-two-hybrid screen

| p-value | q-value | pathway | source |
|---|---|---|---|
| 0.000214797 | 0.000945107 | Processing and activation of SUMO | Reactome |
| 0.000355359 | 0.001465857 | Signaling events mediated by HDAC Class I | PID |
| 0.000411644 | 0.001598146 | AndrogenReceptor | NetPath |
| 0.000538773 | 0.001871527 | Regulation of IFNG signaling | Reactome |
| 0.000538773 | 0.001871527 | sumoylation by ranbp2 regulates transcriptional repression | BioCarta |
| 0.000708275 | 0.002337307 | Hedgehog Signaling Pathway | Wikipathways |
| 0.000900261 | 0.002829392 | JAK-STAT-Ncore | Signalink |
| 0.001004619 | 0.003010155 | Interferon gamma signaling | Reactome |
| 0.001048993 | 0.003010155 | Signaling by Hedgehog | Reactome |
| 0.001114519 | 0.003064327 | fas signaling pathway (cd95) | BioCarta |
| 0.00120627 | 0.003184553 | C-MYB transcription factor network | PID |
| 0.001477203 | 0.003749824 | IL11 | NetPath |
| 0.001746219 | 0.004268536 | Hedgehog | NetPath |
| 0.003795858 | 0.005947379 | mRNA Processing | Wikipathways |
| 0.004010665 | 0.00912772 | Signaling events mediated by HDAC Class II | PID |
| 0.004230525 | 0.009307155 | TGF beta Signaling Pathway | Wikipathways |
| 0.004694393 | 0.009994524 | Ubiquitin mediated proteolysis - *Homo sapiens* (human) | KEGG |
| 0.004881859 | 0.010068834 | Hedgehog off state | Reactome |
| 0.005112111 | 0.010224223 | FAS pathway and Stress induction at HSP regulation | Wikipathways |
| 0.005347296 | 0.010380046 | Interleukin-11 Signaling Pathway | Wikipathways |
| 0.006082205 | 0.0114693 | IL6-mediated signaling events | PID |
| 0.007129675 | 0.01387107 | Hedgehog signaling pathway - *Homo sapiens* (human) | KEGG |
| 0.007965137 | 0.014288082 | Interferon type I signaling pathways | Wikipathways |
| 0.008252996 | 0.01433415 | Basal cell carcinoma - *Homo sapiens* (human) | KEGG |
| 0.008664299 | 0.01466266 | RNA transport - *Homo sapiens* (human) | KEGG |
| 0.008943913 | 0.014757456 | TGF_beta_Receptor | NetPath |

Figure 1C:
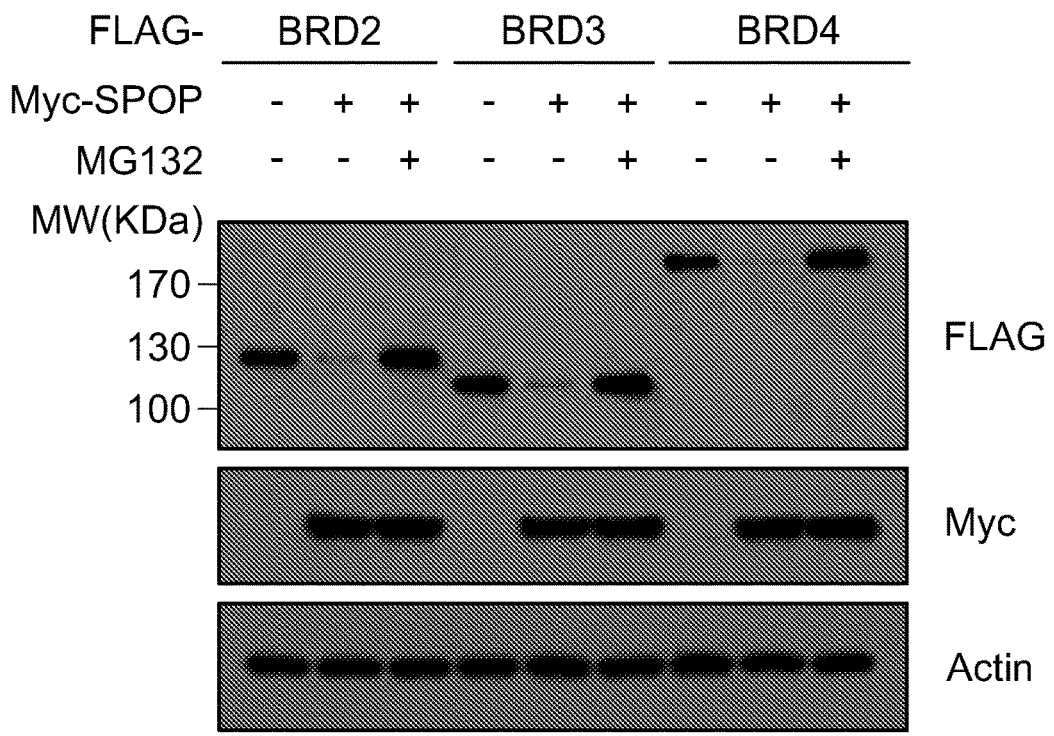
Figure 1D:
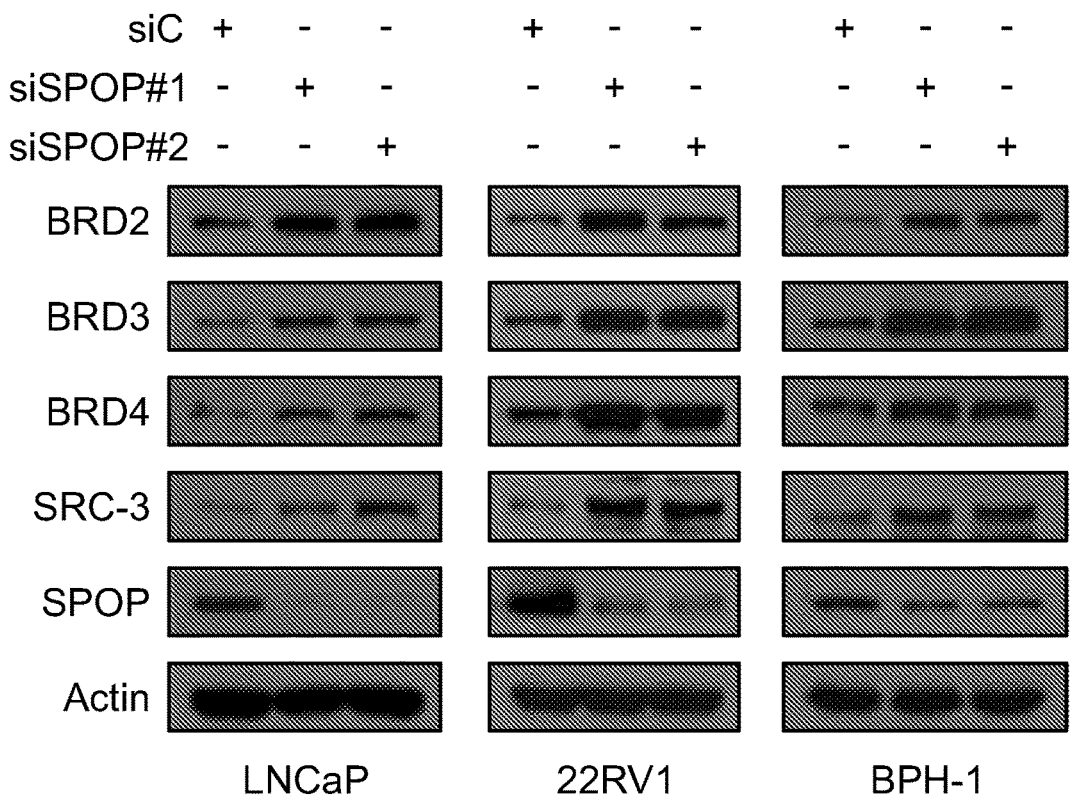
Figure 1E:
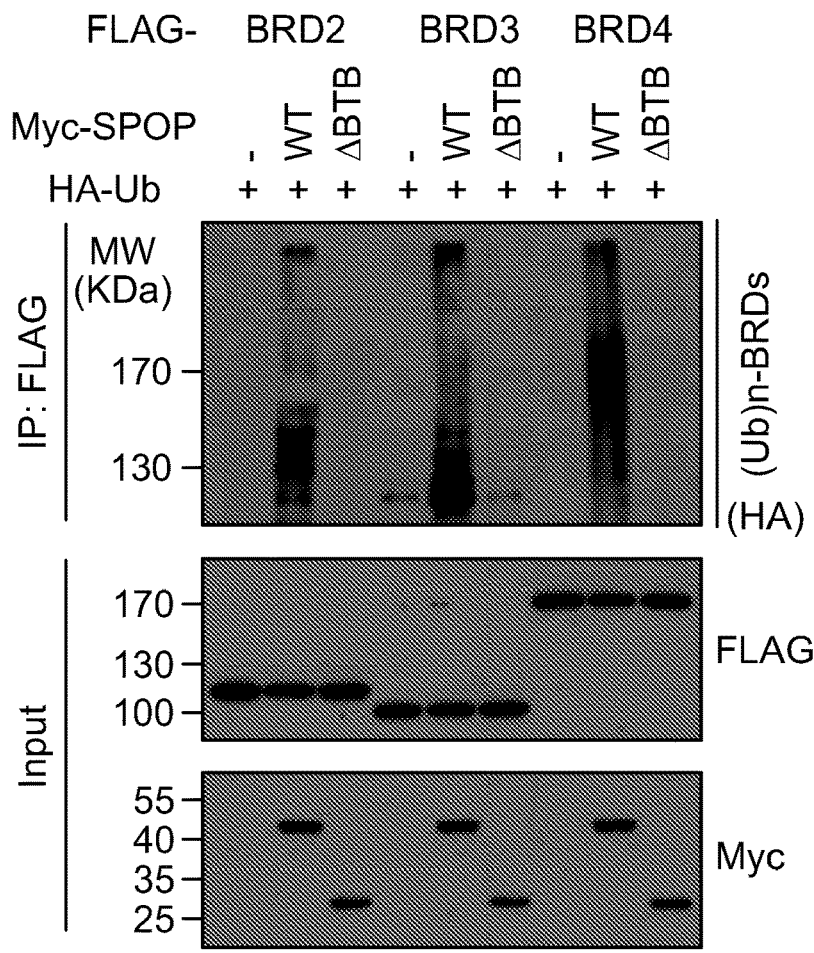
Figure 1F:
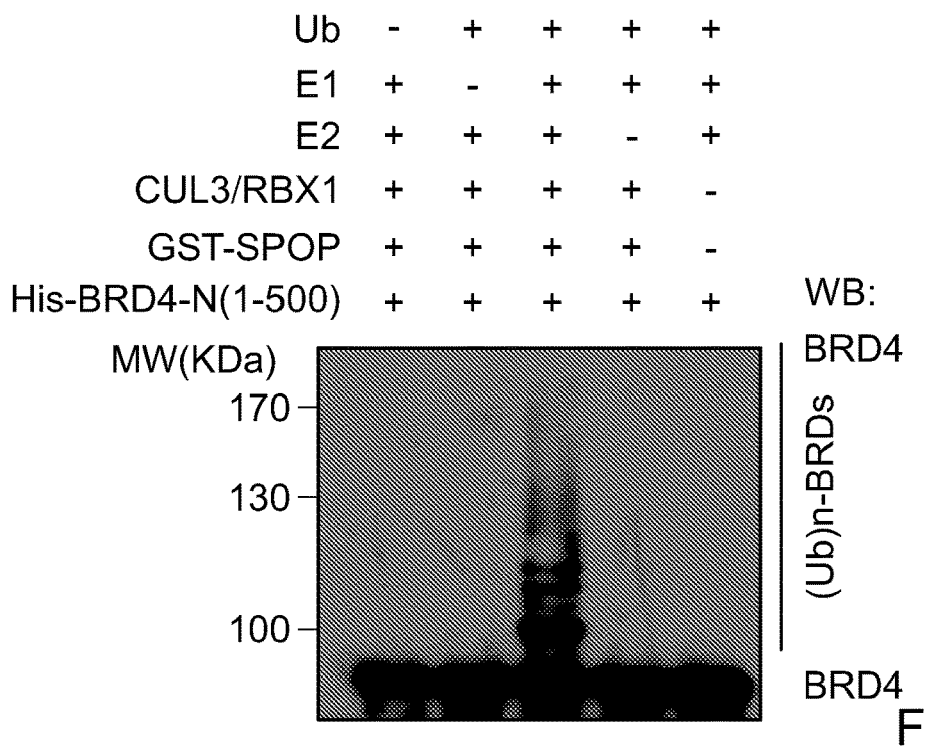
Figure 2D:
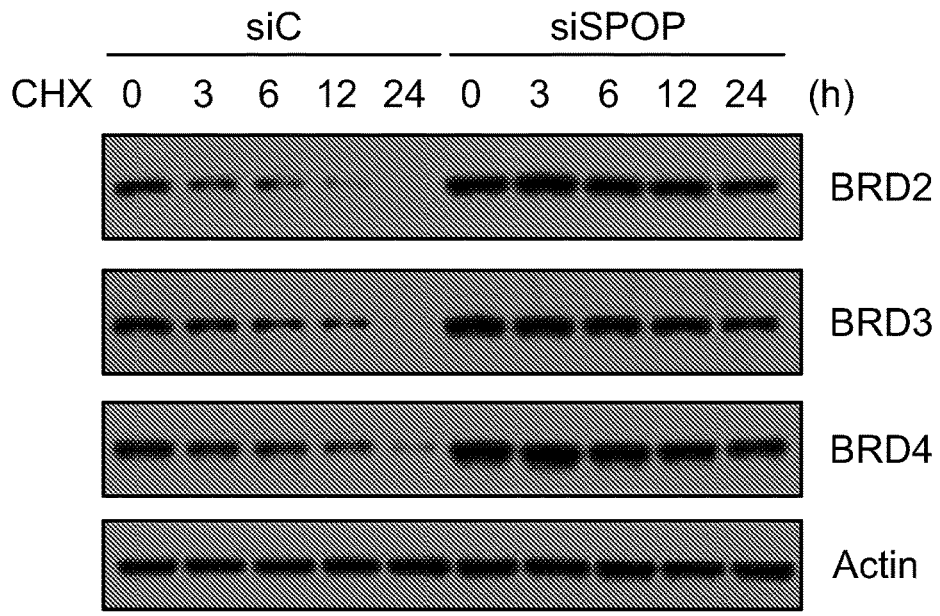
Figure 2E:
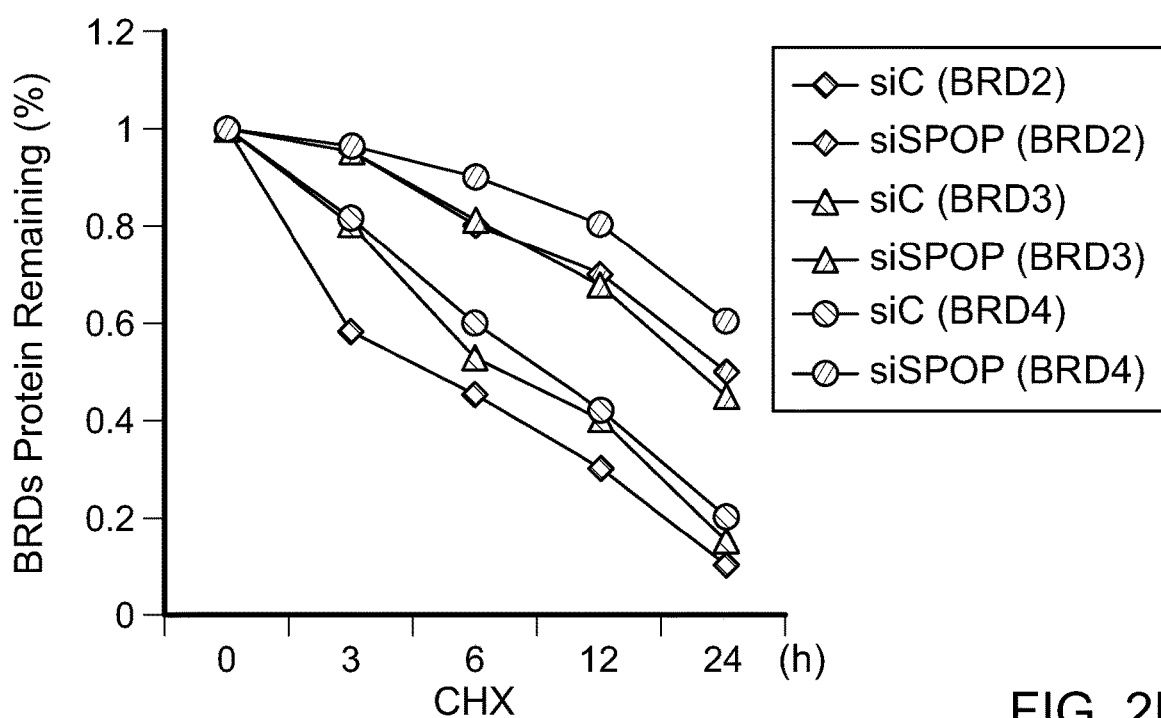
Figure 2F:
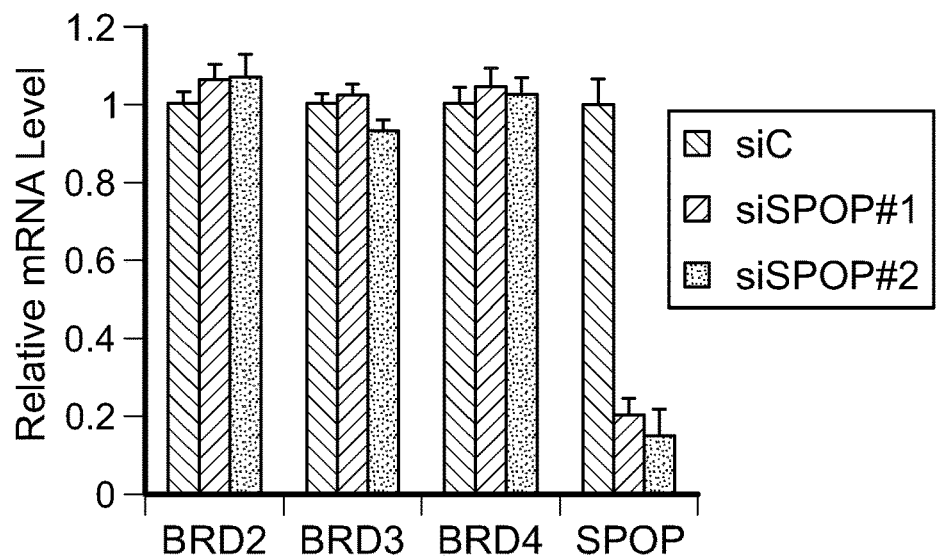
Figure 2G:
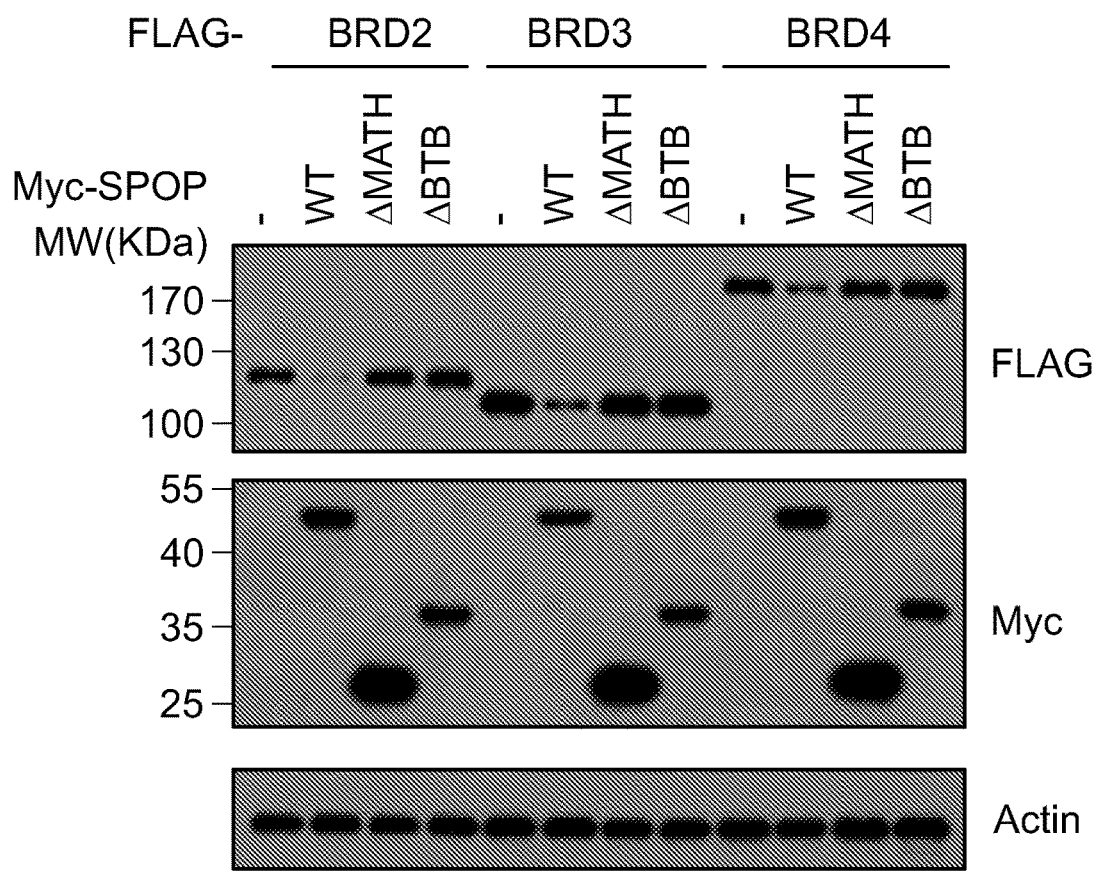
Figure 2H:
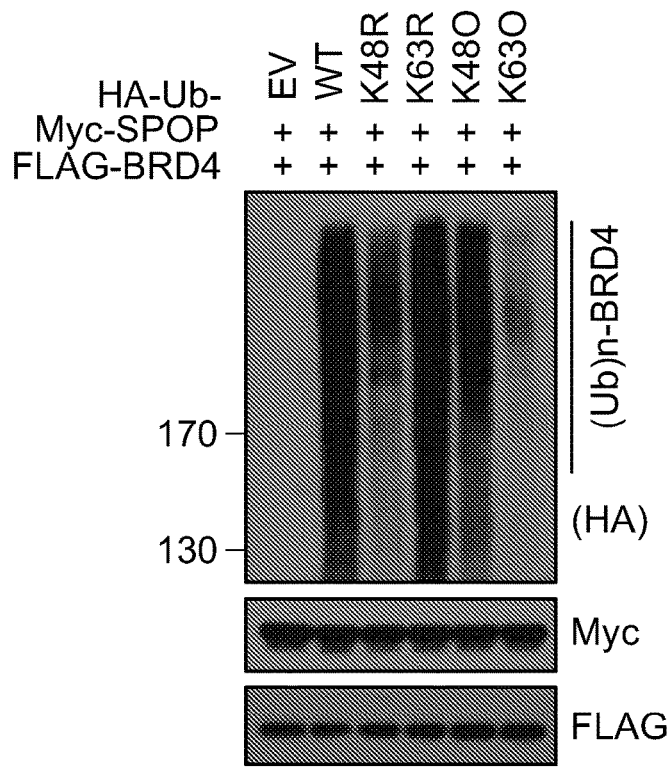
Figure 2I:
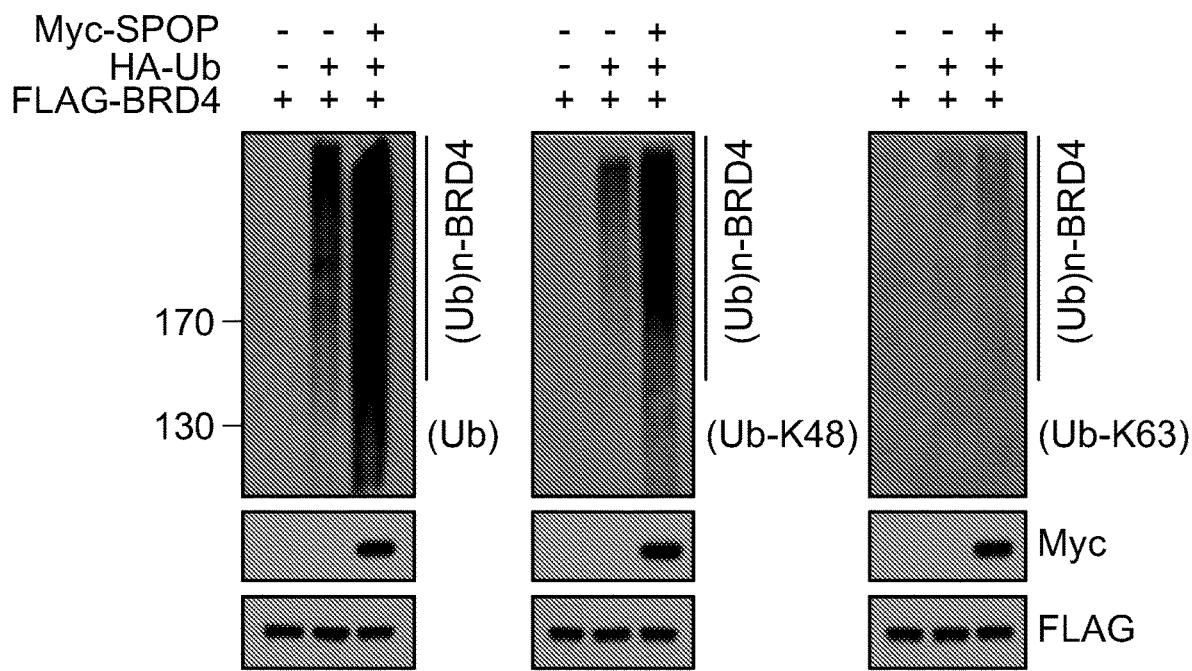

BET proteins play roles in epigenetic regulation and cancer, but little is known about their post-translational modifications and downstream functions. Treatment of LNCaP cells with proteasome inhibitors, Bortezomib and MG132, increased BRD2/3/4 protein, but not mRNA expression (FIGS. 2b and 2c). MLN4924, a small molecule inhibitor of NEDD8-activating enzyme that is required for activation of CRLs, also caused accumulation of BRD2/3/4 at protein level (FIGS. 2b and 2c). Expression of wild-type SPOP markedly decreased BRD2/3/4 proteins, and this effect was completely reversed by MG132 treatment (FIG. 1c). Knockdown of SPOP increased the steady-state level of endogenous BRD2/3/4 protein and prolonged the protein half-life, while having no overt effect on mRNA expression in LNCaP cells (FIGS. 1d and 2d-f). Similar results were obtained in 22Rv1 and BPH-1 prostatic cell lines (FIG. 1d). Moreover, only wild-type SPOP, but not substrate binding- and CUL3 binding-deficient mutants (AMATH and ABTB, respectively) degraded BRD2/3/4 proteins (FIG. 2g). Wild-type SPOP induced K48-dependent polyubiquitination of these proteins in cells, and this effect relied on its enzymatic activity (FIGS. 1e and 2h-i). The SPOP-CULLIN3-RBX1 complex was shown to catalyzed BRD4 ubiquitination in vitro (FIG. 1f). Thus, functioning as a CRL substrate-binding adaptor, SPOP promoted ubiquitination and proteasomal degradation of BRD2/3/4 proteins in prostate cancer cells.

Figure 3A:
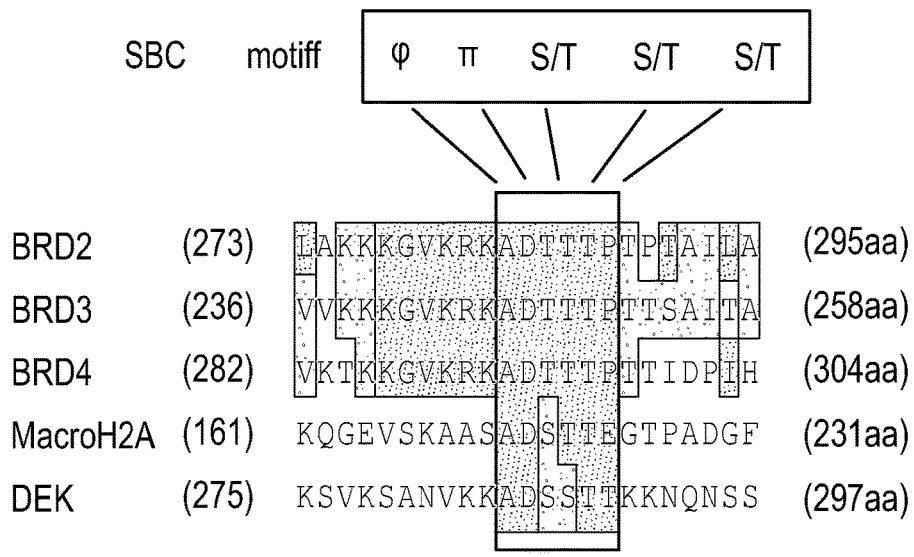
FIGS. 3A-3G. The SBC motif in BRD2/3/4 is a SPOP-recognized degron.
Figure 3B:
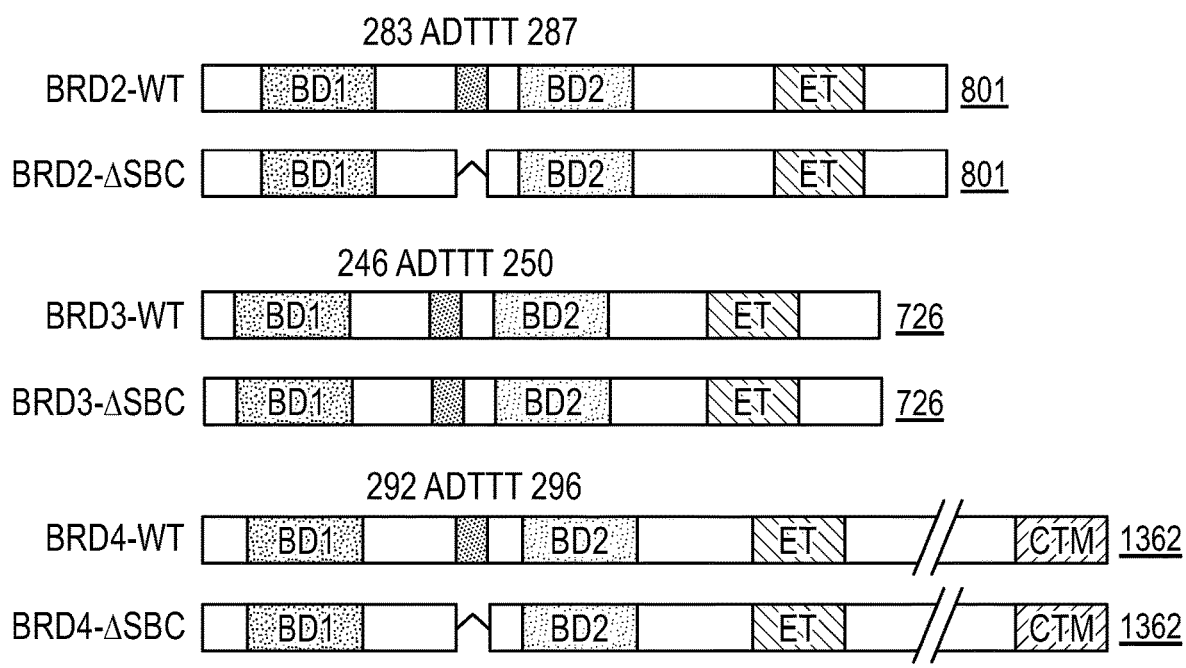
Figure 3C:
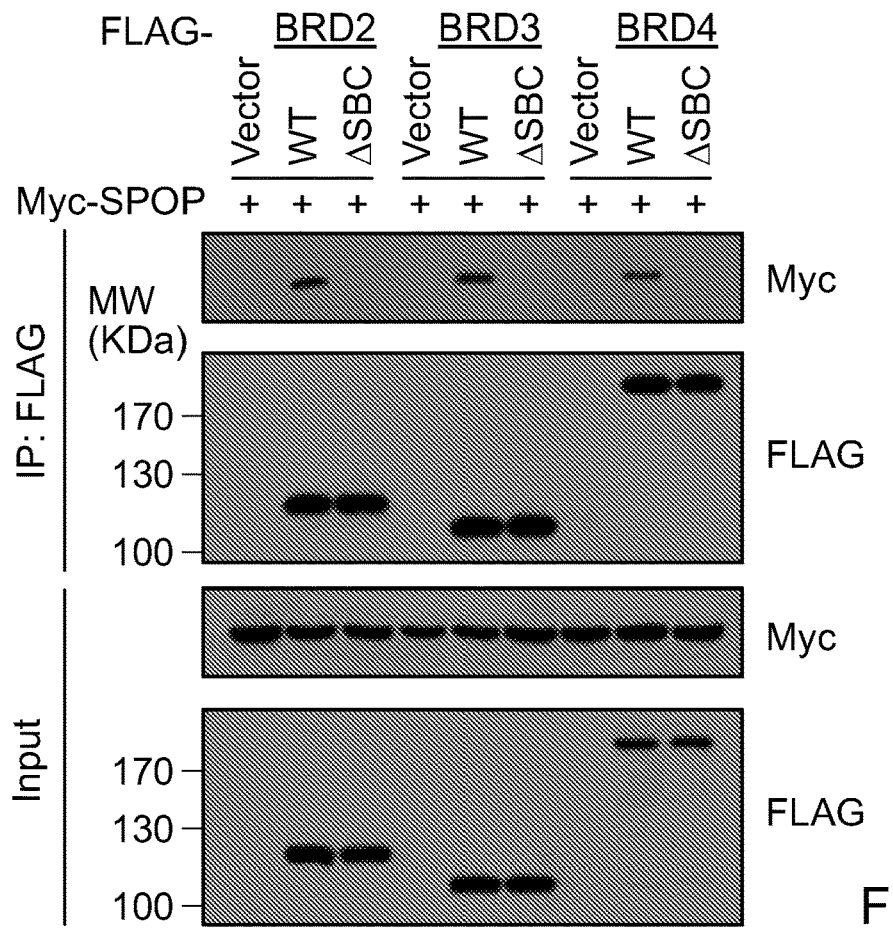
Figure 3D:
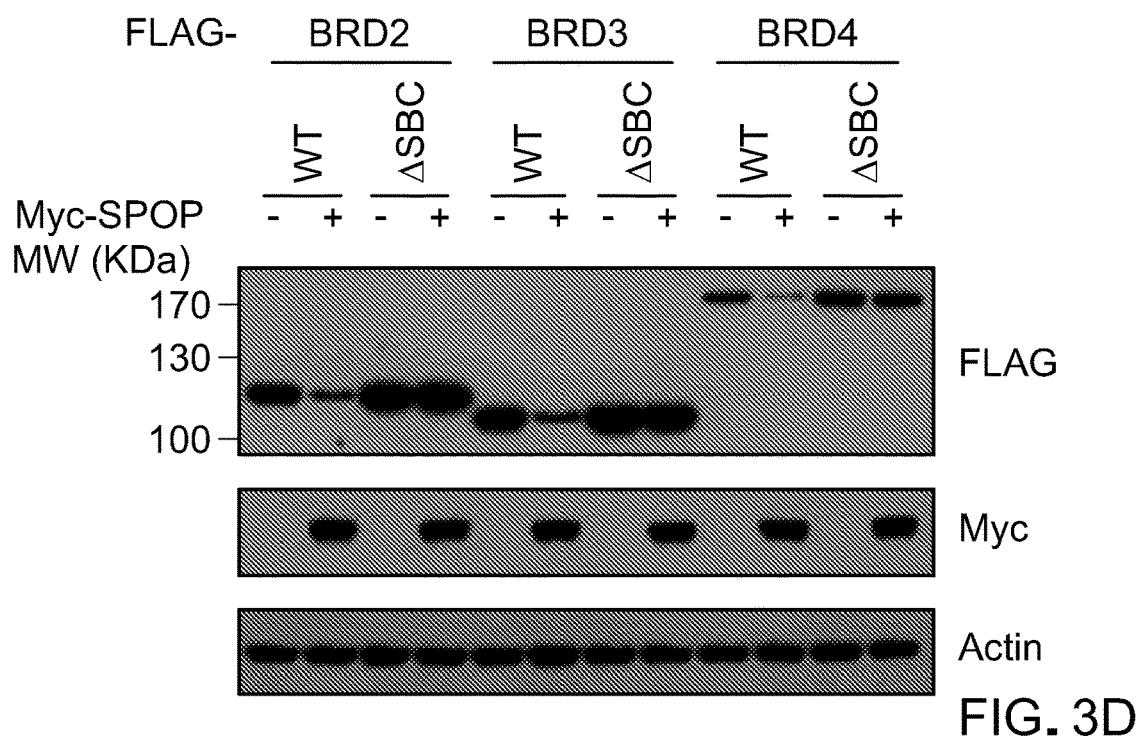
Figure 3E:
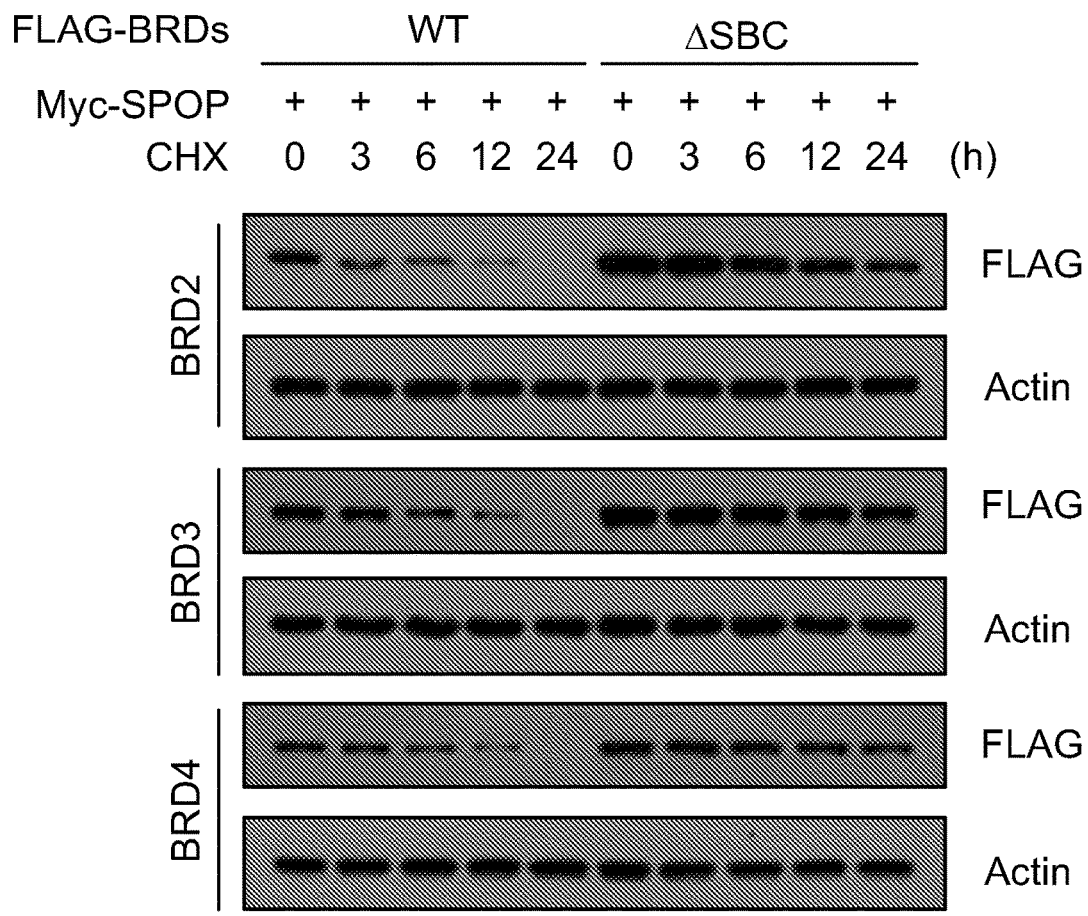
Figure 3F:
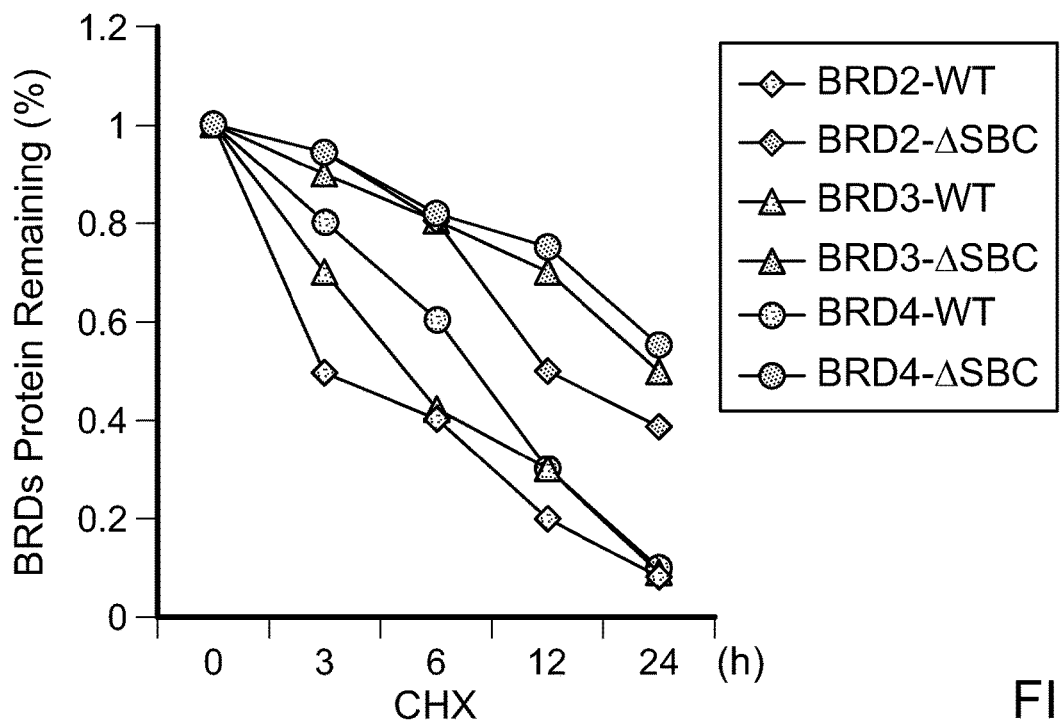
Figure 3G:
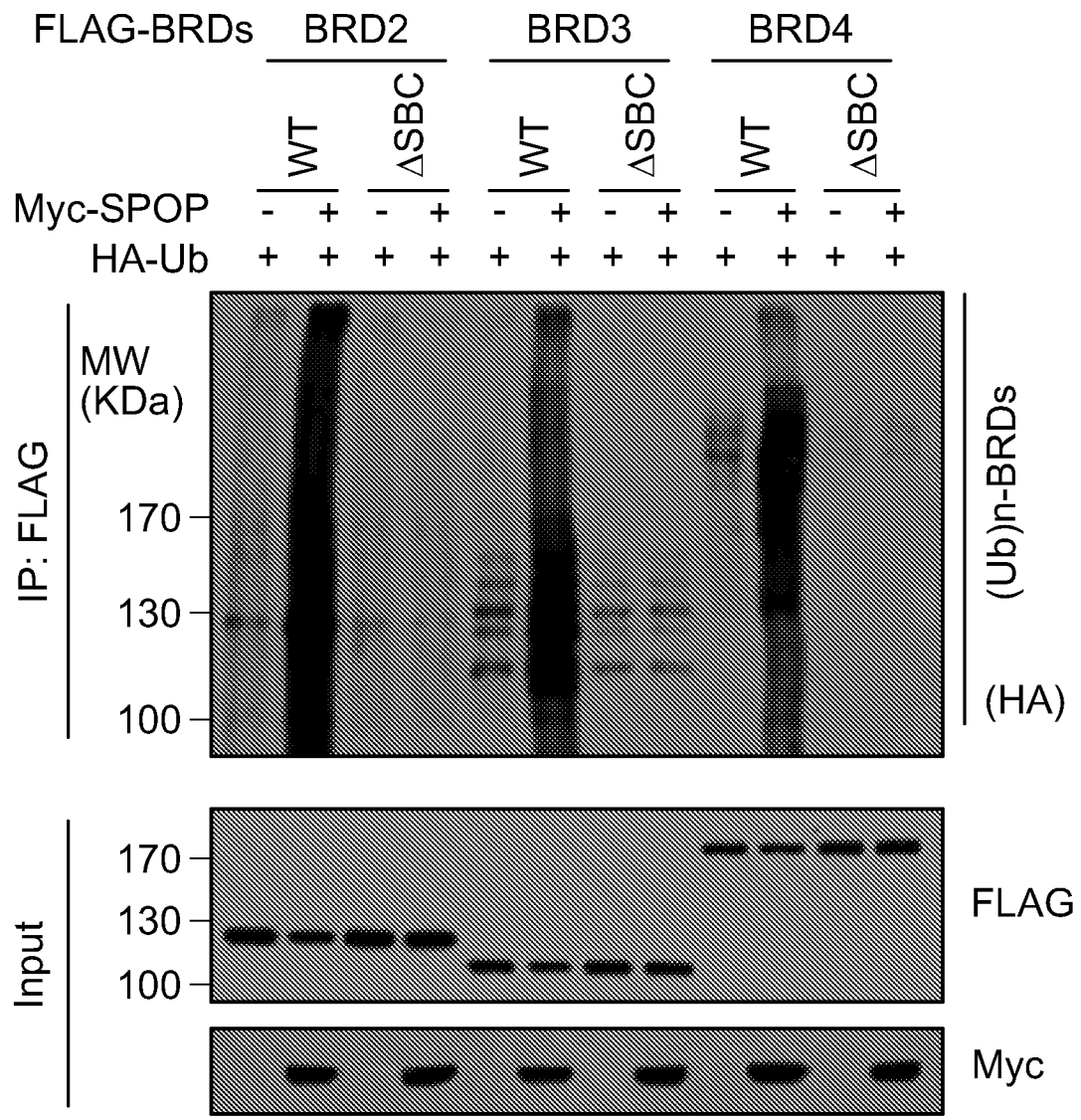

Substrate-binding consensus (SBC) motifs (Φ-π-S/T-S/T-S/T, where Φ is a nonpolar residue, and x is a polar residue (Zhuang et al., *Mol. Cell*, 36:39-50 (2009)) have been well characterized in known SPOP substrates such as MacroH2A and DEK12. The existence of a perfectly matched SBC motif in the region between bromodomain-1 (BD1) and BD2 in BRD2/3/4 proteins was found (FIGS. 3a and 3b), which also localized within the minimal SPOP-interaction region defined by yeast two-hybrid clones of BRD2/3/4 (FIG. 1a). Co-IP assays revealed that deletion of the putative SBC motif in BRD2/3/4 not only abolished SPOP binding and SPOP-mediated ubiquitination and degradation of BRD2/3/4, but also significantly prolonged the half-life of these proteins (FIGS. 3b-g). Thus, a common, functionally conserved SBC motif was identified in BRD2/3/4 proteins that was required for SPOP-dependent ubiquitination and degradation.

Figure 4B:
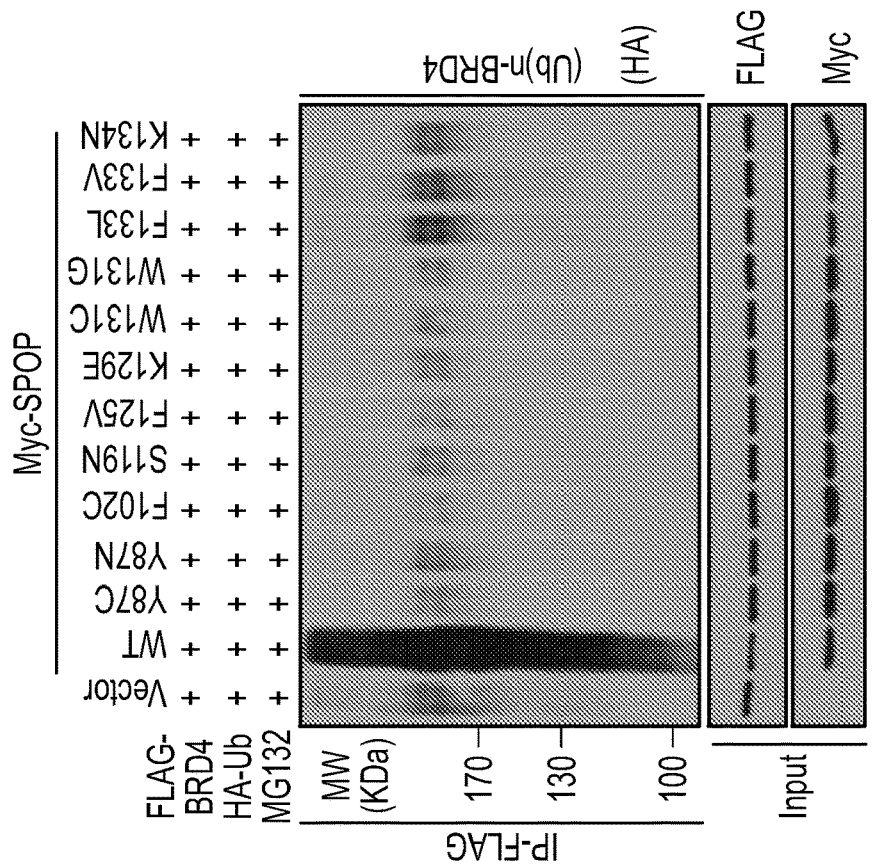
FIGS. 4A-4E. Expression of BET proteins is elevated in SPOP mutant-expressing prostate cancer cells and patient specimens.
Figure 4A:
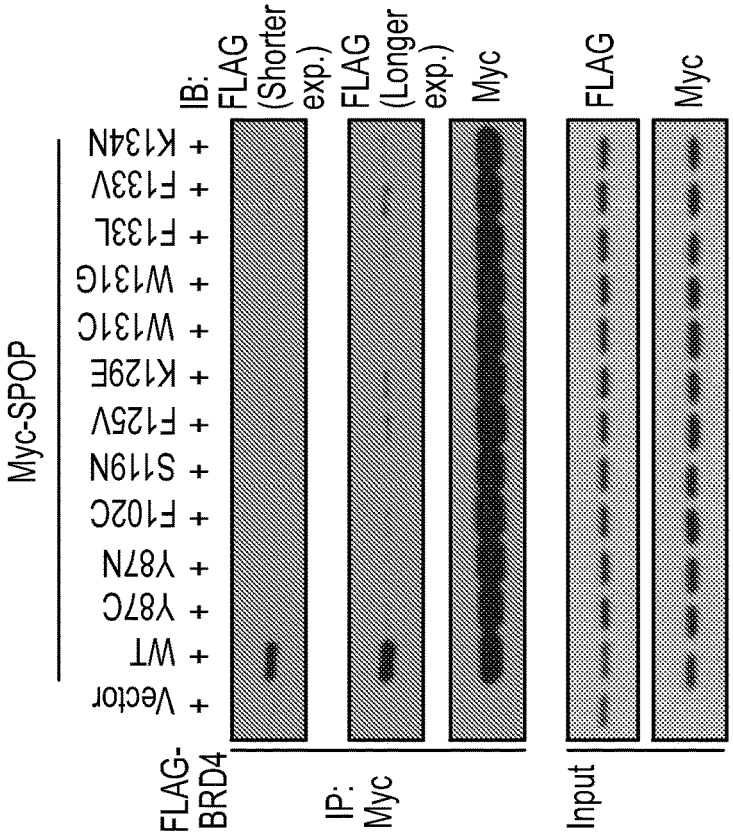
Figure 4C:
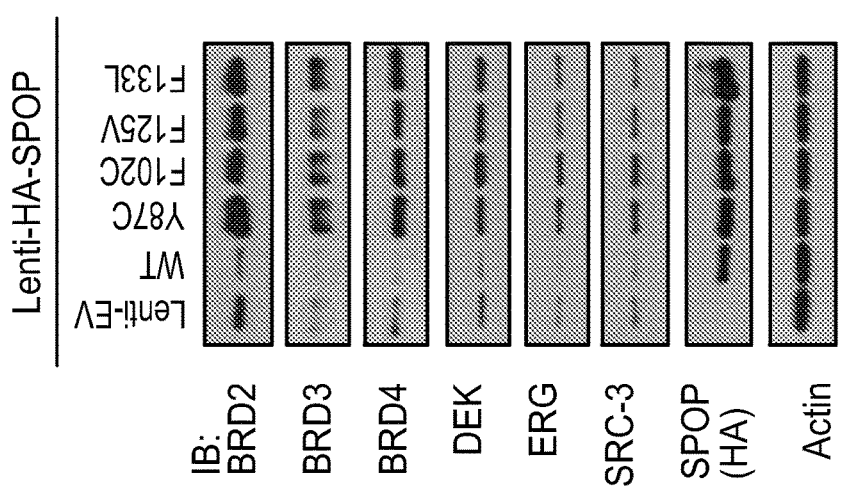
Figure 5A:
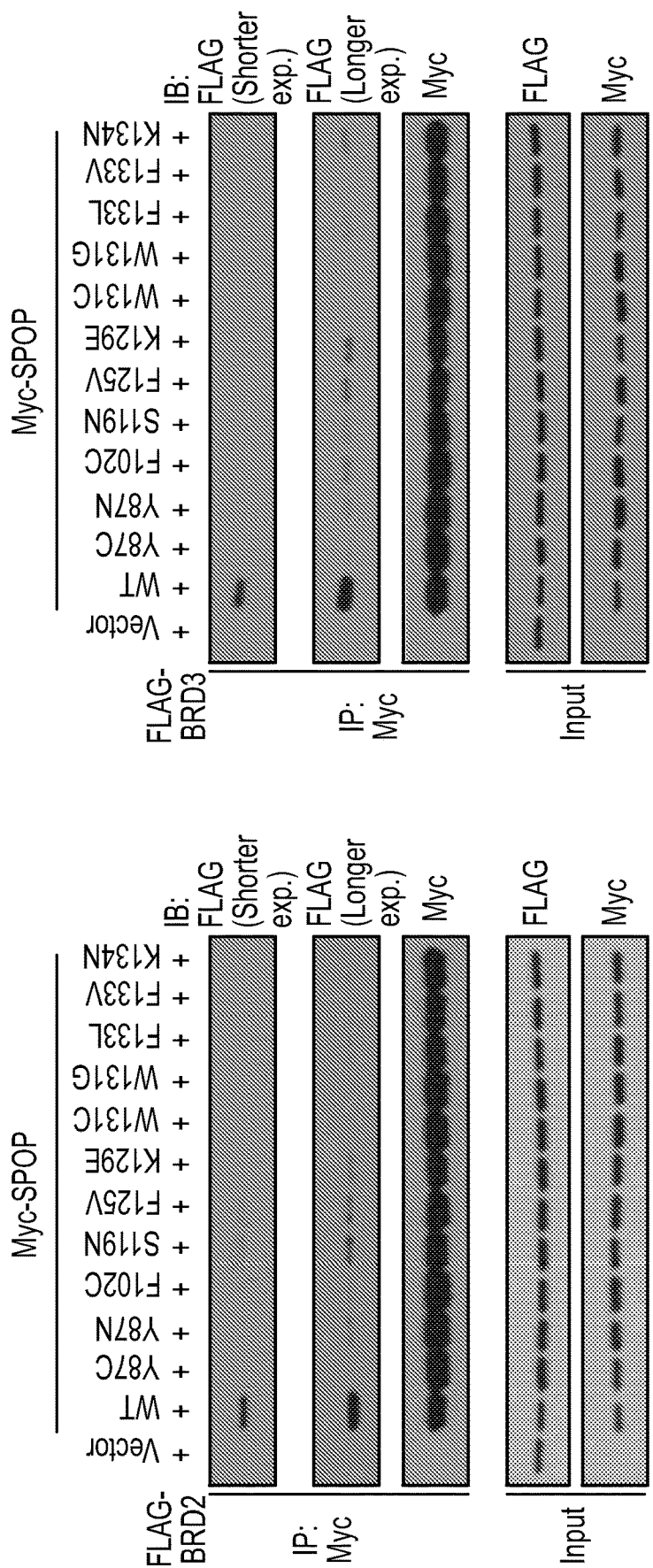
FIGS. 5A-5D. The ability of prostate cancer-associated SPOP mutants to promote BRD2/3 protein degradation and ubiquitination, and expression of BRD2/3/4 mRNA in prostate cancer patient specimens.
Figure 5B:
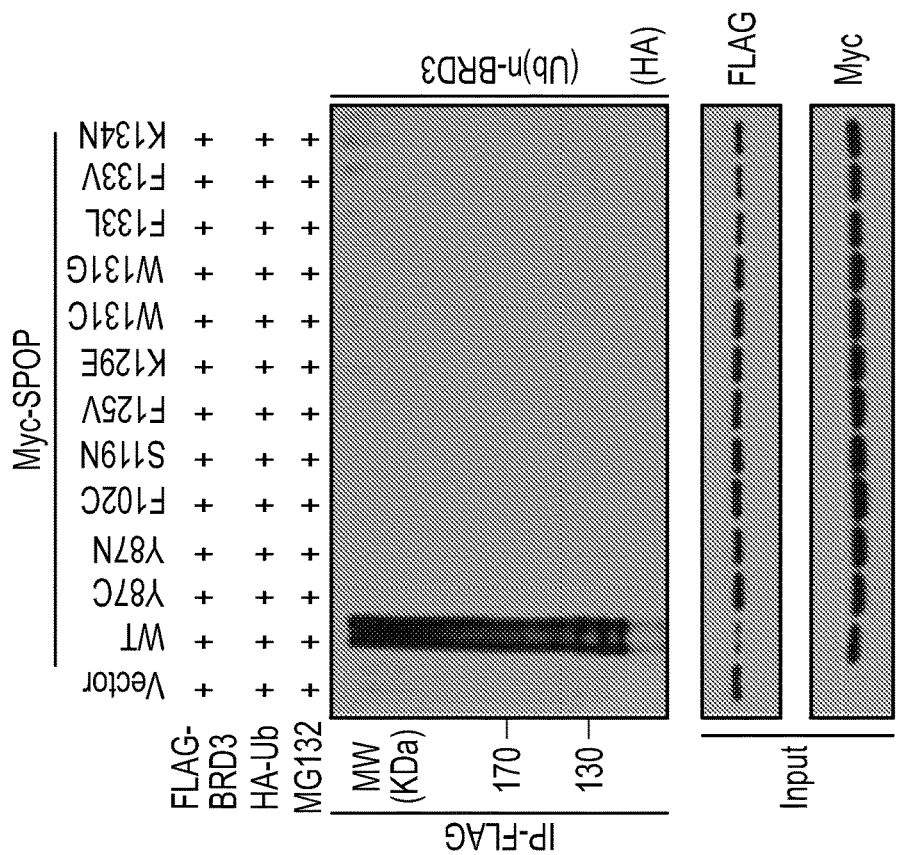
Figure 5B:
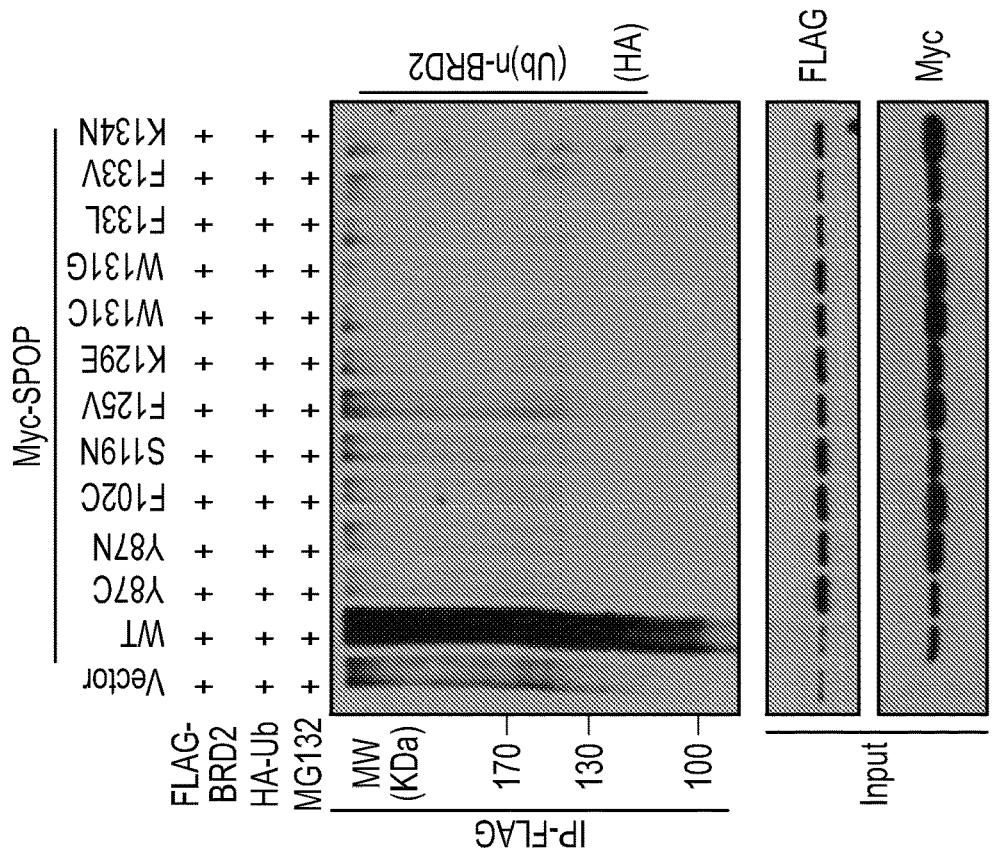

Because SPOP mutations in prostate cancers occur in the MATH domain that is responsible for substrate binding (Blattner et al., Neoplasia, 16:14-20 (2014)), it was hypothesized that prostate cancer-associated mutations impair the ability of SPOP to degrade BRD2/3/4. 11 prostate cancer-associated SPOP mutants were generated. Co-IP assays demonstrated that the BRD2/3/4-binding ability of all 11 SPOP mutants was largely impaired compared with wild-type SPOP (FIGS. 4a and 5a). SPOP-mediated ubiquitination of these proteins also was markedly attenuated by these mutations (FIGS. 4b and 5b). SPOP mutants failed to degrade, but rather elevated endogenous BRD2/3/4 protein levels, a dominant-negative effect similarly occurred to known SPOP substrates such as DEK, ERG and SRC-3 (FIG. 4c; Theurillat et al., *Science*, 346:85-89 (2014); Geng et al., *Proc. Natl. Acad. Sci. USA*, 110:6997-7002 (2013); and An et al., *Mol. Cell*, 59:904-916 (2015)). Thus, prostate cancer-associated SPOP mutants resulted in the stabilization of BRD2/3/4 proteins in prostate cancer cells.

To examine the effect of SPOP mutations on BET protein levels in patient specimens, BRD2/3/4 protein levels were analyzed in two cohorts constituting 99 primary prostate tumors (Table 4). 13 SPOP-mutated tumors were identified through whole-genome sequencing and/or Sanger sequencing. The SPOP mutation frequency in these samples was consistent with the previous findings in different cohorts of prostate cancer (Barbieri et al., *Nat. Genet.*, 44:685-689 (2012); and The Molecular Taxonomy of Primary Prostate Cancer, *Cell*, 163:1011-1025 (2015)). IHC revealed that approximately 85%, 92%, and 85% of SPOP-mutated tumors exhibited strong or intermediate straining of BRD2, BRD3 and BRD4 proteins, respectively (FIGS. 4d and 4e).

Figure 4D:
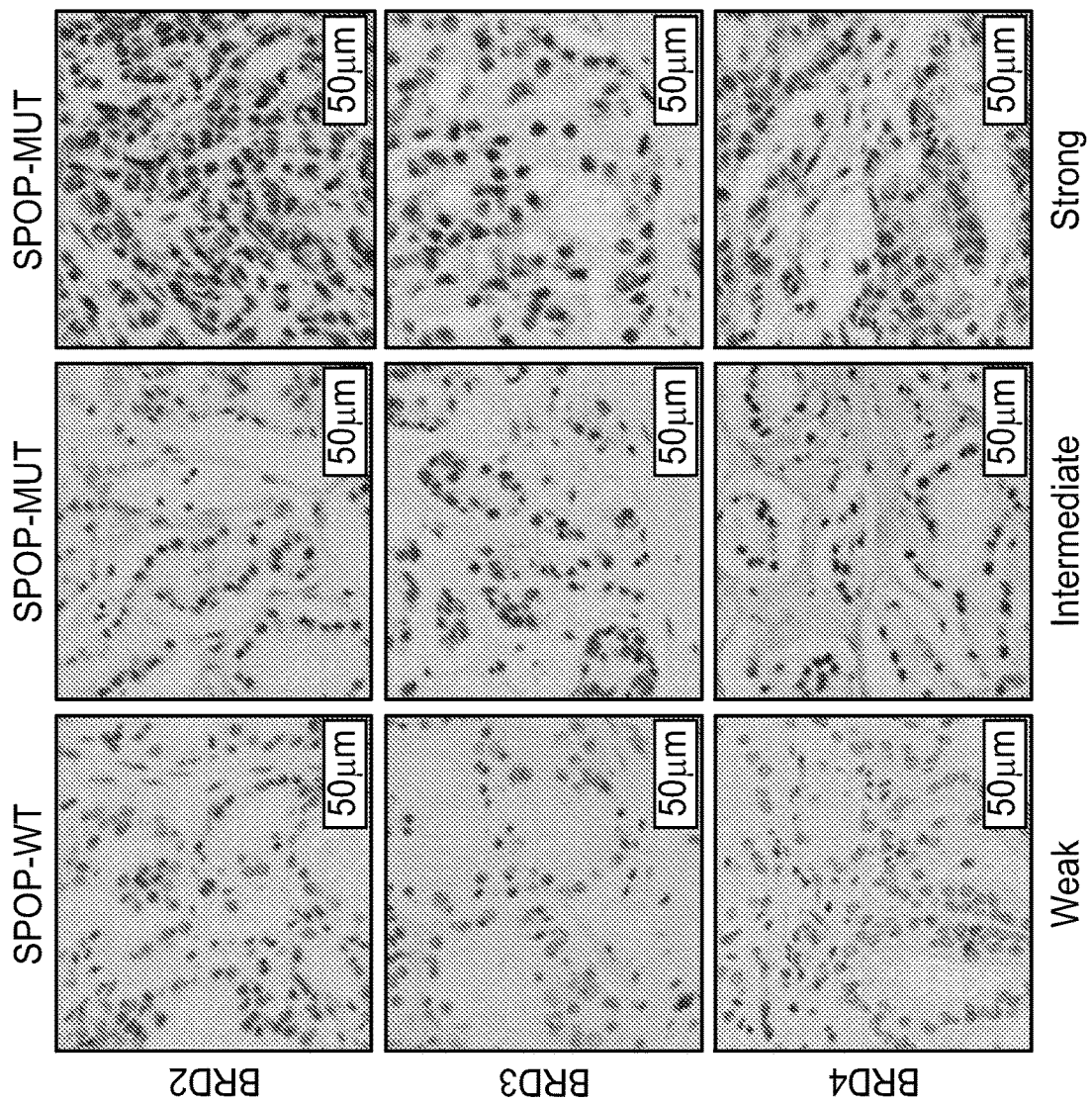
Figure 4E:
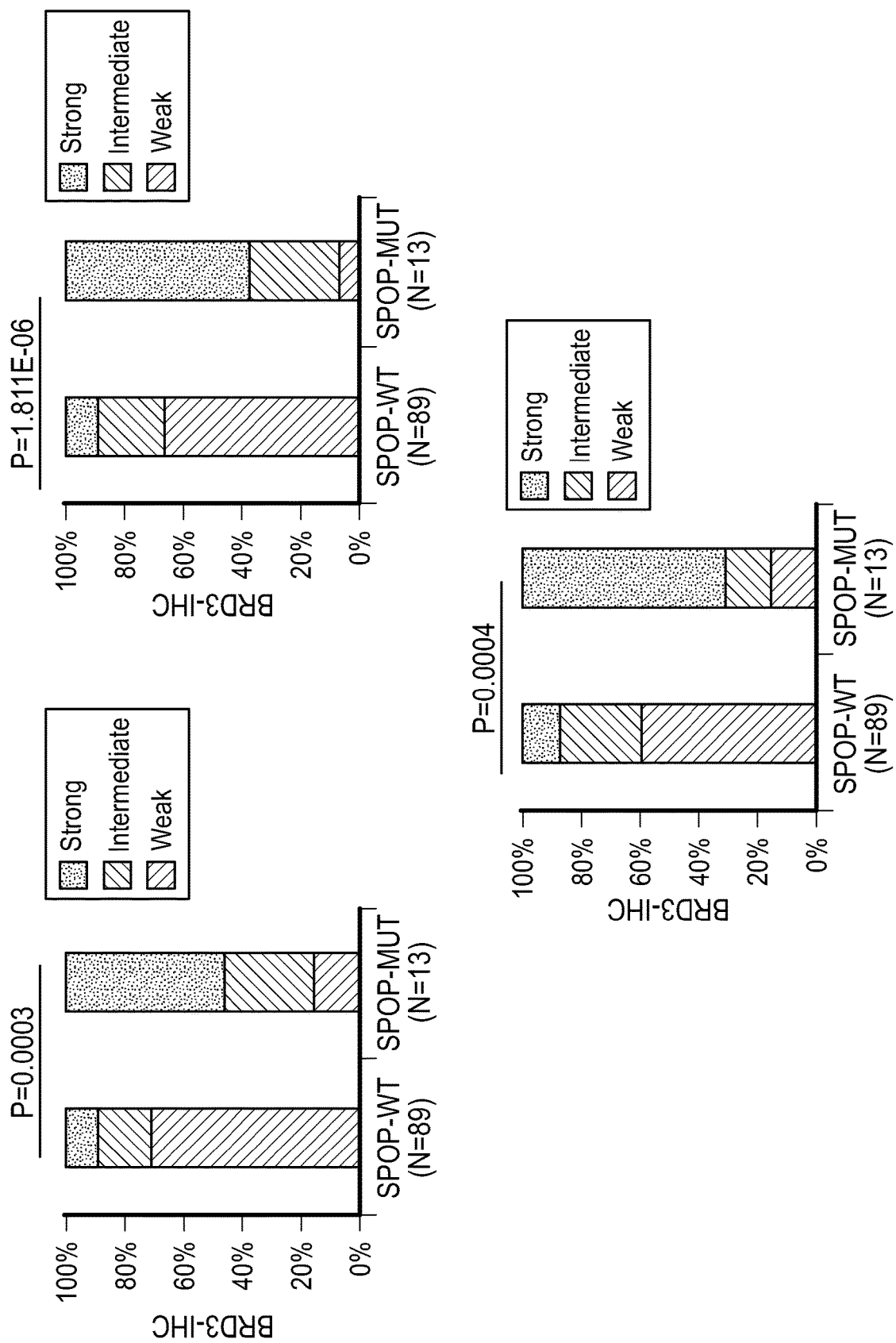
Figure 5C:
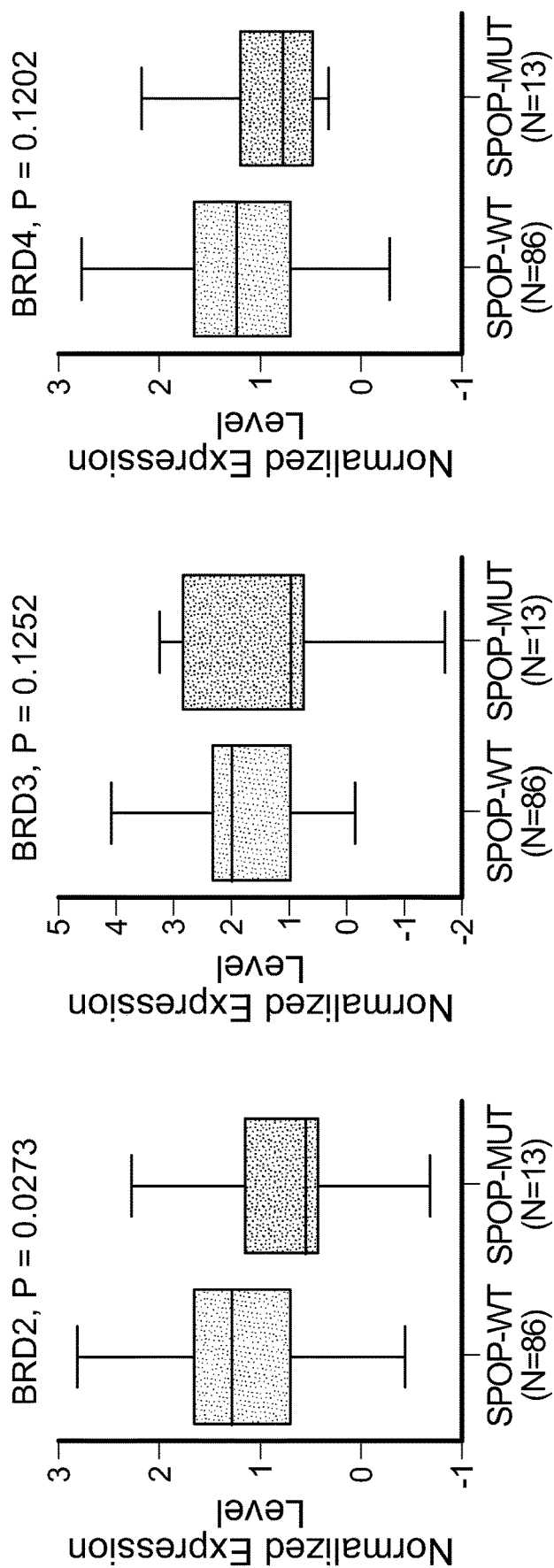
Figure 5D:
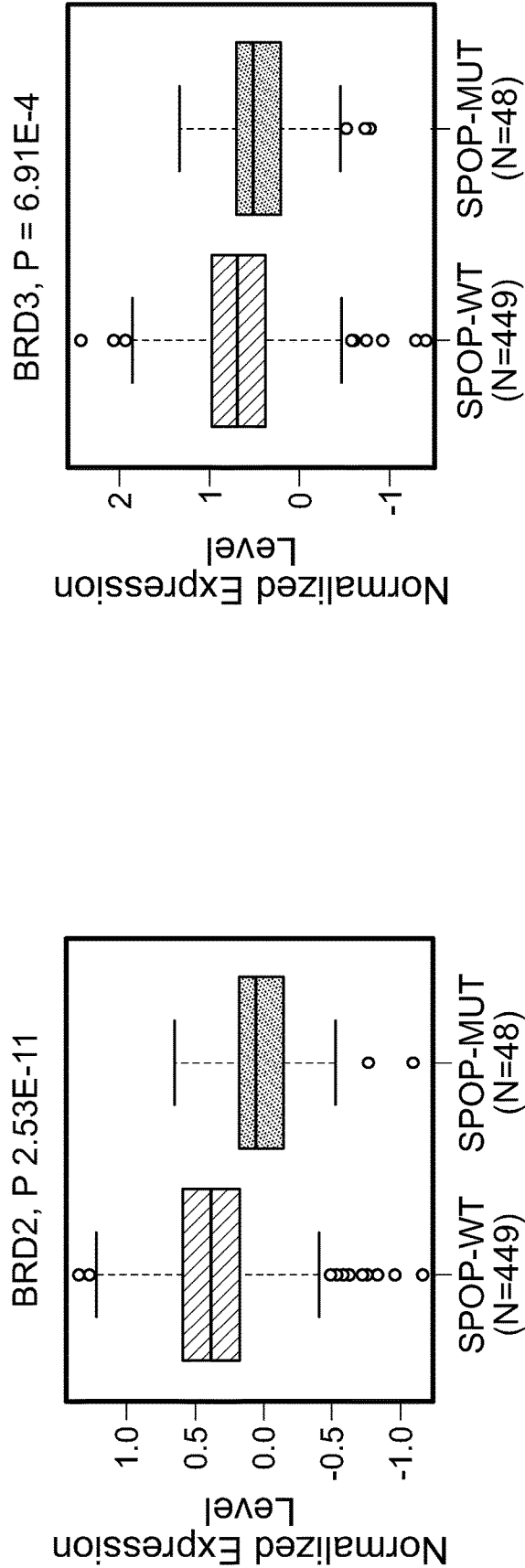
Figure 5D:
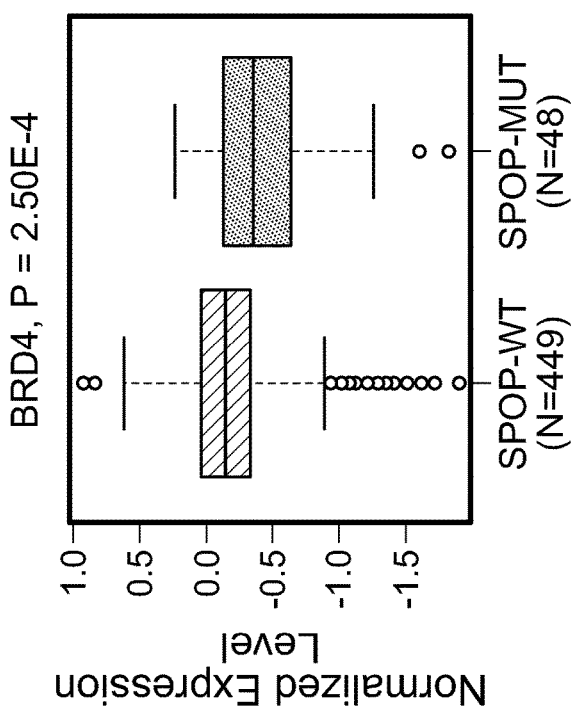

In contrast, only 40% or less of SPOP-WT tumors exhibited strong or intermediate straining, whereas majority of them (approximately 71%, 66%, and 59% for BRD2, BRD3 and BRD4, respectively) exhibited weak staining (FIGS. 4d and 4e). BRD2/3/4 mRNA expression was relative lower in SPOP-mutated tumors than that in SPOP-WT specimens in these cohorts, although the difference did not reach statistical significance (except BRD2) (FIG. 5c). A similar trend was observed in The Cancer Genome Atlas (TCGA) dataset (FIG. 5d). These findings indicate that BRD2/3/4 protein levels were elevated in SPOP-mutated prostate cancer specimens and that this was unlikely caused by increases in mRNA levels.

TABLE 4

Table 4 SPOP mutation status, BRD2/3/4 IHC scores in 99 cases of prostate cancer specimens and the associated clinical i

| patient ID | SPOP Status(Two alies) | BRD2 IHC intensity | BRD3 IHC intensity | BRD4 IHC intensity | Age | Preoperative BMI (kg/m2) | Preoperative PSA level (ng/ml) | Clinical stage |
|---|---|---|---|---|---|---|---|---|
| CHH1 | WT/WT | 1 | 3 | 1 | 65 | 26.85 | 6.37 | T1 |
| CHH2 | WT/WT | 1 | 2 | 2 | 65 | 23.88 | 69.89 | T1 |
| CHH3 | WT/WT | 1 | 2 | 1 | 67 | 24.71 | 10.23 | T1 |
| CHH4 | WT/WT | 1 | 1 | 2 | 66 | 25.16 | 11.10 | T2 |
| CHH5 | F102C/WT | 2 | 2 | 2 | 78 | 26.81 | 22.75 | T2 |
| CHH6 | WT/WT | 1 | 2 | 2 | 65 | 23.20 | 14.14 | T2 |
| CHH7 | WT/WT | 1 | 1 | 1 | 64 | 25.39 | 52.23 | T2 |
| CHH8 | WT/WT | 1 | 1 | 2 | 78 | 25.59 | 8.01 | T1 |
| CHH9 | F102V/WT | 1 | 1 | 1 | 68 | 24.38 | 9.85 | T2 |
| CHH10 | WT/WT | 1 | 2 | 3 | 77 | 21.08 | 41.78 | T1 |
| CHH11 | WT/WT | 1 | 1 | 1 | 69 | 23.26 | 12.80 | T1 |
| CHH12 | WT/WT | 1 | 1 | 2 | 75 | 22.04 | 10.71 | T2 |
| CHH13 | F125C/WT | 3 | 3 | 3 | 68 | 26.50 | 9.68 | T2 |
| CHH14 | WT/WT | 1 | 2 | 1 | 74 | 24.53 | 8.96 | T2 |
| CHH15 | WT/WT | 1 | 1 | 2 | 67 | 25.15 | 21.12 | T1 |
| CHH16 | WT/WT | 1 | 3 | 1 | 73 | 23.23 | 23.62 | T2 |
| CHH17 | WT/WT | 1 | 2 | 1 | 75 | 26.33 | 18.47 | T2 |
| CHH18 | WT/WT | 1 | 1 | 2 | 70 | 28.37 | 8.68 | T2 |
| CHH19 | WT/WT | 1 | 2 | 2 | 74 | 25.26 | 63.83 | T2 |
| CHH20 | WT/WT | 2 | 2 | 1 | 76 | 23.44 | 11.56 | T1 |
| CHH21 | WT/WT | 3 | 3 | 3 | 55 | 20.76 | 87.11 | T2 |
| CHH22 | WT/WT | 1 | 1 | 2 | 70 | 20.95 | 10.07 | T2 |
| CHH23 | F133L/WT | 1 | 2 | 3 | 61 | 25.10 | 7.90 | T2 |
| CHH24 | WT/WT | 1 | 3 | 2 | 65 | 24.91 | 9.03 | T1 |
| CHH25 | WT/WT | 1 | 1 | 1 | 79 | 26.03 | 20.21 | T1 |
| CHH26 | WT/WT | 1 | 3 | 3 | 67 | 25.80 | 39.60 | T1 |
| CHH27 | WT/WT | 1 | 1 | 1 | 62 | 20.07 | 7.96 | T1 |
| CHH28 | WT/WT | 1 | 2 | 2 | 78 | 27.68 | 35.43 | T1 |
| CHH29 | WT/WT | 1 | 1 | 1 | 56 | 25.31 | 5.96 | T2 |
| CHH30 | WT/WT | 1 | 1 | 1 | 68 | 22.58 | 7.49 | T2 |
| CHH31 | WT/WT | 1 | 1 | 1 | 71 | 24.91 | 8.76 | T2 |
| CHH32 | W131G/WT | 2 | 2 | 3 | 70 | 23.44 | 31.19 | T2 |
| CHH33 | F102C/WT | 3 | 3 | 2 | 60 | 22.86 | 9.94 | T1 |
| CHH34 | WT/WT | 1 | 2 | 2 | 54 | 20.62 | 13.00 | T1 |
| CHH35 | F133V/WT | 2 | 2 | 1 | 73 | 23.15 | 21.79 | T1 |
| CHH36 | F133L/WT | 3 | 3 | 3 | 66 | 25.82 | 70.97 | T2 |
| CHH37 | WT/WT | 1 | 1 | 1 | 77 | 20.52 | 13.50 | T2 |
| CHH38 | T133L/WT | 3 | 3 | 3 | 76 | 27.18 | 9.87 | T1 |
| CHH39 | WT/WT | 1 | 1 | 1 | 61 | 23.88 | 14.87 | T2 |
| CHH40 | WT/WT | 2 | 1 | 1 | 60 | 25.61 | 10.67 | T1 |
| CHH41 | W131G/WT | 2 | 3 | 3 | 51 | 22.95 | 27.04 | T2 |
| CHH42 | WT/WT | 1 | 1 | 1 | 71 | 22.32 | 21.37 | T2 |
| CHH43 | WT/WT | 1 | 1 | 2 | 77 | 25.39 | 47.43 | T2 |
| CHH44 | WT/WT | 2 | 1 | 2 | 74 | 24.49 | 26.90 | T2 |
| CHH45 | WT/WT | 1 | 1 | 1 | 75 | 23.88 | 12.57 | T2 |
| CHH46 | WT/WT | 1 | 1 | 1 | 69 | 24.61 | 89.63 | T2 |
| CHH47 | WT/WT | 1 | 1 | 2 | 62 | 29.41 | 7.95 | T2 |
| CHH48 | WT/WT | 1 | 1 | 1 | 50 | 25.39 | 8.01 | T2 |
| CHH49 | WT/WT | 1 | 1 | 1 | 66 | 25.51 | 6.78 | T2 |
| CHH50 | WT/WT | 2 | 1 | 2 | 60 | 28.34 | 10.09 | T1 |
| CHH51 | WT/WT | 1 | 1 | 3 | 71 | 21.77 | 51.65 | T1 |
| CHH52 | WT/WT | 1 | 2 | 2 | 62 | 21.11 | 5.80 | T2 |
| CHH53 | WT/WT | 1 | 1 | 1 | 72 | 21.11 | 7.40 | T2 |
| CHH54 | WT/WT | 3 | 2 | 3 | 74 | 22.84 | 18.74 | T2 |
| CHH55 | WT/WT | 1 | 1 | 1 | 55 | 26.30 | 7.44 | T1 |
| CHH56 | WT/WT | 1 | 1 | 1 | 65 | 26.22 | 7.60 | T2 |
| CHH57 | WT/WT | 1 | 1 | 1 | 80 | 21.34 | 16.54 | T2 |
| CHH58 | WT/WT | 1 | 1 | 1 | 61 | 25.35 | 14.58 | T2 |
| CHH59 | WT/WT | 2 | 2 | 1 | 50 | 27.10 | 14.87 | T1 |
| CHH60 | WT/WT | 1 | 1 | 2 | 55 | 25.76 | 30.82 | T1 |
| CHH61 | WT/WT | 1 | 1 | 1 | 73 | 19.61 | 13.11 | T1 |
| CHH62 | WT/WT | 2 | 2 | 1 | 68 | 24.69 | 14.00 | T2 |
| CHH63 | F133V/WT | 3 | 3 | 3 | 67 | 26.30 | 13.95 | T1 |
| CHH64 | WT/WT | 1 | 1 | 1 | 69 | 23.88 | 2.52 | T2 |

TABLE 4-continued

Table 4 SPOP mutation status, BRD2/3/4 IHC scores in 99 cases
of prostate cancer specimens and the associated clinical i

| patient ID | SPOP Status(Two alies) | BRD2 IHC intensity | BRD3 IHC intensity | BRD4 IHC intensity | Age | Preoperative BMI (kg/m2) | Preoperative PSA level (ng/ml) | Clinical stage |
|---|---|---|---|---|---|---|---|---|
| CHH65 | WT/WT | 1 | 1 | 2 | 72 | 24.22 | 29.96 | T1 |
| CHH66 | WT/WT | 1 | 1 | 1 | 69 | 22.23 | 4.50 | T2 |
| CHH67 | WT/WT | 1 | 1 | 1 | 72 | 25.47 | 21.91 | T2 |
| CHH68 | WT/WT | 1 | 2 | 1 | 56 | 22.86 | 4.00 | T1 |
| CHH69 | F102S/WT | 3 | 3 | 3 | 72 | 23.44 | 48.13 | T1 |
| CHH70 | F102S/WT | 3 | 3 | 3 | 79 | 23.44 | 21.20 | T2 |
| CHH71 | WT/WT | 2 | 1 | 1 | 64 | 24.80 | 10.30 | T2 |
| CHH72 | WT/WT | 3 | 1 | 3 | 74 | 25.86 | 39.50 | T2 |
| CHH73 | WT/WT | 1 | 1 | 1 | 67 | 23.03 | 46.20 | T1 |
| CHH74 | WT/WT | 3 | 1 | 1 | 72 | 27.47 | 19.76 | T1 |
| CHH75 | WT/WT | 2 | 1 | 1 | 68 | 31.25 | 47.28 | T2 |
| CHH76 | WT/WT | 2 | 1 | 3 | 63 | 23.53 | 16.84 | T1 |
| CHH77 | WT/WT | 3 | 2 | 3 | 67 | 27.78 | 7.66 | T1 |
| CHH78 | WT/WT | 1 | 1 | 1 | 77 | 29.27 | 17.58 | T1 |
| CHH79 | WT/WT | 3 | 3 | 2 | 58 | 24.22 | 24.08 | T2 |
| CHH80 | WT/WT | 1 | 2 | 1 | 77 | 21.48 | 4.62 | T2 |
| CHH81 | WT/WT | 2 | 2 | 3 | 70 | 24.69 | 9.55 | T2 |
| CHH82 | WT/WT | 2 | 2 | 1 | 76 | 20.08 | 9.98 | T2 |
| CHH83 | WT/WT | 1 | 1 | 2 | 70 | 31.77 | 11.56 | T2 |
| CHH84 | WT/WT | 1 | 1 | 1 | 70 | 31.89 | 5.68 | T2 |
| CHH85 | WT/WT | 2 | 1 | 1 | 69 | 24.21 | 6.96 | T2 |
| CHH86 | WT/WT | 2 | 1 | 1 | 70 | 23.14 | 14.20 | T3 |
| CHH87 | WT/WT | 1 | 1 | 1 | 69 | 25.71 | 19.70 | T2 |
| CHH88 | WT/WT | 1 | 1 | 1 | 59 | 23.59 | 5.26 | T2 |
| CHH89 | WT/WT | 1 | 1 | 3 | 60 | 25.39 | 20.45 | T2 |
| CHH90 | WT/WT | 2 | 1 | 1 | 68 | 21.48 | 14.76 | T2 |
| CHH91 | WT/WT | 1 | 1 | 1 | 63 | 26.99 | 17.93 | T2 |
| CHH92 | WT/WT | 2 | 2 | 1 | 75 | 23.66 | 1.29 | T4 |
| CHH93 | WT/WT | 1 | 1 | 2 | 68 | 23.44 | 18.72 | T2 |
| CHH94 | WT/WT | 3 | 1 | 3 | 63 | 23.44 | 8.61 | T2 |
| CHH95 | WT/WT | 1 | 1 | 2 | 69 | 21.71 | 25.72 | T2 |
| CHH96 | WT/WT | 2 | 2 | 2 | 46 | 24.16 | 5.96 | T2 |
| CHH97 | WT/WT | 3 | 1 | 1 | 60 | 24.91 | 164.90 | T4 |
| CHH98 | WT/WT | 1 | 1 | 1 | 64 | 25.40 | 17.94 | T2 |
| CHH99 | WT/WT | 3 | 3 | 1 | 74 | 20.94 | 8.38 | T1 |

Figure 6B:
FIG. 6B and FIG. 6C, C4-2 cells were infected with lentivirus as in (FIG. 6A) and then treated with or without JQ1 (0.25 μM) every other day. Cell growth was measured at indicated time points by cell proliferation assay (FIG. 6B) and trypan blue assay (FIG. 6C). Data are shown as means±SD (n=6 biological replicates).
Figure 6A:
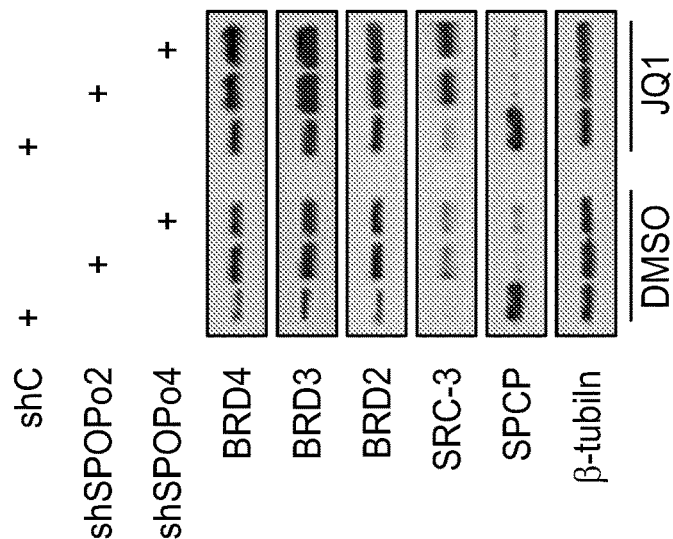
FIGS. 6A-6Q. SPOP knockdown and expression prostate cancer-associated mutant promote JQ1-resistant growth of prostate cancer cells.
Figure 6D:
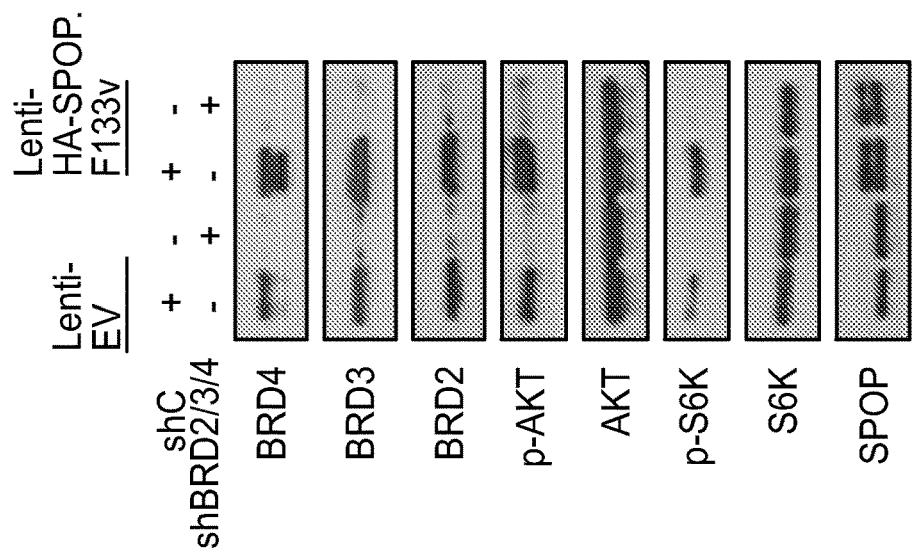
Figure 6C:
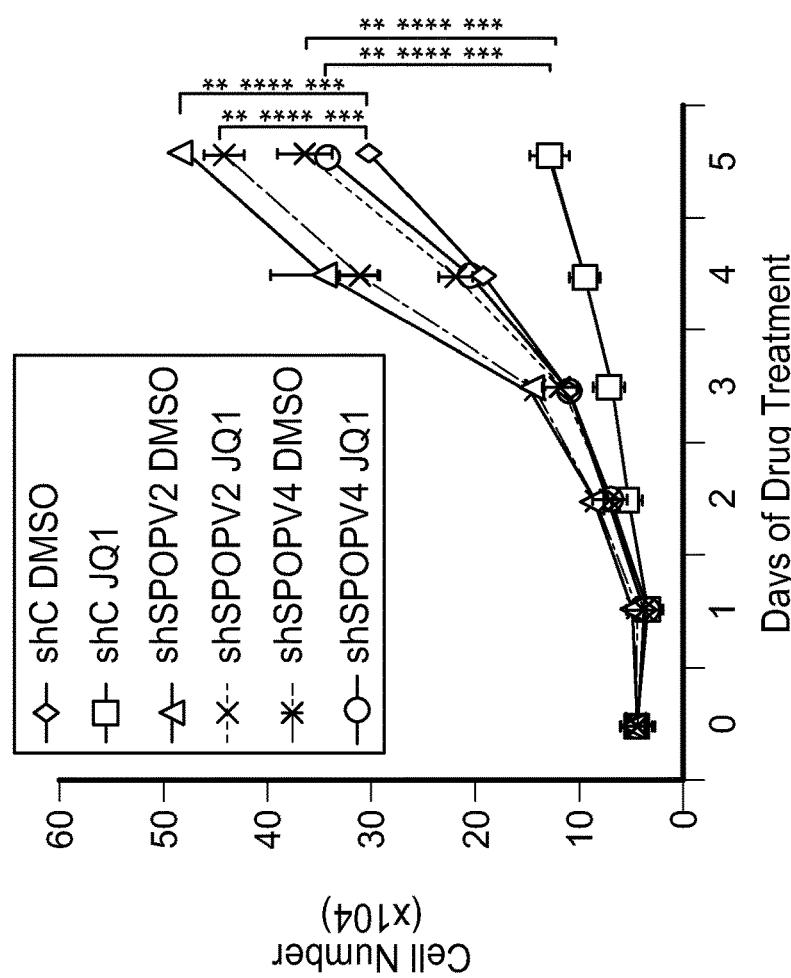
Figure 6E:
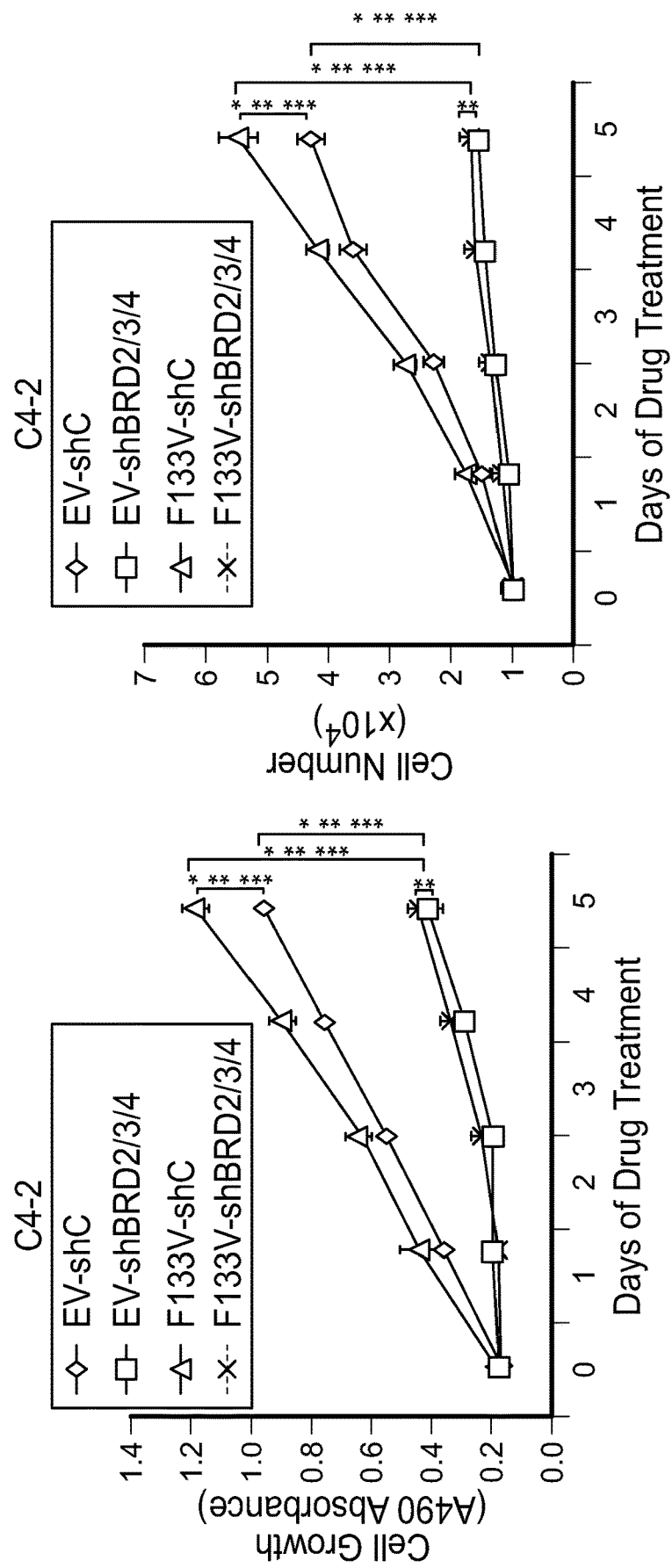
Figure 6F:
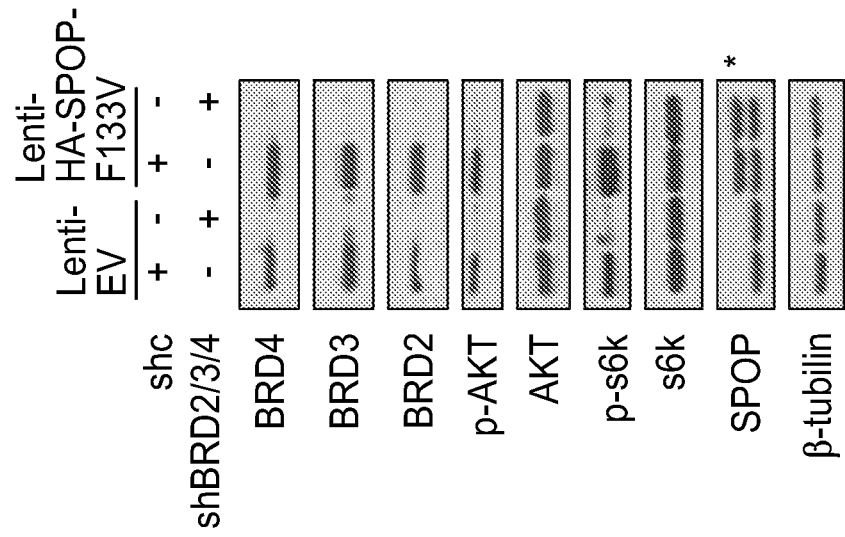
Figure 6G:
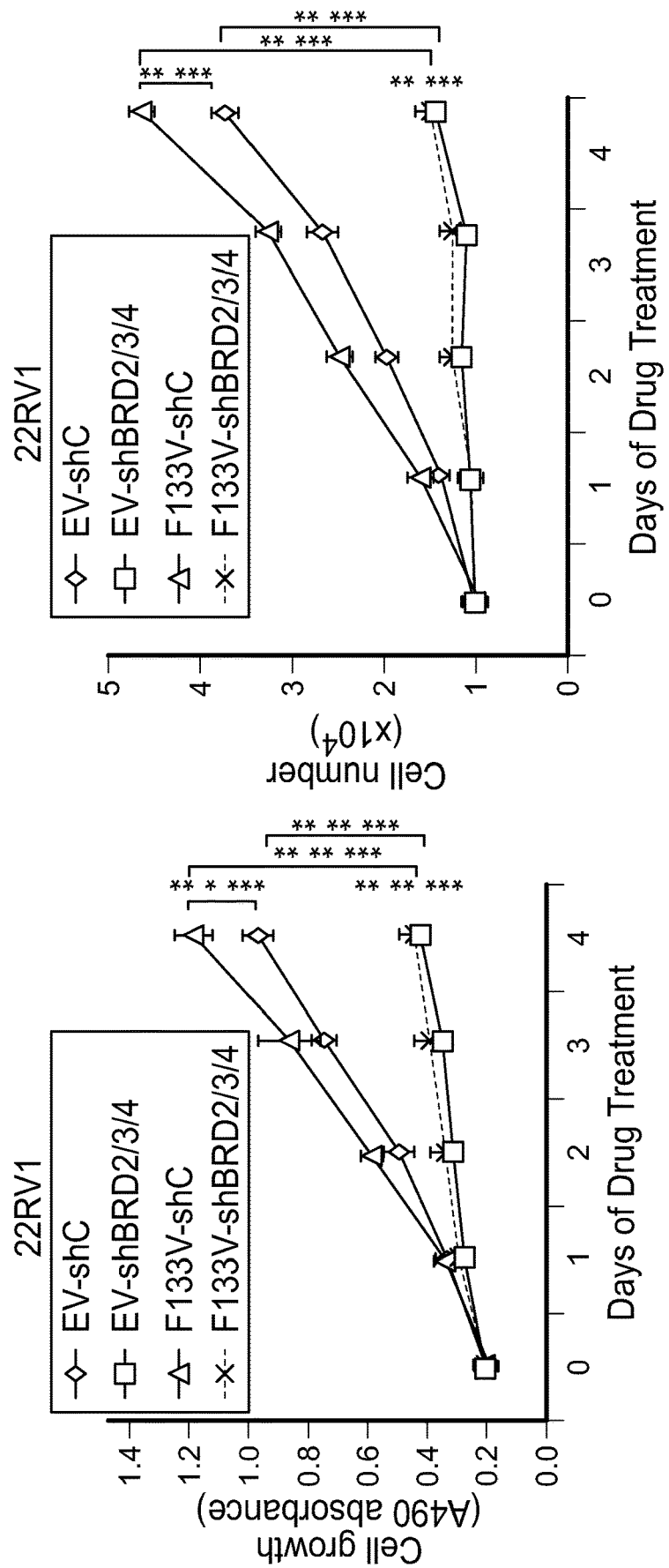
Figure 6I:
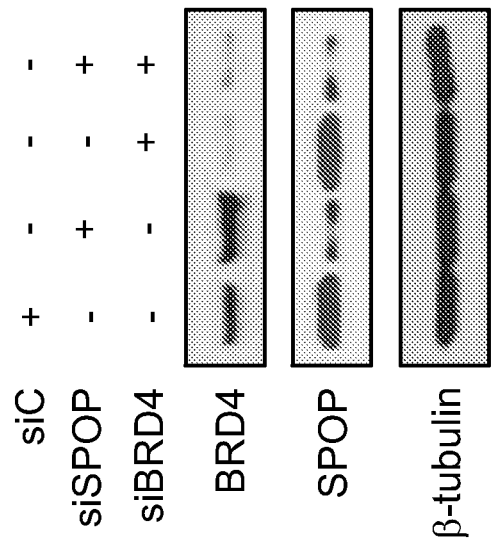
FIG. 6H-6J, C4-2 cells were transfected with control siRNA (siC), a pool of BRD4- and/or SPOP specific siRNAs (siBRD4 or siSPOP) as indicated. At 48 hours after transfection, the first set of cells were harvested for measurement of BRD4 and SPOP mRNA expression by RT-qPCR (FIG. 6H); the second set of cells were harvested for measurement of BRD4 and SPOP protein expression by western blots (FIG. 6I); the third set of cells were treated with different doses of JQ1 for 24 hours, and cell viability were measured by MTS assay (FIG. 6J). Data are shown in (FIG. 6H) as means±SD (n=3 technical replicates), and similar results were obtained from two independent experiments. Data are shown in (FIG. 6J) as means±SD (n=6 replicates). Comparison of the data in cells treated with the highest concentration (500 nM) of JQ1.
Figure 6H:
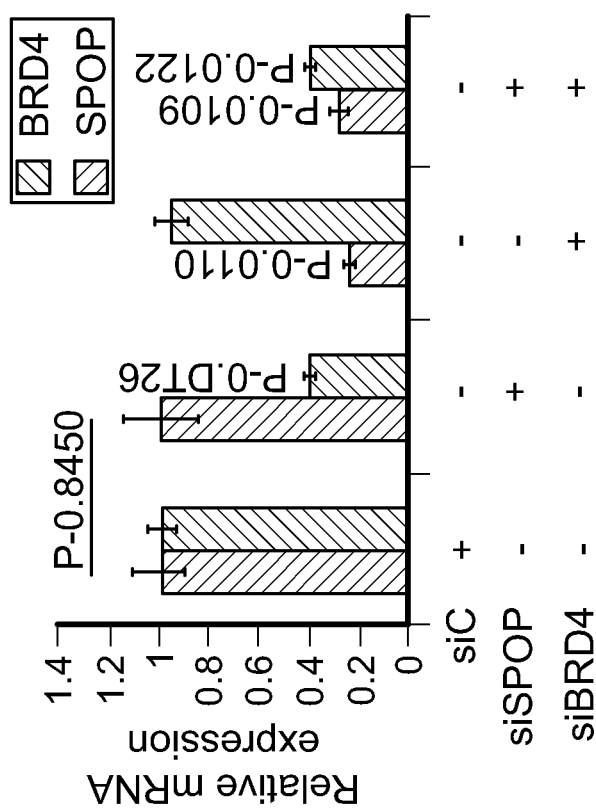
Figure 6K:
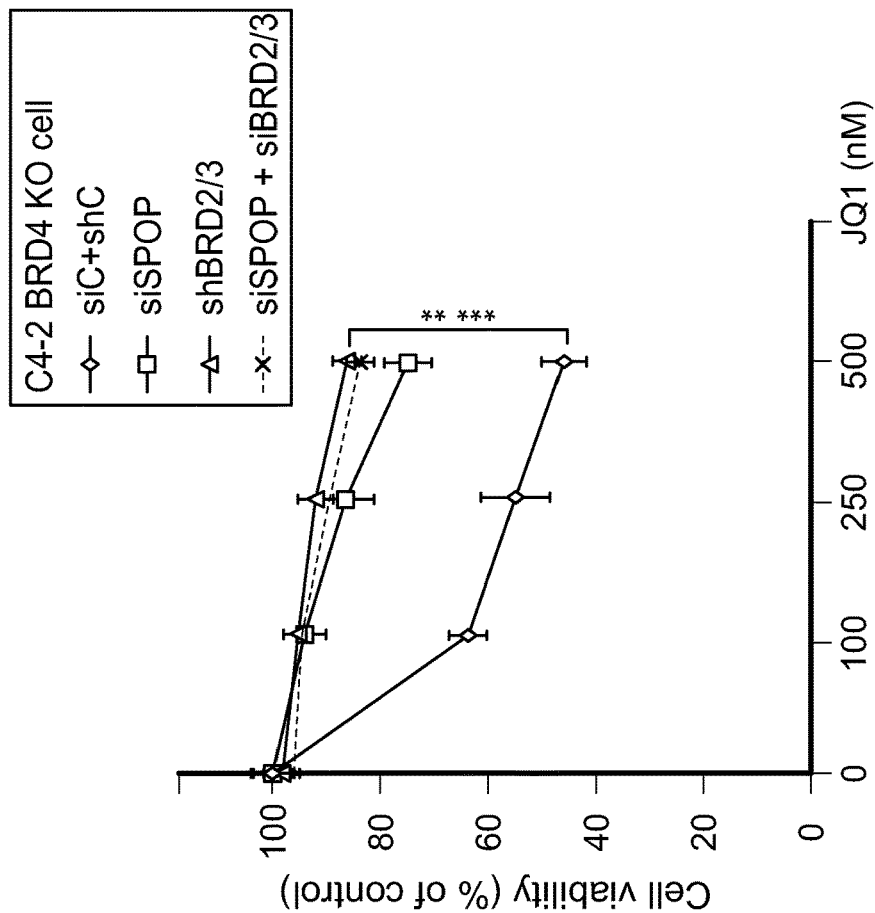
FIG. 6K and FIG. 6L, BRD4 KO C4-2 cells were transfected with control siRNA (siC), pool of SPOP-specific siRNAs, and/or BRD2/3 shRNAs (shBRD2/3 or siSPOP) as indicated. At 48 hours after transfection, the first set of cells were harvested for measurement of BRD2/3/4 and SPOP protein expression by western blots; the second set of cells were treated with different doses of JQ1 for 24 hours, and cell growth were measured by cell proliferation assay. Data are shown as means±SD (n=6 replicates). Statistical significance was determined by two-tailed Student's t-test for cells treated with the highest concentration (500 nM) of JQ1. m, Western blot of indicated proteins including AKT (Ser473) and S6K (Thr389) phosphorylation in WCL of C4-2 (left) and 22Rv1 (right) cells infected with lentivirus expressing empty vector (EV) or SPOP F133V mutant and treated with vehicle (DMSO) or 1 μM JQ1 for 24 hours. Western blot signal intensity of p-AKT and p-S6K was first normalized to pan AKT and S6K level, respectively, and the value was further normalized to the one in cells infected with EV without JQ1 treatment. Asterisk indicates the exogenous HA-SPOPF133V.
Figure 6J:
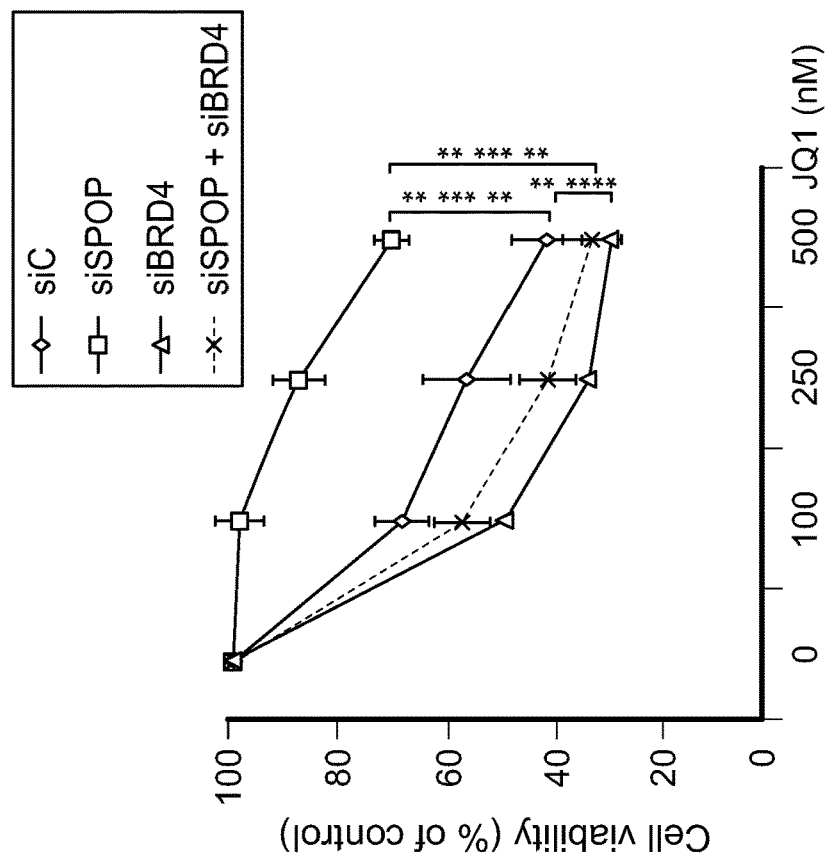
Figures 6L, 6M:
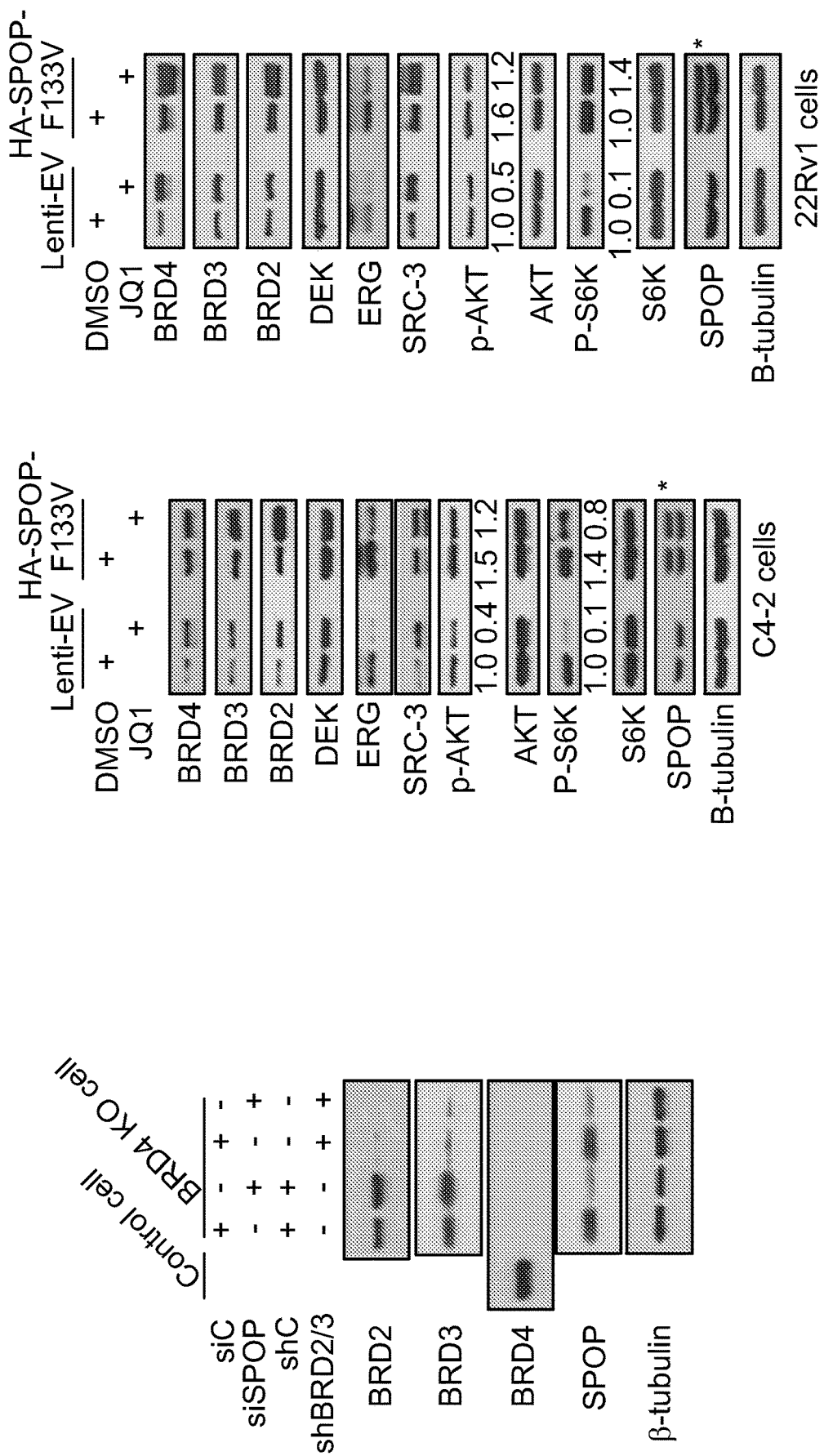

Small molecule inhibitors of BET proteins are being actively tested as promising epigenetic-targeted therapeutics of cancer (Mertz et al., Proc. Natl. Acad. Sci. USA, 108: 16669-16674 (2011); and Loven et al., Cell, 153:320-334 (2013)). The following was performed to examine if SPOP-mediated degradation of BET proteins influences the anti-cancer efficacy of BET inhibitors in prostate cancer cells. Knockdown of endogenous SPOP by small hairpin RNAs (shRNAs) not only increased BRD2/3/4 protein expression, but also enhanced proliferation in C4-2 cells, and this effect was abolished by co-knockdown of BRD2/3/4 proteins (FIGS. 6a-g). Consistent with a previous report (Asangani et al., Nature, 510:278-282 (2014)), the BET inhibitor JQ1 robustly inhibited prostate cancer cell growth, but this effect was largely attenuated in SPOP-knockdown cells (FIGS. 6a-c). SPOP depletion-mediated JQ1 resistance was reversed by knockdown of BRD4 alone (FIGS. 6h-j). However, BRD4 knockout cells became highly resistant to JQ1 when BRD2/3 were largely depleted (FIGS. 6k and 6l). These results are not surprising since little or no druggable targets (BRD2/3/4 proteins) were present in these cells. These data suggest that protein levels of BRD2/3/4 may represent a molecular determinant for JQ1 sensitivity in SPOP-deficient prostate cancer cells.

Figure 6N:
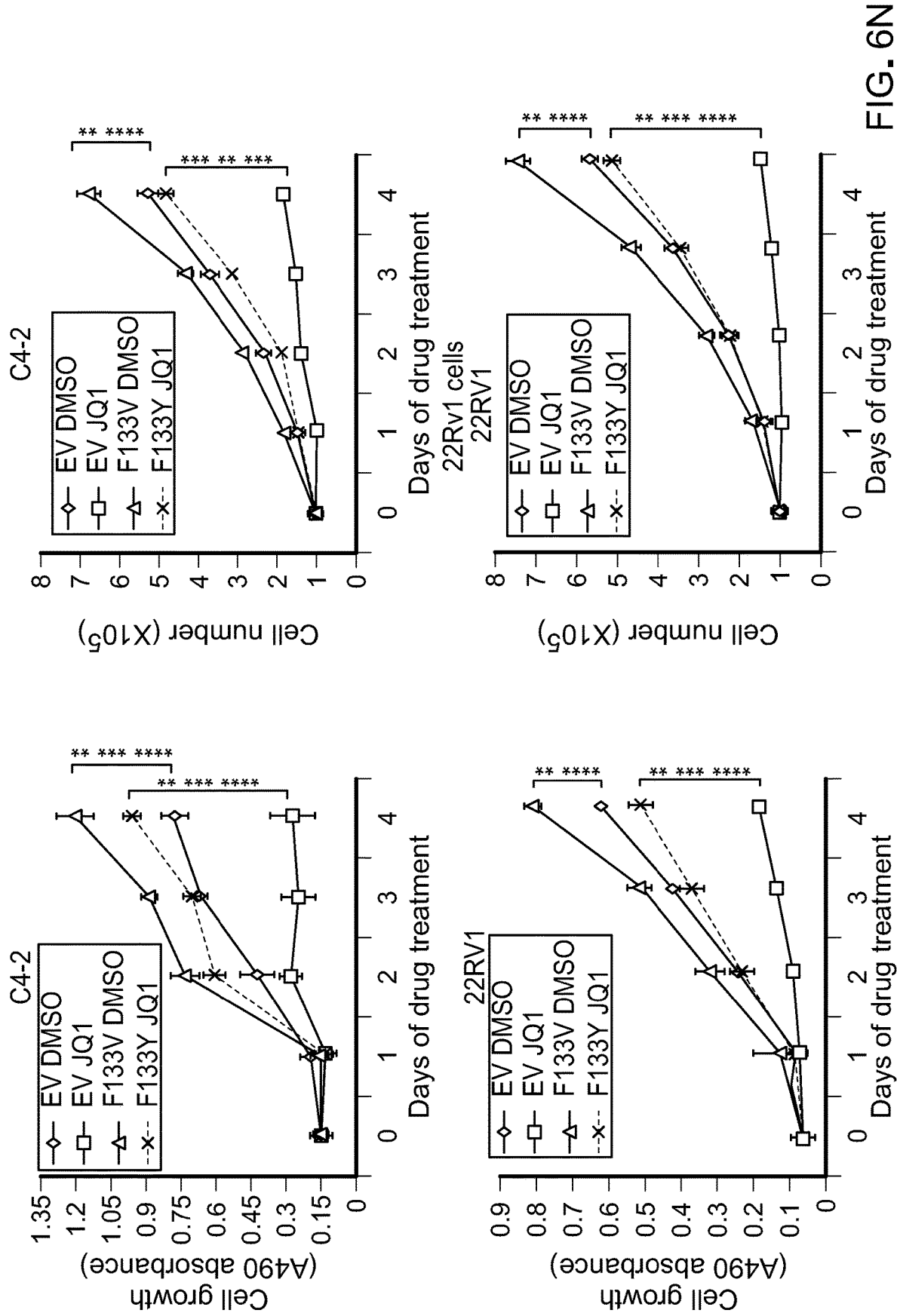
FIG. 6N, C4-2 (top panels) and 22Rv1 (bottom panels) cells were infected with lentivirus as in (FIG. 6M) and then treated with or without JQ1 (0.25 μM) every other day. Cell growth was measured by cell proliferation assay (left panels) and trypan blue assay (right panels). Data are shown as means±SD (n=6 biological replicates).
Figure 6P:
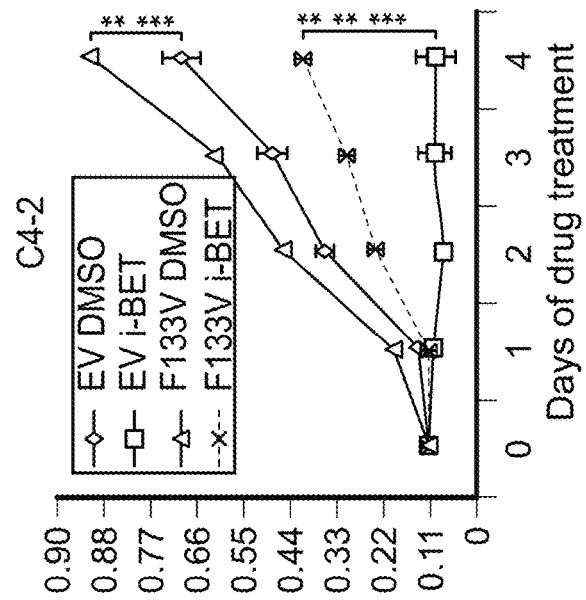
FIG. 6P, C4-2 cell infected with lentivirus as in (FIG. 6O) were treated with vehicle (DMSO) or i-BET762 (i-BET, 0.5 μM) every other day, and cell growth were measured by trypan blue assay at indicated time points. Data are shown as means±SD (n=6 biological replicates).
Figure 6O:
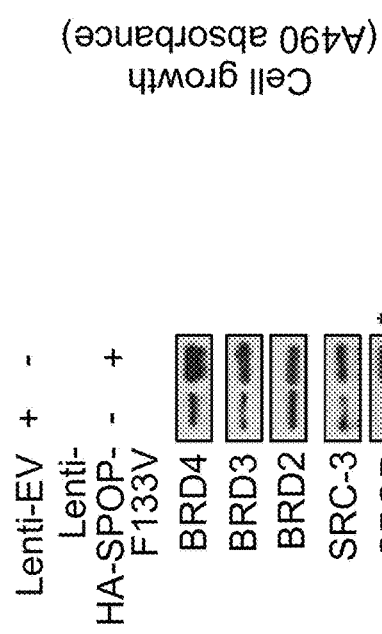
FIG. 6O, Western blot of indicated proteins in WCL of C4-2 cells infected with indicated lentivirus for 48 hours.
Figure 6Q:
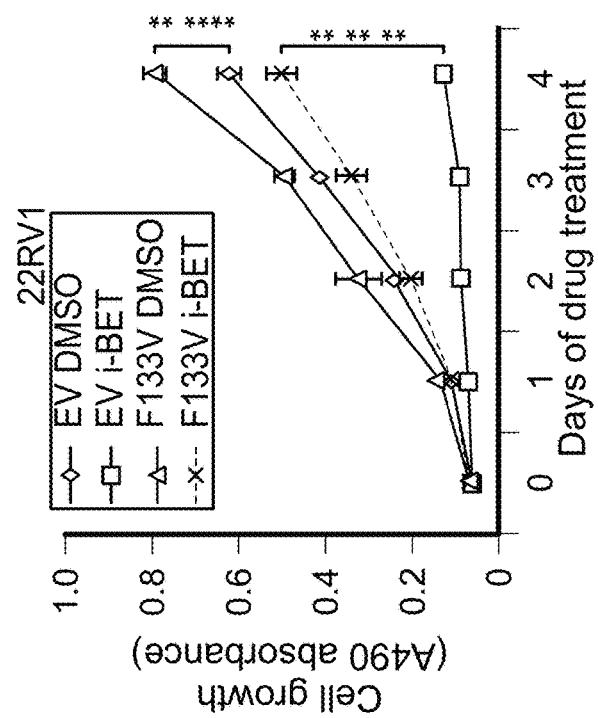
Figure 7B:
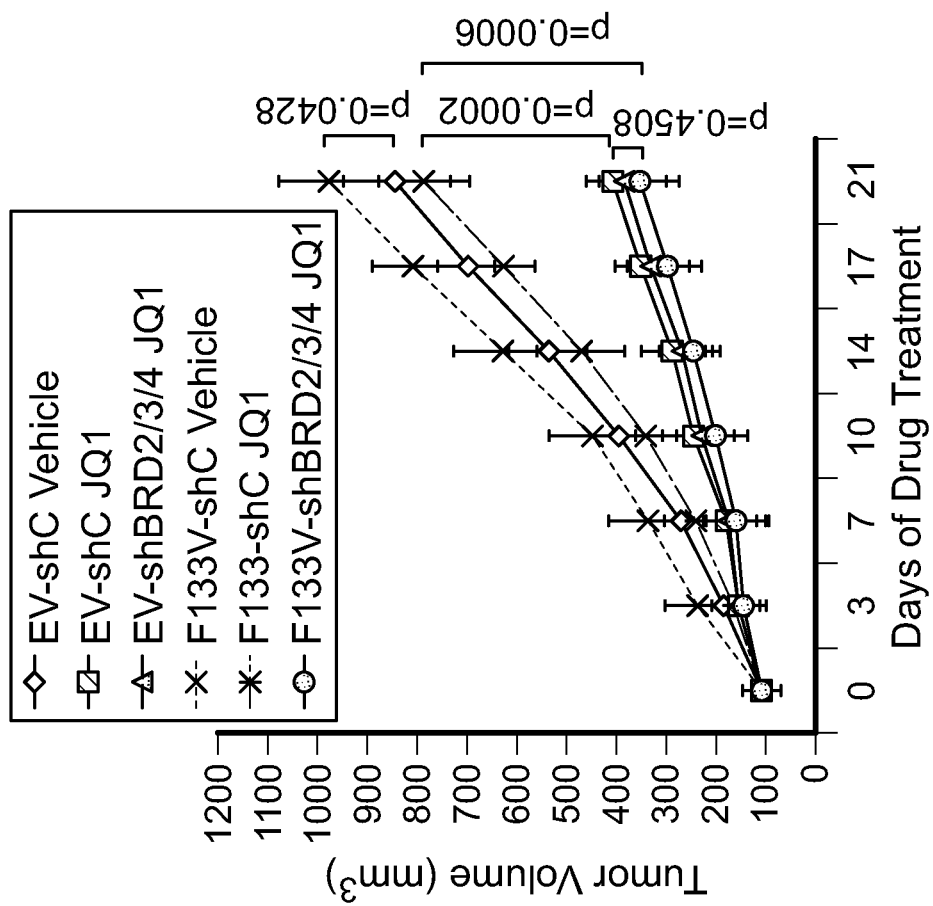
Figure 7A:
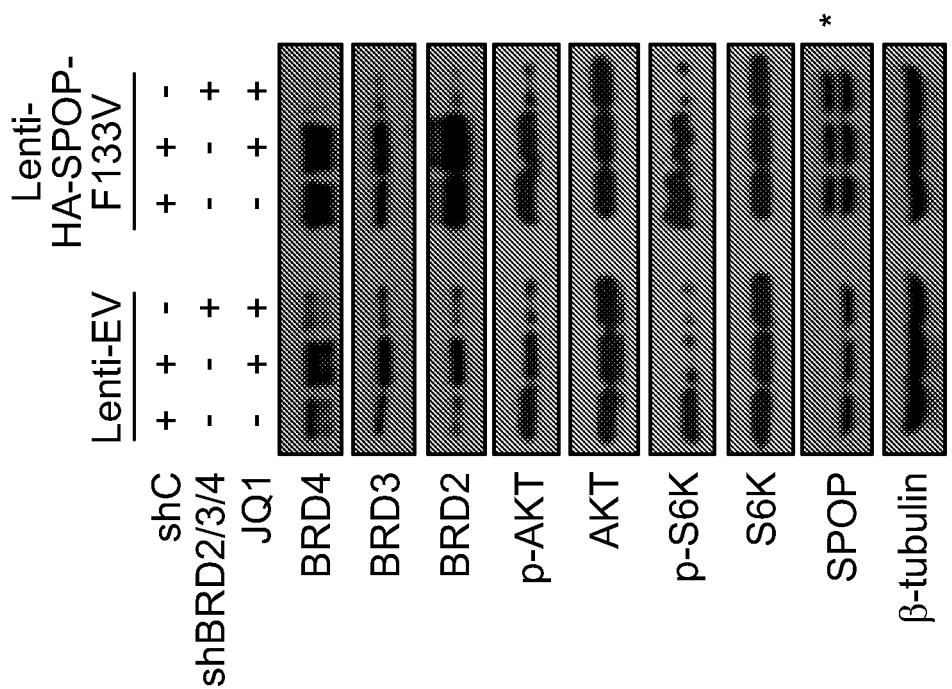
Figure 7D:
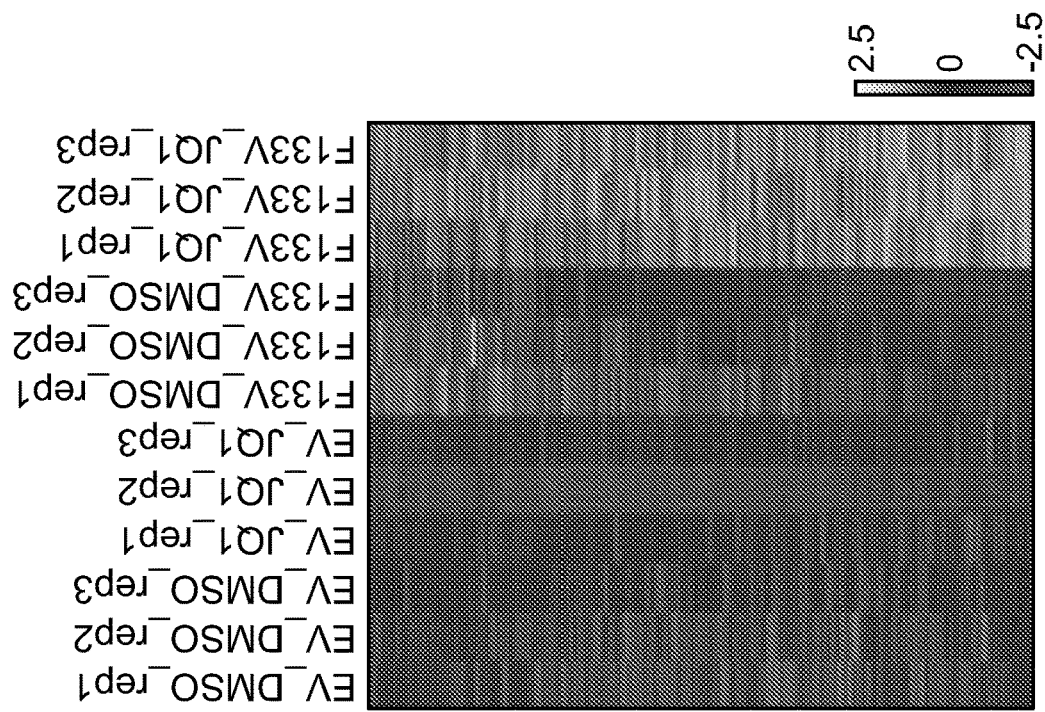
Figure 7C:
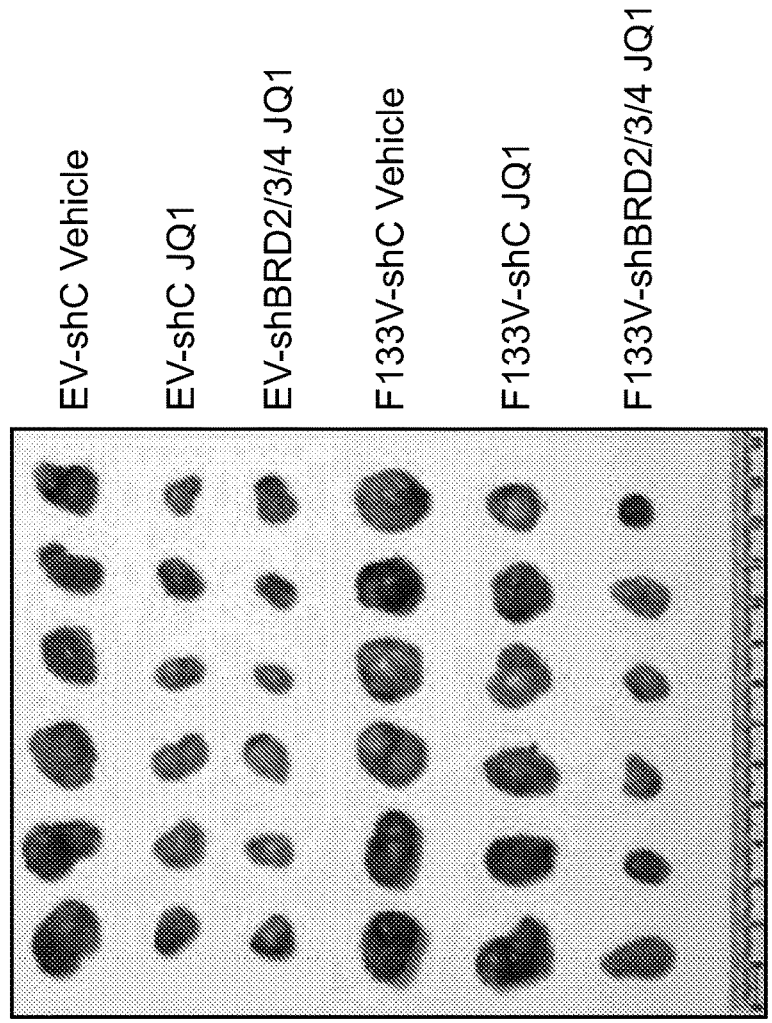
Figure 8A:
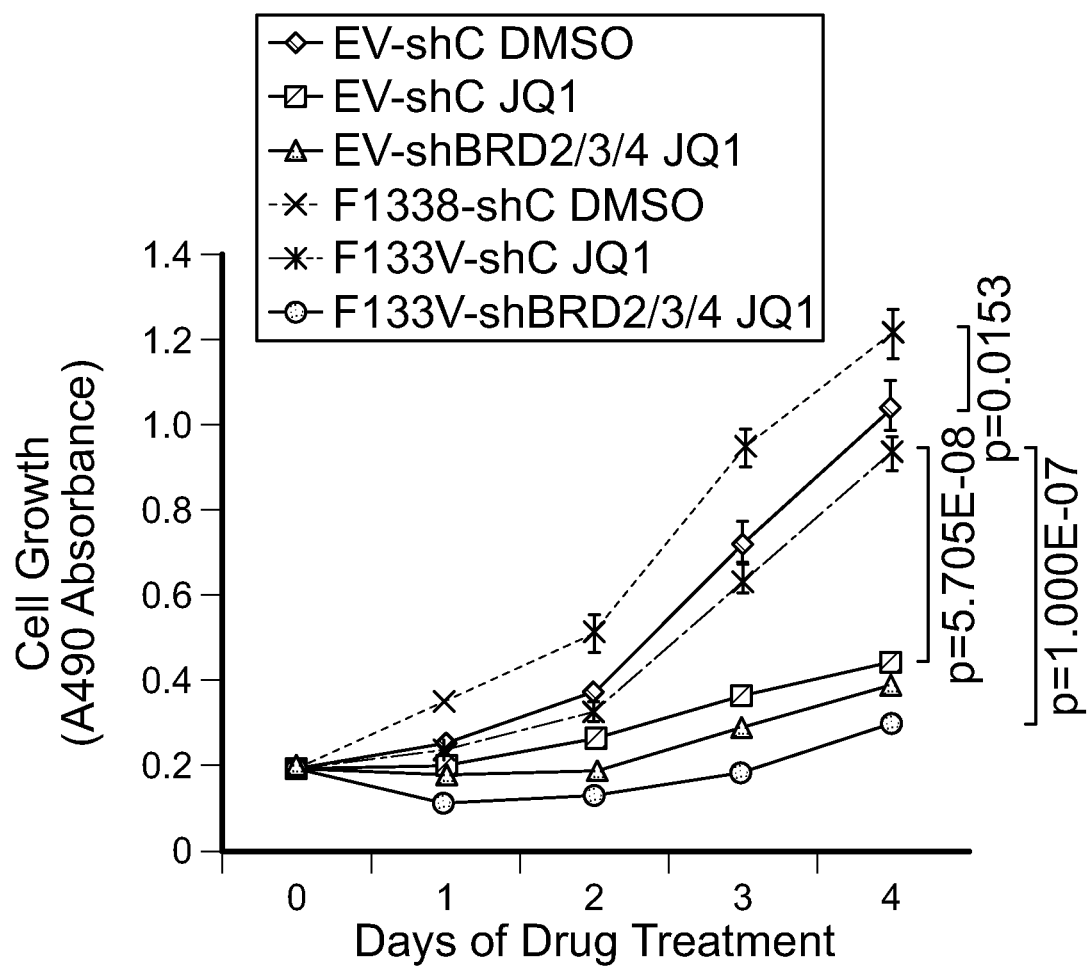
FIGS. 8A-8F. SPOP mutated prostate cancer cells in culture and xenograft tumors in mice and their role in JQ1 resistance in SPOP-mutated cells.
Figure 8B:
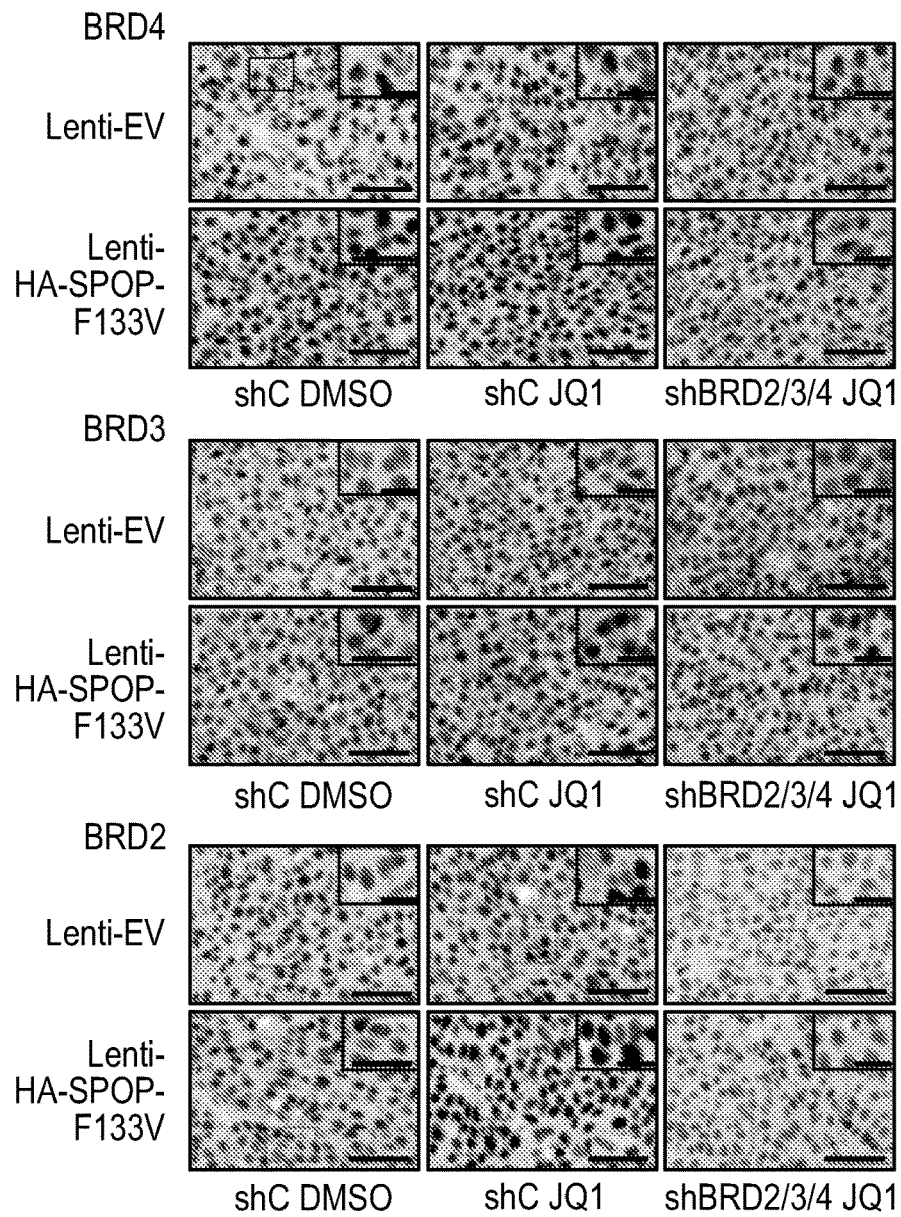
Figure 8C:
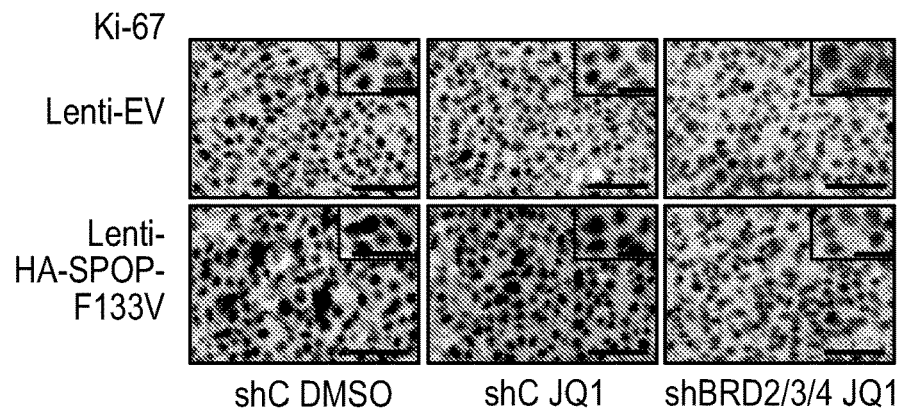
Figures 8D, 8E:
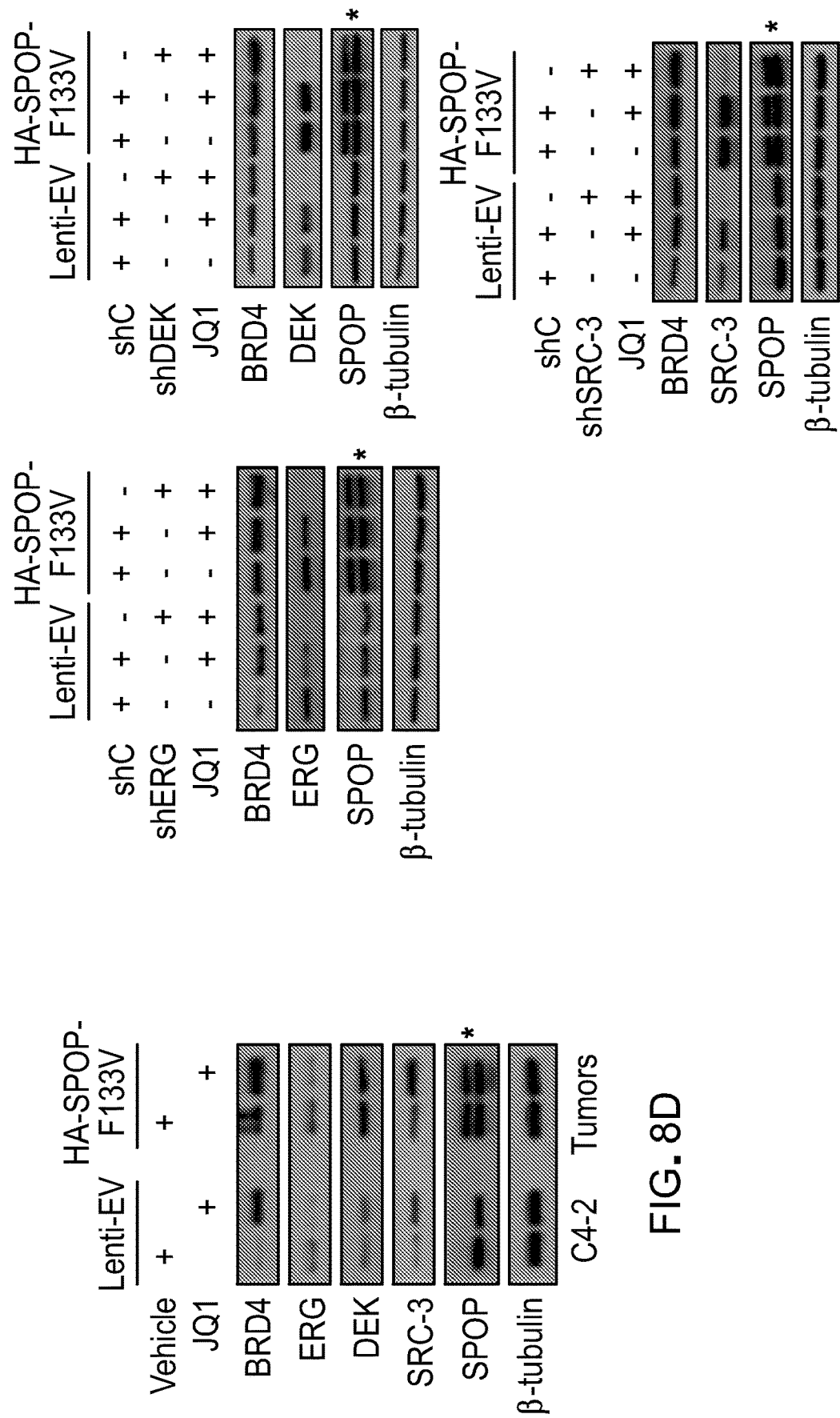
Figure 8F:
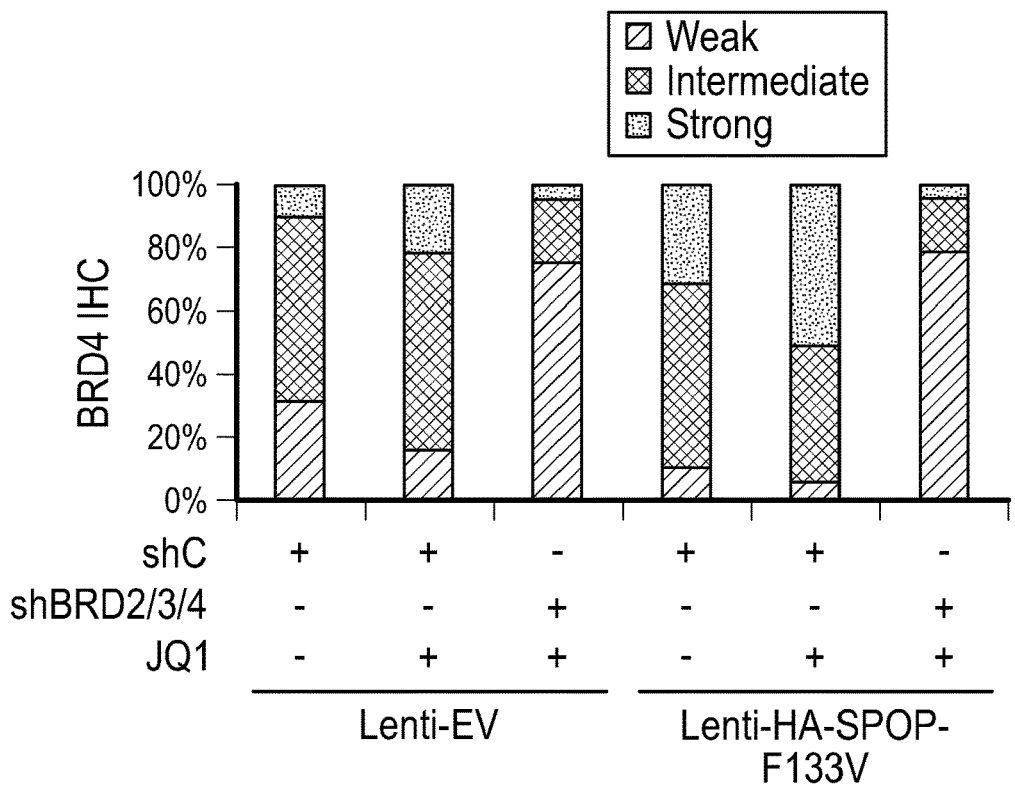
Figure 8F:
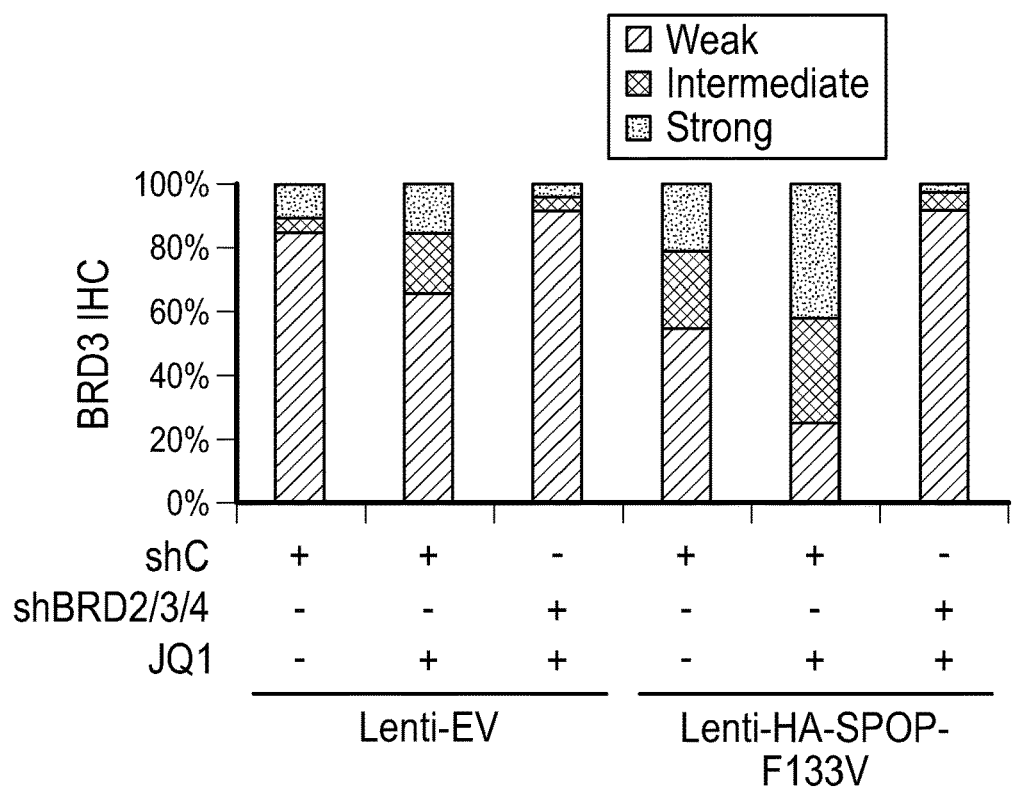
Figure 8F:
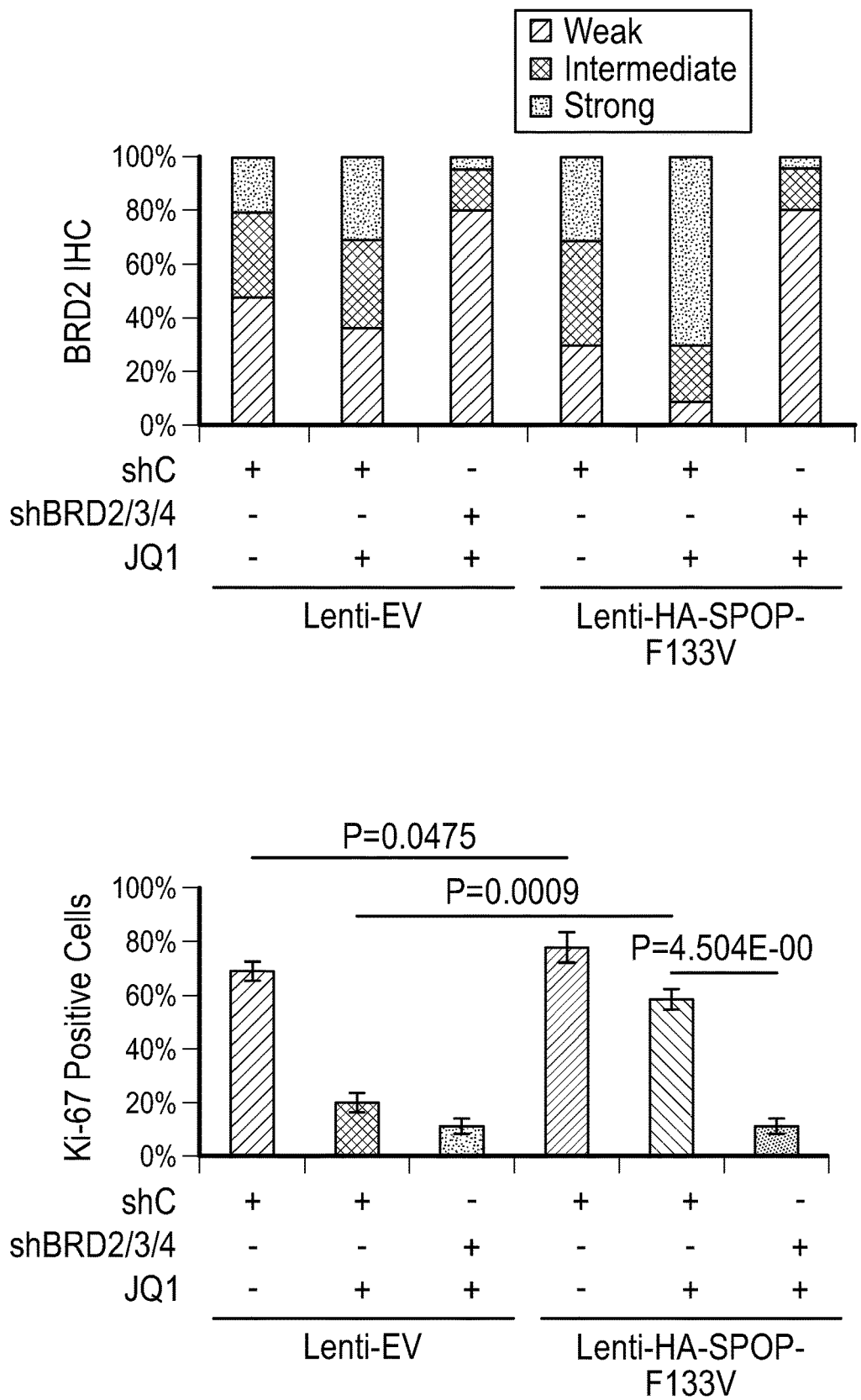
Figure 8F:
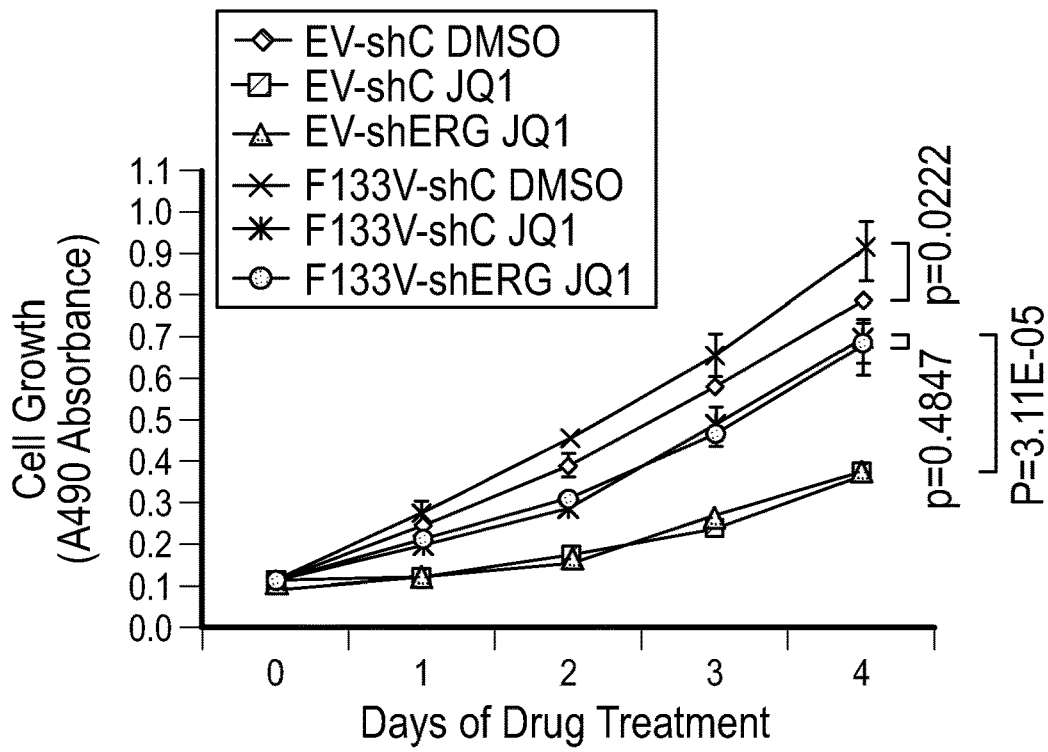
Figure 8F:
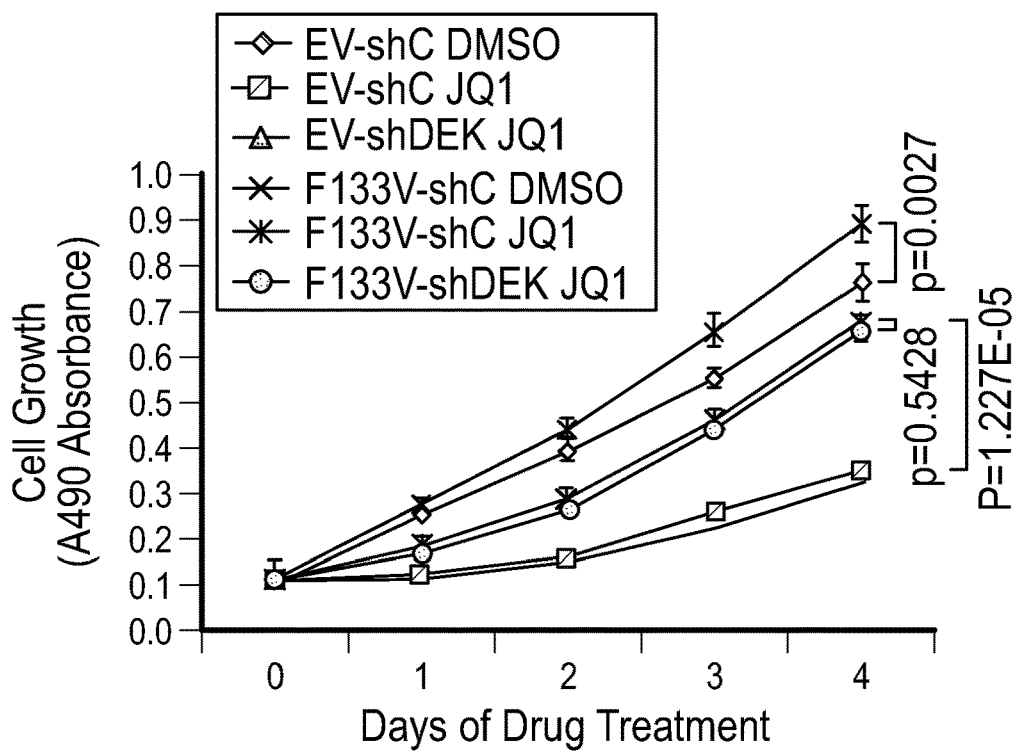
Figure 8F:
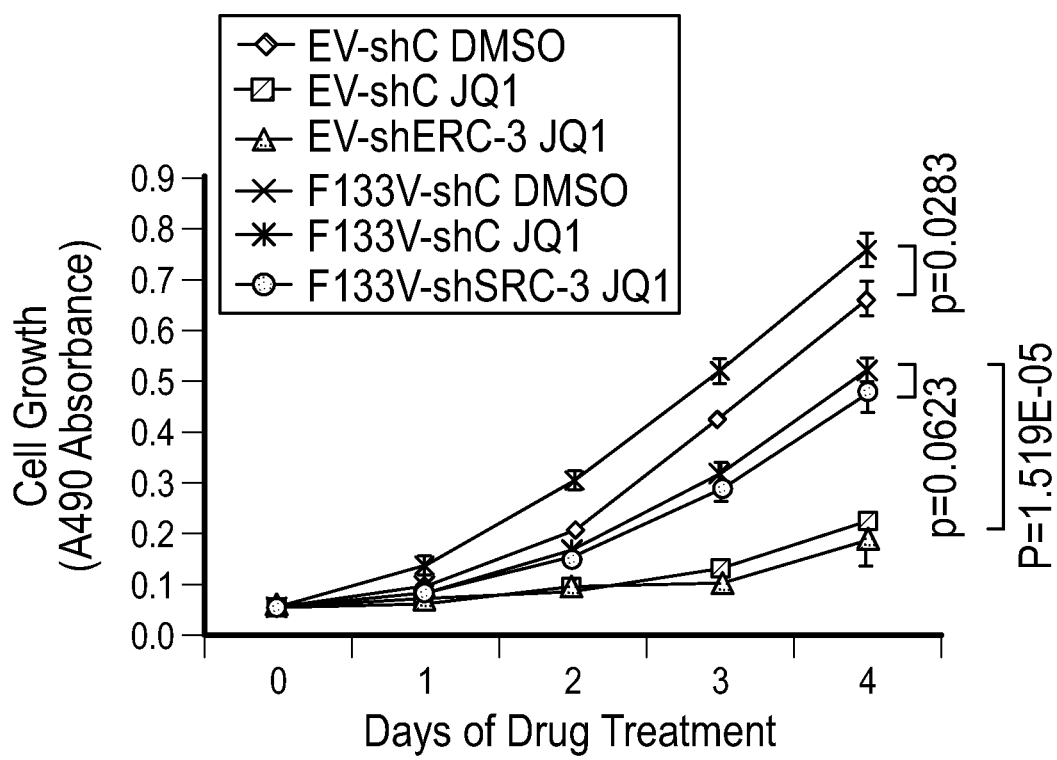

Phenylalanine 133 (F133) is the most frequently mutated residue in SPOP (Barbieri et al., Nat. Genet., 44:685-689 (2012)). To recapitulate the situation in patients, SPOP-F133V mutant was introduced into SPOP-WT-expressing C4-2 and 22Rv1 cells. Expression of SPOP-F133V not only induced accumulation of BRD2/3/4 proteins, but also caused a significant increase in proliferation in both cell lines (FIGS. 6m and 6n). While JQ1 treatment inhibited growth of empty vector (EV)-expressing C4-2 and 22Rv1 cells, the effect of JQ1 was largely impeded in SPOP-F133V-expressing cells (FIG. 6n). SPOP-F133V expression also caused similar resistance to another BET inhibitor (i-BET) in C4-2 and 22Rv1 cells (FIGS. 6o-q). The SPOP-F133V mutant also was shown to confer JQ1-resistance in C4-2 xenograft tumors in mice (FIGS. 7a-c). SPOP-F133V-mediated JQ1-resistance was completely reversed by co-depletion of BRD2/3/4 proteins in C4-2 cells in vitro and in C4-2 xenografts in mice (FIGS. 7a-c and 8a-c). SPOP-F133V expression also induced accumulation of known SPOP substrates ERG, DEK and SRC-3 in C4-2 and 22Rv1 cells and C4-2 tumors in mice (FIGS. 6m and 8d). However, JQ1 treatment largely decreased ERG expression (FIGS. 6m, 8d, and 8e), which was consistent with similar findings in acute myeloid leukemia cells (Roe et al., Mol. Cell, 58:1028-1039 (2015)). Knockdown of ERG by shRNAs had no overt effect on SPOP-F133V-mediated JQ1 resistance in C4-2 cells, and similar results were obtained in DEK-knockdown cells (FIGS. 8e and 8f). SRC-3 knockdown slightly sensitized SPOP-F133V cells to JQ1, but the effect was not statistically significant (FIGS. 8e and 8f). Thus, these results demonstrate that SPOP mutation-conferred BET inhibitor resistance is largely mediated by elevation of BRD2/3/4 proteins in prostate cancer cells.

Figure 9B:
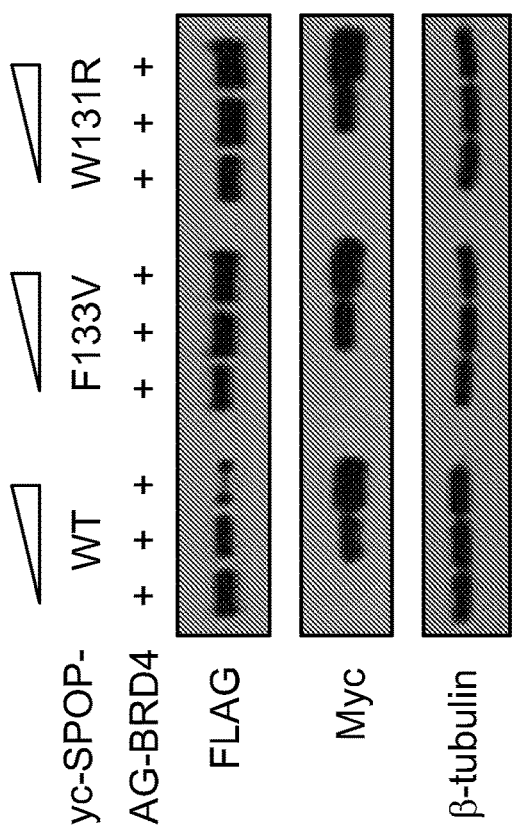
Figure 9A:
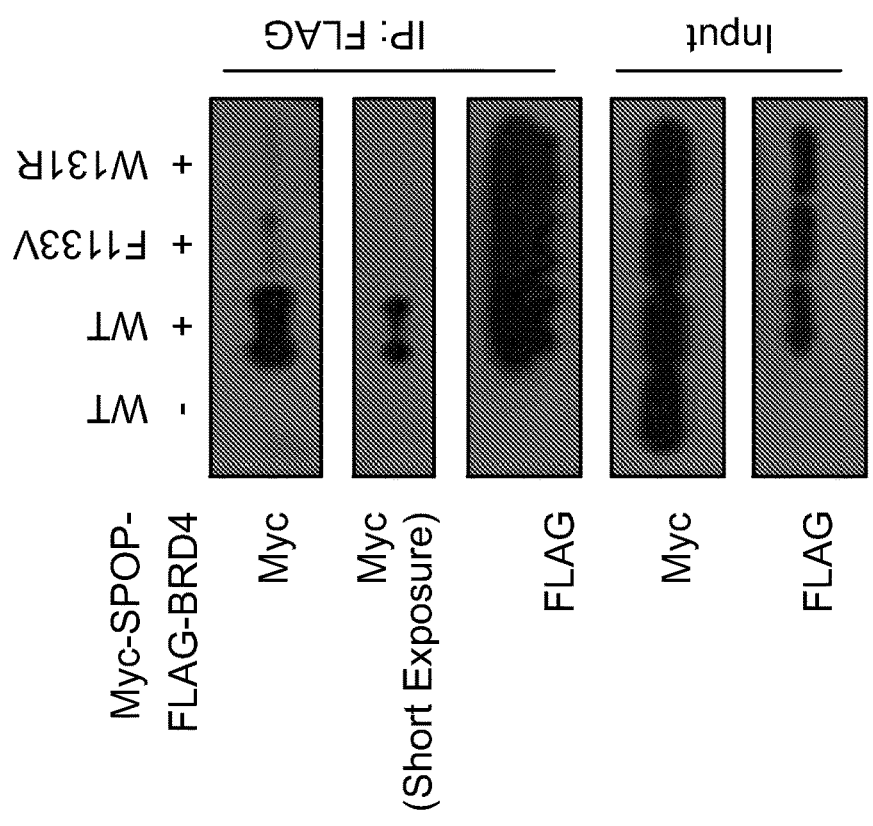
Figure 9G:
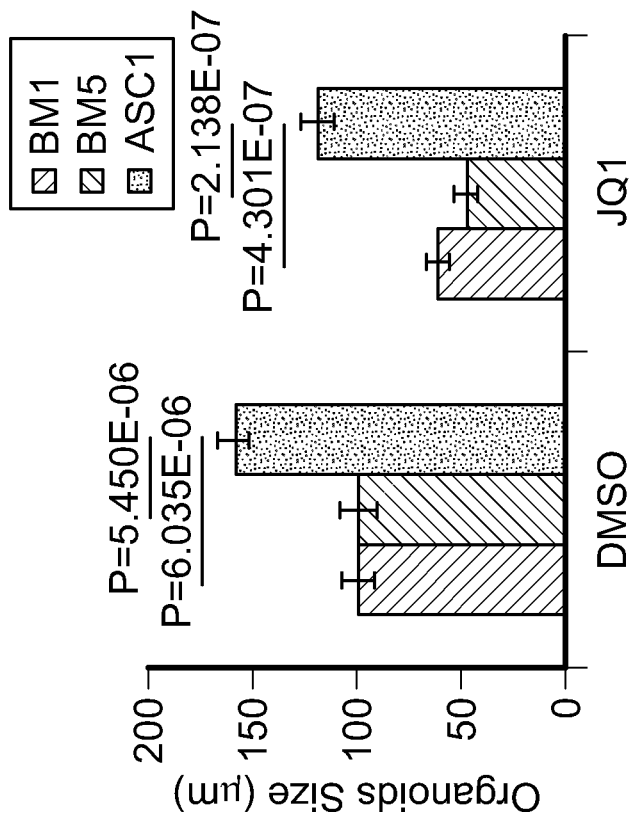
Figure 9F:
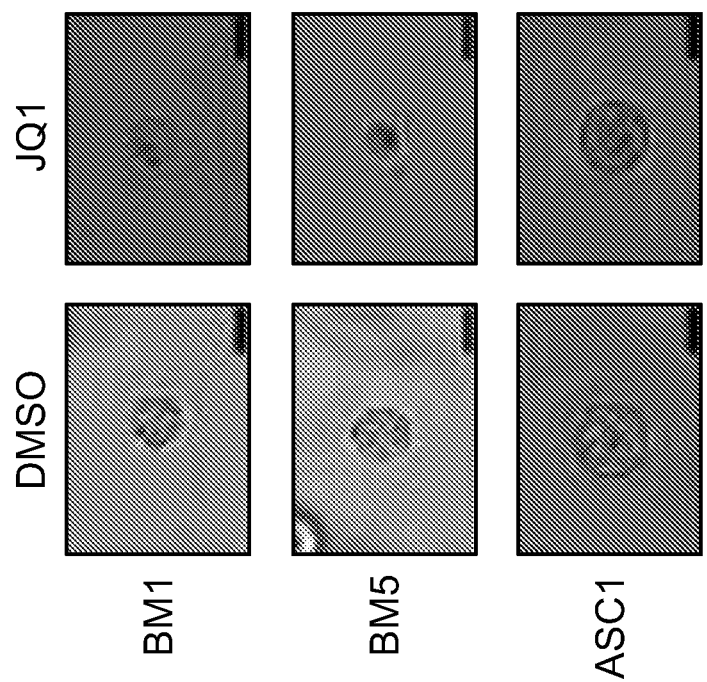
Figure 10A:
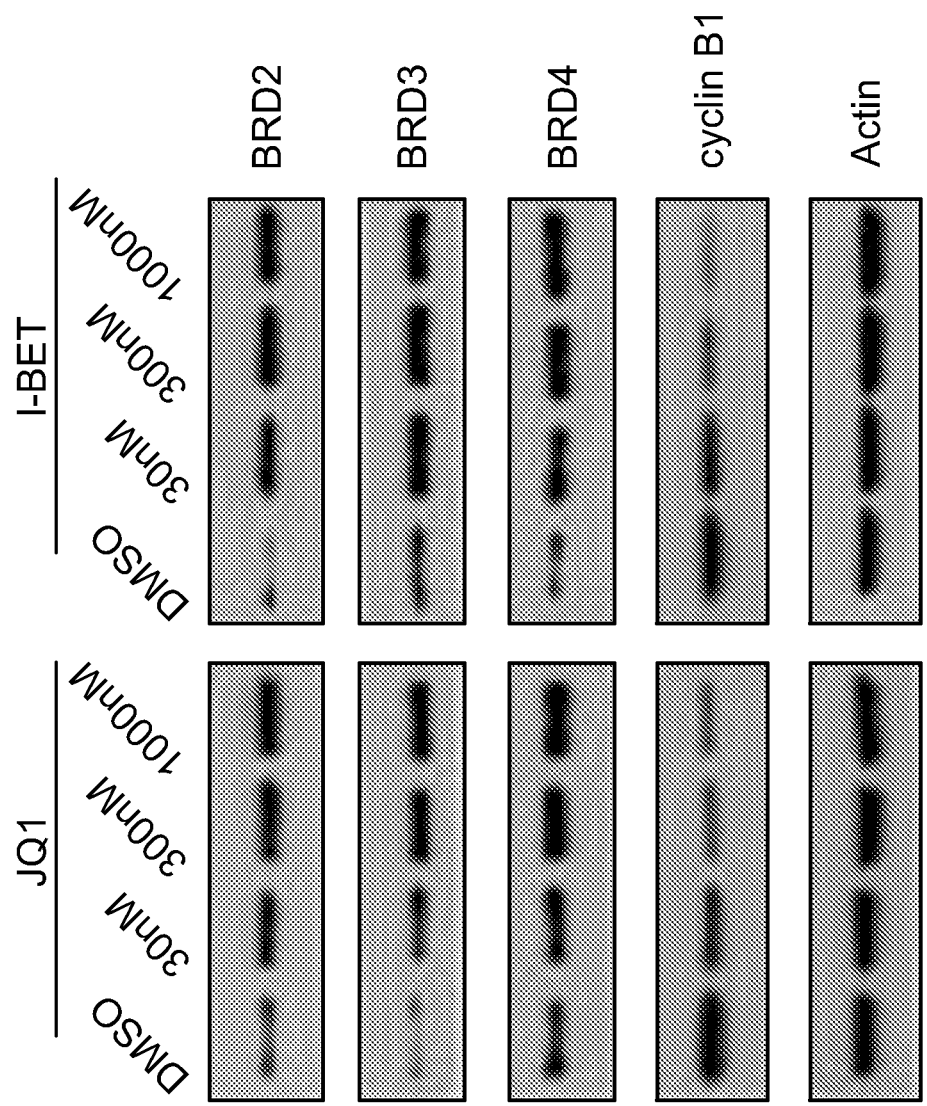
FIGS. 10A-10H. Effects of JQ1 on BRD2/3/4 protein stability, the interaction between SPOP and BRD2/3/4, SPOP mediated ubiquitination and degradation of BRD2/3/
Figure 10B:
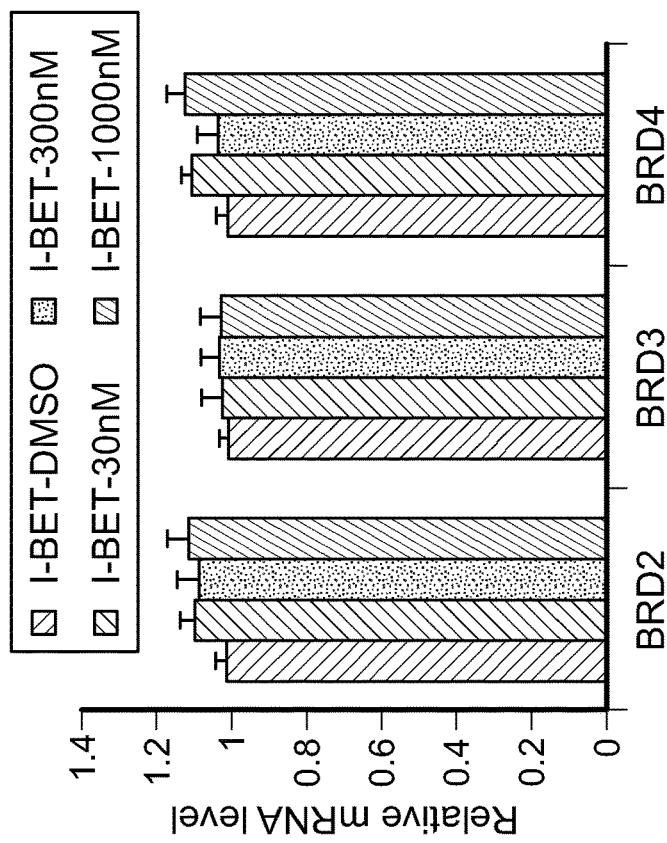
Figure 10B:
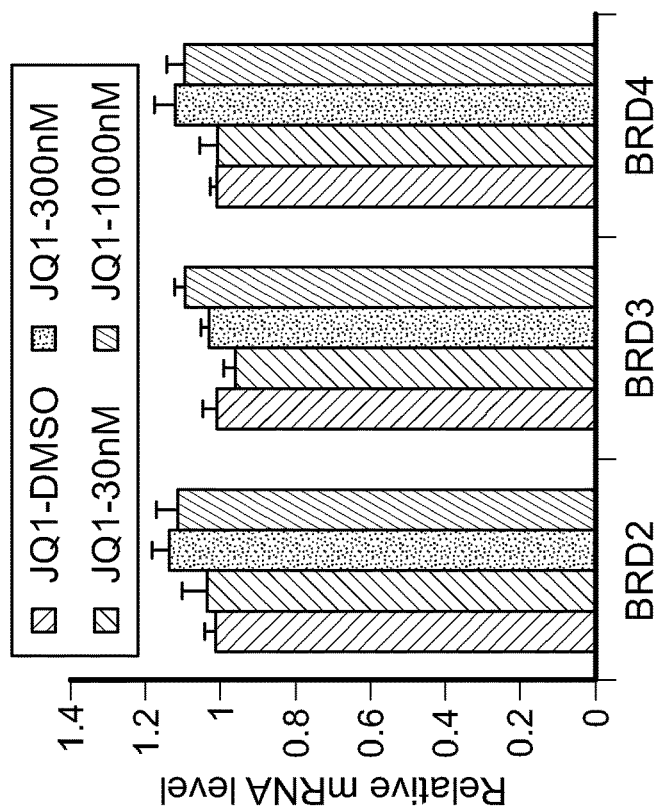
Figure 10C:
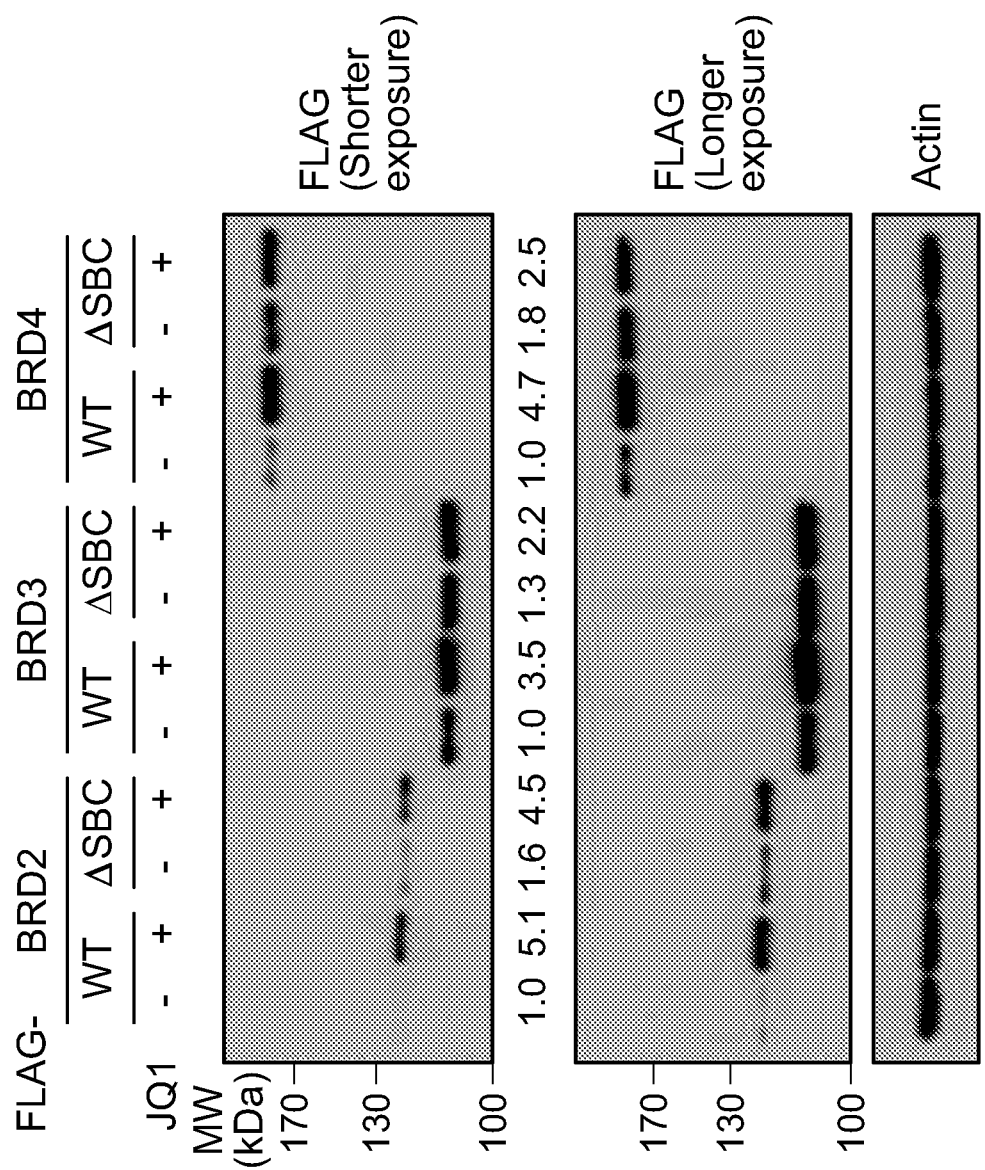
Figure 10C:
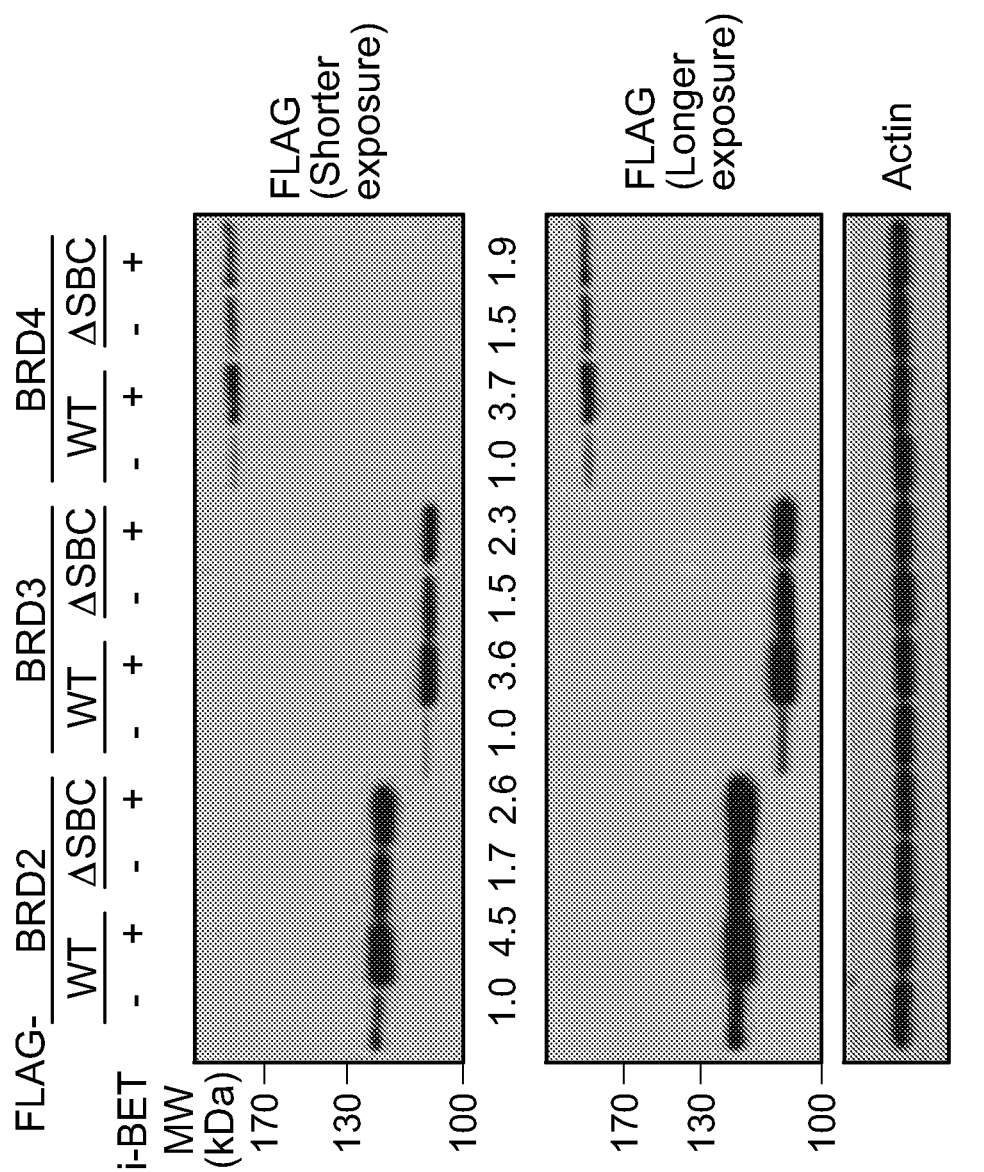
Figure 10D:
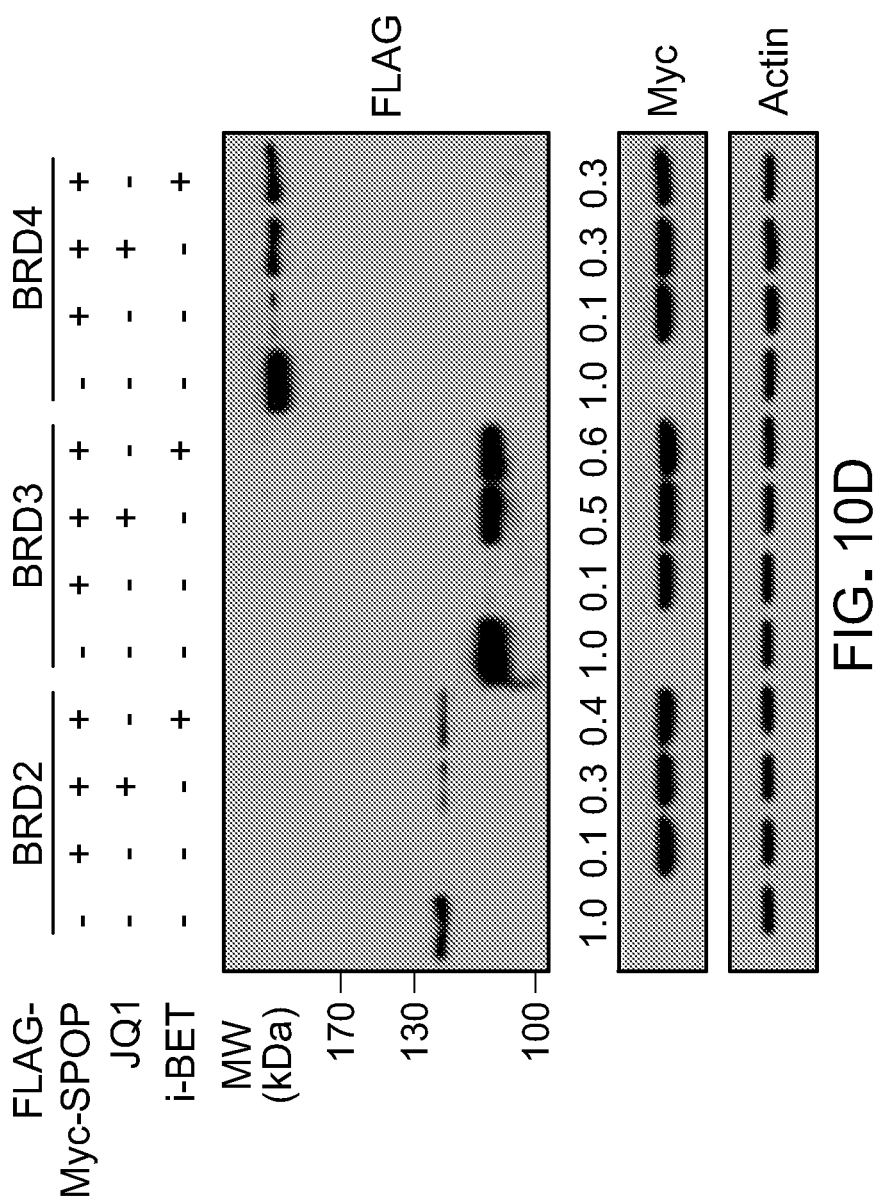
Figures 10E, 10F:
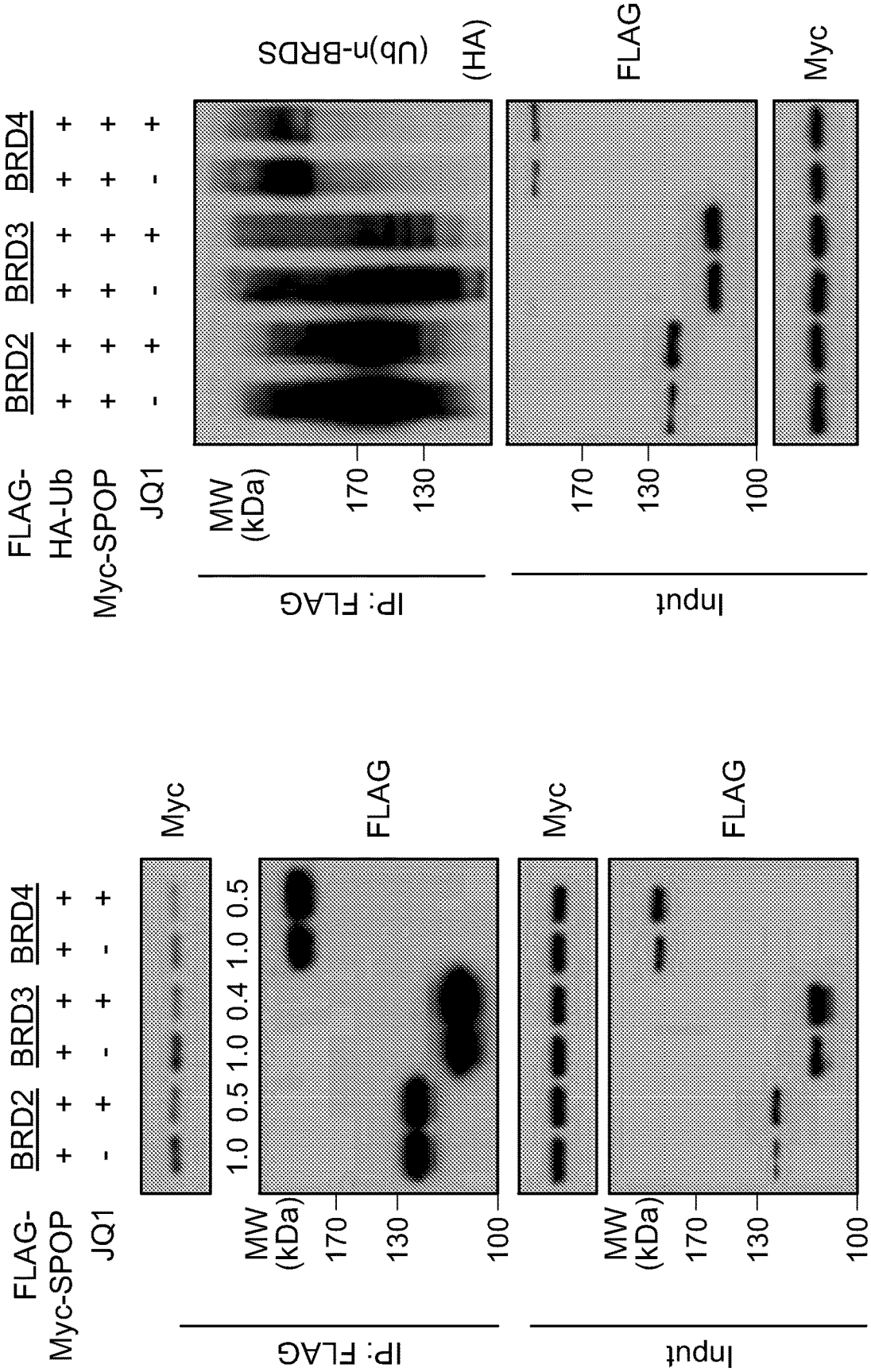
Figure 10G:
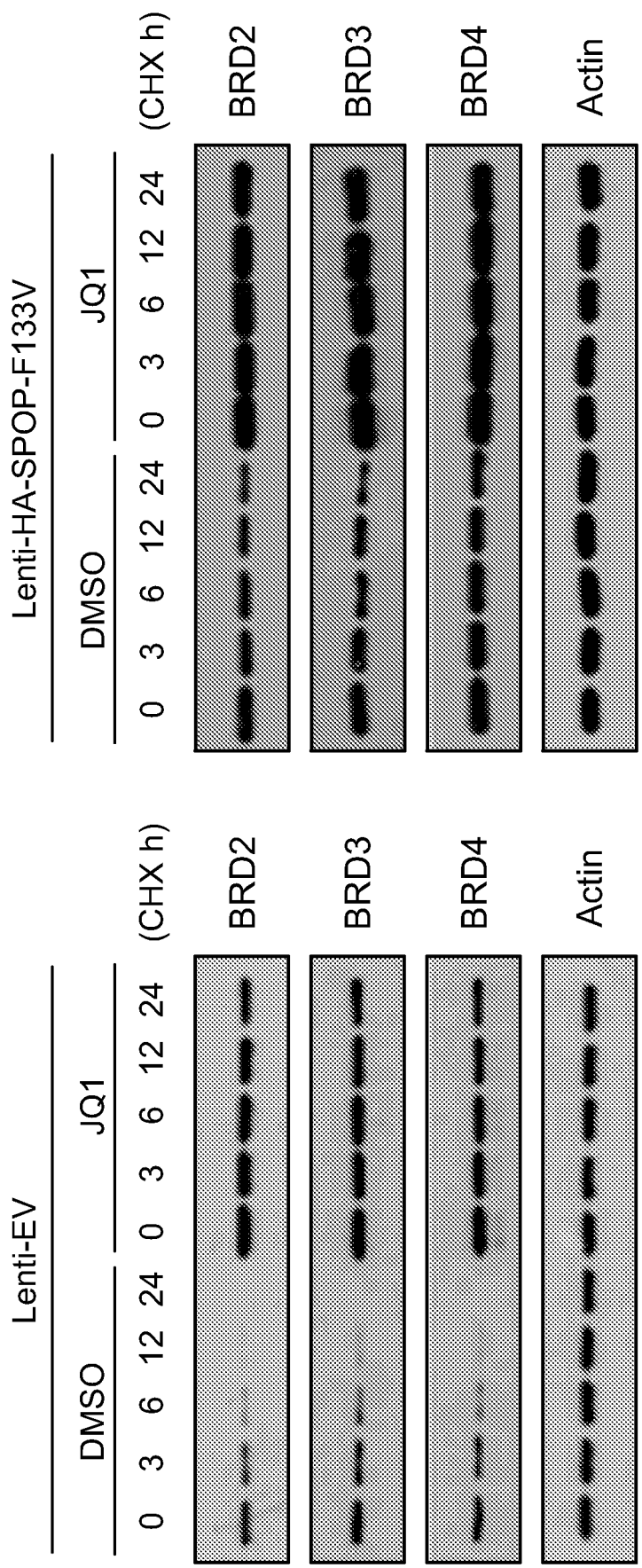
Figure 10H:
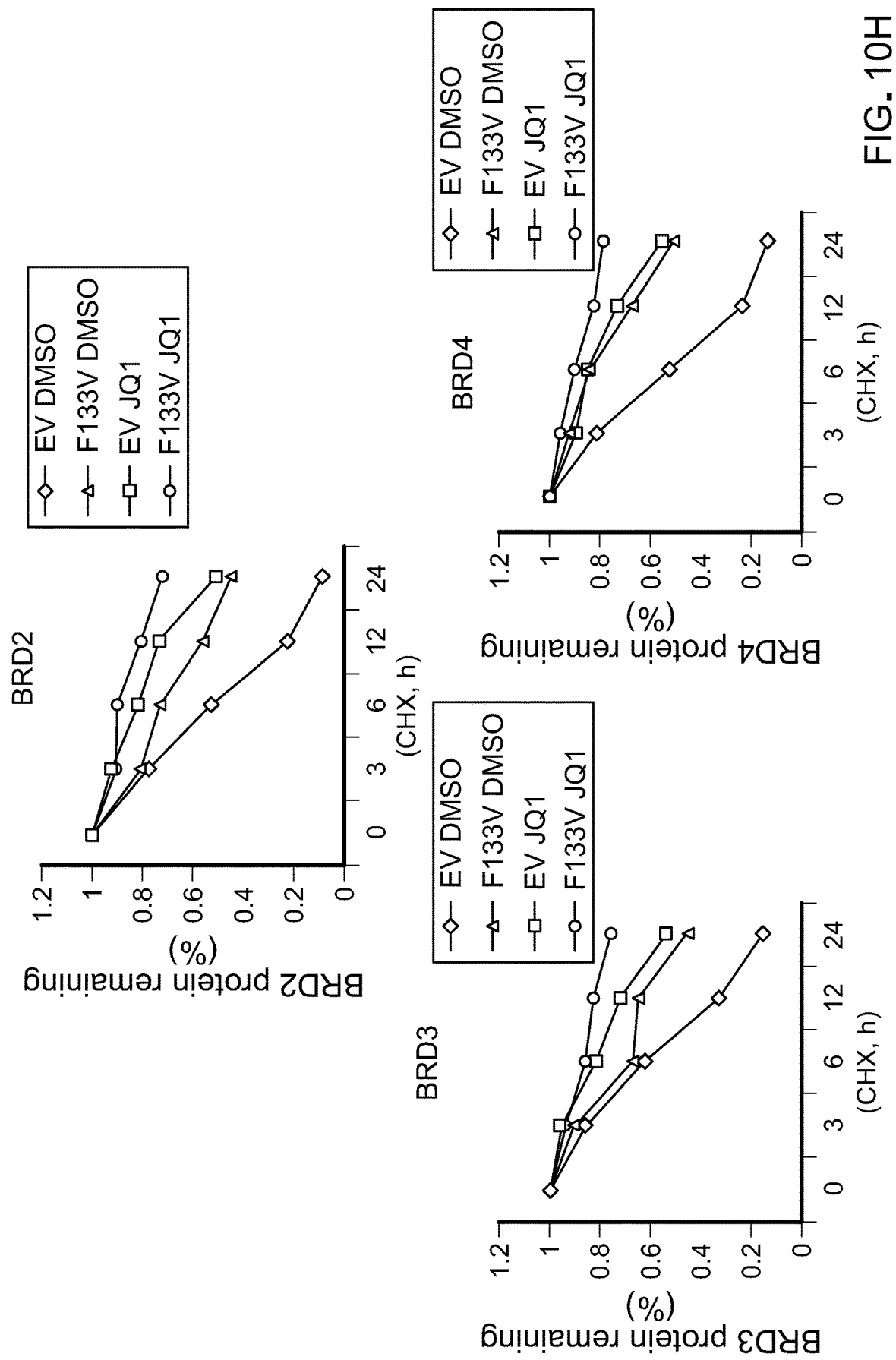

The following was performed to investigate the role of SPOP mutation-induced accumulation of BRD proteins in BET inhibitor resistance in clinically-oriented models. Among three prostate cancer patient-derived organoid lines examined, one harbors a W131R mutation in SPOP. W131 belongs to a conserved residue in the substrate-binding cleft (Barbieri et al., *Nat. Genet.*, 44:685-689 (2012)). W131R mutation was deficient in binding to and mediating ubiquitination and degradation of BRD4 (FIGS. 9a-c). Most importantly, the W131R-expressing organoid expressed more BRD2/3/4 proteins and was resistant to JQ1 compared to two SPOP WT counterparts under both 2D and 3D growth conditions (FIGS. 9d-g). These results indicate that SPOP mutation confers BET inhibitor resistance in patient-derived primary cultures.

It is worth noting that BET inhibitors have been shown to induce BRD4 accumulation in different cell types, but the underlying mechanism was unclear (Asangani et al., *Nature*, 510:278-282 (2014); and Lu et al., *Chem. Biol.*, 22:755-763 (2015)). The effect was shown to occur at post-transcriptional level (FIGS. 6m, 7a, 10a, and 10b). In addition, JQ1 diminished SPOP-BRD2/3/4 protein interaction, partially blocked SPOP-induced BRD2/3/4 ubiquitination and degradation, and prolonged protein half-life even in SPOP-F133V-expressing cells (FIGS. 10c-h). Thus, while inhibiting their activities, BET inhibitors undesirably disturb BET protein proteolysis, and this effect appears to be mediated by SPOP-dependent and -independent mechanisms.

Figure 11A:
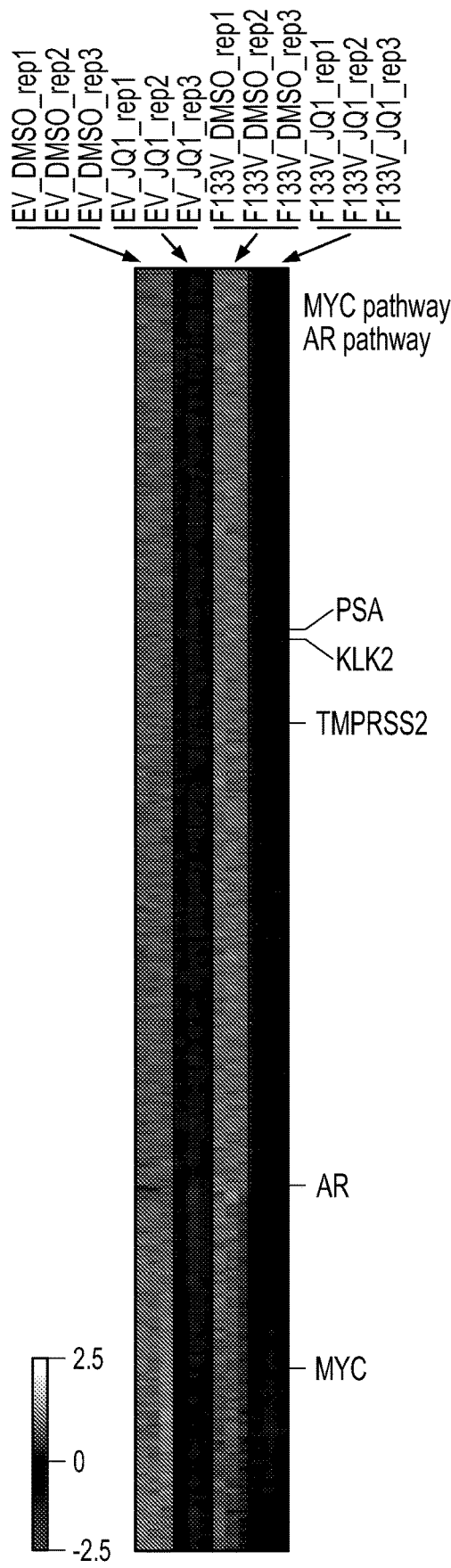
FIGS. 11A-11H. Effect of JQ1 on the MYC and AR signaling pathways in both SPOP wildtype and mutant-expressing prostate cancer cells.
Figure 11B:
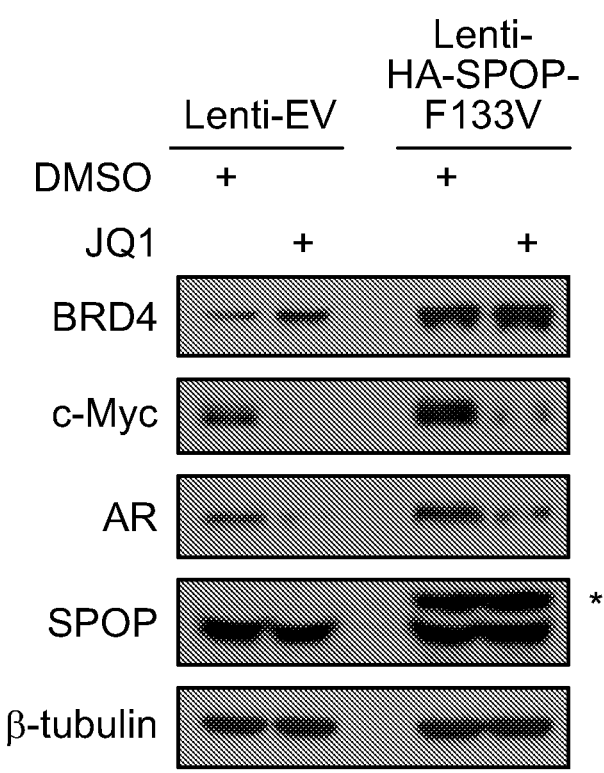
Figure 11C:
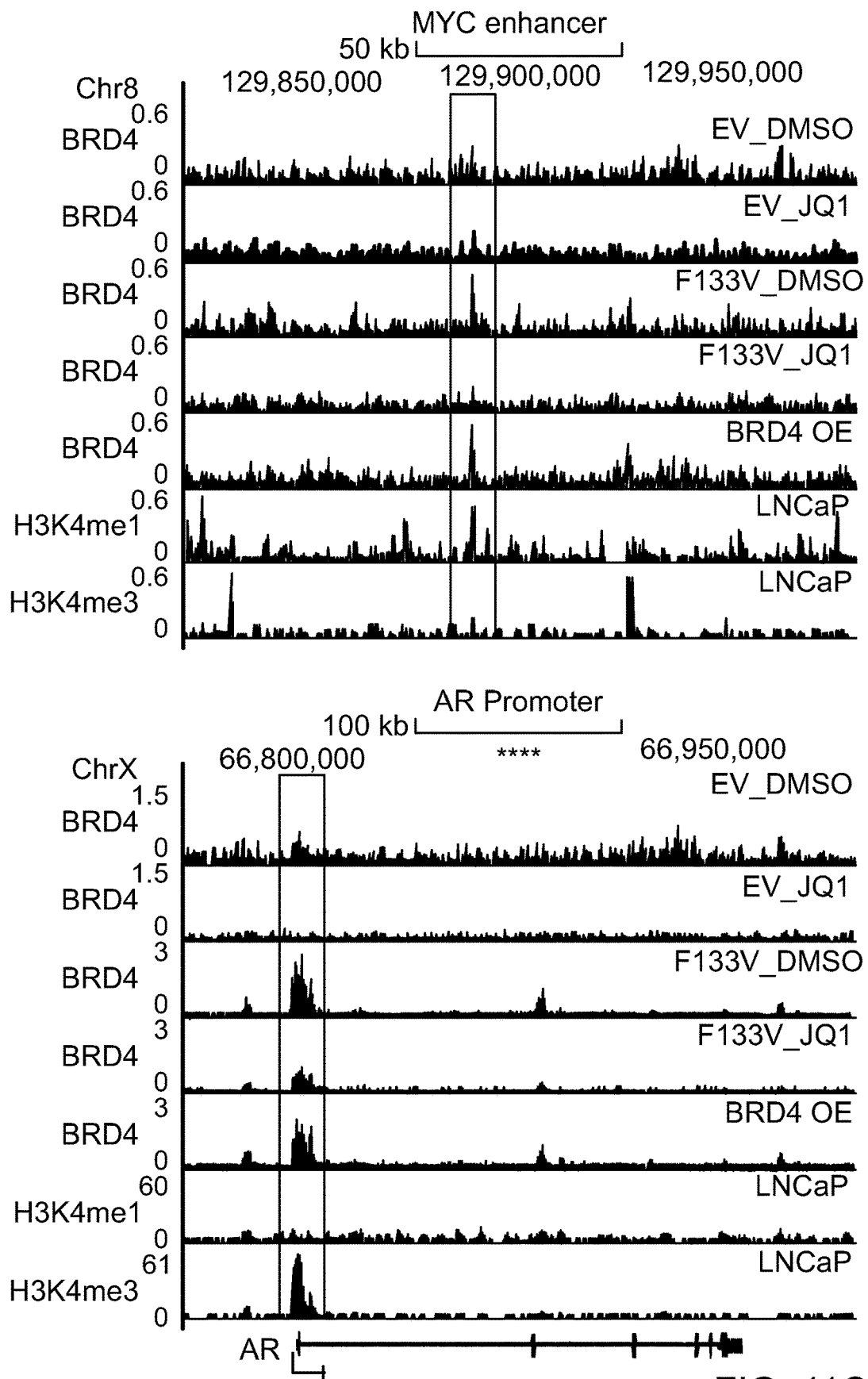
Figure 11D:
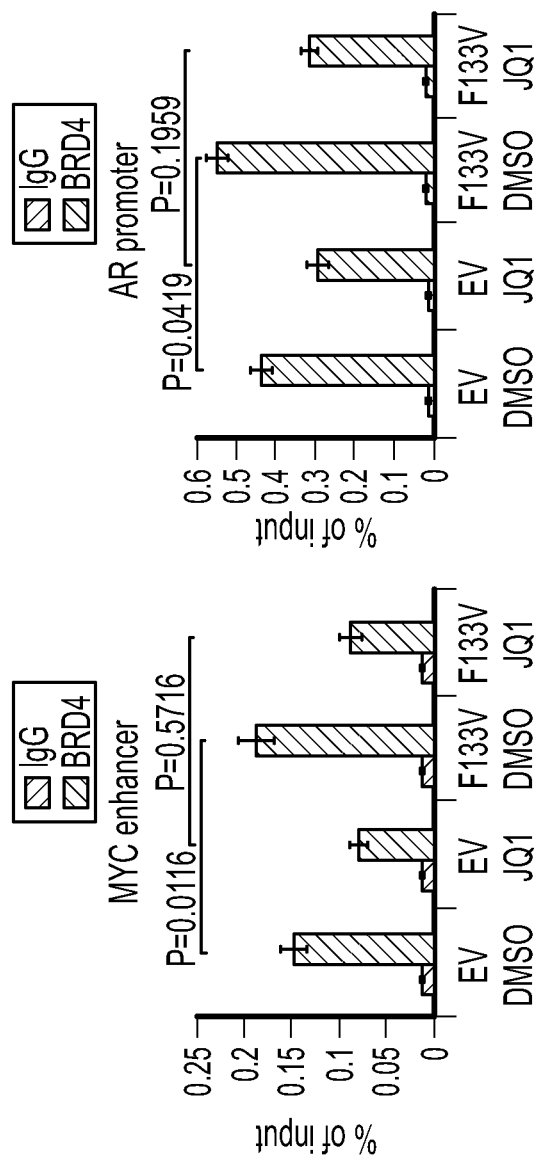
Figure 11E:
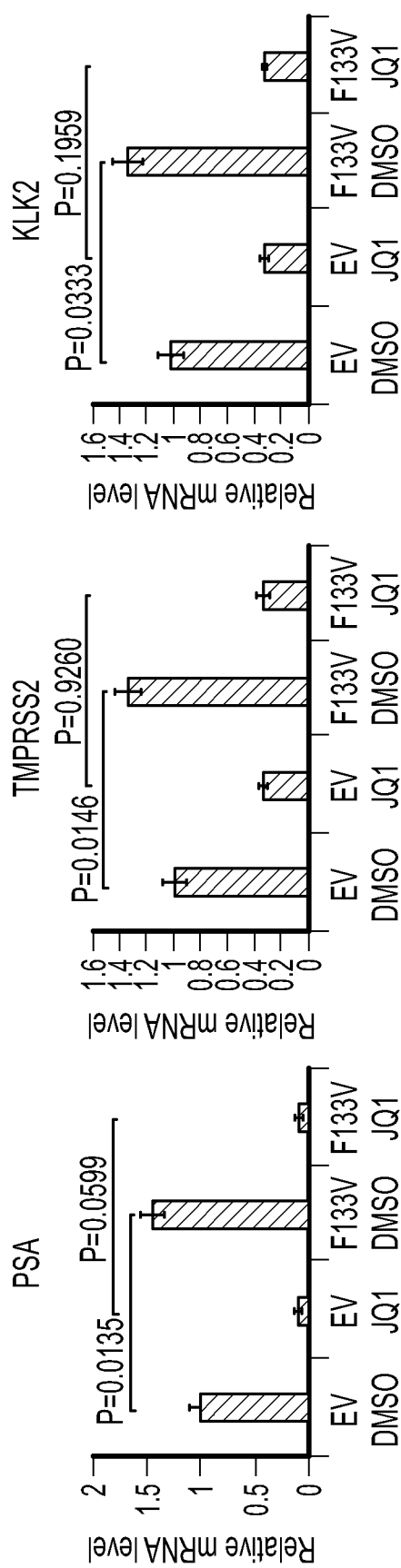
Figure 11F:
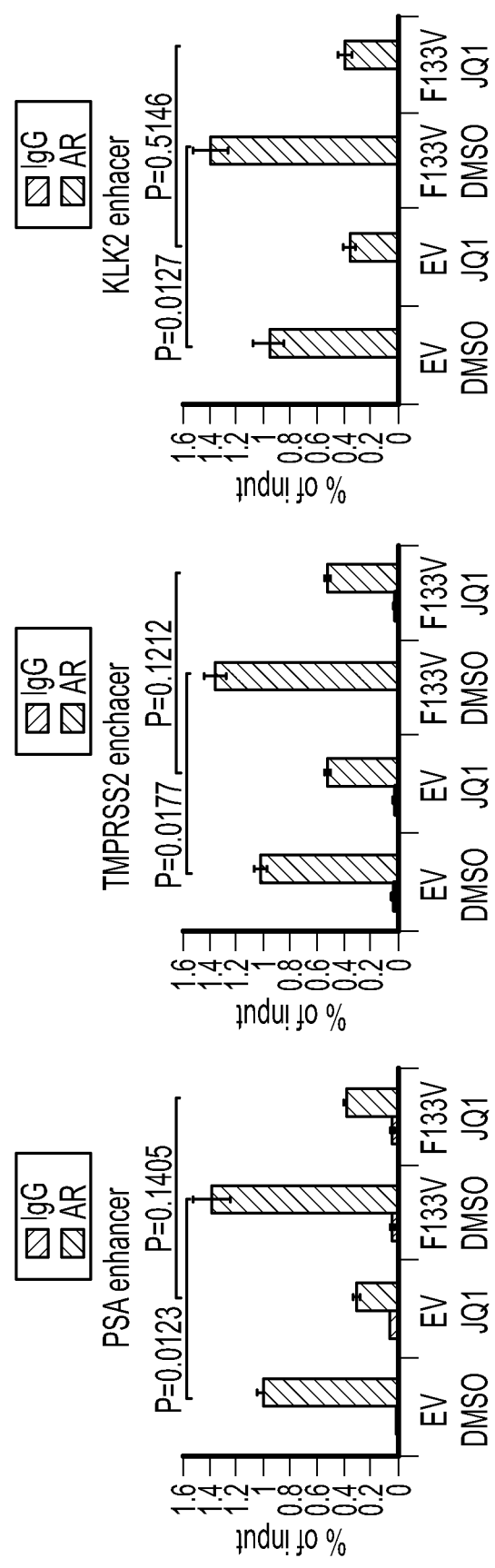
Figure 11H:
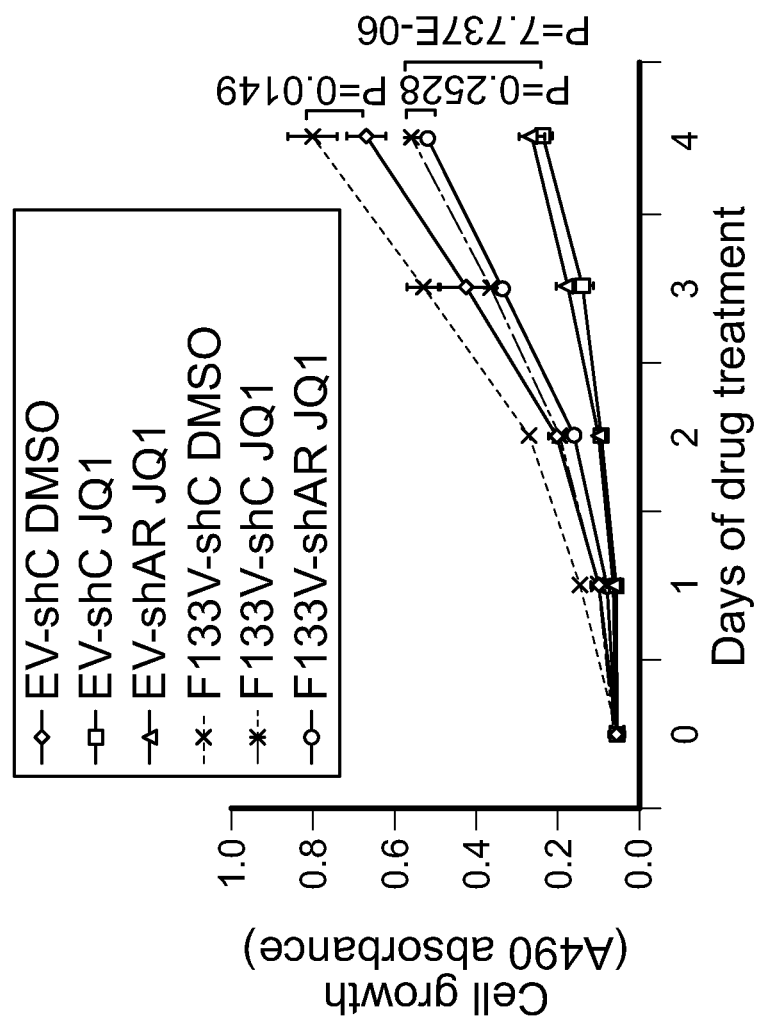
Figure 11G:
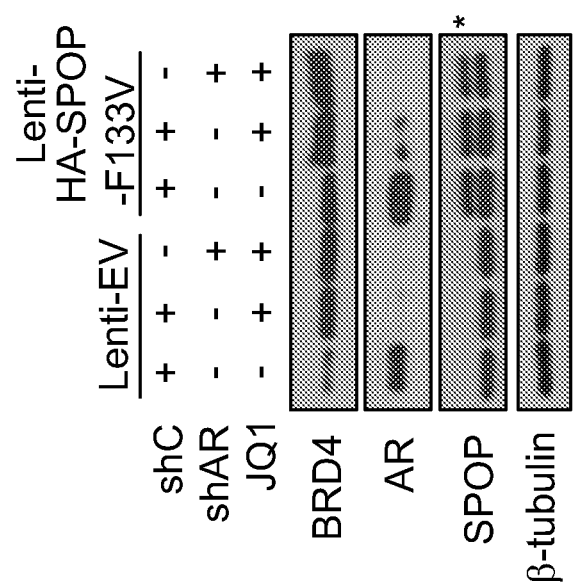

To define the signaling pathways that mediate BET inhibitor resistance in SPOP-mutated cells, transcriptome analysis was performed in control (EV) and SPOP-F133V-expressing C4-2 cells treated with or without JQ1. Through unsupervised cluster analysis, 5,079 JQ1-downregulated genes were identified in both control and SPOP-F133V cells, including MYC and AR, two known targets of BET inhibitors (Delmore et al., *Cell*, 146:904-917 (2011); Zuber et al., *Nature*, 478:524-528 (2011); and Asangani et al., *Nature*, 510:278-282 (2014)) (FIG. 11a). Previous studies suggest that MYC may not be the major anti-cancer target of JQ1 in prostate cancer cells (Asangani et al., *Nature*, 510:278-282 (2014)). In agreement with this report, JQ1 treatment markedly decreased MYC protein expression, which is consistent with substantial reduction of BRD4 binding in the MYC gene enhancer in both JQ1-sensitive (control) and -resistant (SPOP-F133V) C4-2 cells (FIGS. 11b-d). JQ1 also largely decreased AR protein level, BRD4 binding in the AR gene promoter, and AR transcriptional activity in both control and SPOP-F133V cells (FIGS. 11b-f), and further knockdown of AR by shRNAs did not affect JQ1 sensitivity in these cells (FIGS. 11g and 11h). Collectively, these results demonstrate that BET inhibitor resistance in SPOP-mutated prostate cancer cells is likely mediated by MYC- and AR-independent pathways.

Figures 7E, 7F:
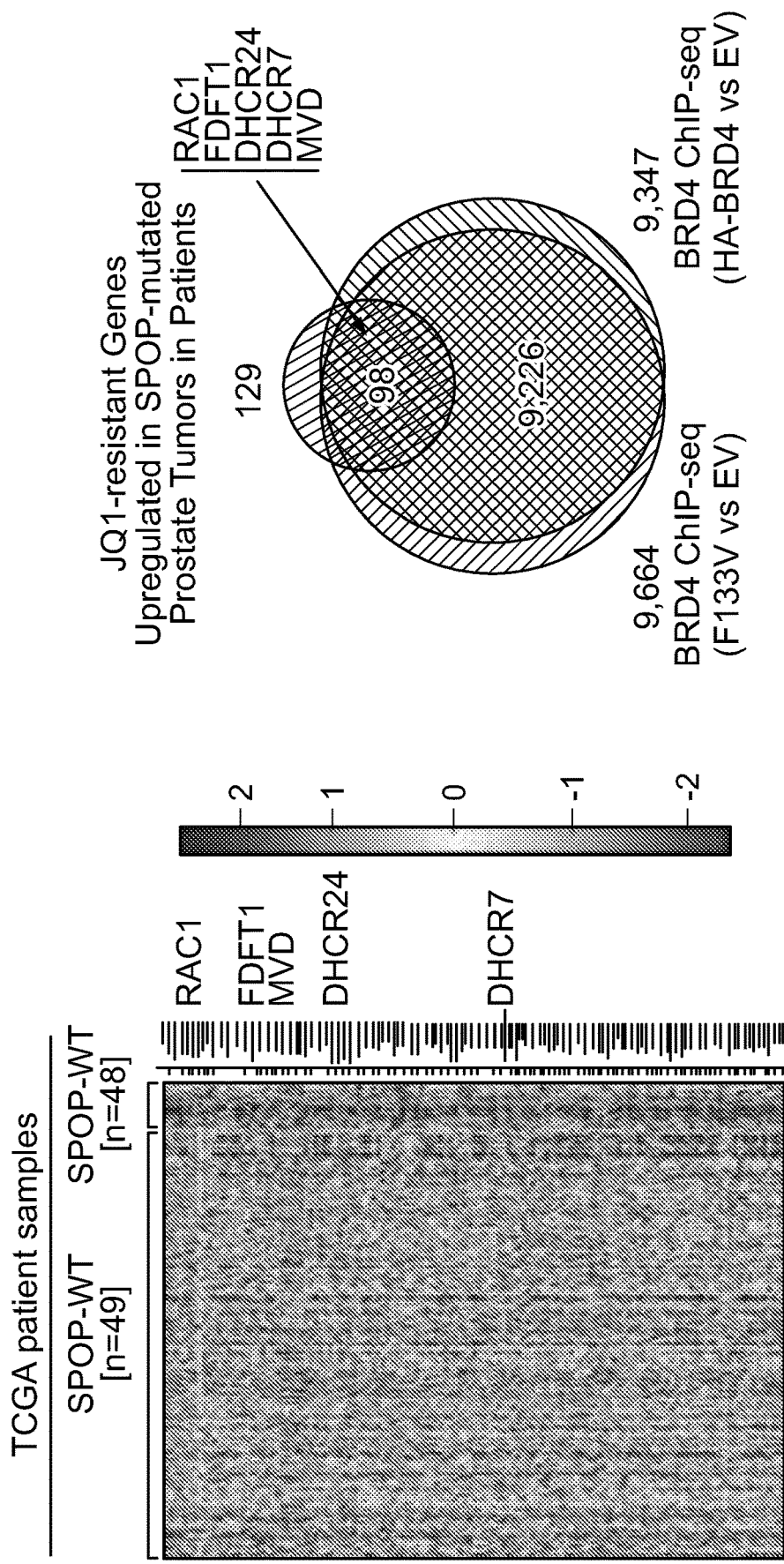

Further analysis of RNA-seq data revealed 1,017 genes whose expression was suppressed by JQ1 in control cells but remained either unchanged or upregulated in F133V-mutant cells (FIG. 7d). 129 of them were highly upregulated in SPOP-mutated prostate tumors compared to SPOP-WT tumors in the TCGA cohort (FIG. 7e and Table 5). Notably, these aberrantly upregulated genes significantly overlapped with the BRD4 target genes commonly identified in C4-2 cells transfected with SPOP-F133V or HA-BRD4 (FIGS. 7f and 12a-c). Ingenuity pathway analysis of the overlapped genes indicated that the top hit was the cholesterol biosynthesis pathway, and four members of this pathway including FDFT1, DHCR24, DHCR7 and MVD were upregulated in SPOP-mutated tumors (FIGS. 7e and 7f).

TABLE 5

Table 5. 129 genes highly expressed in SPOP mutated prostate cancers compared to SPOP wild-type counterparts in the TCGA dataset Gene symbol PREB
PHLDA2
ATPGV0E2
HMG20B
CYP2R1
RAC1
ZNF582
MAGEC2
EIF2AK1
PIGX
SEC61A1
ETHE1
BCAT2
CYP4F11
ENDOG
AF2S1
VGF
PRKRIR
ZDHHC12
FDFT1
ZNF695
GAS2L1
MVD
MEMO1
PCDHA2
PCDHA7
PCDHA4
PCDHA5
PCDHA8
MOSPD3
NRD1
PUSL1
GABRD
MBD3
RTN2
DHCR24
TCTEX1D2
PCDHA12
SLC25A39
TMEM52
FAM84A
PQLC1
FKBP2
ALCAM
NDOR1
CBLN2
DOLK
PCDHA9
ABHD2
GNMT
CKMT1A
CKMT1B
ABHD11
HCN2
E4F1
SCYL1
NANS
TXNL4A
BPGM
PAFAH1B3
SLC25A33
DDAH1
CROT
PCK2
SEC61G
SEPW1
LIN7B
GMPR
TRPM4
FANK1
DHCR7
POLD4
FAM117A
PTS
SIAH2
MERTK TABLE 5-continued Table 5. 129 genes highly expressed in SPOP mutated
prostate cancers compared to SPOP wild-type counterparts
in the TCGA dataset Gene symbol PQLC2
LMO7
NRIP1
NUDT8
ANXA4
FDXR
STK32C
SLC41A3
TMEM134
CTU2
CHMP1A
SNAPC2
HYAL3
TMEFF2
TBC1D4
CNTNAP2
SNHG6
GGH
PPFIA3
TBX10
MFSD5
BCL2L1
TMED1
TCIRG1
SESN2
ATP59L
SERINC2
POLR3H
TMEM120A
THAP10
SLC25A1
PRRG2
PCYT2
ECHS1
TUSC2
POLE4
CD9
GET4
BCL7B
DGKA
BTBD11
CLCF1
GNB2
GLRX2
FKBPL
IL17RC
NPDC1
GRTP1
SCAND1
SND1
MRPL41
PHF1
TTLL12

Figure 12C:
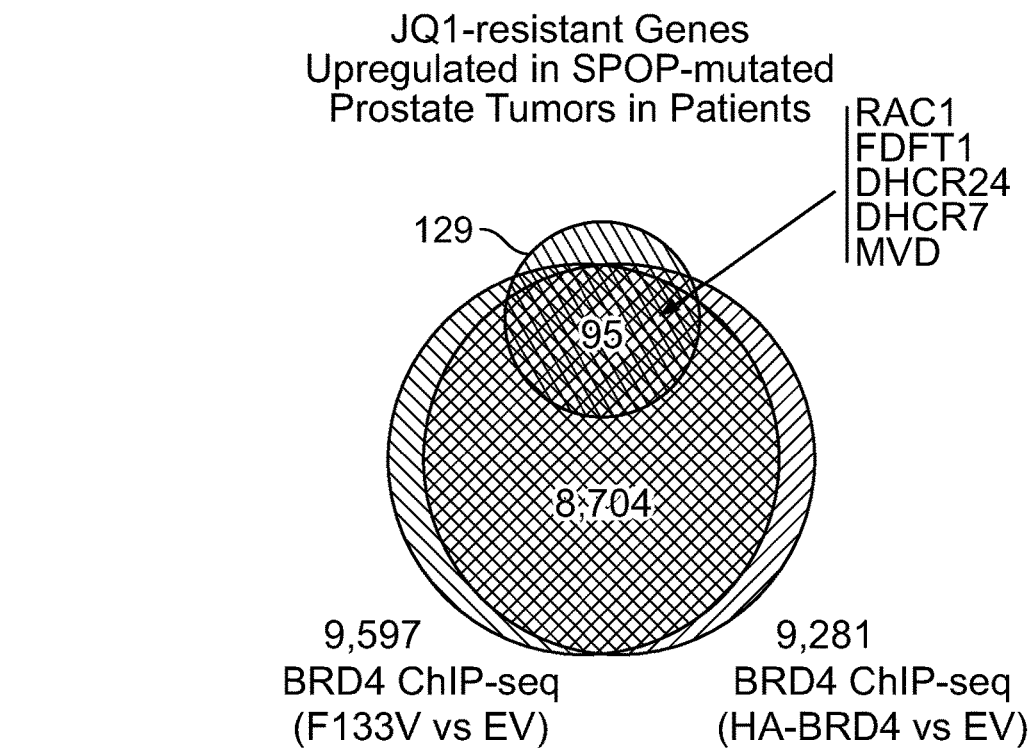
FIG. 12C, Data from a replicate of the experiment shown in FIG. 7F and FIG. 7G. Top, Venn diagram showing the overlap of JQ1-resistant genes upregulated in SPOP-mutated prostate tumors with the common BRD4 target genes induced by SPOP F133V and HA-BRD4 expression in C4-2 cells. The overlap is statistically significant with P=6.591e-13 (Permutation test). Bottom, BRD4 ChIPseq signals in EV- and F133V-expressing C4-2 cells treated with or without JQ1 (1 µM) and H3K4me3 ChIP-seq signals in LNCaP cells (Wang et al., Nature, 474:390-394 (2011)).
Figure 12C:
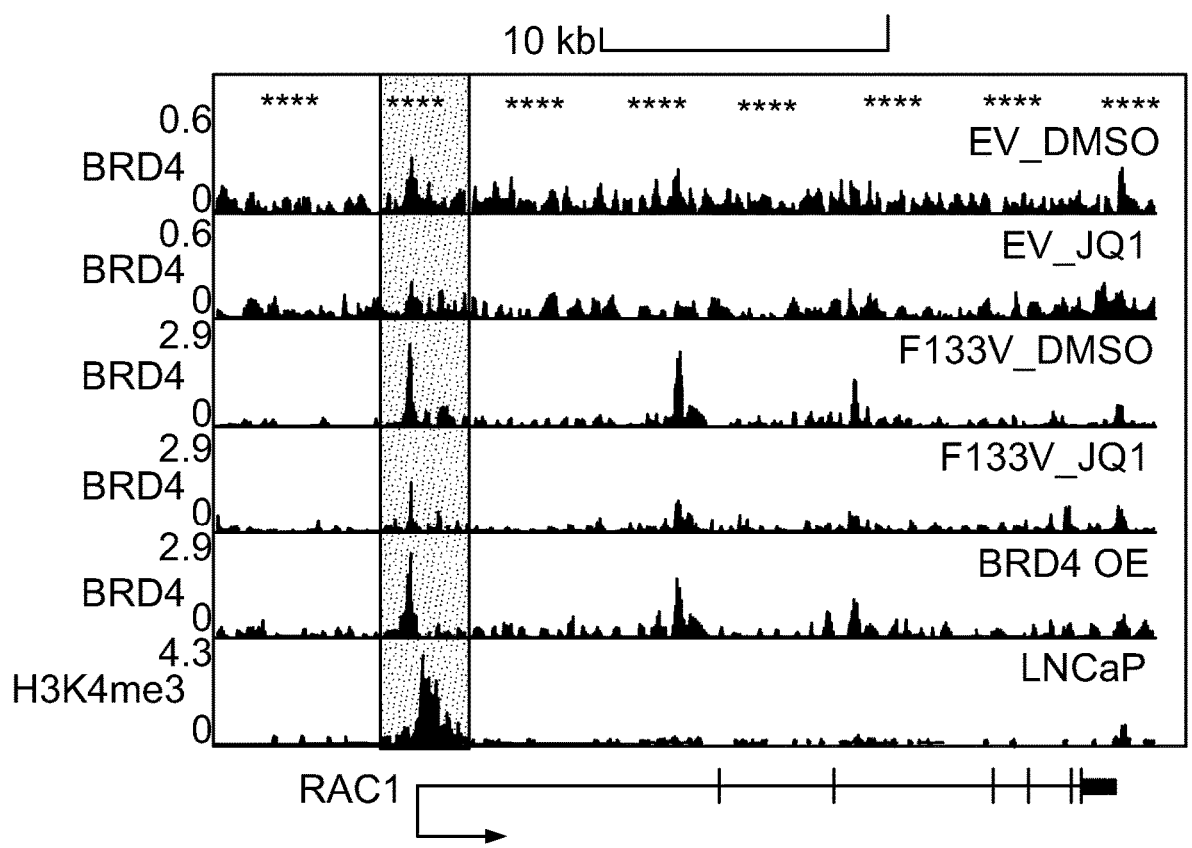
Figure 12D:
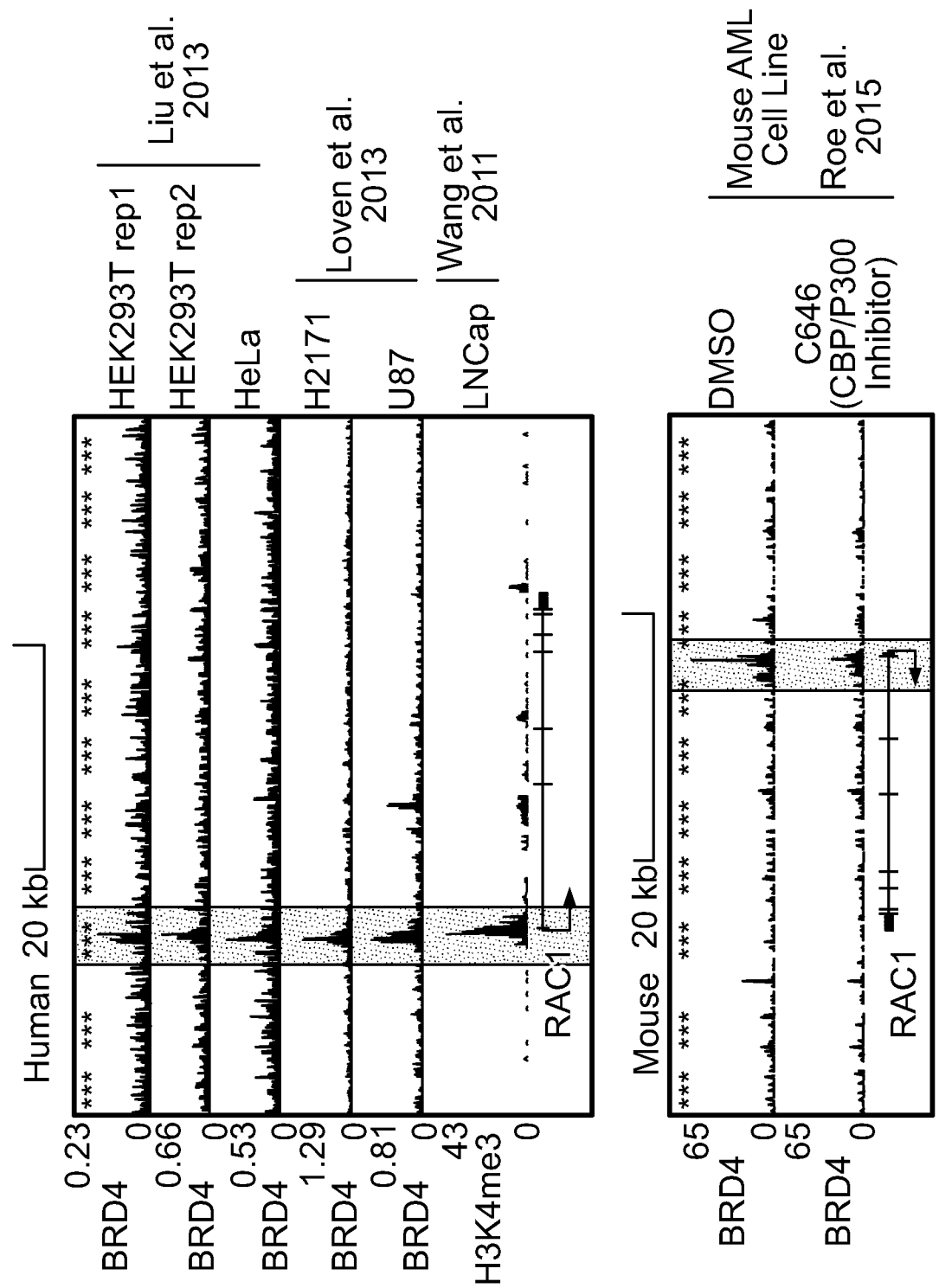
FIG. 12D, BRD4 ChIP-seq signals in the RAC1 promoter in several human cell lines including HEK293T, HeLa, H2171, and U87 and mouse acute myeloid leukemia (AML) cells (Roe et al., Mol. Cell., 58:1028-1039 (2015)). H3K4me3 ChIP-seq signals in LNCaP cells are included.
Figure 12I:
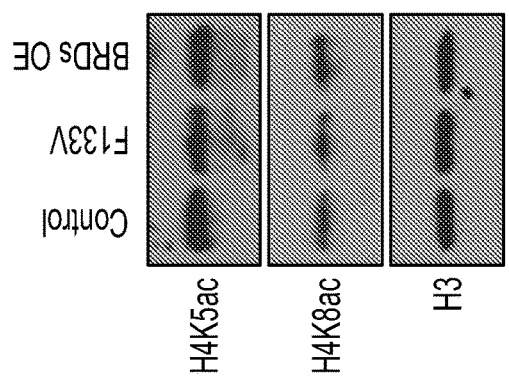
FIG. 12I, Western blot analysis of indicated proteins in whole cell lysate of C4-2 cells infected with empty vector (EV) or SPOP F133V or BRD2/3/4 expressed vectors for 48 hours before being harvested.
Figure 12I:
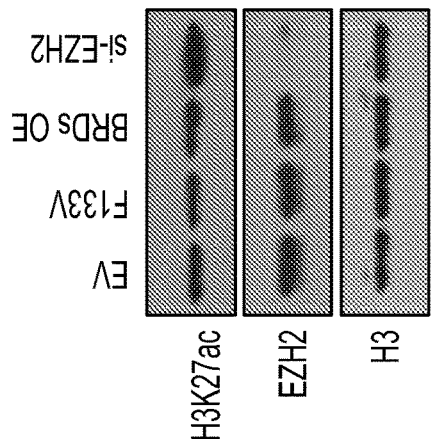
Figure 12H:
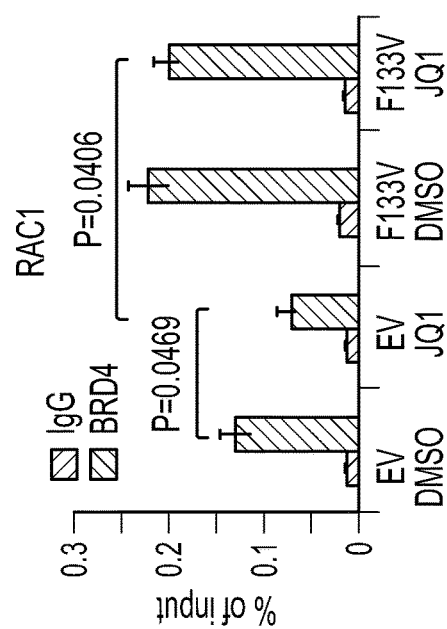
FIG. 12H, ChIP-qPCR analysis of BRD4 binding at the RAC1 promoter in C4-2 cells infected and treated as in (FIG. 12A). All data are shown as mean values±SD (n=3 technical replicates), and similar results were obtained from two independent experiments.
Figure 12J:
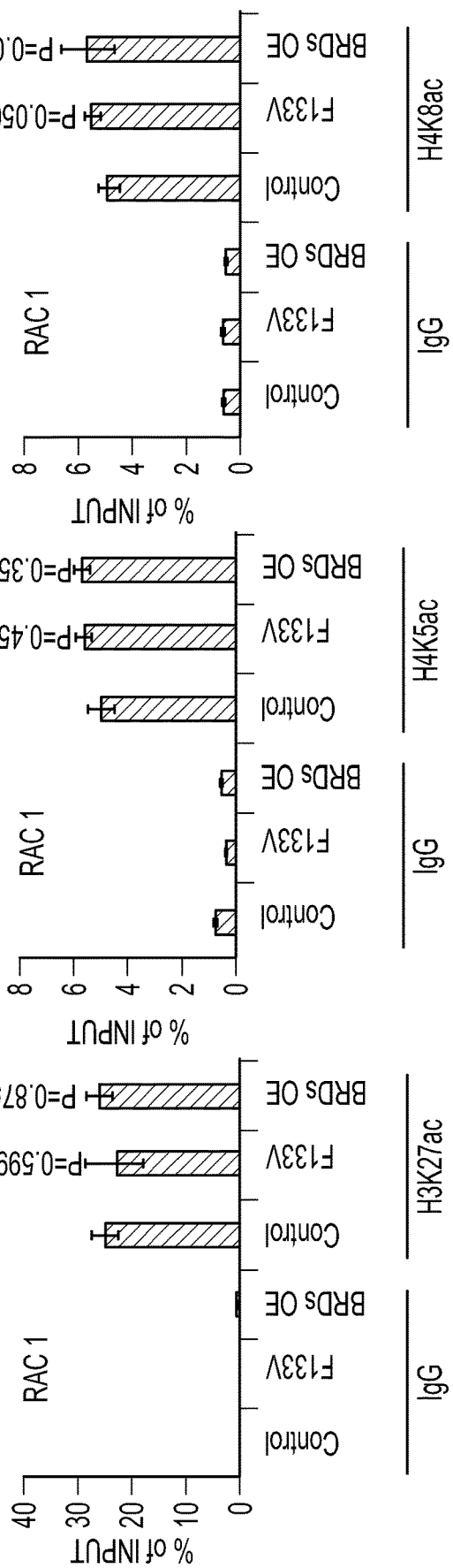
FIG. 12J, ChIP-qPCR analysis of H3K27ac, H4K5ac, and H4K8ac binding at the RAC1 promoter of the indicated genes in C4-2 cells transfected with empty vector (Control), SPOP F133V or BRDs. All data shown are mean values±SD (error bar) from three replicates.
Figure 12I:
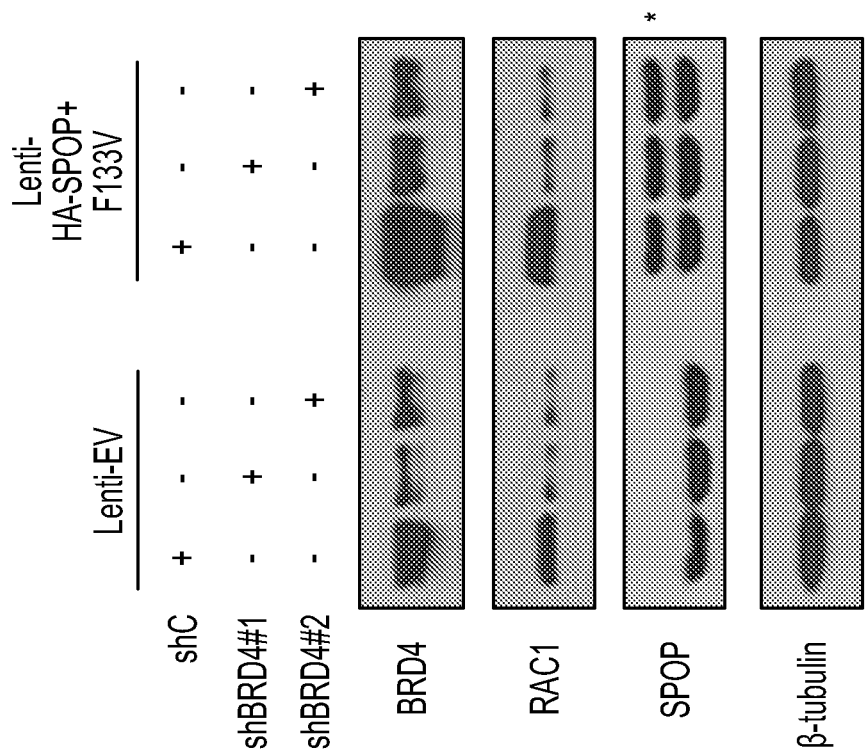
Figure 12K:
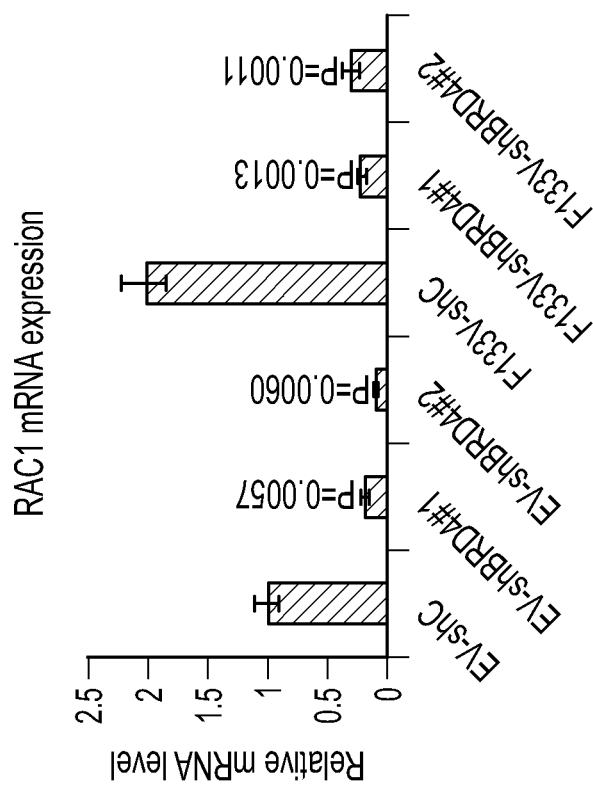
Figure 12M:
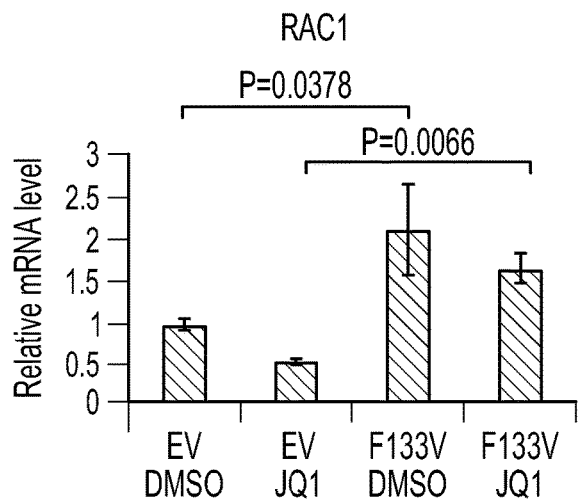
FIG. 12M, RT-qPCR analysis of RAC1 mRNA expression in C4-2 infected with lentivirus and JQ1 as in (FIG. 12A). RAC1 mRNA level was first normalized to the level of GAPDH mRNA and then further normalized to the value in EV-expressed C4-2 cells treated with vehicle. Data are shown as means±SD (n=3 technical replicates), and similar results were obtained from two independent experiments. Two-tailed Student's t test was used.
Figure 12N:
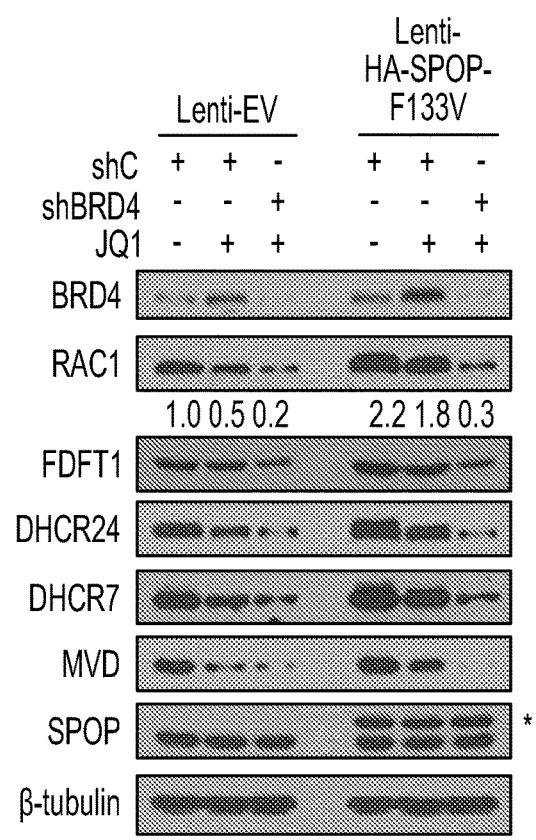
FIG. 12N, Western blot of WCL of C4-2 cells infected with lentivirus as indicated and treated with JQ1 (1 µM) for 24 hours before being harvested. Western blot signal intensity RAC1 was first normalized to β-tubulin level, and the value was further normalized to the one in control cells.
Figure 12O:
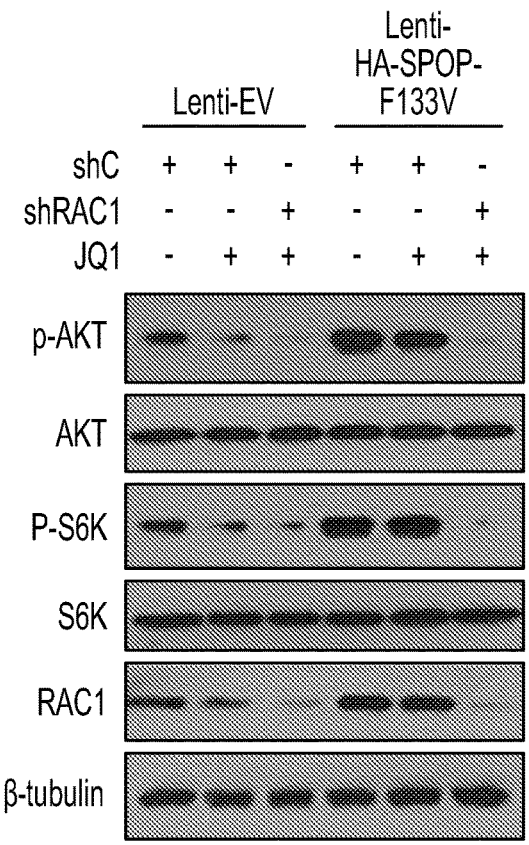
FIG. 12O, Western blot of WCL of C4-2 cells infected with lentivirus expressing empty vector (EV) or SPOPF133V in combination with control shRNA (shC) or RAC1-specific shRNAs and treated with or without JQ1 (1 µM) for 24 hours before being harvested.
Figure 12P:
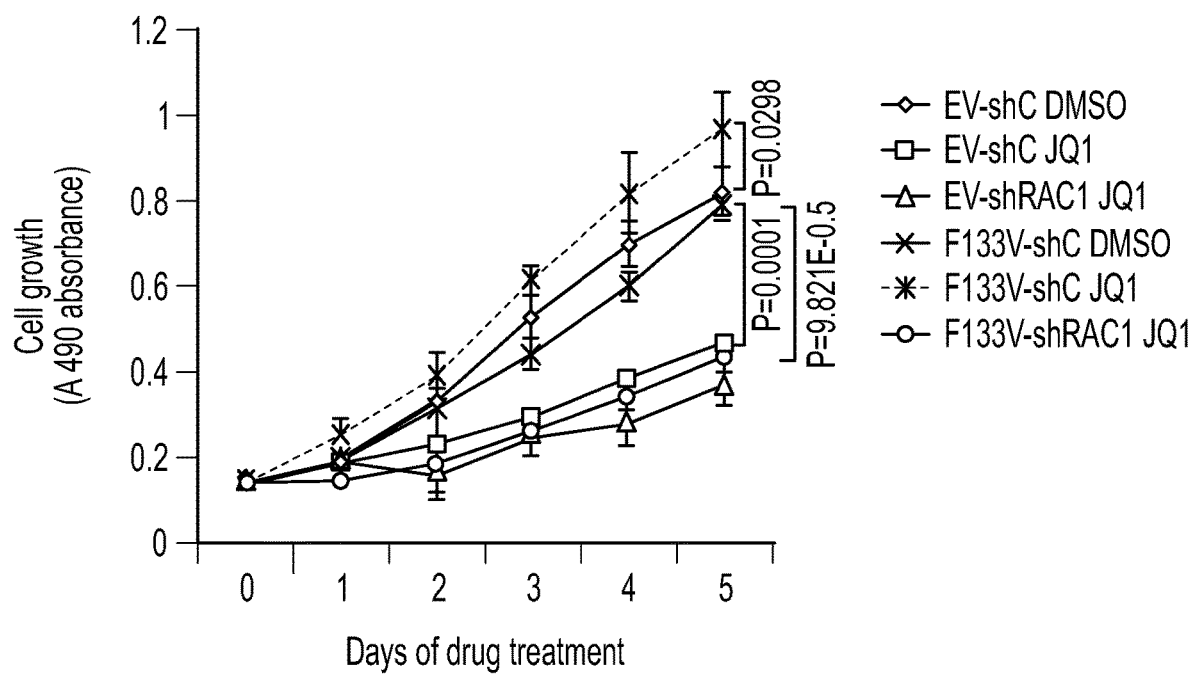

RAC1, a RHO GTPase family member, was upregulated in SPOP-mutated tumors (FIG. 7e). Meta-analysis also showed BRD4 binding at the RAC1 locus in different cell types (FIG. 12d). RNA-seq analysis revealed that global transcriptional changes caused by BRD2/3/4 overexpression in C4-2 cells significantly overlapped with the genes associated with JQ1 resistance in F133V-mutant cells, including RAC1 (FIGS. 12e-g). ChIP-seq and ChIP-qPCR assays revealed that BRD4 readily bound at the RAC1 gene promoter in control cells, but the binding was largely enhanced by expression of SPOP-F133V or HA-BRD4 (FIGS. 7f, 7g, 12c, and 12h). Increased BRD4 binding was unlikely caused by histone acetylation changes since expression of SPOP F133V or BRD proteins had no effect on the level of H3K27ac, H4K5ac, and H4K8ac, both globally and in the RAC1 locus (FIGS. 12i and 12j). BRD4-dependent regulation of RAC1 was confirmed by gene knockdown experiments (FIGS. 12k and 12l), providing further evidence that RAC1 was a bona fide BRD4 target gene. Additionally, increased BRD4 binding and RAC1 mRNA and protein expression correlated with high levels of BRD4 proteins in JQ1-resistant SPOP-F133V cells compared to JQ1-untreated control cells (FIGS. 7g, 12c, 12m, and 12n). Furthermore, SPOP-F133V expression substantially increased phosphorylation of AKT and S6K, a downstream kinase of mTORC1, in both C4-2 and 22Rv1 cells regardless of JQ1 treatment (FIGS. 6m and 12o). Knockdown of RAC1 not only inhibited SPOP-F133V-augmented AKT and S6K phosphorylation, but also abolished SPOP-F133V-mediated JQ1 resistance in C4-2 cells (FIGS. 12o and 12p).

Figure 13A:
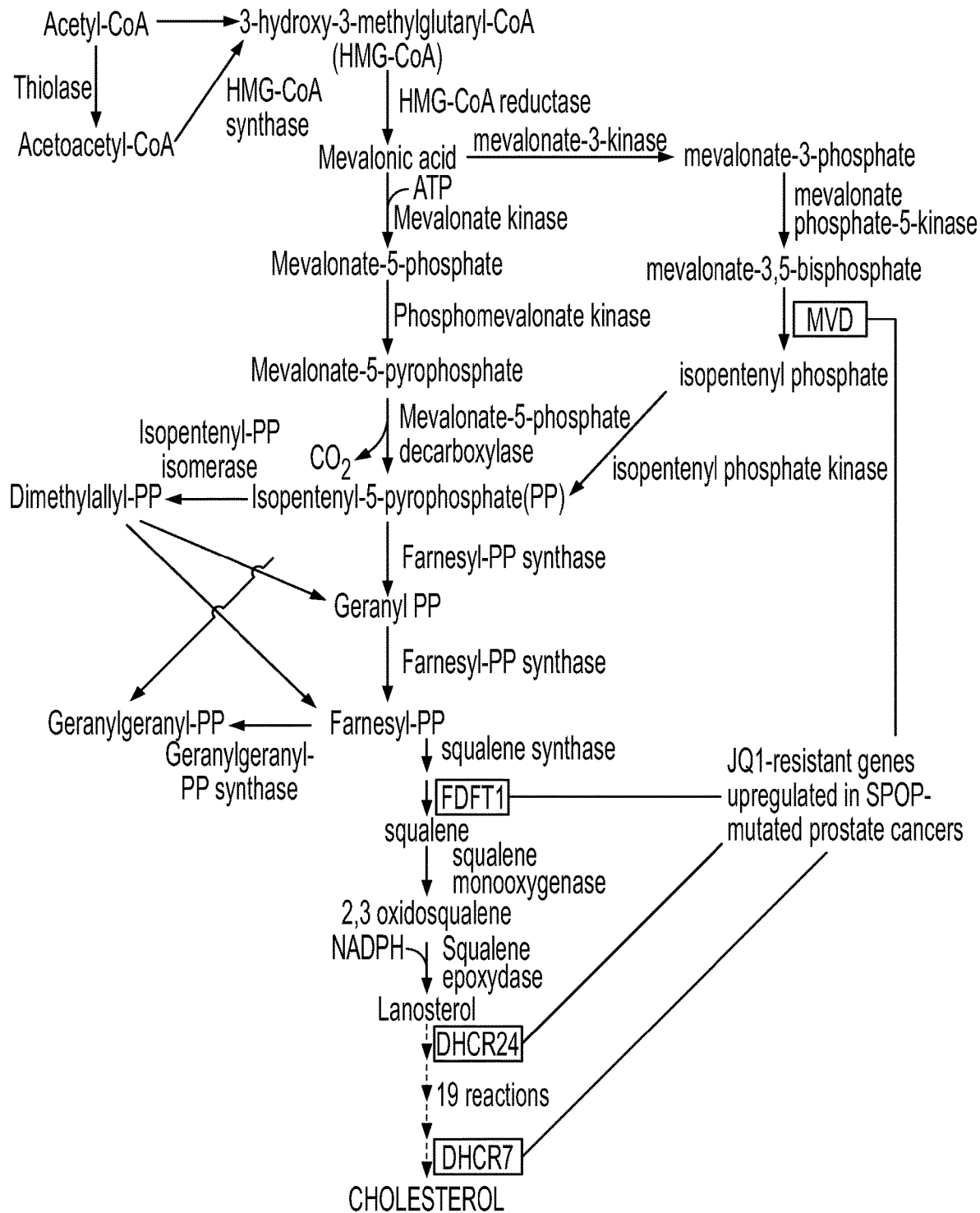
FIGS. 13A-13P. Cholesterol biosynthesis genes are BRD4-binding targets and contribute to JQ1 resistance in SPOP-mutated prostate cancer cells.
Figure 13B:
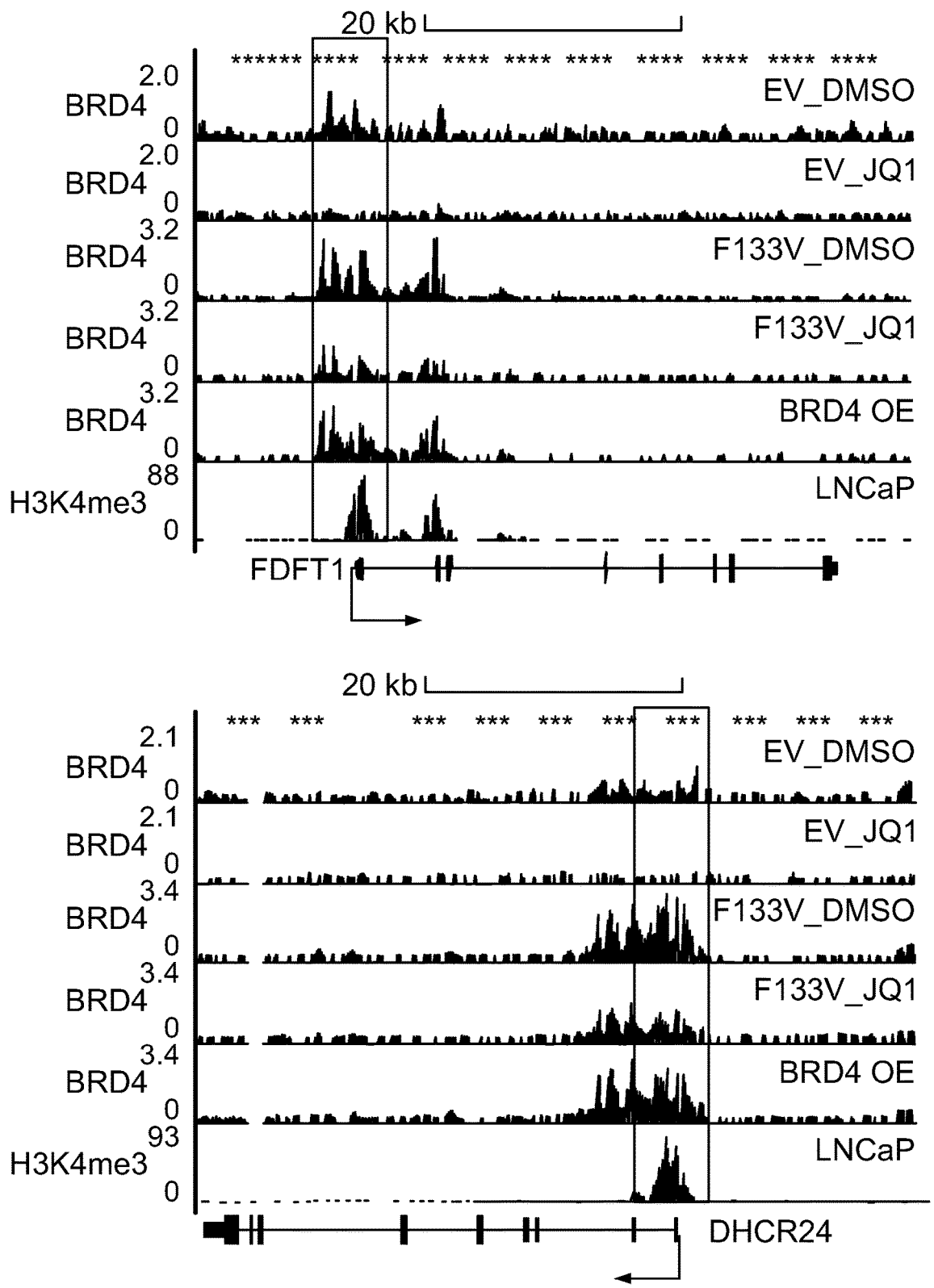
FIG. 13B, BRD4 ChIP-seq signals in the cholesterol synthesis gene promoters in C4-2 cells infected with lentivirus expressing empty vector (EV) or SPOP-F133V mutant or transfected with HA-BRD4 expression vector and treated with or without JQ1 (1 µM) for 24 hours. H3K4me3 ChIP-seq signals in LNCaP cells are included.
Figure 13B:
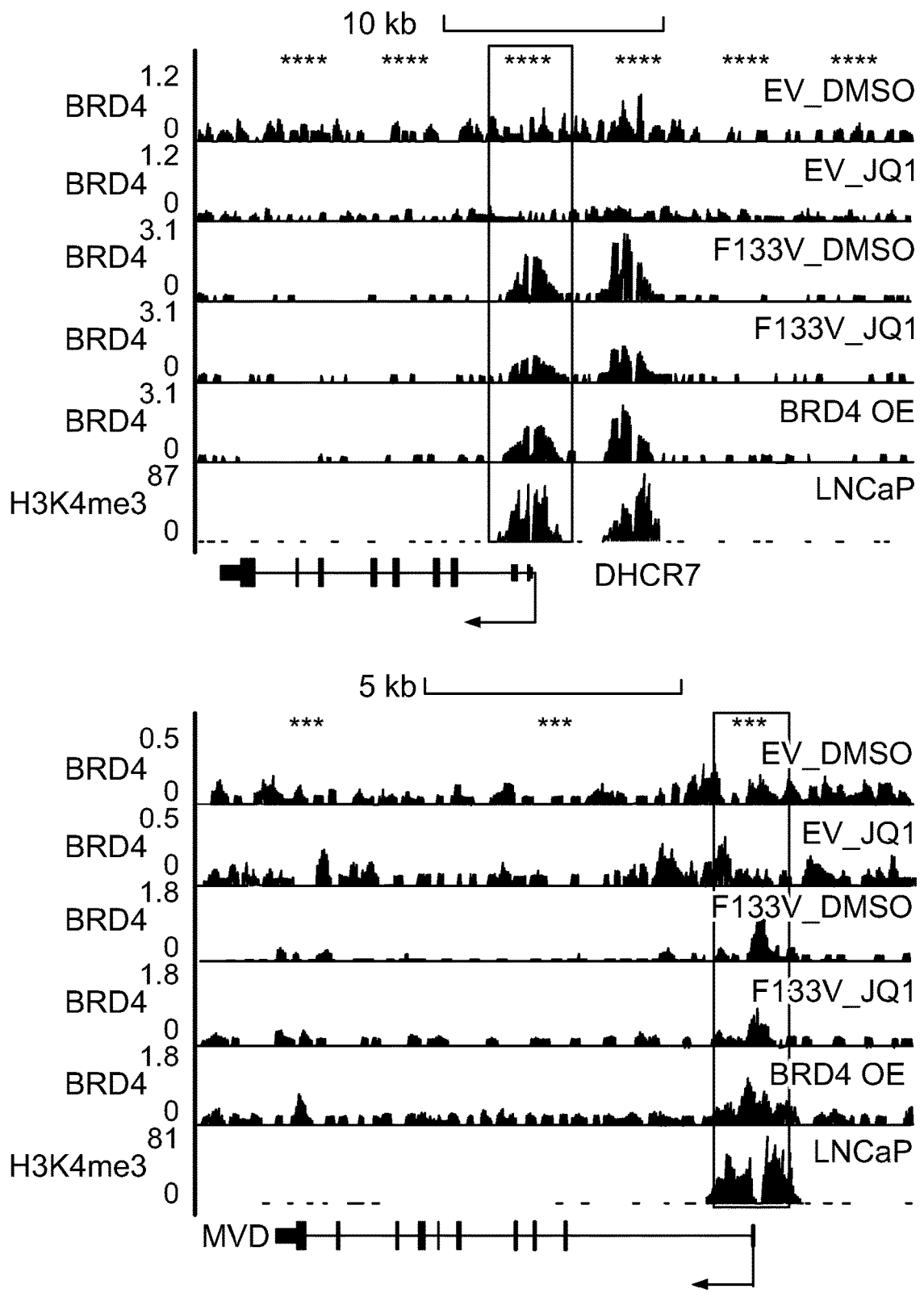
Figure 13C:
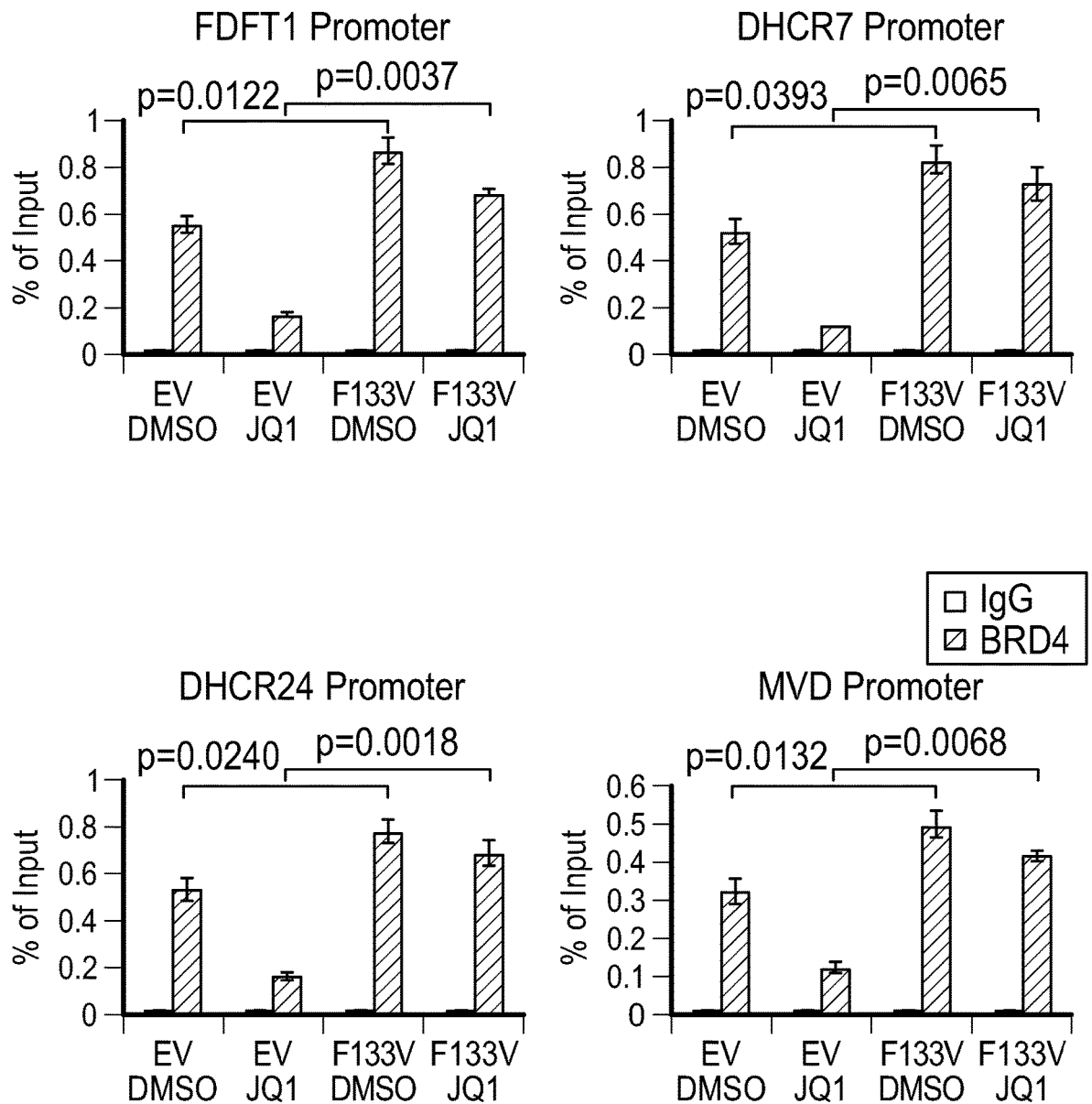
FIG. 13C, ChIP-qPCR analysis of BRD4 binding at the cholesterol synthesis gene promoters in C4-2 cells infected with lentivirus and treated with or without JQ1 as in (FIG. 13B). Data are shown as mean values±SD (n=3 technical replicates), and similar results were obtained in two independent experiments.
Figure 13D:
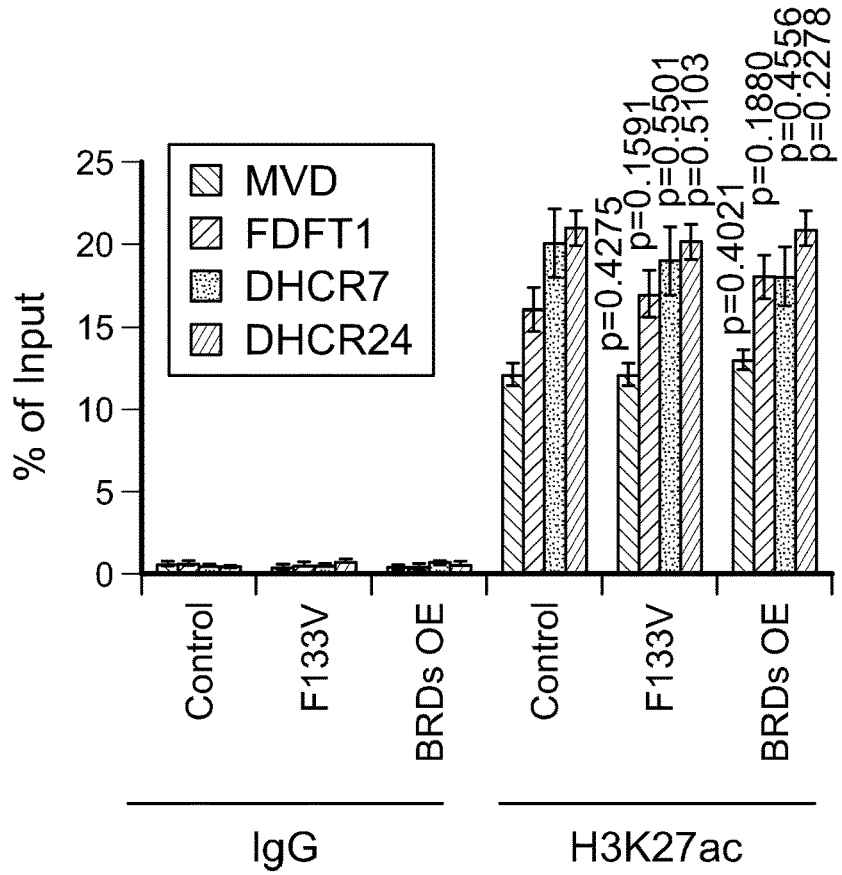
FIG. 13D, ChIP-qPCR analysis of H3K27ac, H4K5ac, and H4K8ac binding at the MVD, FDFT1, DHCR7, and DHCR24 gene promoters in C4-2 cells transfected with empty vector (Control), SPOP F133V, or BRDs. All data shown are mean values±SD (error bar) from three replicates.
Figure 13D:
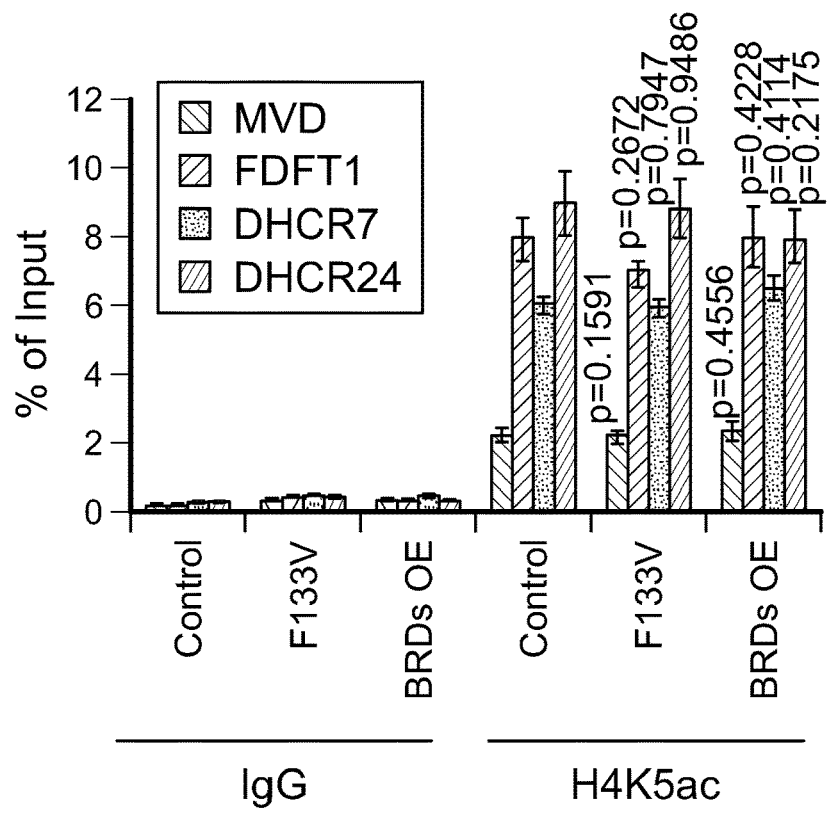
Figure 13D:
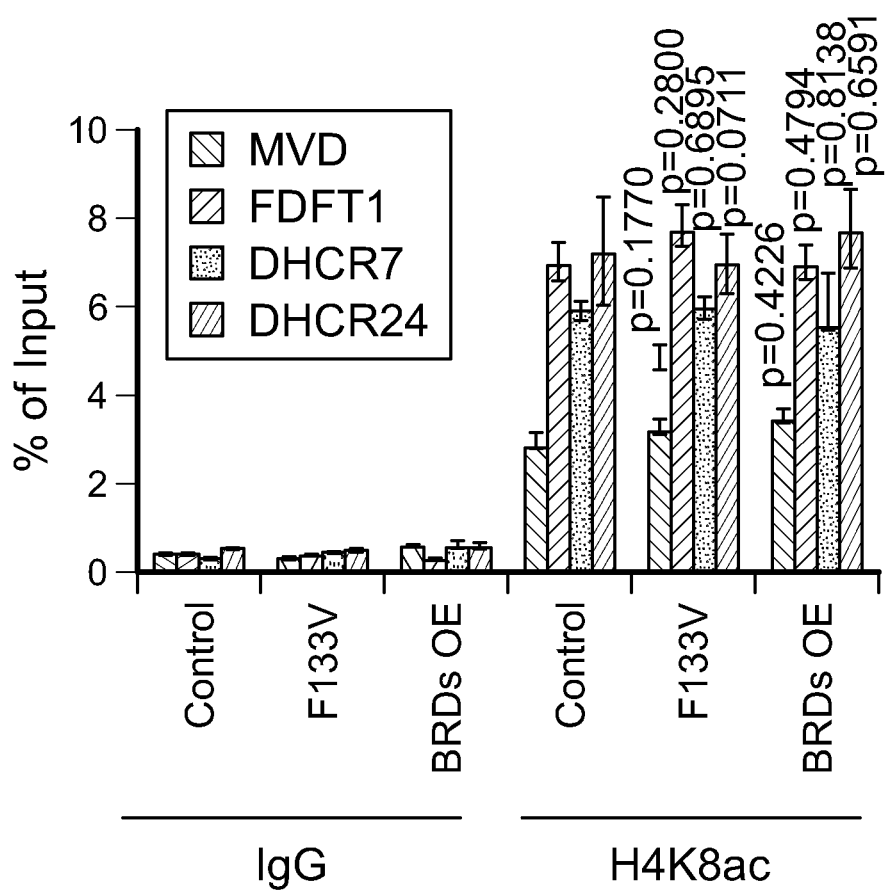
Figure 13E:
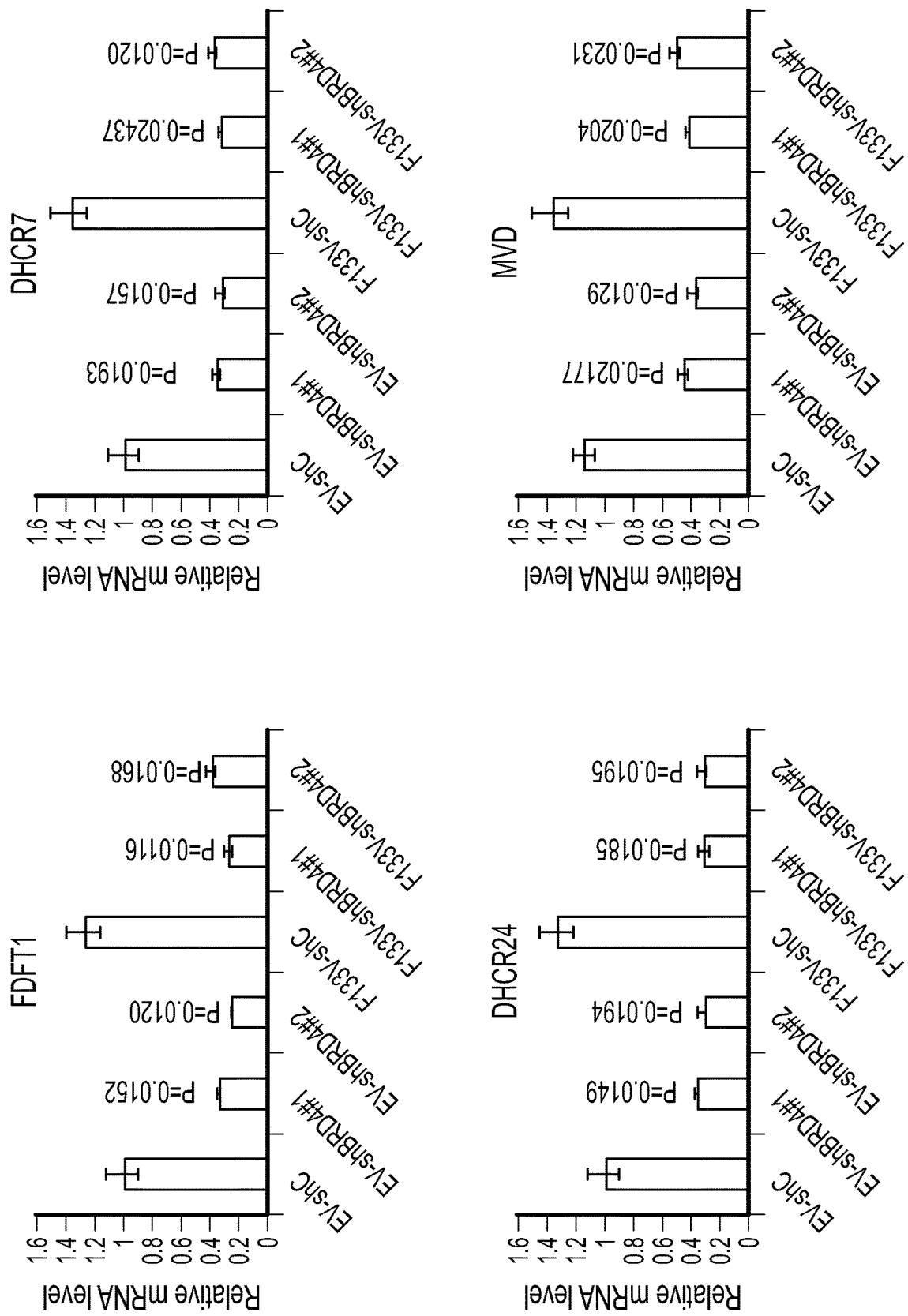
FIG. 13E, RT-qPCR analysis of FDFT1, DHCR24, DHCR7, and MVD mRNA expression in RNA samples infected with indicated lentivirus. Target gene mRNA level was first normalized to GAPDH mRNA and then further normalized to the value in control cells. Data are shown as means±SD (n=3 technical replicates), and similar results were obtained from two independent experiments.
Figure 13F:
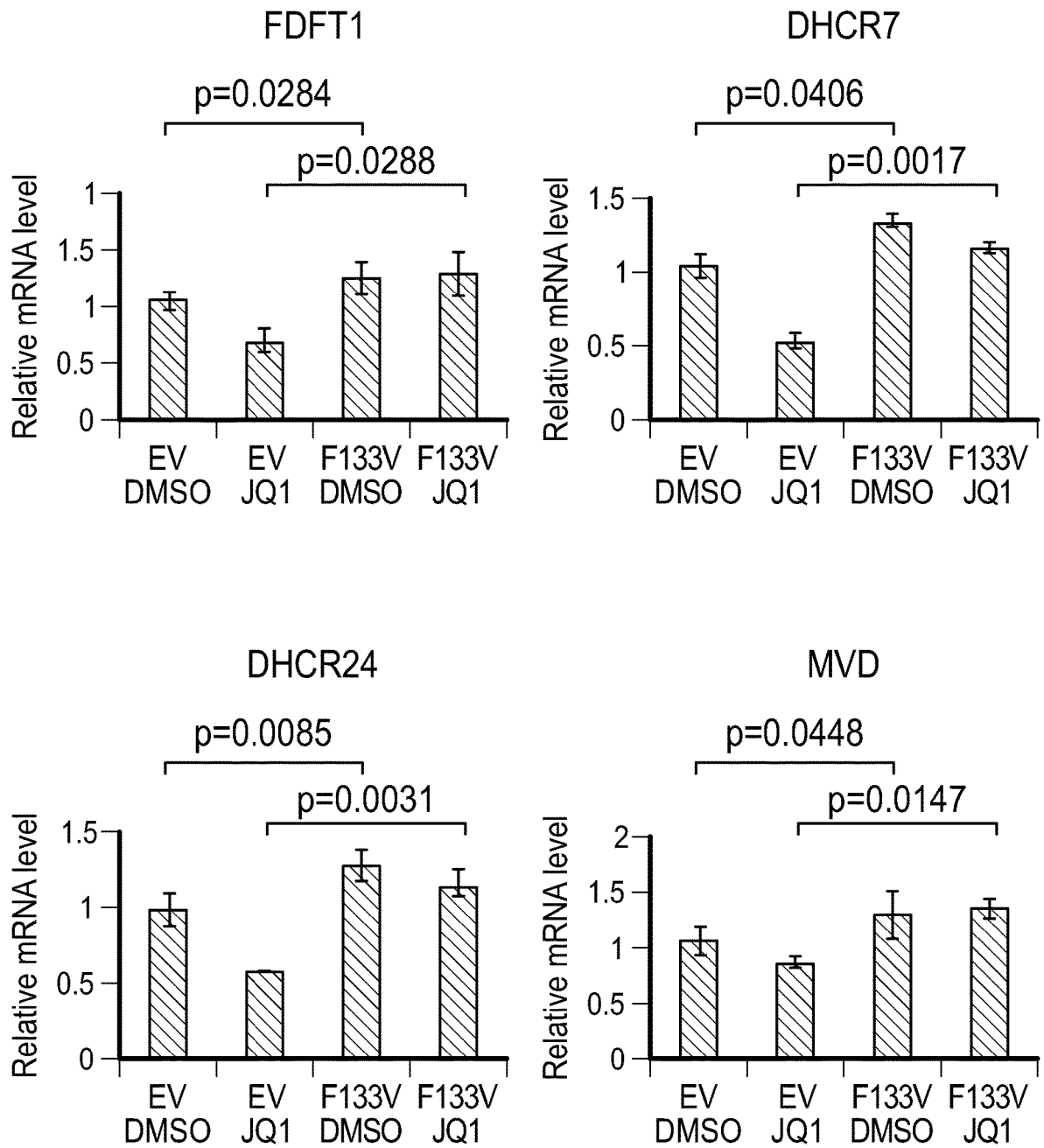
FIG. 13F, RT-qPCR analysis of FDFT1, DHCR24, DHCR7, and MVD mRNA expression in C4-2 cells infected with lentivirus and treated with JQ1 as in (FIG. 13C). Data are shown as mean values±SD (n=3 technical replicates), and similar results were obtained from two independent experiments. Two tailed Student's t test was used.
Figures 13G, 13H:
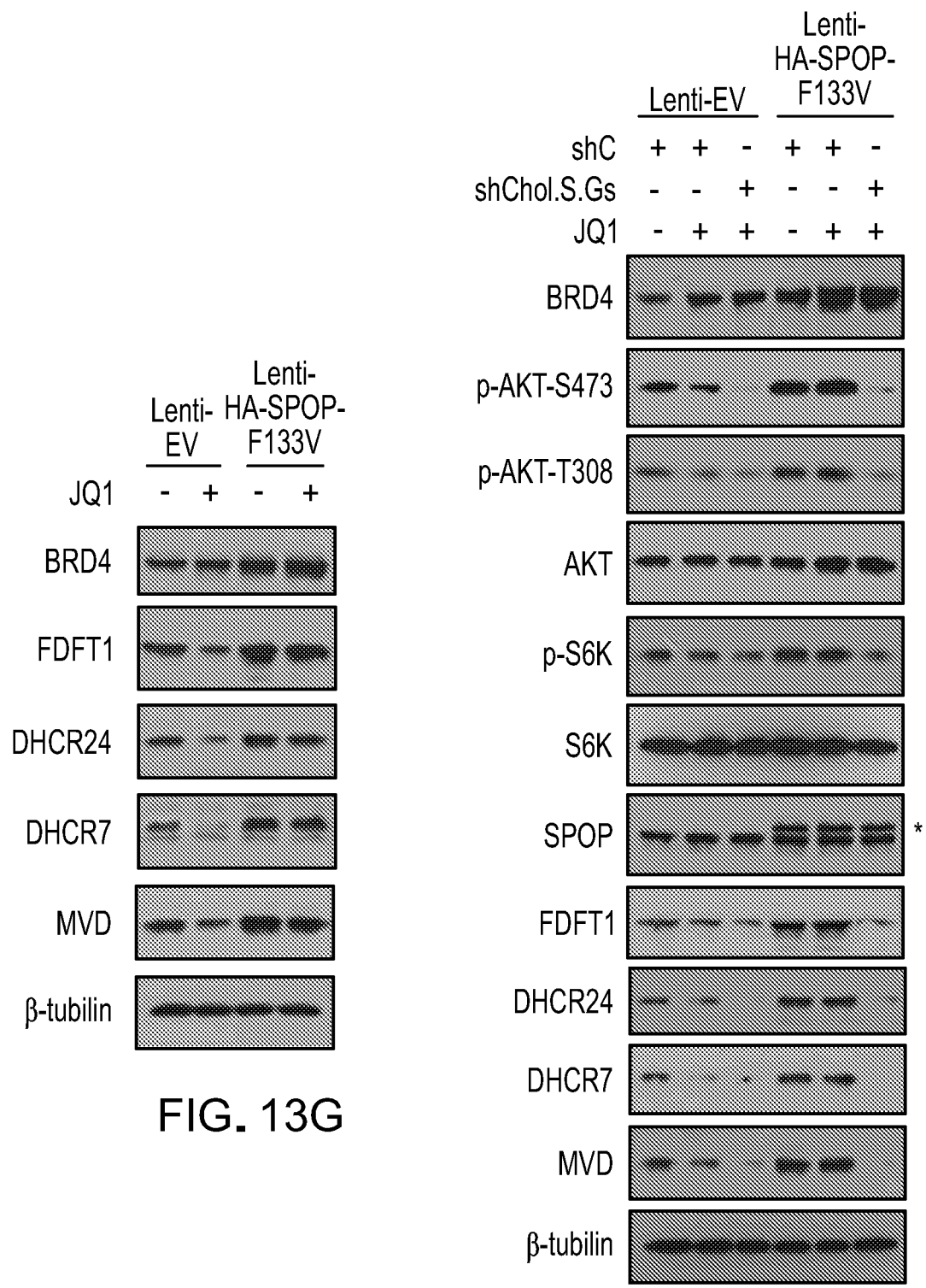
FIG. 13G, Western blot of WCL of C4-2 cells infected with lentivirus and treated with JQ1 as in (FIG. 13C) for 24 hours before being harvested.
FIG. 13H, Western blot of WCL of C4-2 cells infected with lentivirus expressing empty vector (EV) or SPOP F133V in combination with control shRNA (shC) or gene-specific shRNAs for cholesterol synthesis genes including FDFT1, DHCR24, DHCR7, and MVD and treated with or without JQ1 (1 µM) for 24 hours before being harvested. Asterisk indicates the exogenous HA-SPOP-F133V.
Figure 13I:
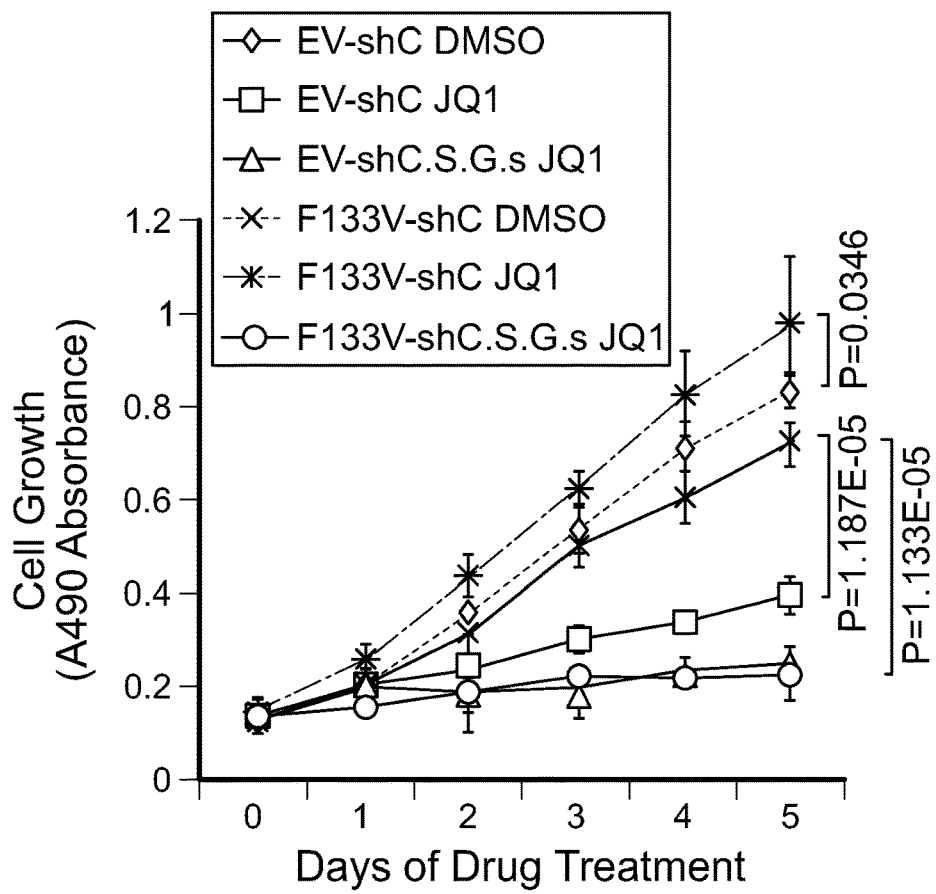
FIG. 13I, C4-2 cells were infected with lentivirus and treated with JQ1 as in (FIG. 13H). Cell growth was measured by cell proliferation assay. Data are shown as mean values±SD (n=6 biological replicates).
Figure 13J:
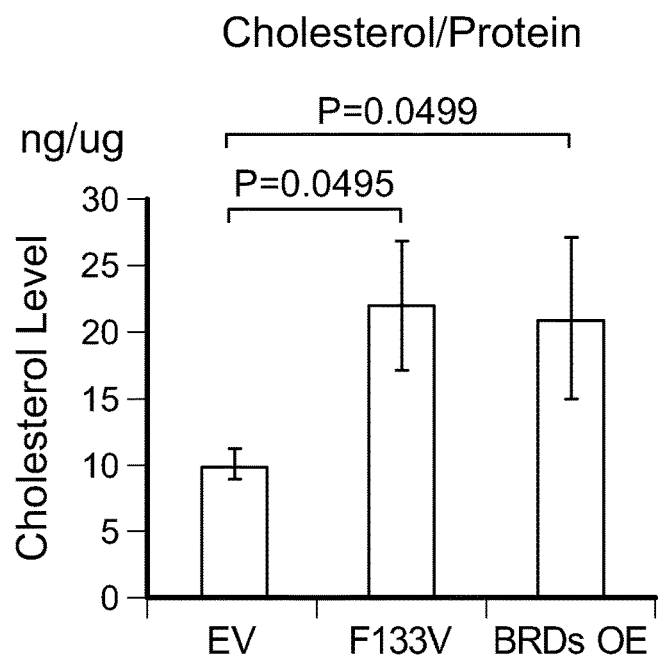
FIG. 13J, Cholesterol level analysis in C4-2 cells transfected with empty vector (Control), SPOP F133V, or BRDs. The cholesterol/protein ratio was determined in the whole cell lysis. All data shown are mean values±SD (error bar) from three replicates.
Figure 13K:
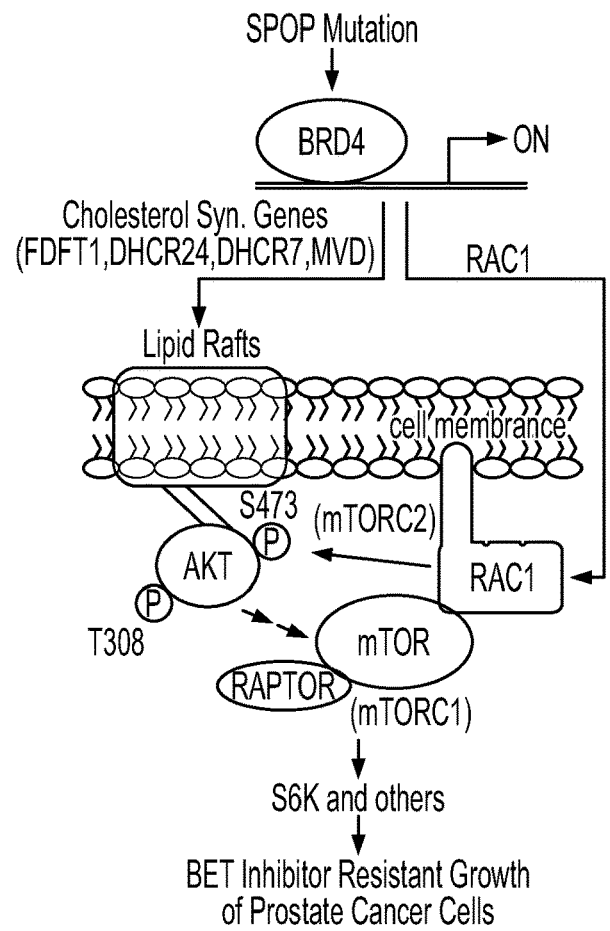
FIG. 13K, A schematic diagram depicts a model where both RAC1 and cholesterol synthesis pathways are needed for BET inhibitor resistance in SPOP-mutated prostate cancer cells. Elevation of BRD4 due to SPOP mutation in prostate cancer cells leads to increased expression of RAC1 and cholesterol synthesis genes, both of which are needed for hyperactivation of the AKT-mTORC1 pathway, given that RAC1 directly binds to mTOR and activates AKT and mTORC1 and that formation of cholesterol and glycosphingolipid-enriched lipid rafts/membrane microdomains is needed for AKT activation.

ChIP-seq and ChIP-qPCR assays showed that BRD4 readily bound in the promoters of cholesterol synthesis genes FDFT1, DHCR24, DHCR7 and MVD in control cells and that the binding was enhanced by SPOP-F133V (FIGS. 13a-c). This effect was unlikely caused by global or locus-specific histone acetylation changes (FIGS. 12i and 13d). Knockdown of BRD4 largely decreased expression of these genes at mRNA and protein levels in both control and SPOP-F133V cells (FIGS. 12n and 13e). With concomitant induction of BRD4 protein levels, SPOP-F133V upregulated the expression of cholesterol synthesis genes at both mRNA and protein levels and enhanced BRD4 binding in their promoters (FIGS. 13b, 13c, 13e, and 13f). JQ1 treatment largely inhibited expression of these genes and BRD4 binding at their promoters in control cells, but the effect was not pronounced in SPOP-F133V cells (FIGS. 13b, 13c, 13f, and 13g). Co-depletion of these cholesterol synthesis genes abolished SPOP-F133V-induced activation of the AKT-mTORC1 pathway and JQ1-resistance in C4-2 cells (FIGS. 13h and 13i). Similar to SPOP mutant, moderate overexpression of BRD2/3/4 increased cholesterol biosynthesis and AKT/mTORC1 activation (FIGS. 12e and 13j). These results demonstrate that both RAC1 and cholesterol synthesis pathways are involved in mediating SPOP mutation-induced AKT/mTORC1 activation and JQ1 resistance (FIG. 13k).

Figure 13L:
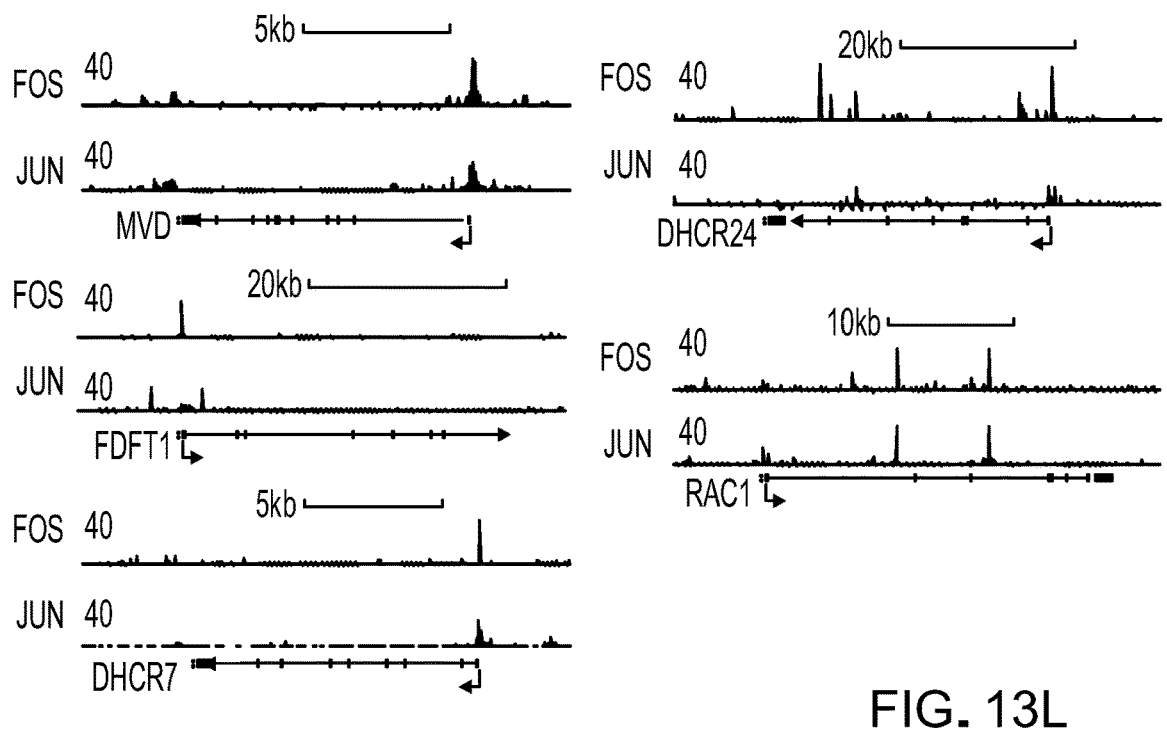
FIG. 13L, UCSC genome browser screen shots showing signal profiles of FOS and JUN ChIP-seq in the gene region of the MVD, FDFT1, DHCR7, DHCR24, and RAC1 genes in HeLa (FOS) and K562 (JUN) cells.
Figure 13M:
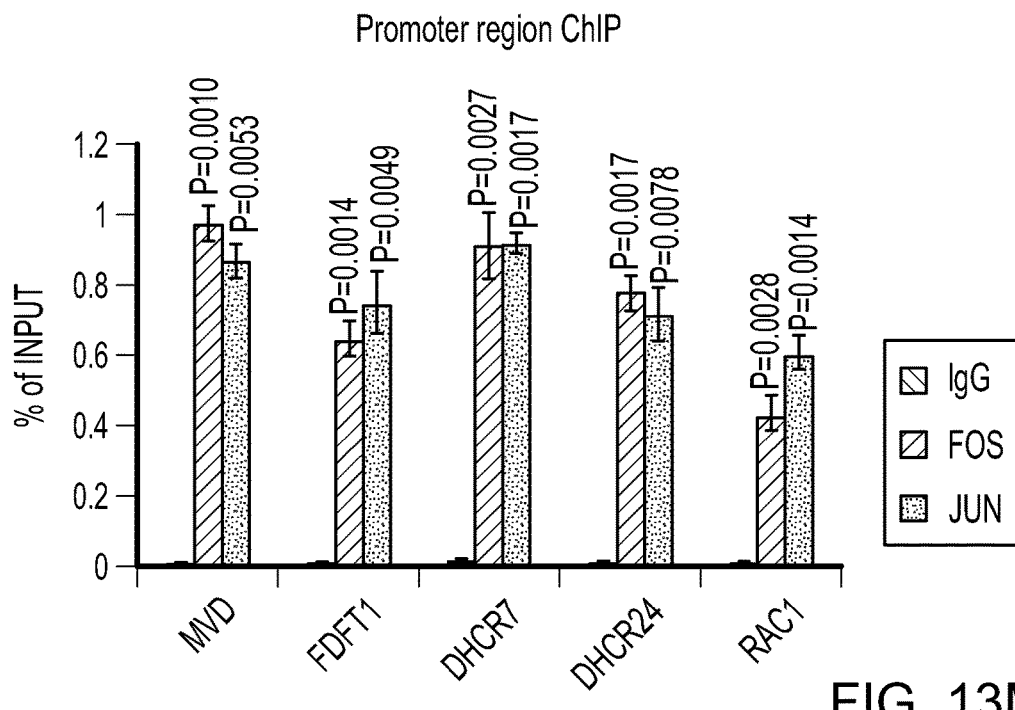
FIG. 13M, ChIP-qPCR analysis of FOS and JUN binding at the MVD, FDFT1, DHCR7, and DHCR24 promoters of the indicated genes in C4-2 cells. All data shown are mean values±SD (error bar) from three replicates. FOS/JUN ChIP vs IgG.
Figure 13N:
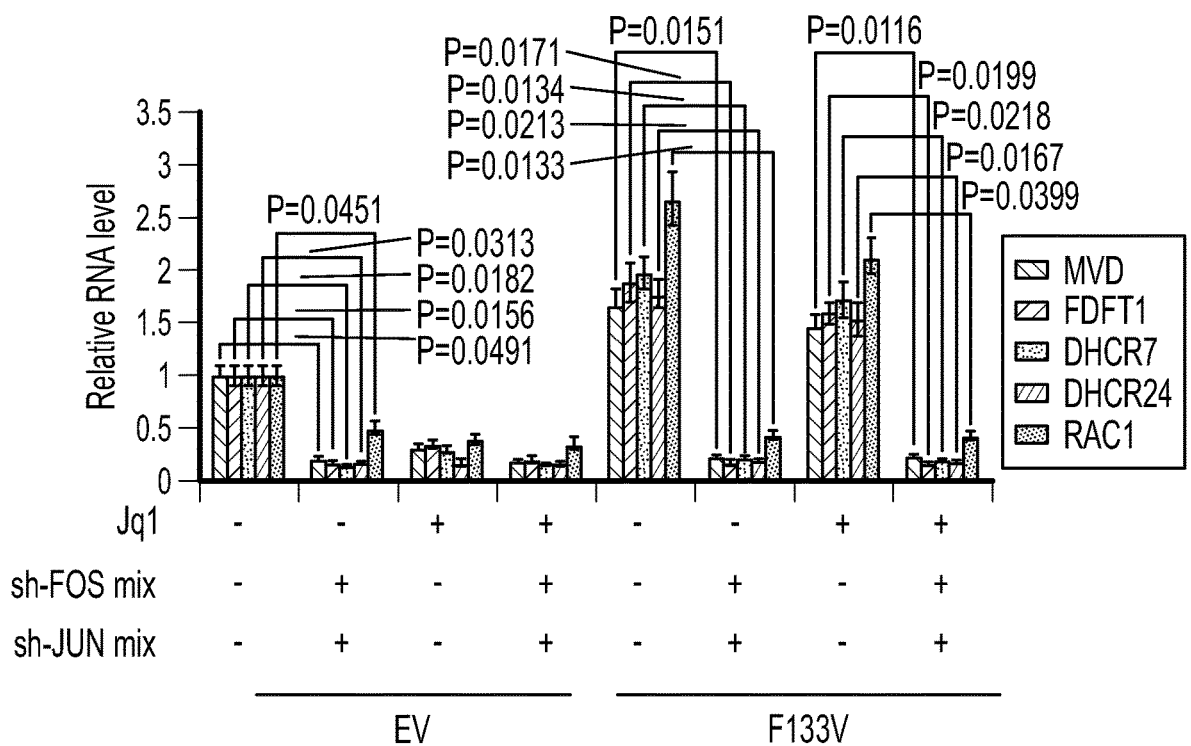
FIG. 13N and FIG. 13O, RT-qPCR (FIG. 13N) and Western blot (FIG. 13O) analysis of indicated proteins in whole cell lysate of C4-2 cells infected with empty vector (EV) or SPOP F133V expressed vectors and with or without FOS or JUN knockdown for 48 hours before being harvested.
Figure 13O:
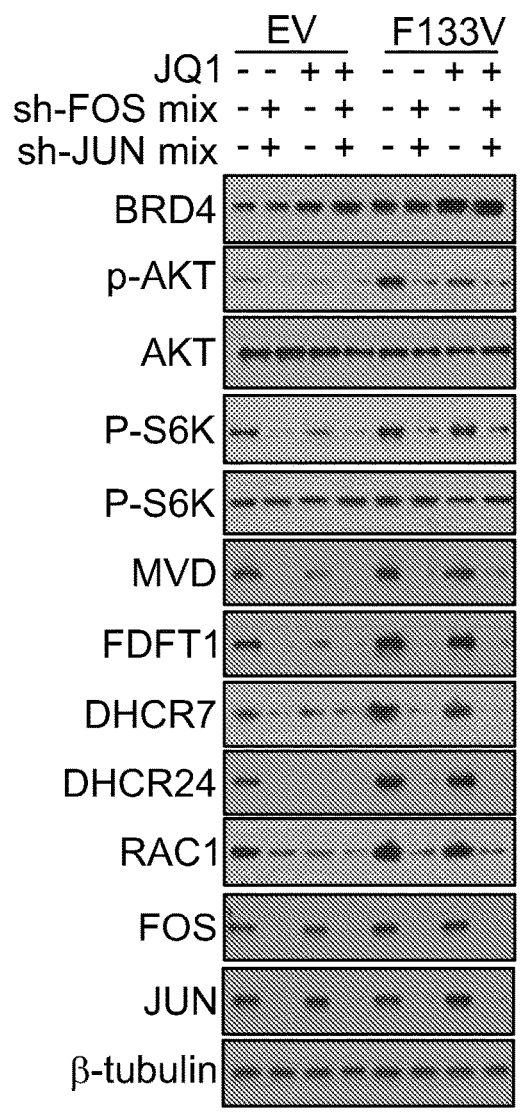
Figure 13P:
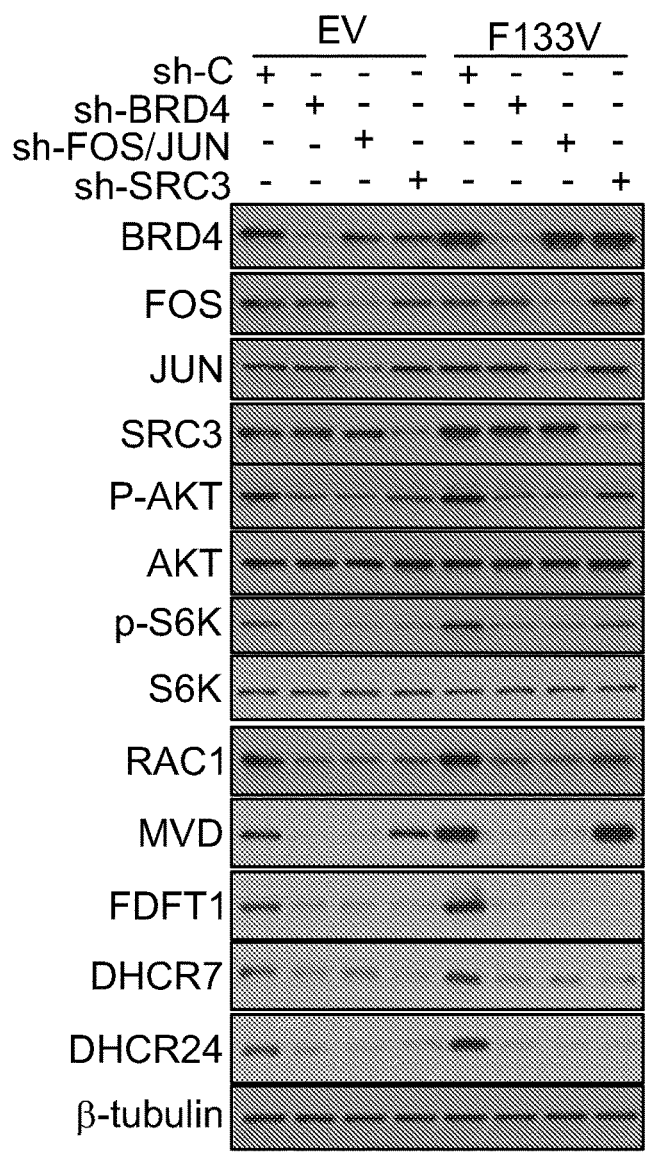

The transcription activator protein 1 (AP-1, a dimer of c-JUN and c-FOS) was demonstrated to bind to RAC1 and cholesterol synthesis gene promoters (FIGS. 13l and 13m). Although expression of c-JUN and c-FOS was not affected by SPOP mutation, knockdown of both abolished SPOP F133V-induced upregulation of RAC1 and cholesterol synthesis genes and activation of AKT/mTORC1 without disturbing BRD4 expression (FIGS. 13n-p). It has been shown that AKT/mTORC1 pathway is activated in the prostate of SPOP F133V knock-in mice and that this effect is mediated partially by increased SRC-3 expression (Blattner et al., Cancer Cell, 31:436-451 (2017)). Results provided herein demonstrate that SRC-3 knockdown only partially decreased SPOP F133V-induced AKT/mTORC1 activation by selectively affecting expression of RAC1 and the cholesterol synthesis genes and slightly, but did not significantly, diminish F133V-mediated JQ1 resistance (FIGS. 8f and 13p), reinforcing a partial, co-activator role of SRC-3 in SPOP F133V-mediated AKT/mTORC1 activation. In contrast, depletion of BET proteins almost completely abolished F133V-induced AKT/mTORC1 activation, upregulation of RAC1 and cholesterol synthesis genes, and BET inhibitor resistance (FIGS. 7a-c and 13p).

Figure 7I:
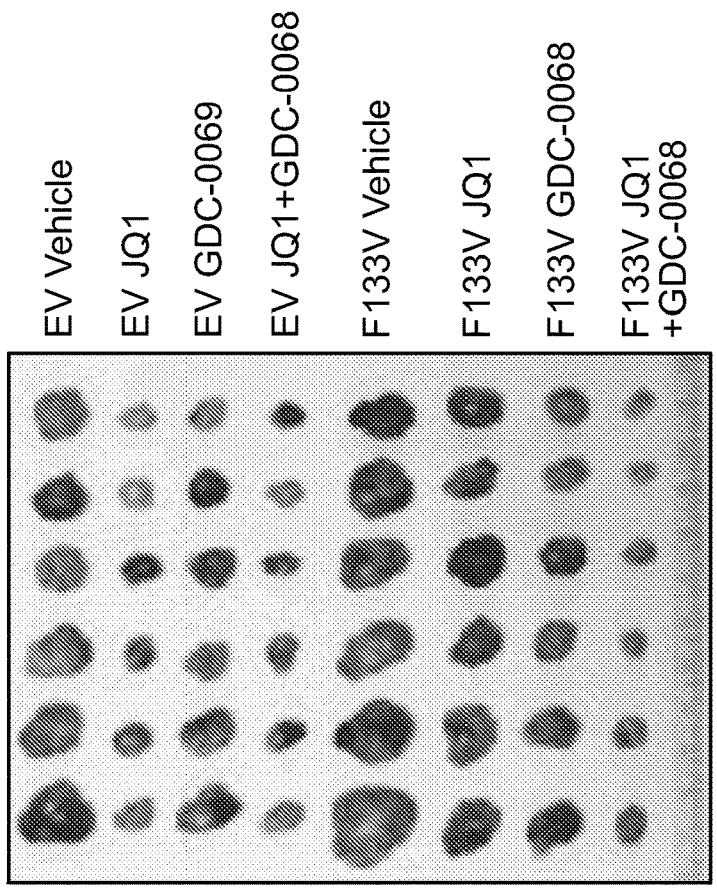
Figure 7H:
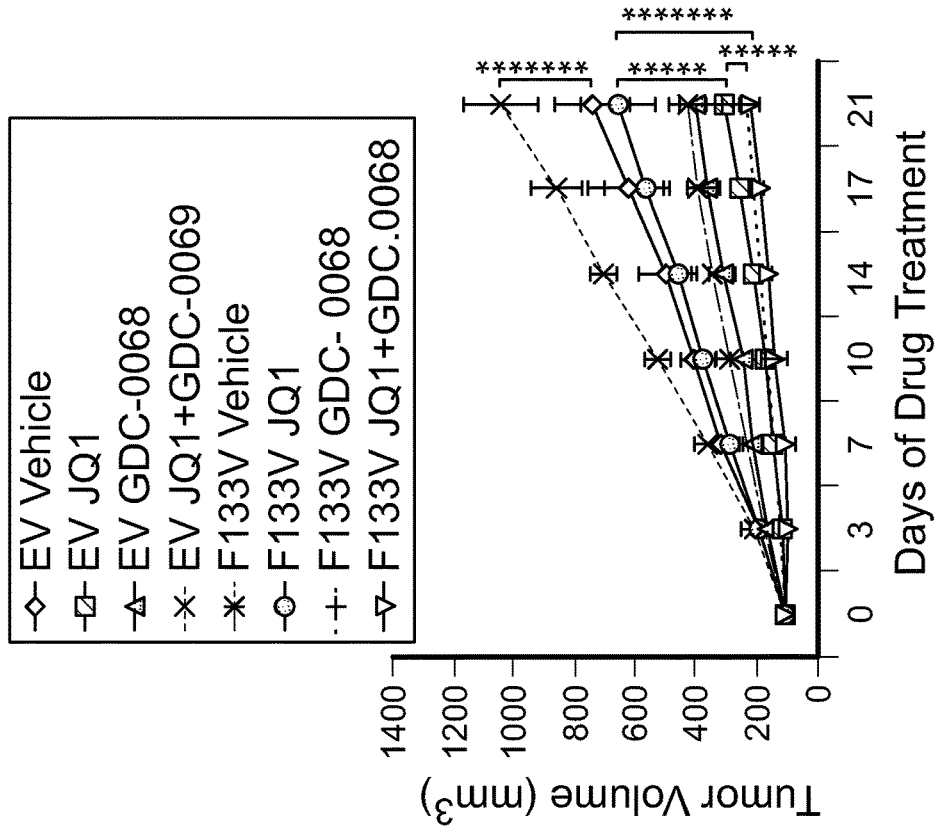
Figure 14A:
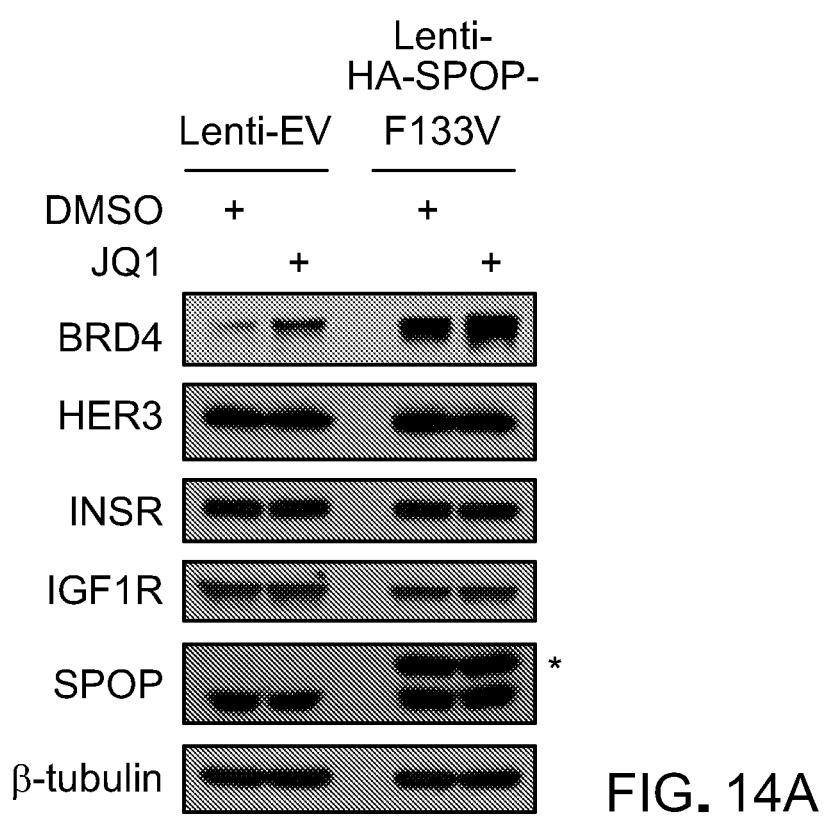
FIGS. 14A-14J. Assessment of the effect of the AKT pathway on SPOP F133V-mediated JQ1 resistance and a hypothetical model for the current study.
Figure 14B:
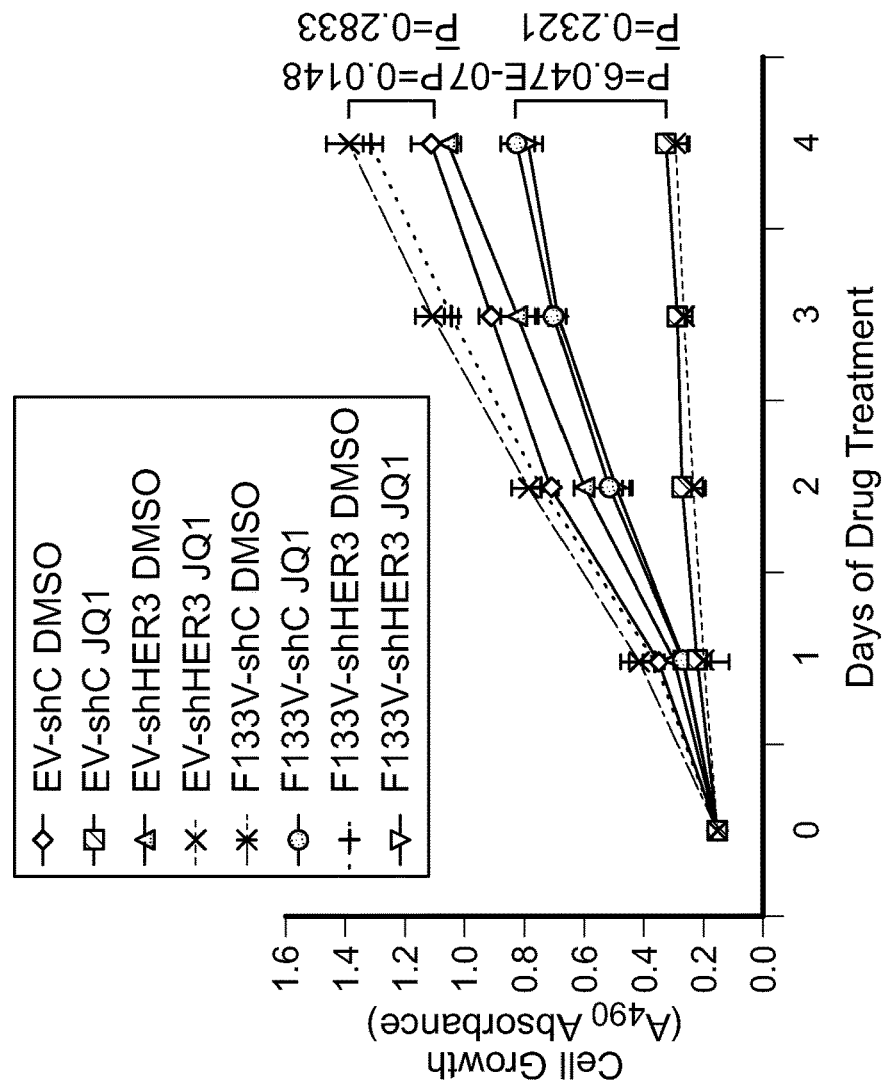
Figure 14C:
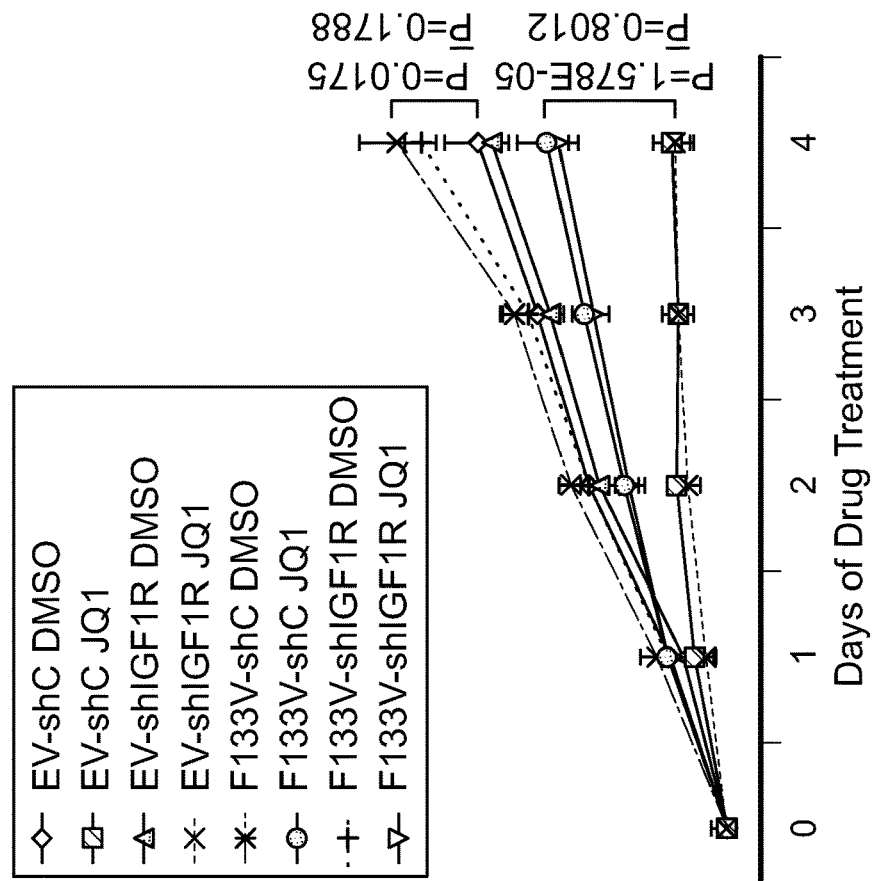
Figure 14C:
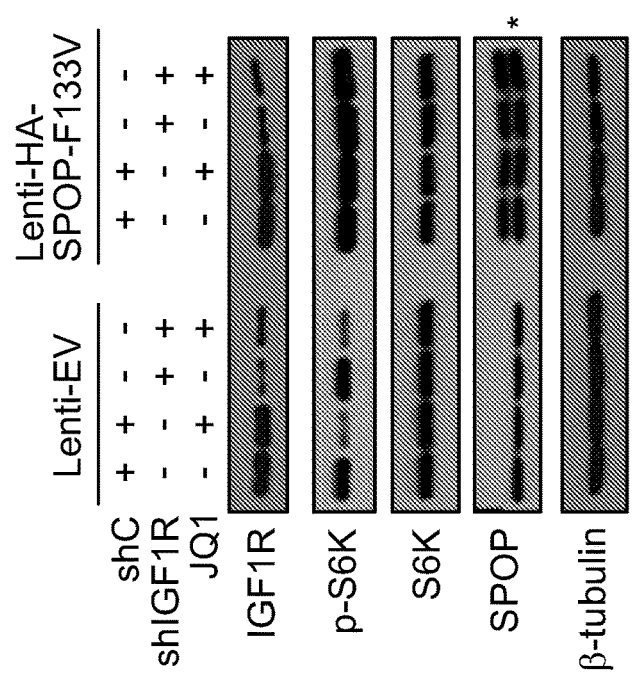
Figure 14D:
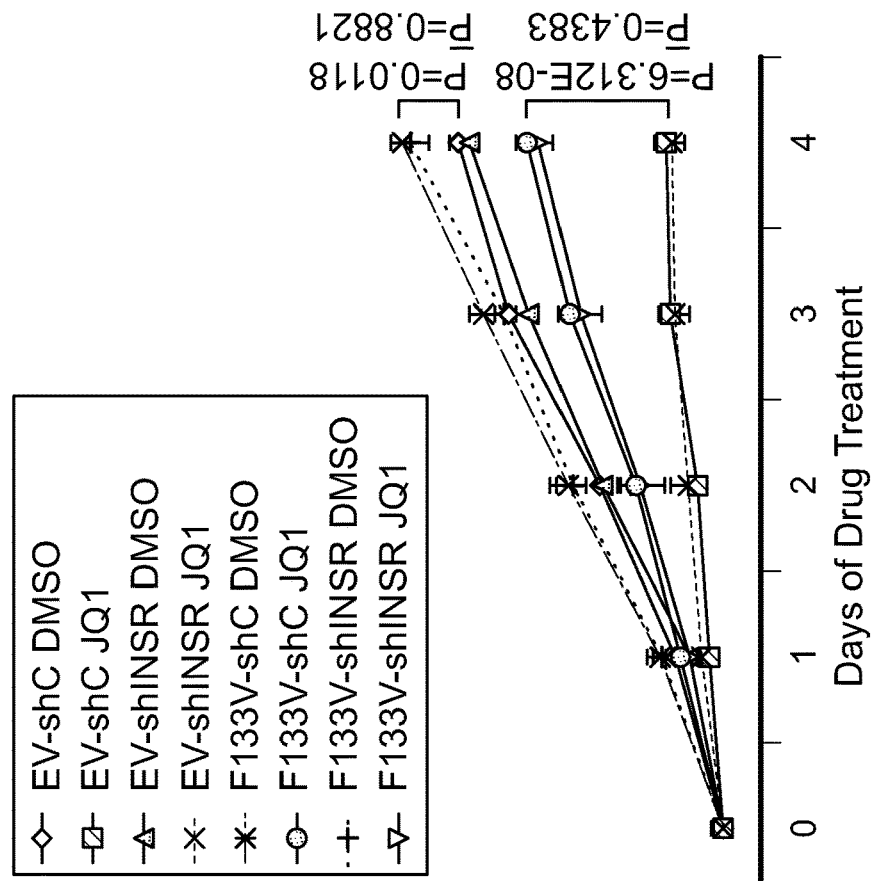
Figure 14D:
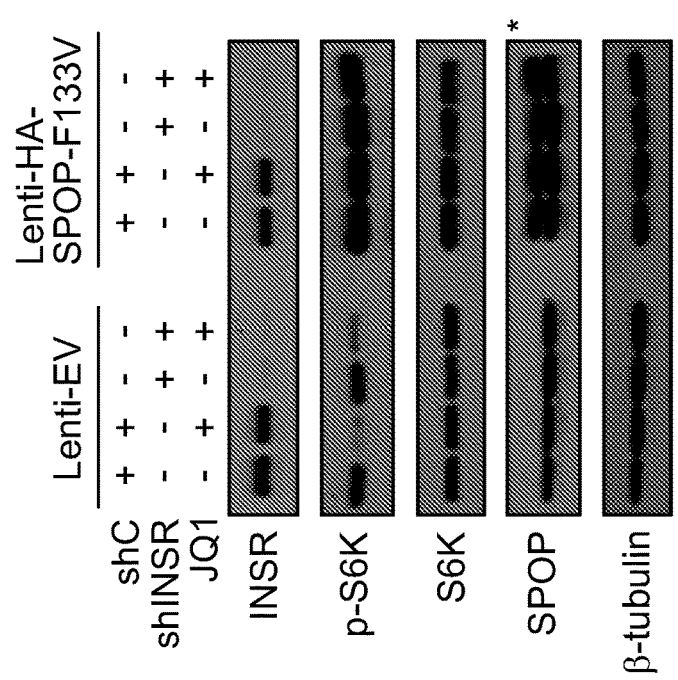
Figure 14E:
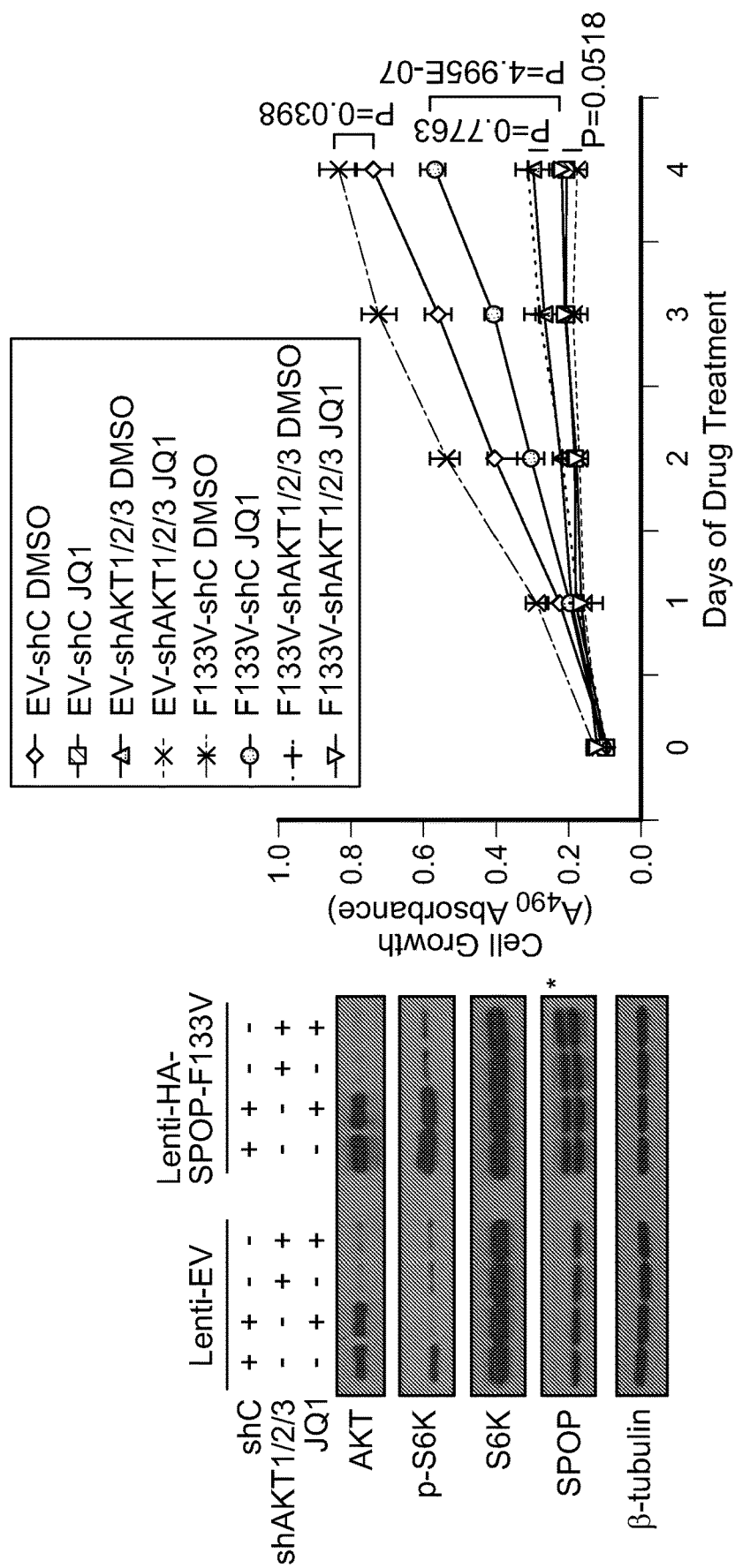
Figure 14F:
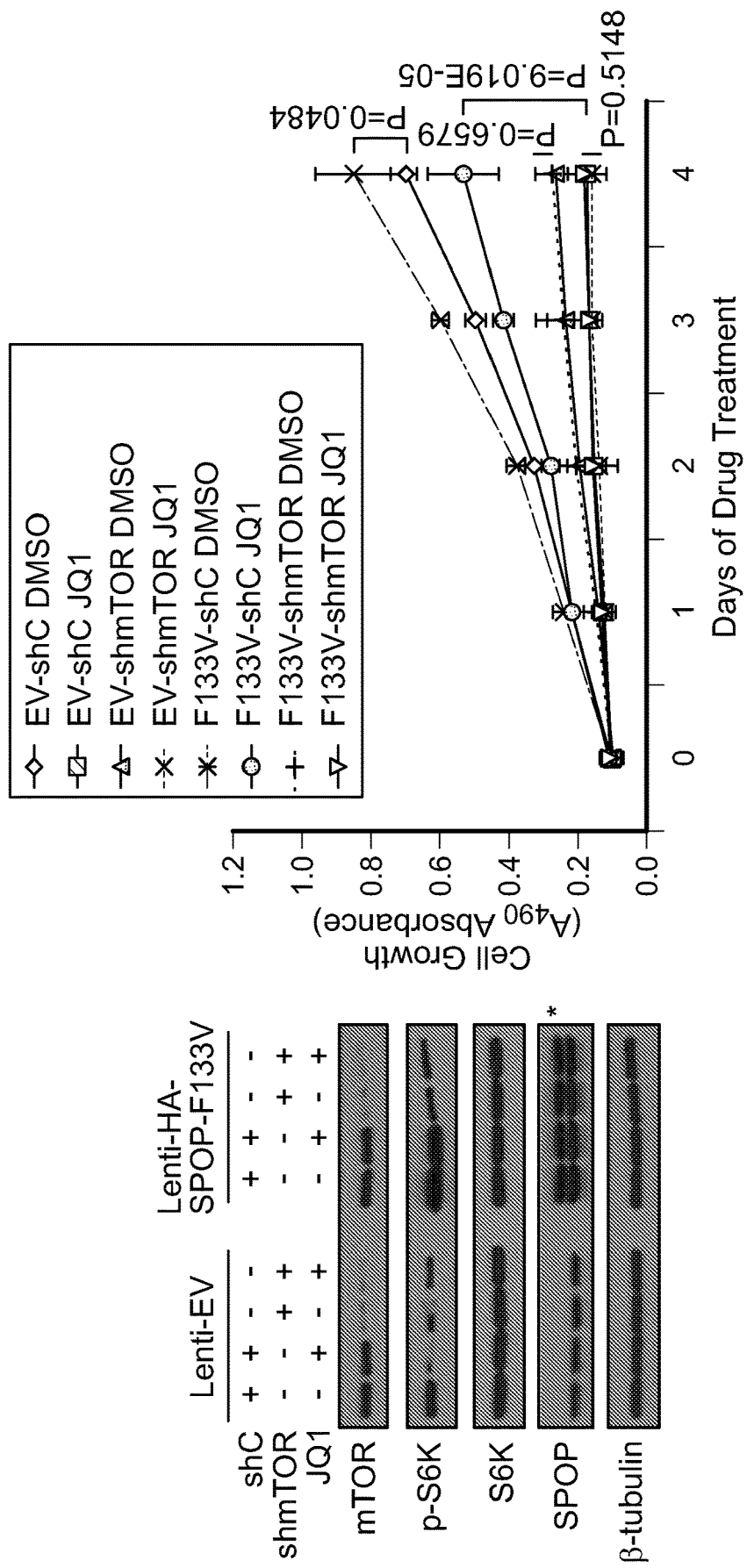
Figure 14G:
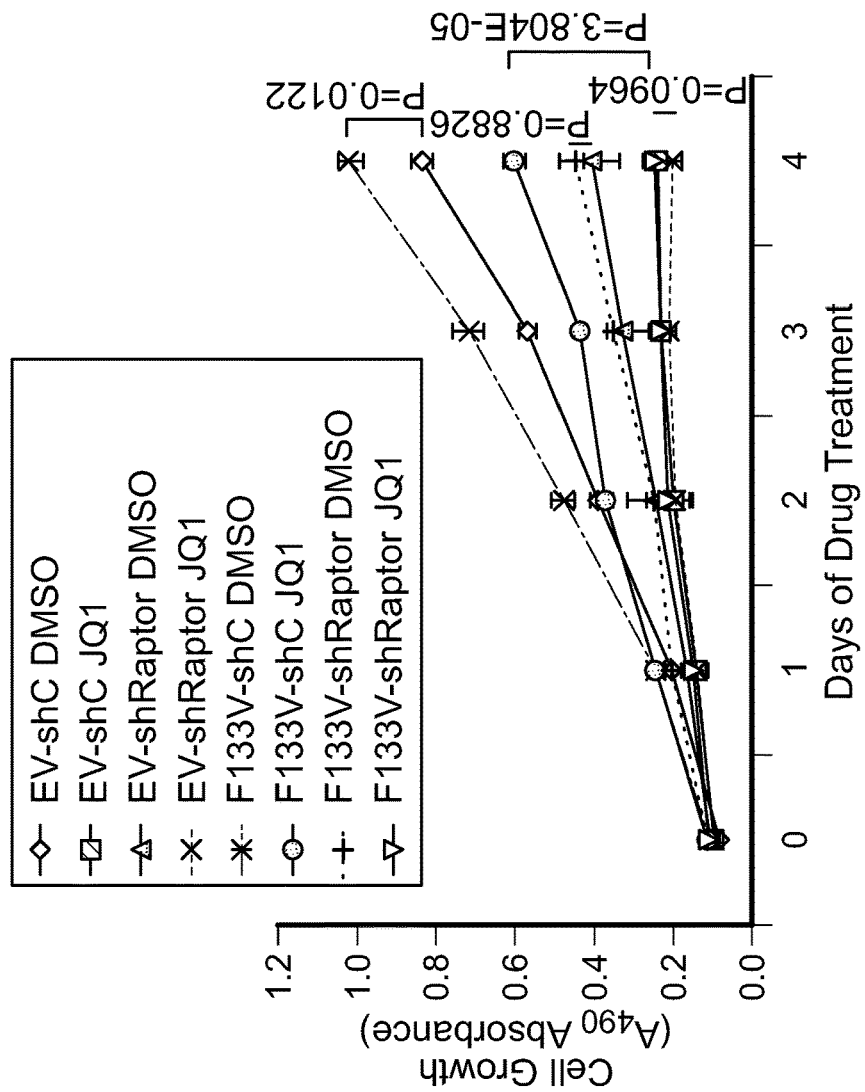
Figure 14H:
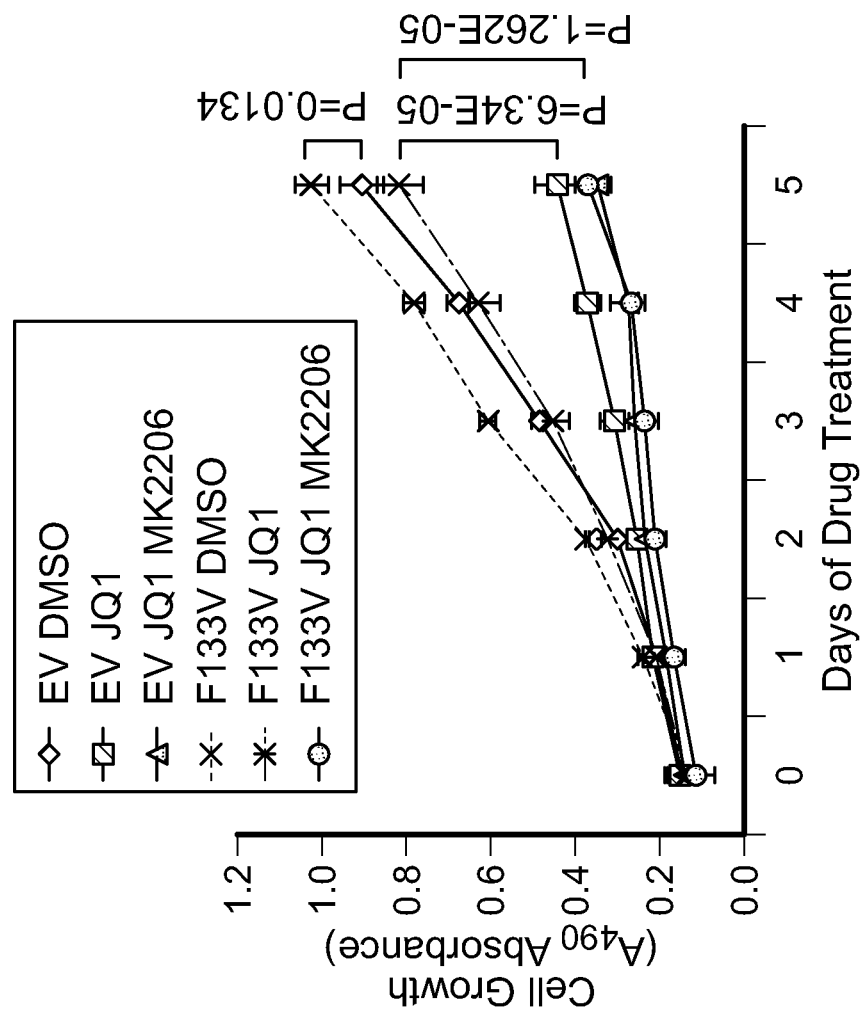
Figure 14H:
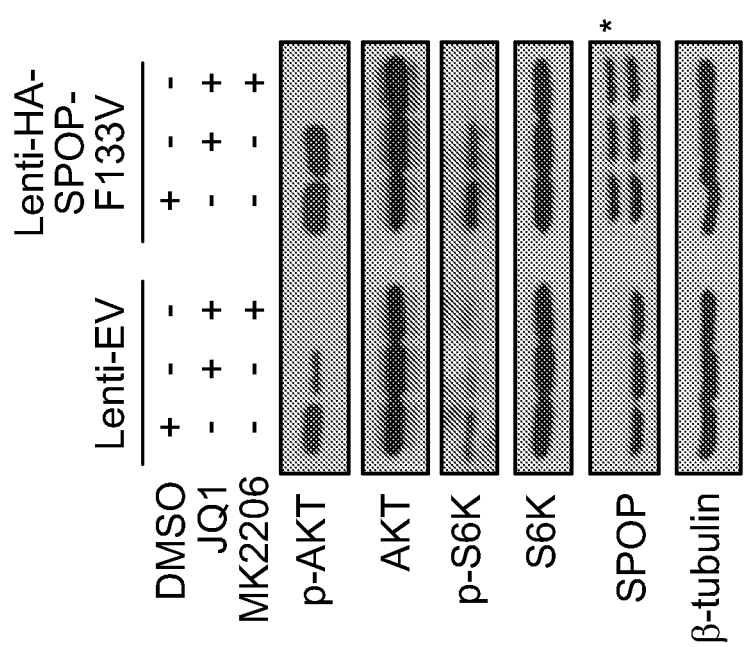
Figure 14I:
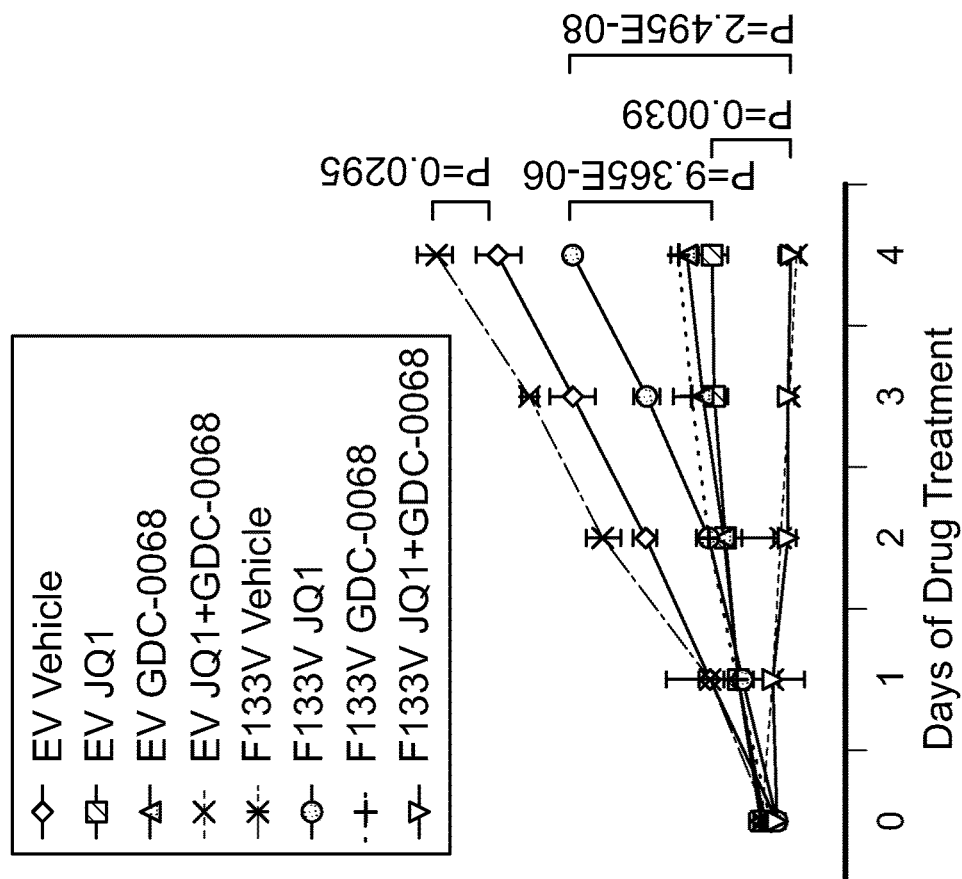
Figure 14I:
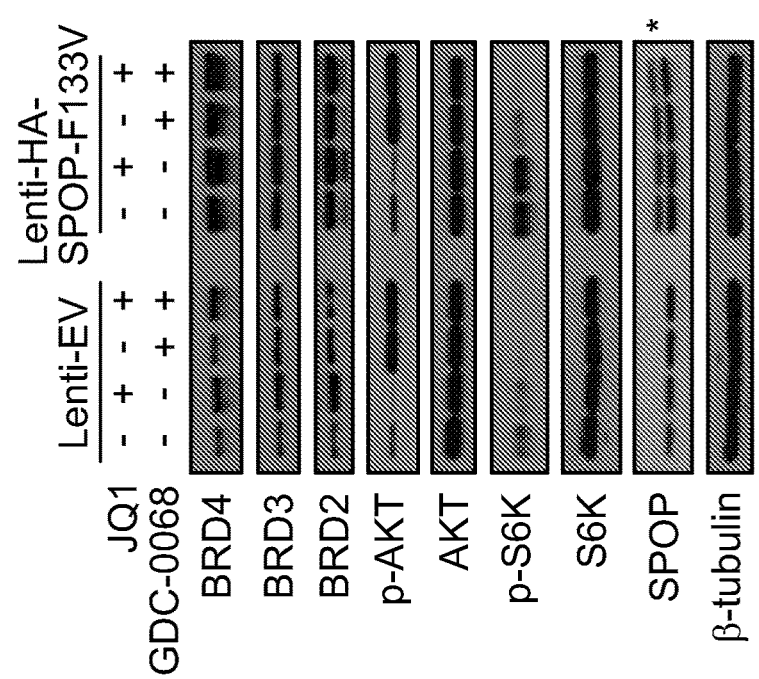
Figure 14J:
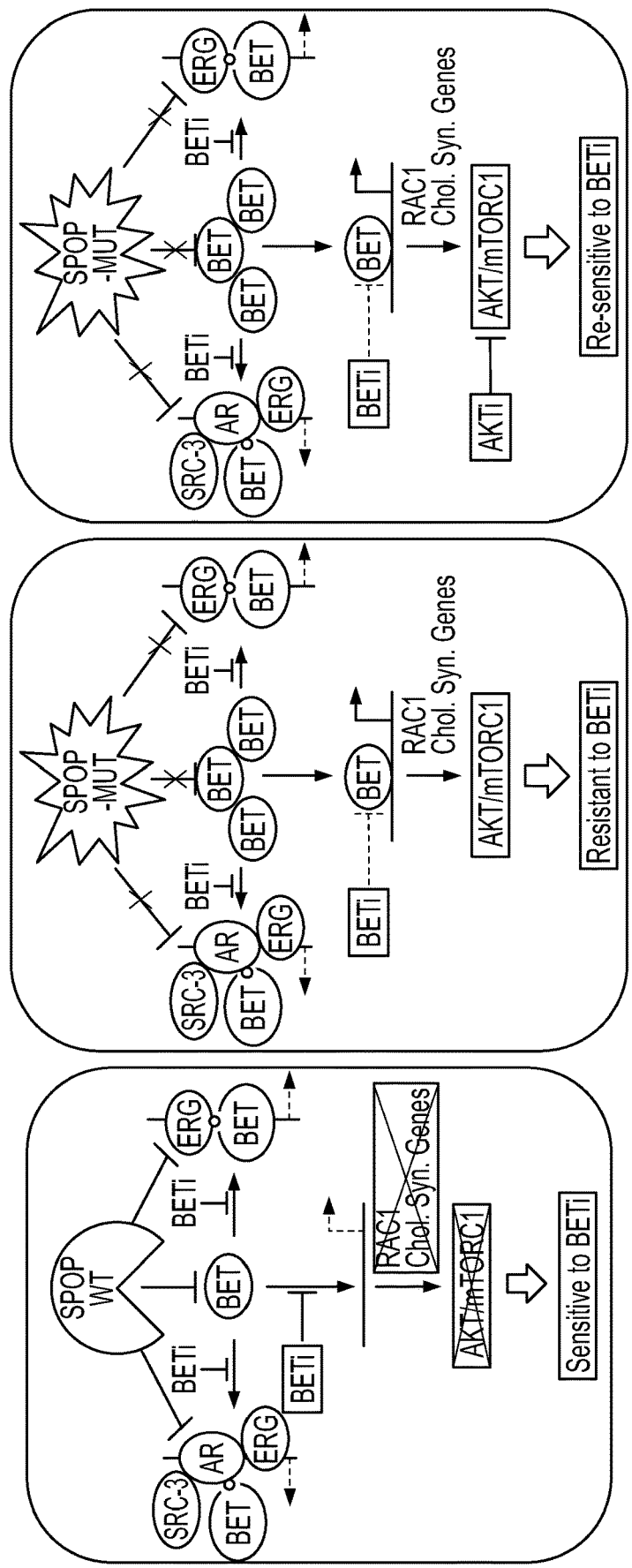

It has been shown that PI3K inhibitor treatment induced expression of receptor tyrosine kinases (RTKs) including HER3, IGF1R and INSR, and the induction was mediated by BRD4, but blocked by BET inhibitor (Stratikopoulos et al., Cancer Cell, 27:837-851 (2015)). However, BET inhibitor treatment alone had no effect on RTK expression (Stratikopoulos et al., *Cancer Cell*, 27:837-851 (2015)). Similarly, no effect of JQ1 on expression of these proteins was detected in either JQ1-sensitive (control) or -resistant (SPOP-F133V) C4-2 cells (FIG. 14a). In addition, neither mTORC1 activity (S6K phosphorylation) nor JQ1-resistant growth was affected by knockdown of HER3, IGF1R, or INSR individually in SPOP F133V expressing C4-2 cells (FIGS. 14b-d). These results ruled out the potential role of these RTKs in F133V-induced AKT activation and JQ1 resistance in these cells. In contrast, knockdown of AKT (AKT1, AKT2 and AKT3), mTOR, or Raptor alone abolished JQ1-resistant growth of SPOP F133V-expressing C4-2 cells (FIGS. 14e-g). Similar results were obtained by treating SPOP-F133V cells with the allosteric AKT inhibitor, MK2206 (FIG. 14h). Ipatasertib (GDC-0068), an ATP-competitive AKT inhibitor, has been shown to exhibit effective antitumor efficacy in patients with solid tumors (Saura et al., *Cancer Discov.*, 7:102-113 (2017)). GDC-0068 treatment of SPOP mutant expressing cells not only abolished SPOP mutation-induced activation of AKT downstream pathways, but also completely overcame SPOP mutation-conferred resistance to BET inhibitor in C4-2 cells in culture and tumors in mice (FIGS. 7h, 7i, and 14i). These results demonstrate the significance of AKT inhibition in overcoming BET inhibitor resistance in SPOP-mutated prostate cancer (FIG. 14j).

Taken together, the results provided herein demonstrate that BRD2/3/4 proteins are degradation substrates of SPOP. SPOP mutation not only induced accumulation of these proteins, but also conferred intrinsic resistance to BET inhibitors in prostate cancer cells, suggesting that besides SPOP mutations, elevation of BET proteins can be a biomarker to predict BET inhibitor resistance in prostate cancer patients.

The results provided herein also demonstrate that (i) expression of mutant SPOP (e.g., an SPOP-F133V mutant) not only increases the basal levels of phosphorylation of AKT-mTORC1 pathway proteins, but also largely impedes JQ1-induced inhibition of their phosphorylation, and (ii) that targeting the AKT pathway using therapeutic agents such as an AKT inhibitor (e.g., Ipatasertib) can be a viable treatment option to overcome BET inhibitor resistance in SPOP-mutated cancer (e.g., SPOP-mutated prostate cancer).

Example 2—DUB3 Promotes BET Inhibitor Resistance and Cancer Progression by Deubiquitinating BRD4

Cell Culture and Transfection

C4-2, PC-3, and DU145 cells were cultured in RPMI medium supplemented with 10% fetal bovine serum (FBS). 293T cells were cultured in DMEM medium supplementary with 10% FBS. All cell lines were kept in a 37° C. incubator at 5% $CO_2$. Transfections were performed by using Lipofectamine 2000 (Thermo Fisher Scientific).

RNA Interference

Lentivirus-based control and gene-specific small hairpin RNAs (shRNAs) were purchased from Sigma-Aldrich. Viral packaging plasmids (pEXQV and pVSV-G) and shRNA plasmid were transfected to 293T cells by using Lipofectamine 2000. After 24 hours, virus culture medium was replaced with DMEM containing 10% FBS with 1:100 of sodium Pyruvate. 48 hours post transfection, medium was collected and added to prostate cancer cells added with 12 µg/mL of polybrene. Prostate cancer cells were harvested 48 hours after puromycin selection. shRNA sequence information is provided in Table 6.

TABLE 6

Real-time RT-PCR primer sequences.

| Species | Gene | Forward (5'-3') | Reverse (5'-3') |
|---|---|---|---|
| Human | GAPDH | ACCCAGAAGA CTGTGGATGG (SEQ ID NO: 57) | TTCAGCTCAG GGATGACCTT (SEQ ID NO: 58) |
| Human | β-actin | GACCTCTATG CCAACACAGT (SEQ ID NO: 59) | AGTACTTGCG CTCAGGAGGA (SEQ ID NO: 60) |
| Human | BRD4 | GGAAGAGGAC AAGTGCAAGC (SEQ ID NO: 61) | GCTTCAGGGT CTCAAAGTCG (SEQ ID NO: 62) |
| Human | NCOR2 | GTGTACCCGC TGCTGTACC (SEQ ID NO: 63) | CTGGTGTTGC CTGGAGACTT (SEQ ID NO: 64) |
| Human (ChIP target: BRD4) | NCOR2 | CCCCCTCTGG CTCCTTAAA (SEQ ID NO: 65) | AGGAGAAGAG GGAGGGGAAG (SEQ ID NO: 66) |
| Human (ChIP target: NCOR2) | DUB3 | GGCCACACAG TTGCCTTATT (SEQ ID NO: 67) | ATGACGGTAG CTGCCAAAAG (SEQ ID NO: 68) |
| Human (ChIP target: HDAC10) | DUB3 | GGCCACACAG TTGCCTTATT (SEQ ID NO: 67) | ATGACGGTAG CTGCCAAAAG (SEQ ID NO: 68) |

Tissue Microarray and Immunohistochemistry (IHC) Scoring

The prostate cancer tissue microarray (TMA) slides including 53 cases of prostate cancer TMA specimens, were stained with NCOR2, BRD4, and DUB3 antibodies by standard immunohistochemistry procedures. The IHC staining was scored based on staining intensity and ratio of positive cells as described elsewhere (Jin et al., *Cancer Res.*, 77:4328-4341 (2017)). A final IHC staining index (SI) score for each specimen was determined using the following formula: ratio of positive cells Xintensity.

Co-Immunoprecipitation (Co-IP) Cells were harvested and lysed by IP buffer (50 mM Tris-HCl, pH 7.4, 150 mM NaCl, 1% Triton X-100, 1% sodium deoxycholate and 1% protease inhibitor cocktails) on ice for more than 15 minutes. Cell lysate was centrifuged for 15 minutes at 13,000 rpm at 4° C., and the supernatant was incubated with primary antibodies and protein A/G agarose beads (Thermo Fisher Scientific) with rotating at 4° C. overnight. The next day, the pellet was washed at least six times with 1×IP buffer on ice, and then subjected to western blotting analysis.

Western Blotting

Cells were harvested and lysed by IP buffer (50 mM Tris-HCl, pH 7.4, 150 mM NaCl, 1% Triton X-100, 1% sodium deoxycholate and 1% protease inhibitor cocktails) on ice for more than 15 minutes. Cell lysate was centrifuged for 15 minutes at 13,000 rpm at 4° C., and the supernatant was quantified by BCA protein quantification assay. Equal amounts of protein sample were added into 4× sample buffer and boiled for 5 minutes. The sample was subjected to SDS-PAGE analysis and transferred to nitrocellulose membrane. The membrane was blocked by 5% milk for 1 hour at room temperature and incubated with primary antibody at 4° C. overnight. The next day, the membrane was washed three times with 1×TBST and incubated with horseradish peroxidase-conjugated secondary antibodies for 1 hour at room temperature. The protein bands were visualized by SuperSignal West Pico Stable Peroxide Solution (Thermo Fisher Scientific).

Quantitative RT-PCR

Total RNA was isolated using TRIzol reagent (Thermo Fisher Scientific). The NanoDrop 2000 spectrophotometer (Thermo Fisher Scientific) was used to assess RNA yield and quality. RNA was reversely transcribed using Superscript II reverse transcriptase (Thermo Fisher Scientific) following manufacturer's instructions. Quantitative real-time PCR was performed by mixing cDNA, gene-specific primers and IQ SYRB Green Supermix and detected by iCycler QTX detection system (Bio-Rad). The 2-ΔCt method was used to quantitate fold changes by normalizing to GAPDH. Primer for RT-qPCR is provided in Table 6.

Chromatin Immunoprecipitation (ChIP) and ChIP-reChIP Assay

ChIP was performed as described elsewhere (Boyer et al., Cell, 122:947-956 (2005)). For ChIP-reChIP assay DNA, cell lysates were sonicated and subjected to immunoprecipitation using NCOR2 antibody. After washed by RIPA buffer (50 mM Hepes-KOH, pH 7.6, 500 mM LiCl, 1 mM EDTA, 1% NP-40, 0.7% Na-Deoxycholate), the protein-DNA complexes were eluted by elution buffer (10 mM Tris, 1 mM EDTA, 2% SDS, and 20 mM DTT, PH 7.5) for 30 minutes at 37° C. Then, the supernatant was diluted 20 times and subjected to the second ChIP using IgG or HDAC10 antibodies using the method described elsewhere (Li et al., Nature, 513:251-255 (2014)). DNA pulled down by antibodies or nonspecific IgG was amplified by real-time PCR. The information for ChIP primers is provided in Table 6.

Cell Proliferation

Cell proliferation was measured by using the MTS assay (Promega). Prostate cancer cells (2,000 per well) were seeded in 96-well plates with 100 µL of culture medium. Each well was added with 20 µL of CellTiter 96R AQueous One Solution Reagent (Promega) and absorbance was measured in a microplate reader at 490 nm.

Colony Formation Assay

An appropriate number of cells for different dosages of JQ1 were plated onto 6-well plate and treated with JQ1 for three days. After three-day treatment, the medium was changed with fresh medium without drugs for another 8 days. The colonies were fixed with acetic acid: methanol (1:7) for 30 minutes and stained with crystal violet (0.5% w/v) for 1 hour. Colonies with more than 50 cells were counted. The linear regression was applied to generate the survival curve.

Generation and Treatment of Prostate Cancer Xenografts in Mice 6-week-old NOD-SCID IL-2-receptor gamma null (NSG) mice were generated in house and used for animal experiments. All mice were housed in standard conditions with a 12 hour light/dark cycle and access to food and water ad libitum. For studies with tumors treated with JQ1 and the CDK4/6 inhibitor PD0332991, DU145 cells ($5\times10^6$) infected with lentivirus expression shRNA control or DUB3-specific shRNA (in 50 µL 1×PBS plus 50 µL Matrigel (BD Biosciences)) were injected s.c. into the right flank of mice. After xenografts reached a size of approximately 100 mm³, vehicle (10% β-cyclodextrin (intraperitoneal injection) and saline (oral administration)), JQ1 (50 mg per kg bodyweight (intraperitoneal injection)), and PD0332991 (150 mg per kg bodyweight (oral administration)) were administrated individually or in combination 5 days per week. The volume of xenografts was measured every other day for 21 days and estimated using the formula $L\times W^2\times 0.5$ (L: length, W: width). Upon the completion of measurement, tumor grafts were harvested.

Quantification and Statistical Analysis

All values were expressed as means±SD. Statistical analyses were performed with Student t test for single comparison and one way ANOVA and a post hoc test for multiple comparisons. P values<0.05 are considered statistically significant. Pearson's product-moment correlation was used to calculate the correlation between NCOR2, BRD4, and DUB3 staining index in prostate cancer TMAs.

Reagents

Other reagents used are listed in Table 7.

TABLE 7

| REAGENT or RESOURCE | SOURCE | IDENTIFIER |
| --- | --- | --- |
| Antibodies | | |
| Mouse monoclonal anti-USP7 | Santa Cruz | Cat# sc-137008 |
| Rabbit polyclonal anti-DUB3 | Abcam | Cat# ab129931 |
| Mouse monoclonal anti-USP10 | Santa Cruz | Cat# sc-365828 |
| Mouse monoclonal anti-USP13 | Santa Cruz | Cat# sc-514416 |
| Mouse monoclonal anti-USP15 | Santa Cruz | Cat# sc-100629 |
| Rabbit polyclonal anti-USP28 | Cell Signaling Technology | Cat# 4217S |
| Rabbit polyclonal anti-USP49 | Abcam | Cat# ab127547 |
| Rabbit monoclonal anti-BRD4 | Abcam | Cat# ab128874 |
| Rabbit monoclonal anti-BRD2 | Abcam | Cat# ab139690 |
| Rabbit polyclonal anti-BRD3 | Bethyl Laboratories | Cat# A302-368A |
| Rabbit polyclonal anti-HDAC10 | Abcam | Cat# ab53096 |
| Rabbit polyclonal anti-NCOR2 | Abcam | Cat# ab24551 |
| Rabbit polyclonal anti-SPOP | Proteintech | Cat# 16750-1-AP |
| Mouse monoclonal anti-ERK2 | Santa Cruz | Cat# sc-135900 |
| Mouse monoclonal anti-c-Myc | Santa Cruz | Cat# sc-40 |
| Mouse monoclonal anti-FLAG M2 | Sigma-Aldrich | Cat#F-3165 |
| Mouse monoclonal anti-HA.11 | Covance | Cat#MMS-101R |
| Peroxidase IgG Fraction Monoclonal Mouse Anti-Rabbit IgG | Jackson ImmunoResearch | Cat#211-032-171 |
| Peroxidase AffiniPure Goat Anti-Mouse IgG | Jackson ImmunoResearch | Cat#115-035-174 |
| Bacterial and Virus Strains | | |
| E. coli DH5α | Thermo Fisher | Cat#18258012 |
| E. coli BL21 | Thermo Fisher | Cat#C600003 |
| lentivirus-expressing HDAC10-shRNAs | Sigma-Aldrich | SHCLNG-NM_032019 |

TABLE 7-continued

| REAGENT or RESOURCE | SOURCE | IDENTIFIER |
|---|---|---|
| lentivirus-expressing NCOR2-shRNAs | Sigma-Aldrich | SHCLNG-NM_006312 |
| lentivirus-expressing BRD4-shRNAs | Sigma-Aldrich | SHCLNG-NM_058243 |
| lentivirus-expressing SPOP-shRNAs | Sigma-Aldrich | SHCLNG-NM_025287 |
| Chemicals, Peptides, and Recombinant Proteins | | |
| MG132 | Sigma-Aldrich | Cat#M8699 |
| Cycloheximide | Sigma-Aldrich | Cat#01810 |
| JQ1 | Sigma-Aldrich | Cat#SML1524 |
| Lipofectamine 2000 reagent | Thermo Fisher | Cat#11668500 |
| I-BET762 | Selleckchem | Cat# S7189 |
| PD0332991 | Selleckchem | Cat# S1116 |
| Critical Commercial Assays | | |
| KOD Plus Mutagenesis Kit | Toyobo | Cat# F0936K |
| Deposited Data | | |
| Raw data and images | This paper and Mendeley Data | http://dx.doi.org/10.17632/s83f5y9ntt.1 |
| Experimental Models: Cell Lines | | |
| Human: C4-2 | Uro Corporation | N/A |
| Human: PC-3 | ATCC | CRL-1435 |
| Human: DU145 | ATCC | HTB-81 |
| Human: HEK293T | ATCC | CRL-11268 |
| Human: MIA PaCa-2 | ATCC | CRL-1420 |
| Human: MCF7 | ATCC | HTB-22 |
| Human: MDA-MB-231 | ATCC | HTB-26 |
| Human: MDA-MB-436 | ATCC | HTB-130 |
| Human: PANC-1 | ATCC | CRL-1469 |
| Human: 22Rv1 | ATCC | CRL-2505 |
| Oligonucleotides | | |
| See Table S1 for primer sequences | | |
| Recombinant DNA | | |
| Flag-DUB3 | Dr. Zhenkun Lou | (Liu et al., 2017) |
| HA-DUB3 | Dr. Zhenkun Lou | (Liu et al., 2017) |
| Flag-BRD3 | Dr. S. Jane Flint | (LeRoy et al., 2008) |
| Flag-BRD2 | Dr. S. Jane Flint | (LeRoy et al., 2008) |
| Flag-BRD4 | Dr. Tasuku Honjo | (Stanlie et al., 2014) |
| Flag-USP7 | Dr. Zhenkun Lou | (Yuan et al., 2010) |
| Flag-USP10 | Dr. Zhenkun Lou | (Yuan et al., 2010) |
| Flag-USP13 | Dr. Zhenkun Lou | (Yuan et al., 2010) |
| Flag-USP15 | Dr. Zhenkun Lou | (Yuan et al., 2010) |
| Flag-USP28 | Dr. Zhenkun Lou | (Yuan et al., 2010) |
| Flag-USP49 | Addgene | Cat##22586 |
| Software and Algorithms | | |
| ImageJ | NIH | N/A |
| GraphPad Prism 5.0 | Graphpad, Inc | N/A |

LeRoy et al., Mol. Cell., 30: 51-60 (2008); Stanlie et al., Mol. Cell., 55: 97-110 (2014); and Yuan et al., Cell, 140: 384-396 (2010).

Results

NCOR2 and HDAC10 Transcriptionally Repress Expression of DUB3

Figure 15A:
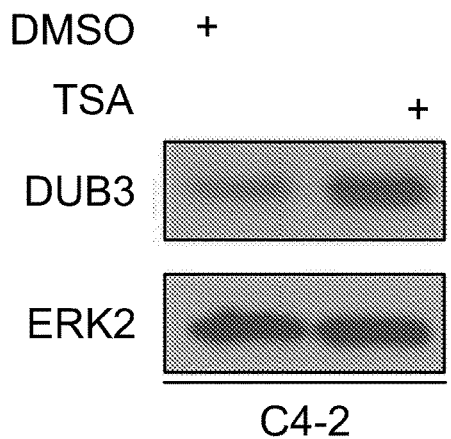
FIGS. 15A-15O. NCOR2 and HDAC10 transcriptionally repress DUB3 expression.
Figure 15B:
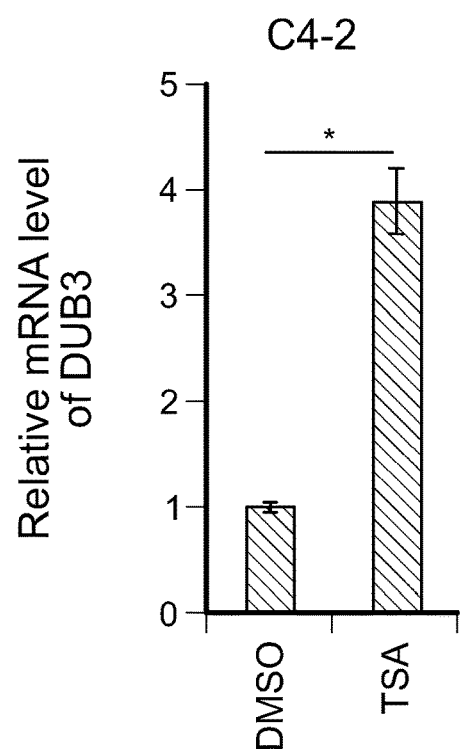
Figure 15C:
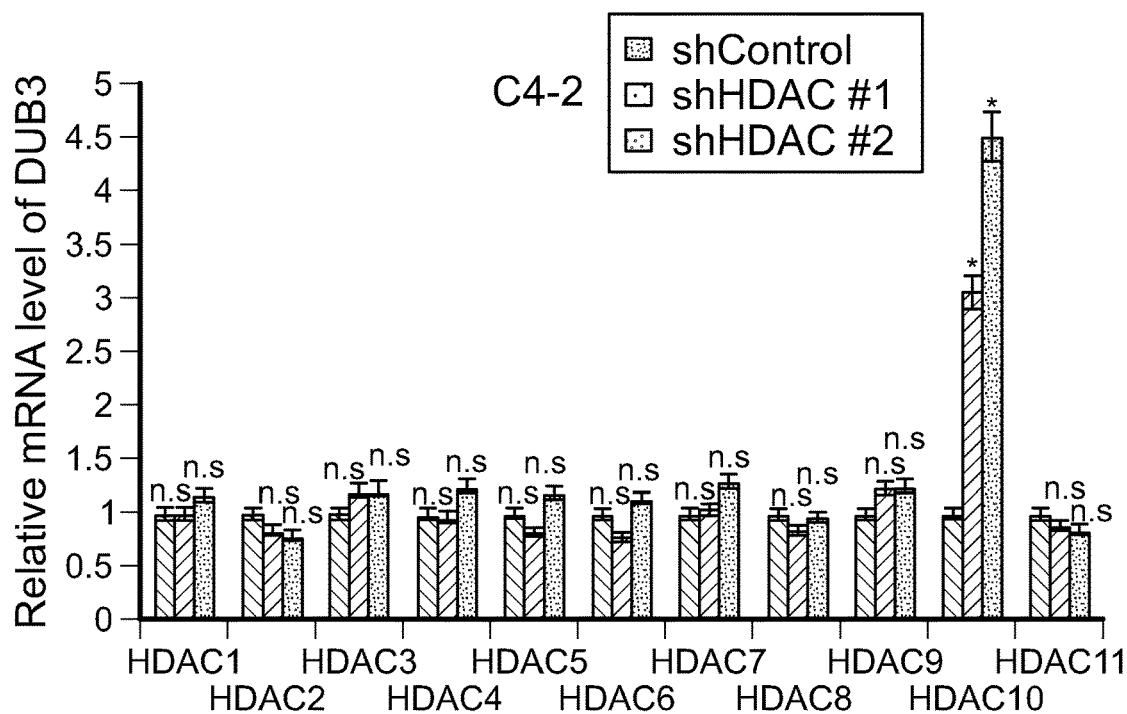
(FIG. 15C), C4-2 cells were infected with lentivirus expressing indicated shRNAs for 48 hours for RT-qPCR. Data are shown as mean±SD (n=3). *P<0.05, n.s., not significant comparing to shControl.

Treatment of pan class I/II HDAC inhibitors induces mRNA expression of USP 17L2 (also known as DUB3 or USP17) in breast cancer cells (Borbely et al., Oncotarget, 6:33623-33635 (2015)). Treatment with the pan histone deacetylase inhibitor trichostatin A (TSA) increased DUB3 protein and mRNA expression in C4-2 prostate cancer cells (FIGS. 15A and 15B). To determine which member(s) in the class I/II HDAC subfamilies mediates the transcriptional repression of DUB3 expression, an unbiased screen was performed by knocking down all eleven class I/II HDACs individually by using small hairpin RNAs (shRNAs). It was demonstrated that only knockdown of HDAC10 specifically resulted in a substantial increase in DUB3 mRNA expression in C4-2 cells (FIG. 15C). HDAC10 knockdown also markedly increased DUB3 protein in C4-2 cells, and similar results were obtained in another prostate cancer cell line PC-3 (FIGS. 15D and 15E).

Figure 15L:
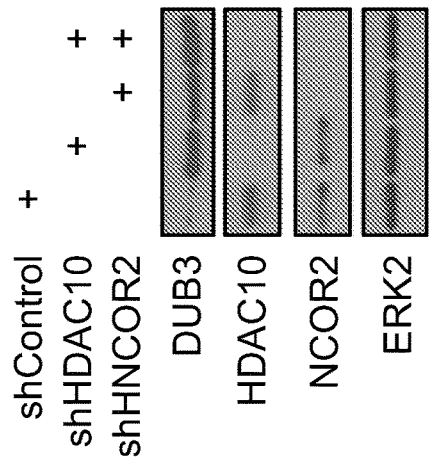
(FIG. 15L), ChIP-reChIP analysis examining the co-localization of HDAC10 and NCOR2 in the DUB3 gene promoters in C4-2 and PC-3 cells. Data are shown as mean±SD (n=3).* P<0.05.
Figure 15M:
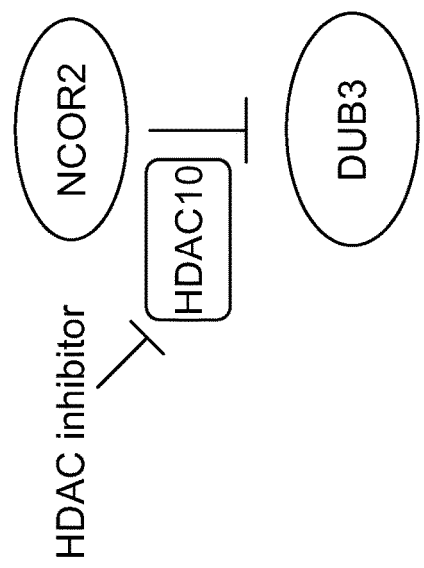
(FIG. 15M, FIG. 15N), C4-2 cells were infected with lentivirus expressing indicated shRNAs for 48 hours for Western blot (FIG. 15M) and RT-qPCR (FIG. 15N). Data are shown as mean±SD (n=3). n.s., not significant.
Figure 15N:
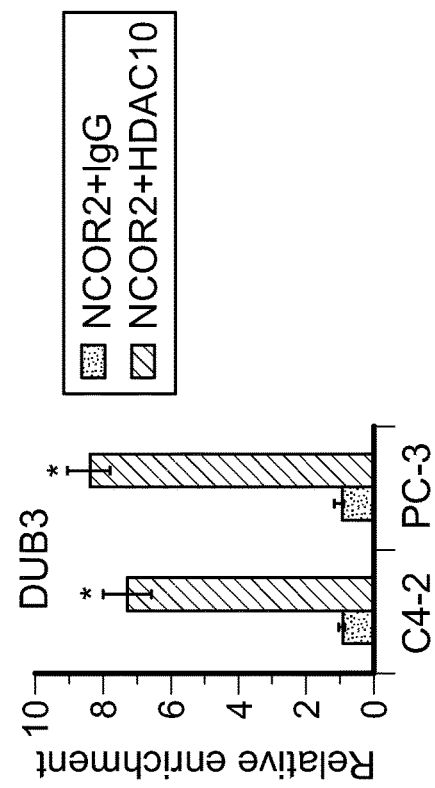
Figure 15O:
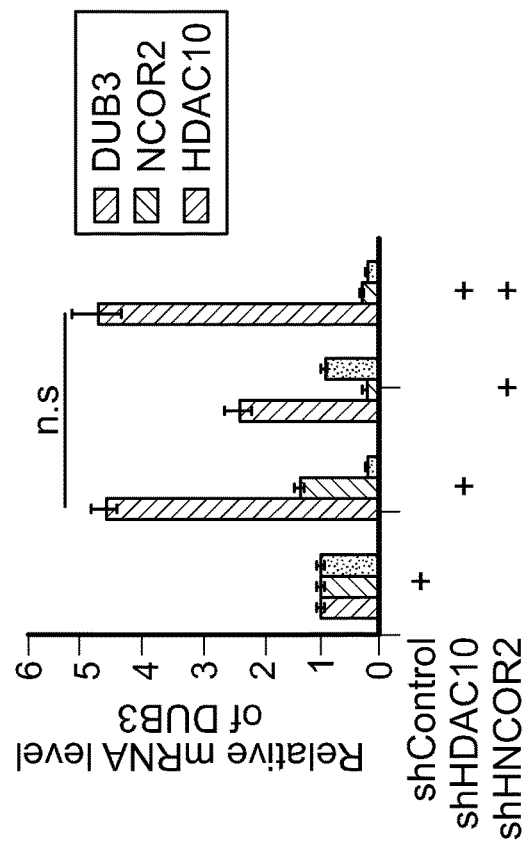

HDAC10 is a class II deacetylase that promotes gene transcription repression by forming a protein complex with nuclear receptor co-repressor (NCOR) proteins (Fischer et al., J. Biol. Chem., 277:6656-6666 (2002)). A study analyzing the co-expression of HDAC and NCOR genes in human gliomas shows that NCOR2 expression is clustered with HDAC10 and HDAC4, whereas NCOR1 is clustered with HDAC8 (Dali-Youcef et al., Sci. Rep., 5:9087 (2015)). The following was performed to examine whether NCOR2 plays any role in regulating DUB3 expression. Reciprocal co-immunoprecipitation (co-IP) revealed that endogenous HDAC10 and NCOR2 proteins interact with each other in C4-2 cells (FIGS. 15F and 15G). Similar to the effect of HDAC10 depletion (FIGS. 15D and 15E), knockdown of NCOR2 by two independent shRNAs increased DUB3 expression at both mRNA and protein level in C4-2 and PC-3 cells (FIGS. 15H and 15I). Chromatin Immunoprecipitation (ChIP) analyses demonstrated that both NCOR2 and HDAC10 occupied in the DUB3 gene promoter in both C4-2 and PC-3 cells (FIGS. 15J and 15K), and their co-occupation in the DUB3 gene promotor was further confirmed by ChIP-reChIP analyses (FIG. 15L). Co-knockdown of NCOR2 and HDAC10 failed to further increase DUB3 expression at both protein and mRNA level in comparison to each knockdown alone (FIGS. 15M and 15N). These data suggest that NCOR2 and HDAC10 work in concert in the same complex to repress expression of DUB3 in prostate cancer cells (FIG. 15O).

BRD4 Represses DUB3 Expression Via Transcriptional Activation of NCOR2

Figure 16A:
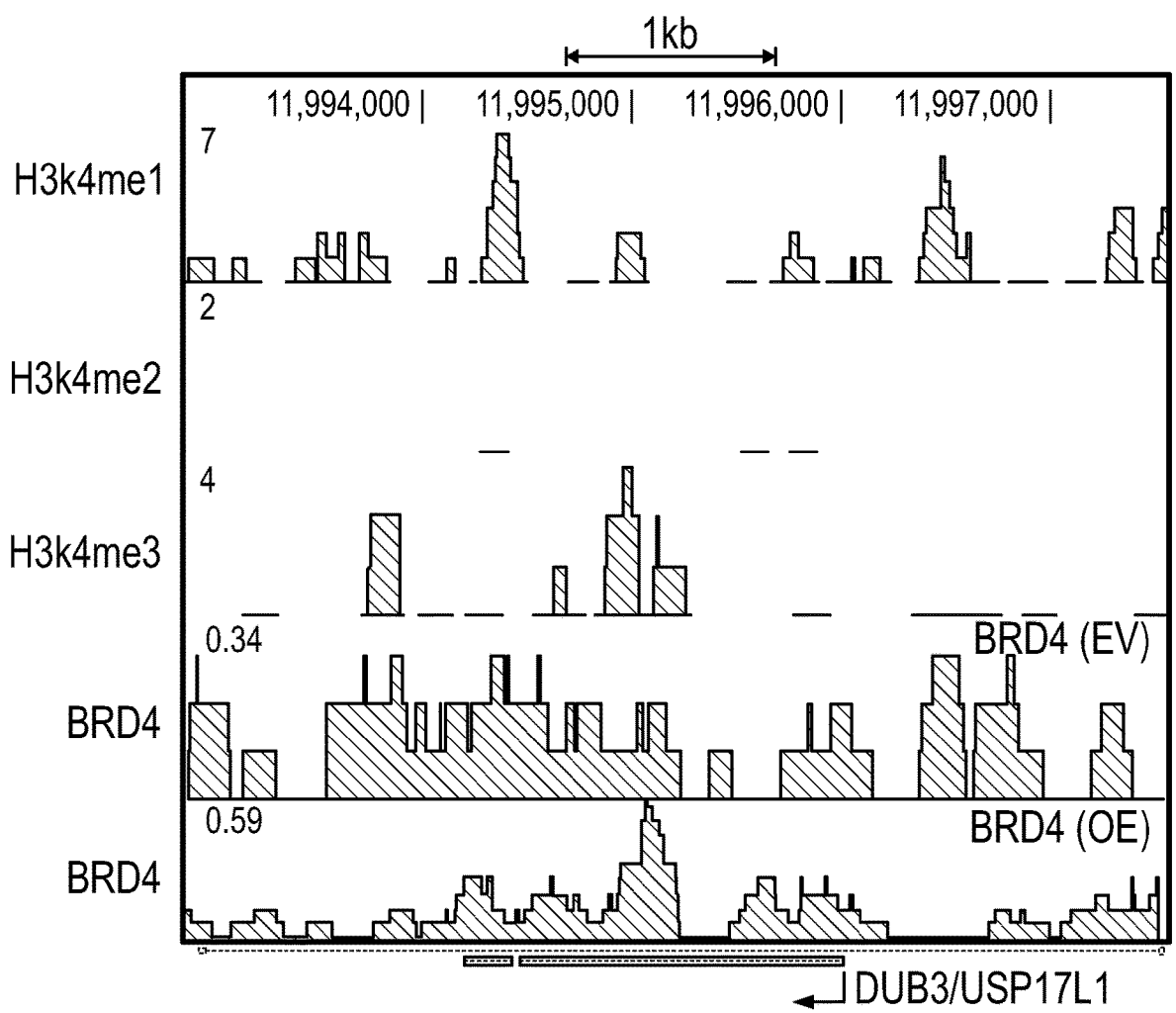
FIGS. 16A-16B. Analysis of BRD4 ChIP-seq data for BRD4 binding at the promoter of DUB3 and HDAC10 genes.
Figure 16B:
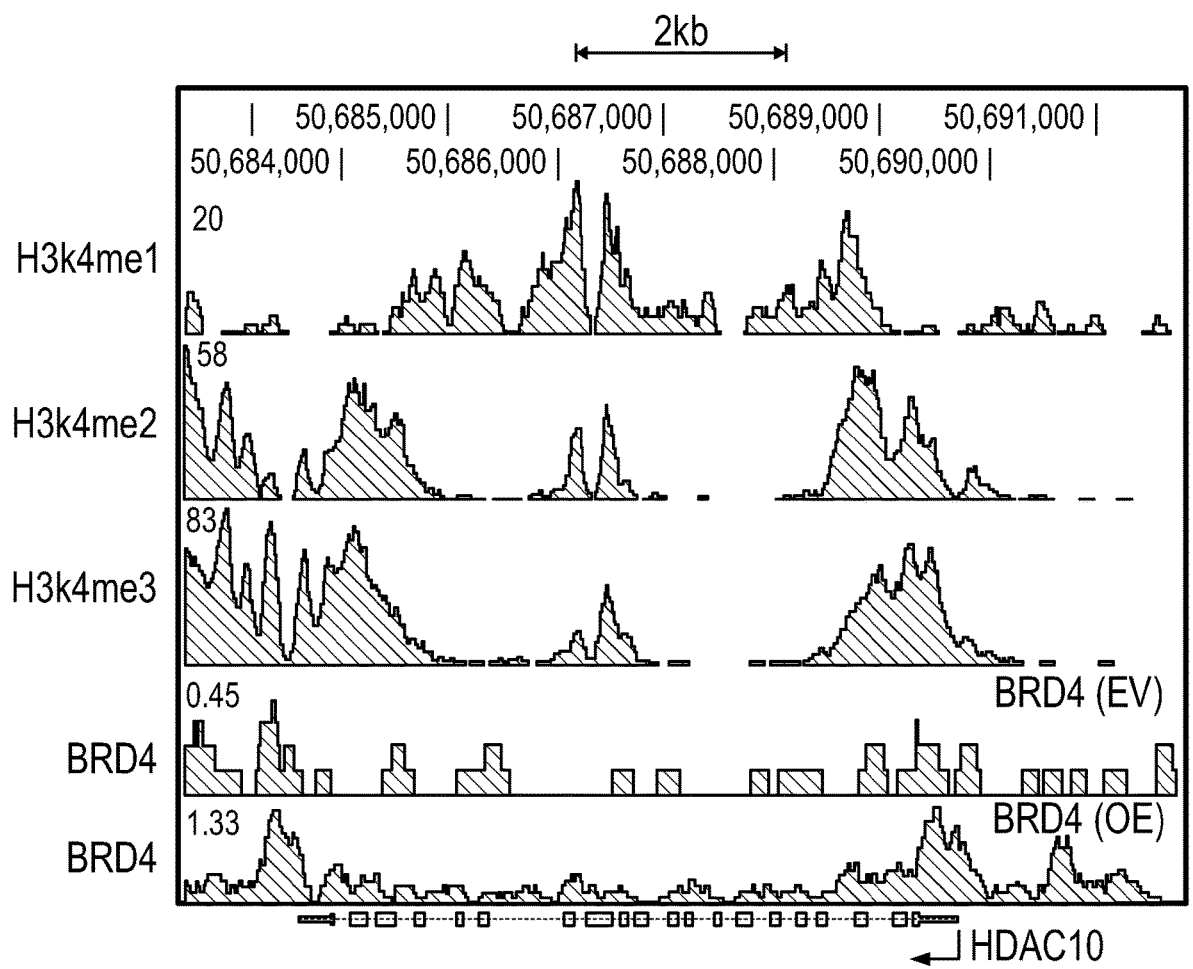
Figure 17F:
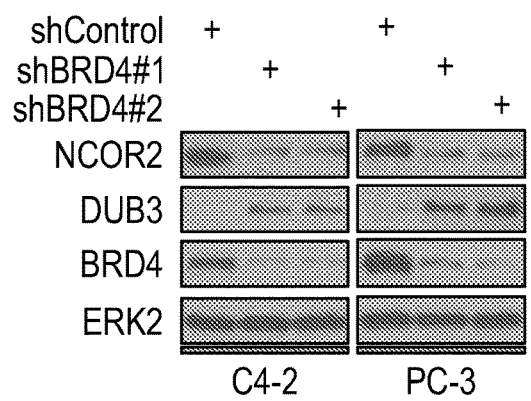
(FIG. 17F), Western blot analysis in C4-2 and PC-3 cells 48 hours after infected with indicated shRNAs.
Figure 17G:
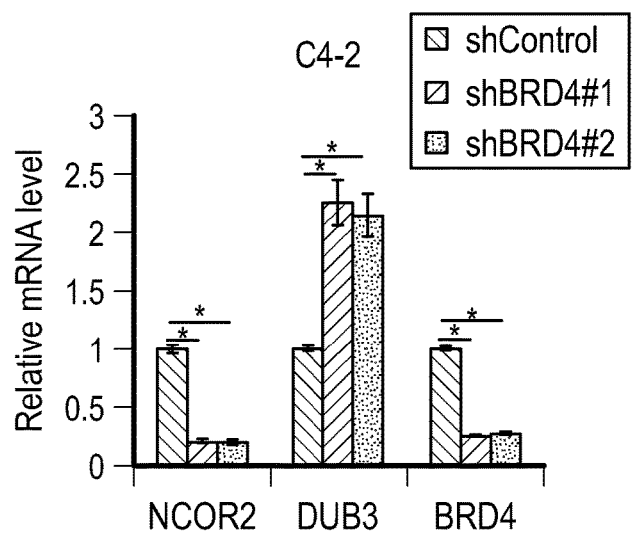
(FIG. 17G), RT-qPCR analysis in C4-2 cells 48 hours post infected with indicated shRNAs. Data are shown as mean±SD (n=3). *P<0.05.
Figure 17H:
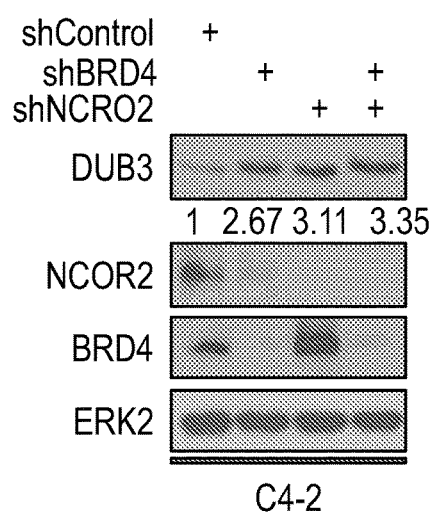
(FIG. 17H), Western blot analysis in C4-2 cells 48 hours post infected with indicated shRNAs. DUB3 proteins were quantified by ImageJ software.
Figure 17I:
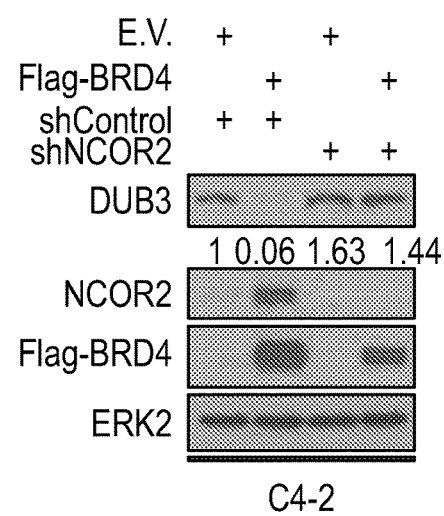
(FIG. 17I), C4-2 cells were infected with indicated shRNAs for 24 hours and further transfected with plasmids for another 24 hours for Western blot.
Figure 17J:
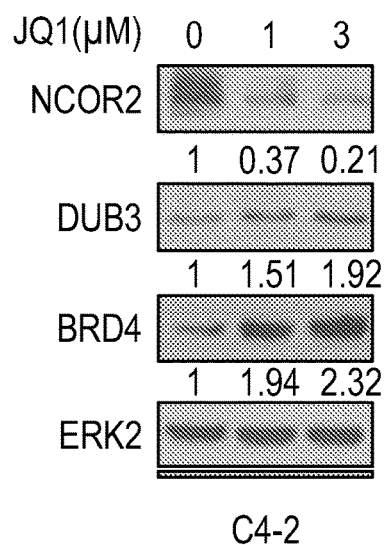
(FIG. 17J, FIG. 17K), C4-2 cells were treated JQ1 for 24 hours for Western blot (FIG. 17J) and RT-qPCR (FIG. 17K). Data are shown as mean±SD (n=3). *P<0.05. n.s., not significant.
Figure 17K:
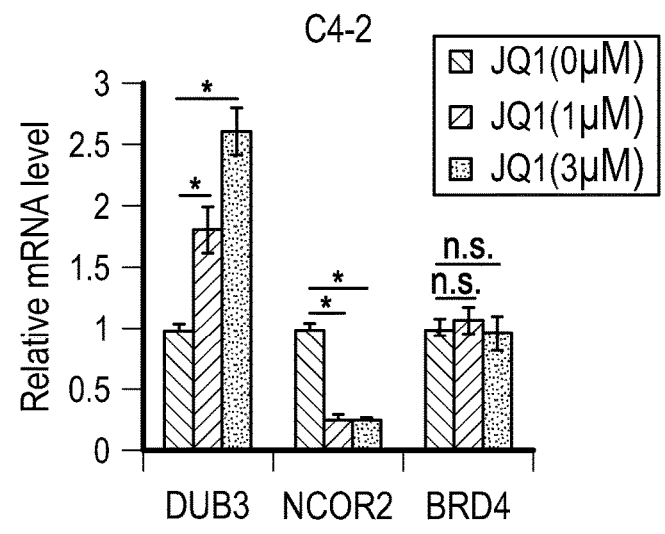
Figure 17L:
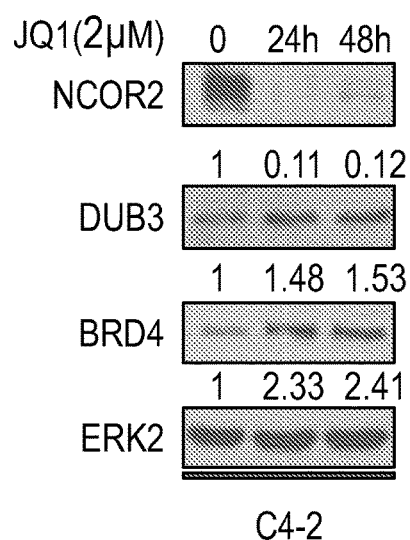
(FIG. 17L, FIG. 17M), C4-2 cells were treated with or without JQ1 for indicated periods for Western blot (FIG. 17J) and RT-qPCR (FIG. 17K). Data are shown as mean±SD (n=3). *P<0.05.
Figure 17M:
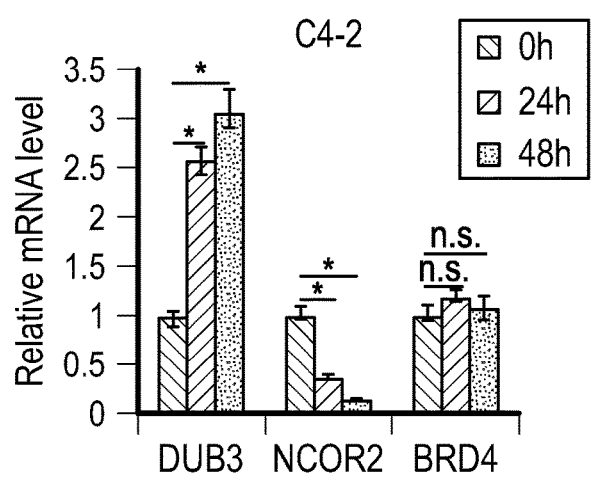
Figure 17N:
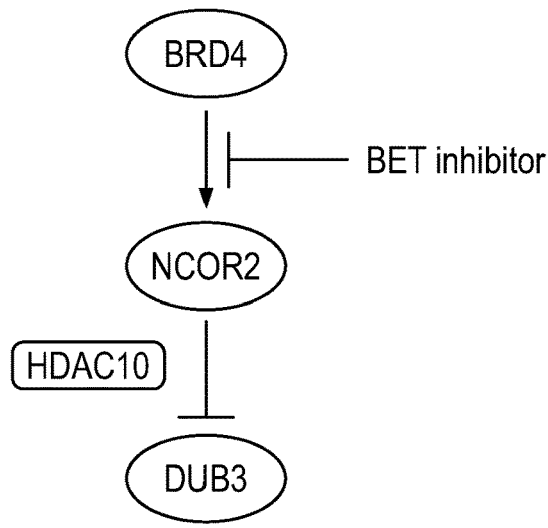

Treatment with the BRD4 inhibitor JQ1 induces rapid upregulation of DUB3 at the mRNA level (Borbely et al., Oncotarget, 6:33623-33635 (2015)). The following was performed to determine how DUB3 expression is regulated by BRD4. Existing BRD4 ChIP-seq data (Zhang et al. Nat. Med., 23:1055-1062 (2017)) were analyzed. There was no obviously detectable BRD4 binding peak in the promoter of DUB3 gene even in BRD4 overexpressing cells (FIG. 16A). These data suggest that BRD4 inhibition-induced downregulation of DUB3 mRNA may be mediated through an indirect mechanism. Since NCOR2 and HDAC10 were identified as upstream repressors of DUB mRNA expression (FIG. 15), the following was performed to determine whether BRD4 modulates DUB3 expression via regulating NCOR2 and/or HDAC10. Re-examination of BRD4 ChIP-seq data revealed a sharp BRD4 binding peak in the promoter of NCOR2, but not HDAC10 gene, in BRD4 over-expressing C4-2 cells (FIGS. 17A and 16B). This result was further confirmed by ChIP-qPCR in both C4-2 and PC-3 cells (FIGS. 17B and 17C). Using a gain-of-function approach, it was demonstrated that overexpression of BRD4 elevated NCOR2 expression but repressed DUB3 at both mRNA and protein levels in C4-2 cells (FIGS. 17D and 17E). In contrast, knockdown of BRD4 by two independent shRNAs decreased NCOR2 but increased DUB3 mRNA and protein expression in both C4-2 and PC-3 cells (FIGS. 17F and 17G). Most importantly, it was demonstrated that both BRD4 knockdown and overexpression-induced upregulation and downregulation of DUB3, respectively were completely abolished by NCOR2 co-knockdown in C4-2 cells (FIGS. 17H and 17I). In a dose- and time-dependent manner, the BRD4 inhibitor JQ1 decreased NCOR2 protein and mRNA expression in C4-2 cells, and the effect of JQ1 on DUB3 protein and mRNA expression was opposite (FIGS. 17J-17M). JQ1 treatment only increased BRD4 protein level, but not mRNA level (FIGS. 17J-17M), which was consistent with previous reports in various cell types (Asangani et al., Nature, 510:278-282 (2014); Lu et al., Chem. Biol., 22:755-763 (2015); and Zhang et al., Nat. Med., 23:1055-1062 (2017)). Taken together, these data indicate that BRD4 induces downregulation of DUB3 through upregulation of NCOR2, which acts as a repressor of DUB3 transcription (FIG. 17N).

DUB3 Promotes Deubiquitination of BRD4 Protein

Figure 18A:
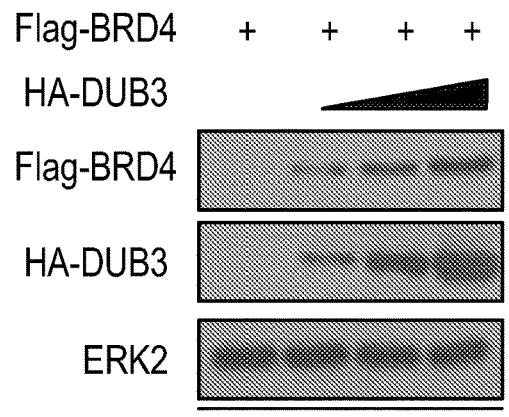
Figure 18B:
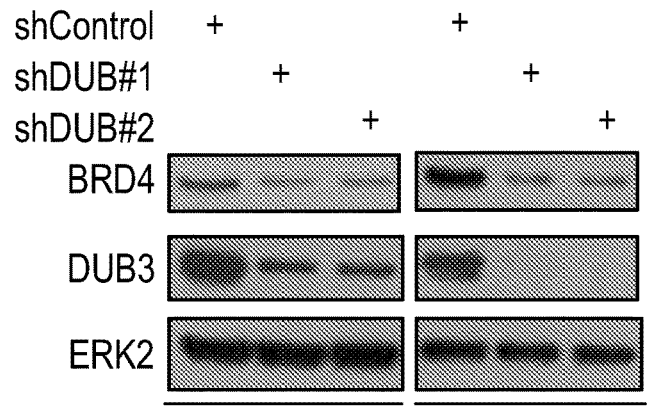
Figure 18F:
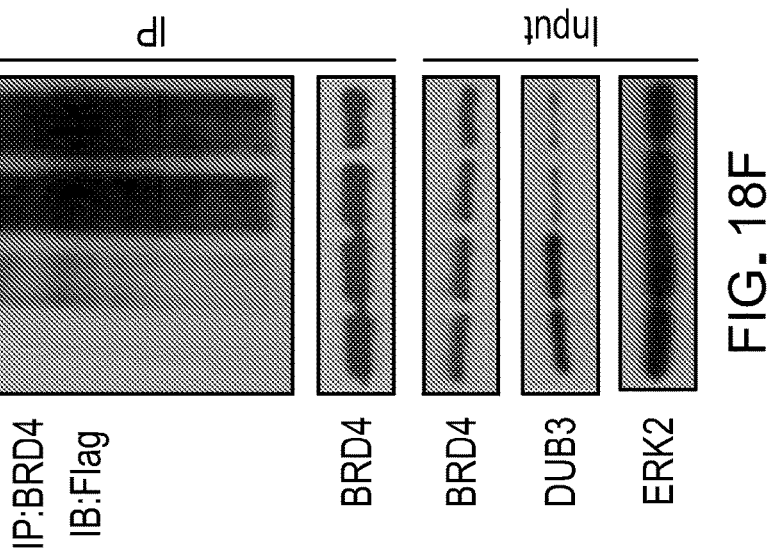
Figure 18E:
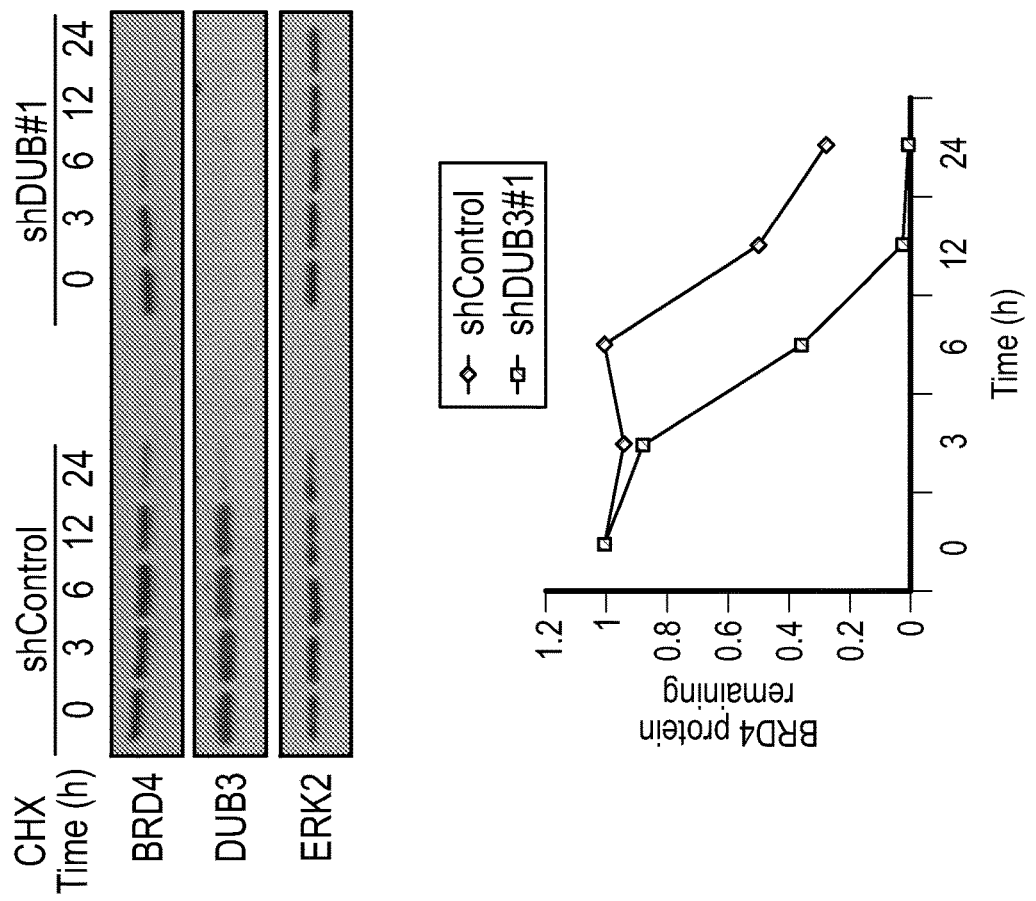
Figure 19C:
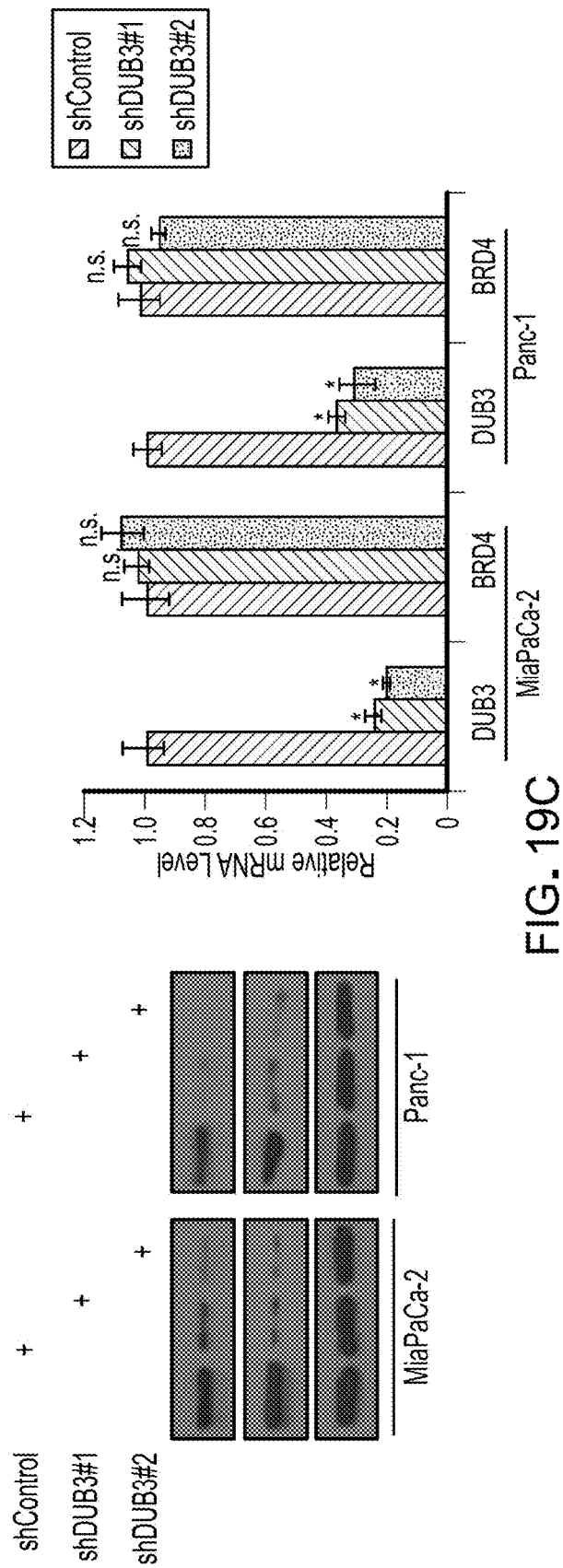
Figure 19D:
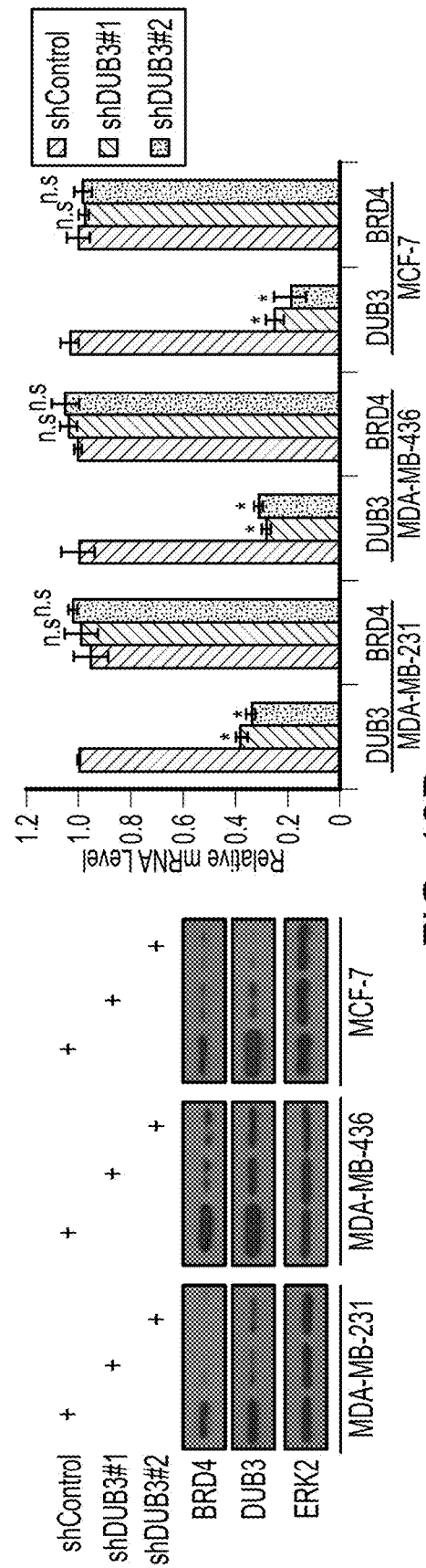
Figure 20A:
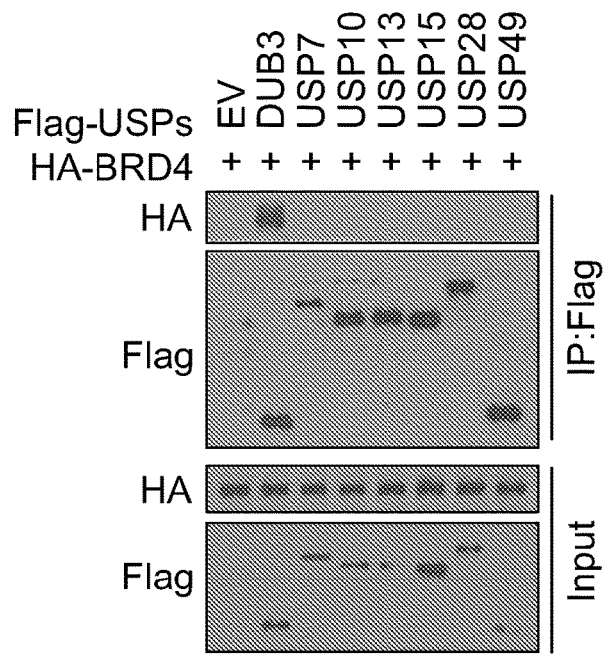
FIGS. 20A-20B. The effect of a number of cancer-relevant DUBs on BRD4 protein expression in prostate cancer cells.
Figure 20B:
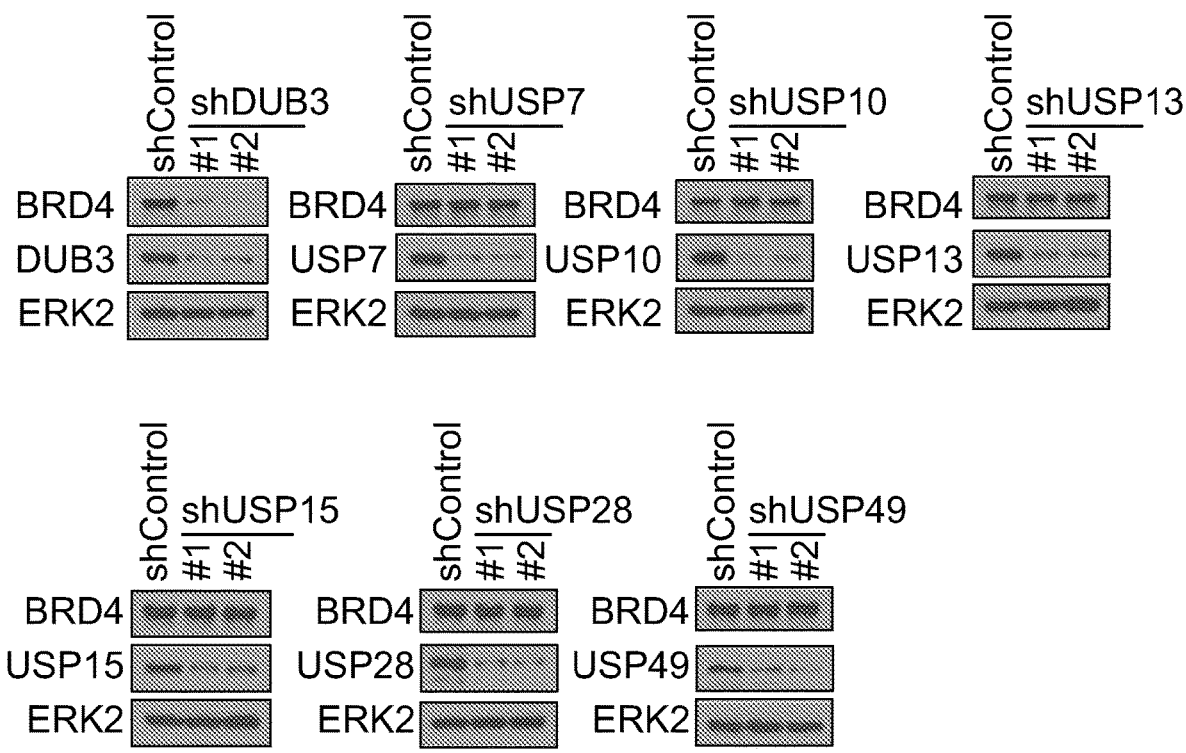

Upon examining the effect of JQ1 on DUB3 expression, JQ1 was found to induce upregulation of DUB3 at both mRNA and protein levels, but only upregulated BRD4 protein level without affecting its mRNA expression (FIG. 17J-17M). Based upon these data, it was hypothesized that DUB3 functions as a DUB that stabilizes BRD4 protein via deubiquitinating BRD4. To test this hypothesis, DUB3 was co-expressed with BRD4 in 293T cells, and DUB3 increased BRD4 protein expression in a dose-dependent manner (FIG. 18A). In contrast, knockdown of DUB3 by two independent shRNAs decreased the level of endogenous BRD4 proteins, but had no overt effect on BRD4 mRNA expression in both PC-3 and DU145 cells (FIGS. 18B and 19A). Similar results were observed in broader cancer cell lines, including two more prostate cancer cell lines, two pancreatic cancer cell lines, and three breast cancer cell lines (FIGS. 19B-19D). Downregulation of BRD4 proteins caused by DUB3 knockdown was reversed by treatment of cells with the proteasome inhibitor MG132 (FIG. 18C). Overexpression of HA-DUB3 WT, but not the deubiquitinase activity-deficient mutant C89S (Wu et al., Nat. Commun., 8:14228 (2017)) increased the level of ectopically expressed Flag-BRD4 protein in a dose-dependent manner in PC-3 cells (FIG. 18D). In agreement with these findings, knockdown of DUB3 shortened BRD4 protein half-life and dramatically increased endogenous BRD4 ubiquitination in PC-3 cells (FIGS. 18E and 18F). In contrast, overexpression of HA-DUB3-WT prolonged the half-life of ectopically expressed Flag-BRD4 protein (FIG. 18G). Forced expression of DUB3-WT, but not the catalytically inactive mutant C89S (CS) (Liu et al., Nat. Commun., 8:13923 (2017)) diminished the ubiquitination level of BRD4 in PC-3 cells (FIG. 18H). The following was performed to determine whether the BRD4 protein level was regulated by other DUBs such as a number of cancer-relevant DUBs including USP7, USP10, USP13, USP15, USP28, and USP49 (Deng et al., Mol. Cell, 61:614-624 (2016); Turnbull et al., Nature, 550:481-486 (2017); Wu et al., Cell Rep., 5:224-236 (2013); and Zhang et al., Genes Dev., 27:1581-1595 (2013)). Unlike DUB3, none of these DUBs either interacted with BRD4 or affected BRD4 protein level in 293T and DU145 cells, respectively (FIGS. 20A and 20B). Thus, DUB3 was identified as a deubiquitinase that specifically promotes deubiquitination of BRD4 in prostate cancer cells. These results suggest that this regulatory mechanism may also exist in other cancer types such as breast and pancreatic cancer.

SPOP is an E3 ubiquitin ligase that promotes ubiquitination and proteasome degradation of BRD4 in prostate cancer cells (Dai et al., Nat. Med., 23:1063-1071 (2017); Janouskova et al., Nat. Med., 23:1046-1054 (2017); and Zhang et al., Nat. Med., 23:1055-1062 (2017)). The following was performed to determine whether DUB3 influences SPOP-mediated ubiquitination and degradation of BRD4. Expression of SPOP markedly decreased the protein level of ectopically expressed BRD4 in PC-3 cells (FIG. 18I). However, this effect of SPOP was largely abolished by expression of DUB3-WT, but not by the C89S mutant (FIG. 18I). Conversely, knockdown of DUB3 largely reduced the level of BRD4 protein in PC-3 cells (FIG. 18J), although SPOP knockdown failed to completely reverse DUB3 knockdown-induced decrease of BRD4 protein levels (FIG. 18J). Moreover, SPOP-mediated polyubiquitination of BRD4 was largely diminished by co-expression of DUB3 WT, but not the C89S mutant (FIG. 18K). These results demonstrate that DUB3 stabilizes BRD4 by promoting BRD4 deubiquitination and SPOP-mediated ubiquitination of BRD4 can be offset by DUB3 (FIG. 18L).

DUB3 Specifically Interacts with BRD4 in Cells

Figure 21A:
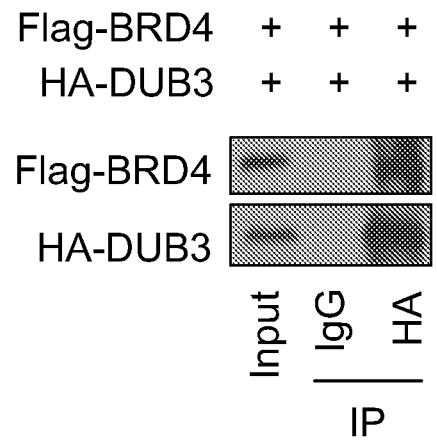
FIGS. 21A-21J. DUB3 interacts with BRD4 in prostate cancer cells.
Figure 21B:
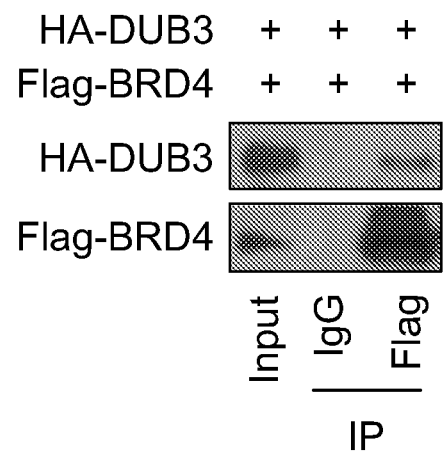
Figure 21C:
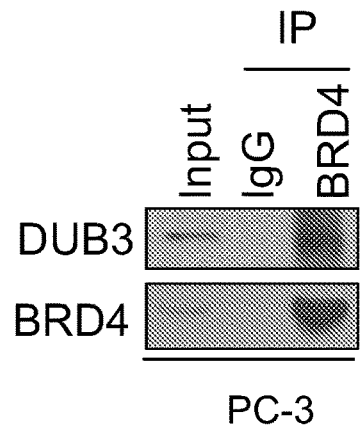
Figure 21D:
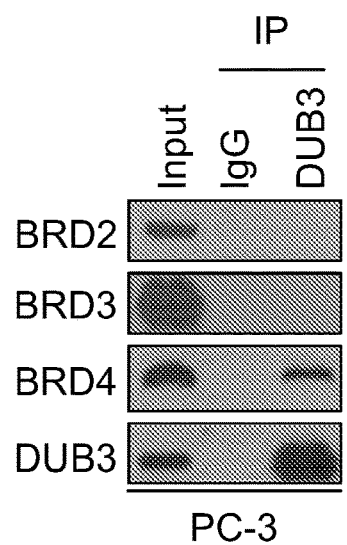
Figure 21E:
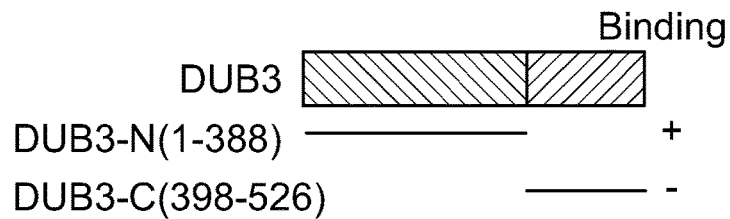
Figure 21F:
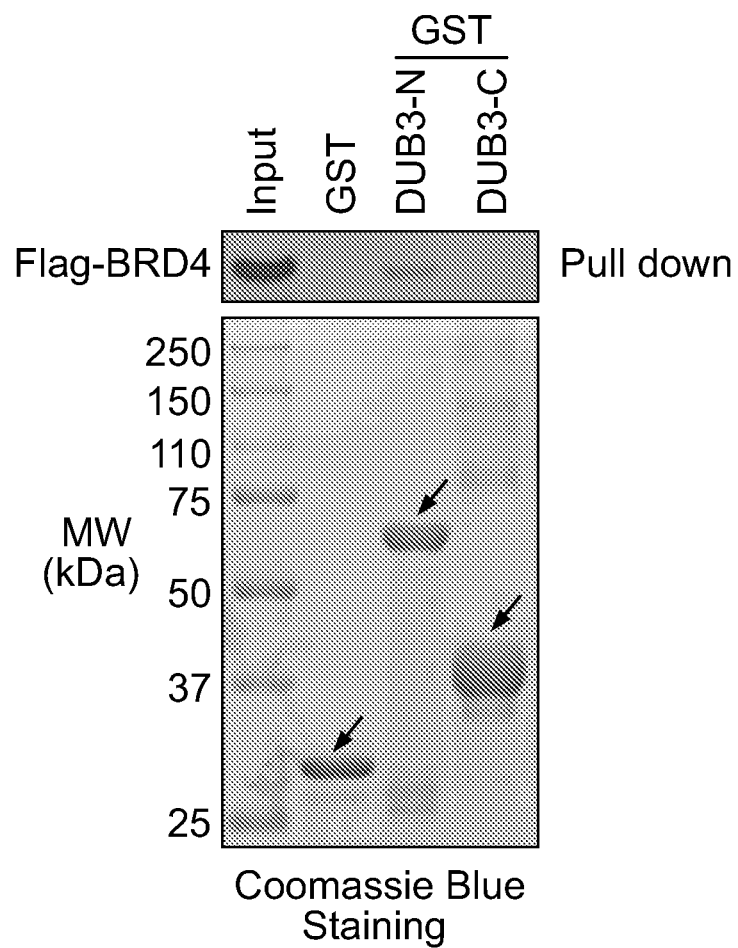
Figure 21G:
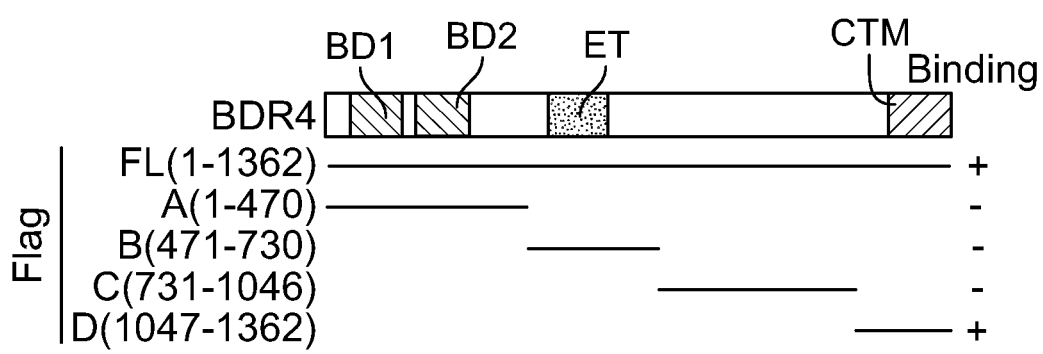
Figure 21H:
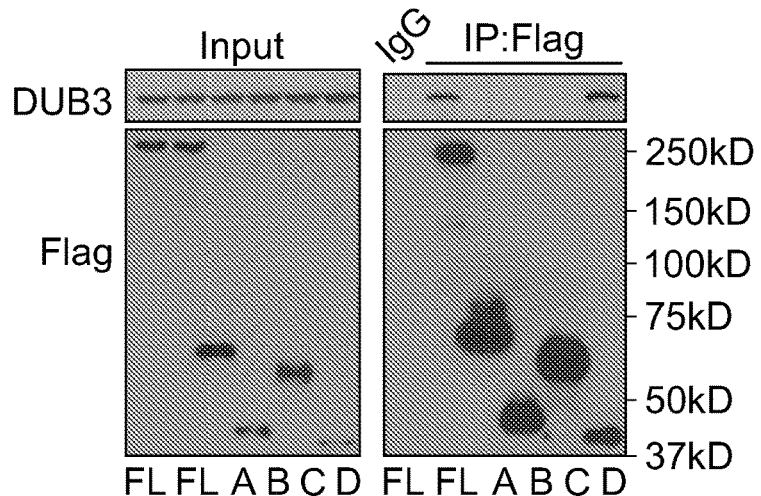
Figure 21I:
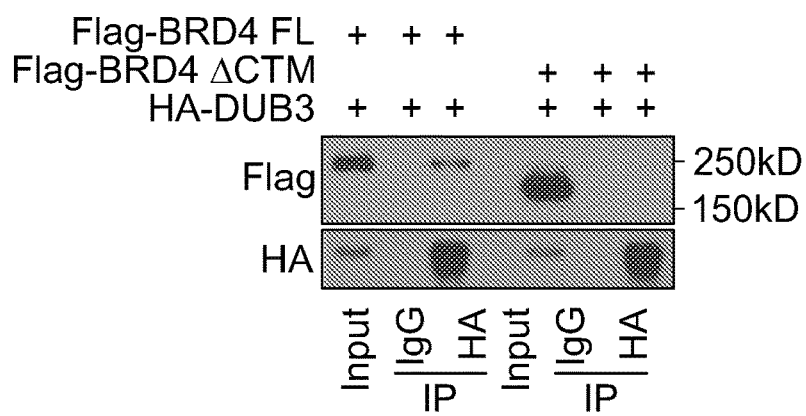
Figure 21J:
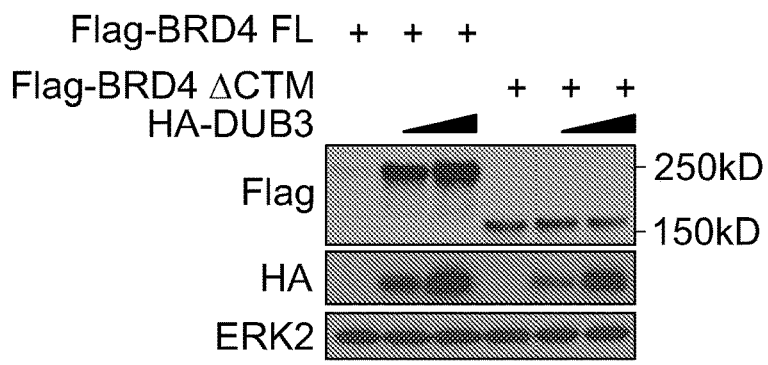
Figures 22A, 22B, 22C, 22D:
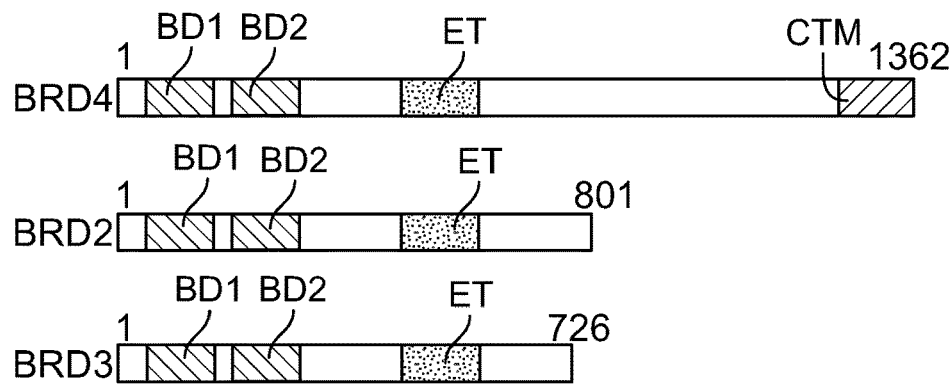
FIGS. 22A-22D. DUB3 does not bind to BRD2 and BRD3 and has no effect on expression level of these two proteins.

To further investigate the relationship between DUB3 and BRD4, reciprocal co-immunoprecipitation (co-IP) assays were performed. Ectopically expressed Flag-BRD4 interacted with ectopically expressed HA-DUB3 in 293T cells (FIGS. 21A and 21B). Interaction between endogenous BRD4 and DUB3 proteins was detected in PC-3 cells (FIGS. 21C and 21D). To define which region(s) in DUB3 interact with BRD4, GST-DUB3 recombinant proteins were generated as reported elsewhere (Wu et al., Nat. Commun., 8:14228 (2017) (FIG. 21E). GST pull-down assays indicated that the N-terminal fragment (aa 1-398) of DUB3, but not the C-terminal fragment or GST alone, bound specifically with BRD4 (FIG. 21F). To determine which region(s) in BRD4 were involved in DUB3 binding, BRD4 deletion constructs were constructed as reported elsewhere (Shi et al., Cancer Cell, 25:210-225 (2014) (FIG. 21G) and co-expressed with DUB3 in 293T cells. Co-IP assays revealed that the C-terminal end of BRD4 containing amino acids (aa) 1047-1362 interacted with DUB3 (FIG. 21H). Given that the C-terminal region in three ubiquitously expressed BET proteins including BRD2, BRD3, and BRD4 is very much diversified and only BRD4 contains the C-terminal motif (CTM) (FIG. 22A), the following was performed to investigate whether the interaction between BRD4 and DUB3 is specific. Co-IP assays revealed that while DUB3 bound to BRD4, it did not bind to BRD2 and BRD3 in PC-3 cells (FIG. 21D). BRD4-DUB3 interaction was mediated through the CTM motif in BRD4 (FIG. 21I). Overexpression of DUB3 increased the level of ectopically expressed full-length BRD4 protein in a dose-dependent manner, but had no effect on BRD4AC™ mutant, BRD2 or BRD3 in PC-3 cells (FIGS. 21J, 22B and 22C). Furthermore, knockdown of DUB3 also failed to affect the expression of endogenous BRD2 and BRD3 proteins in PC-3 cells (FIG. 22D). These results indicate that DUB3 specifically interacts with and modulates BRD4 expression at the protein level.

Figure 23C:
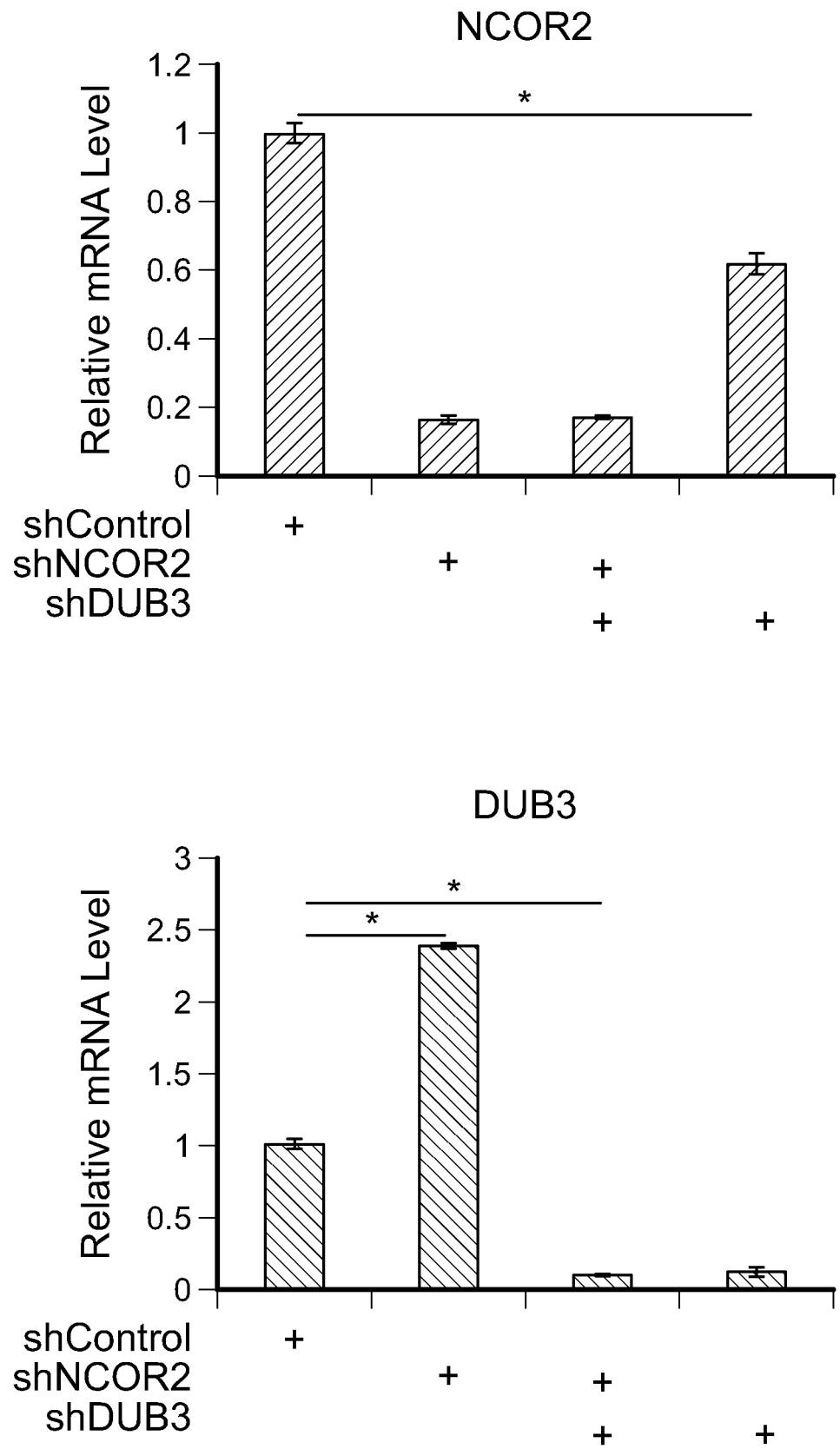
Figure 24A:
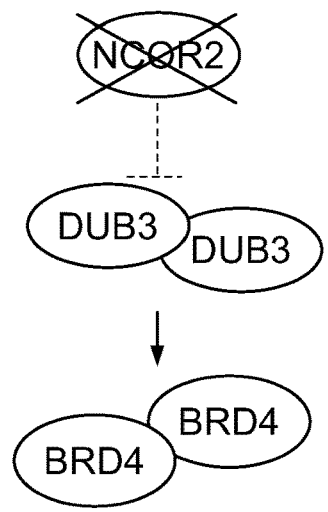
FIGS. 24A-24N. Decreased NCOR2 expression correlates with increased expression of DUB3 and BRD4 in prostate cancer cells and patient specimens.
Figure 24B:
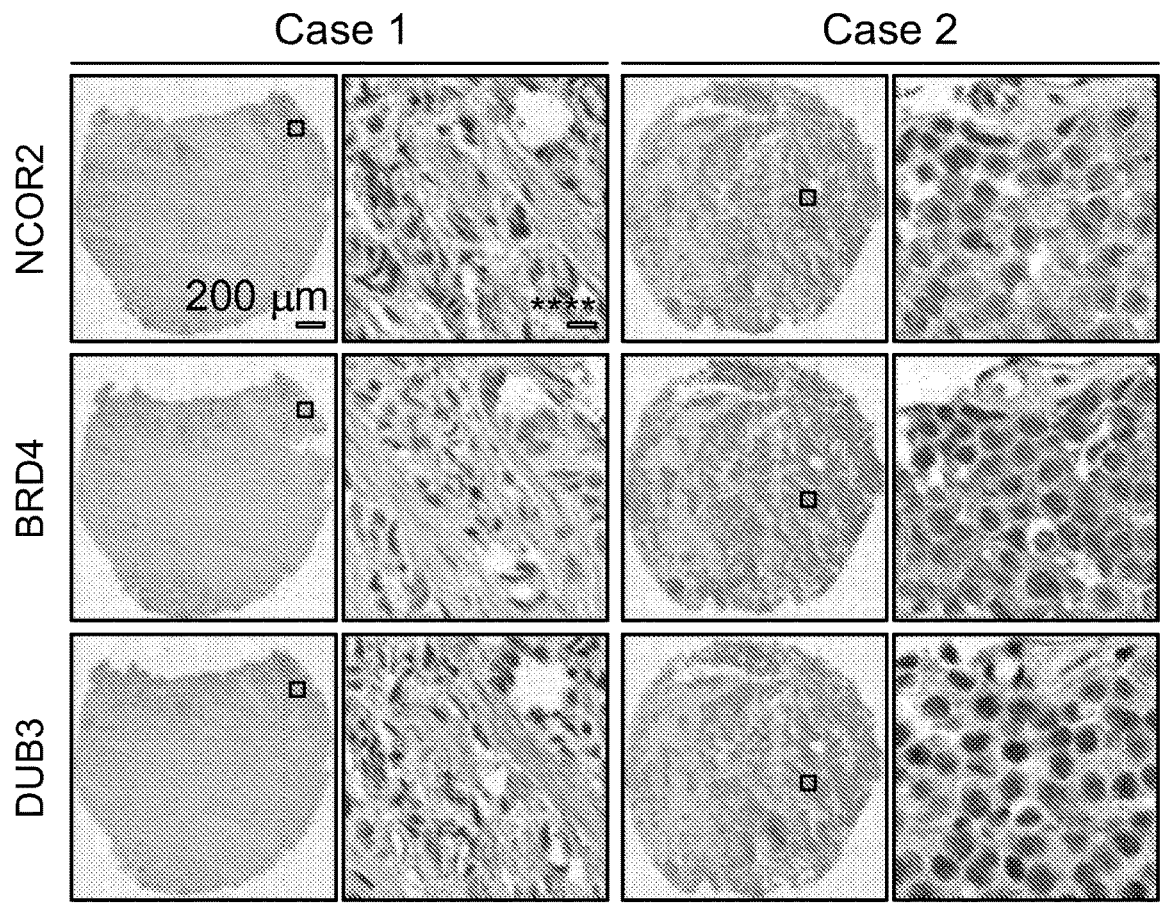
(FIG. 24B), representative images of IHC for NCOR2, DUB3, BRD4 proteins on TMA (n=53) of prostate cancer specimens. Scale bars are indicated.
Figure 24C:
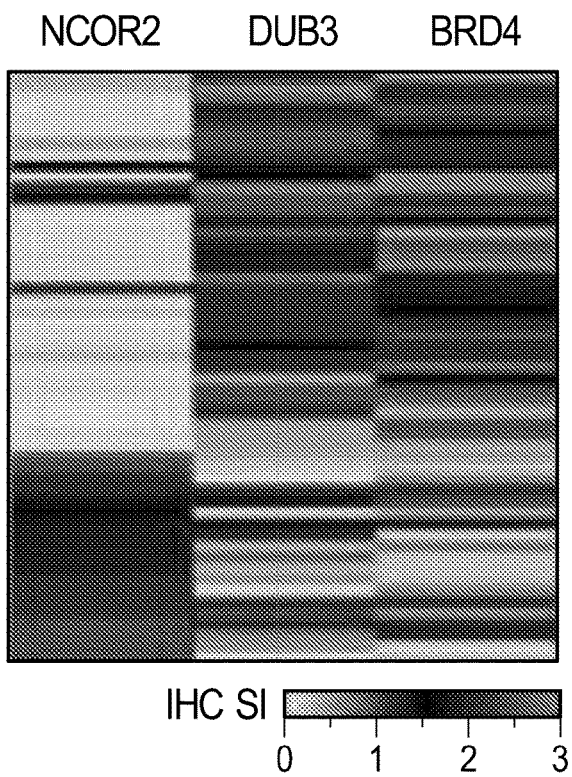
(FIG. 24C), heatmap showing the staining index (SI) of NCOR2, DUB3 and BRD4 proteins in TMA.
Figure 24D:
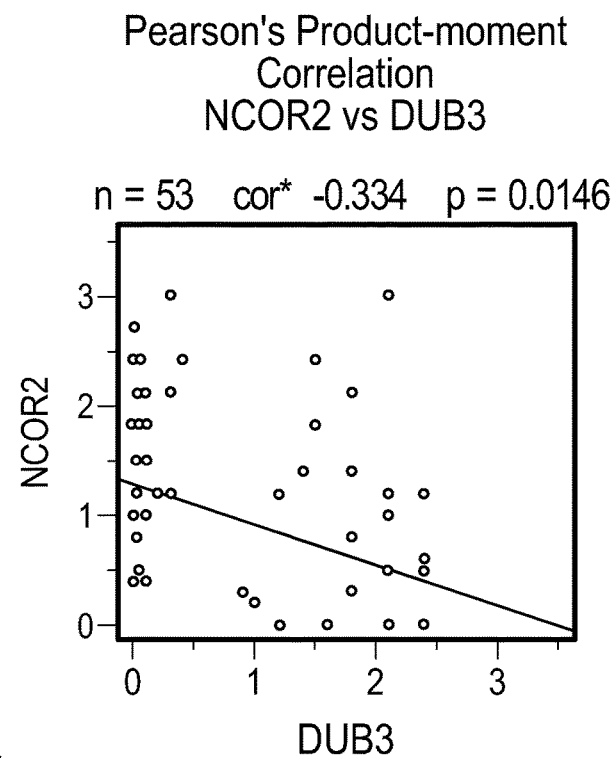
(FIG. 24D), correlation analysis of the SI of NCOR2 and DUB3 proteins in TMA.
Figure 24E:
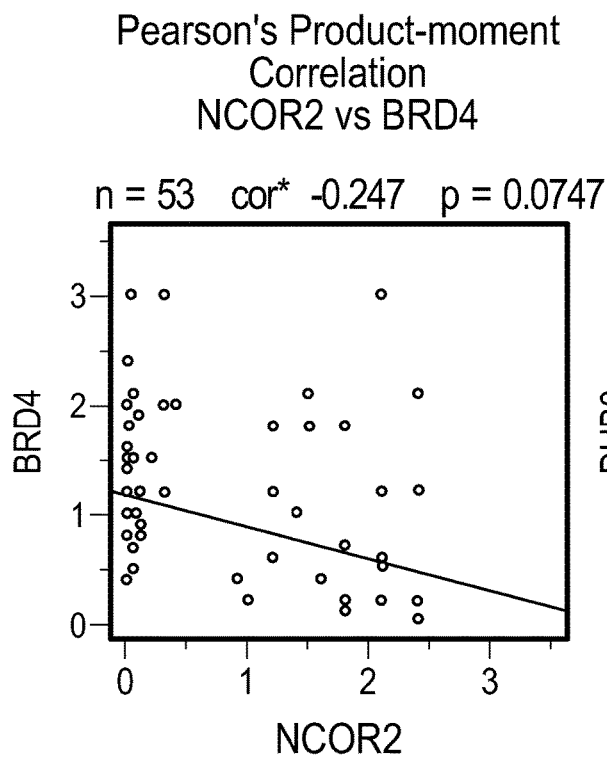
(FIG. 24E), correlation analysis of the SI of NCOR2 and BRD4 proteins in TMA.
Figure 24F:
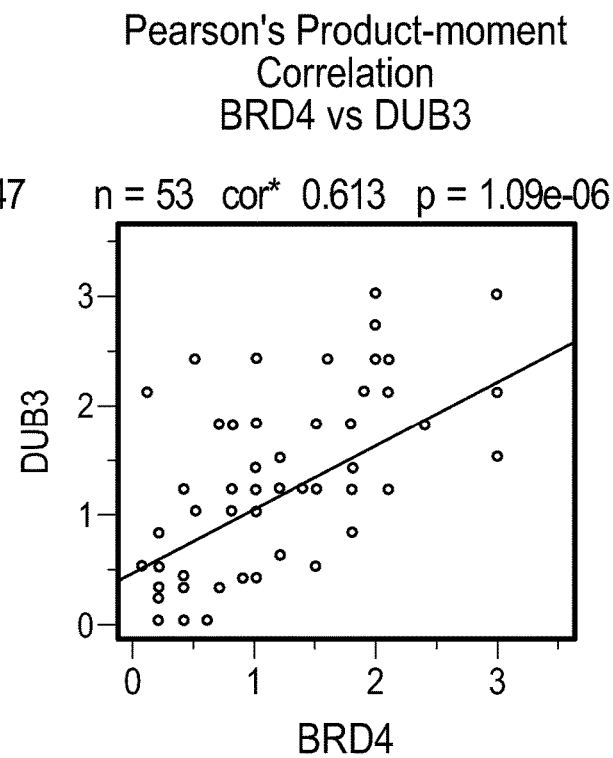
(FIG. 24F), correlation analysis of the SI of DUB3 and BRD4 proteins in TMA.

NCOR2 Regulates DUB3 and BRD4 Expression and its Expression Inversely Correlates with DUB3 and BRD4 Protein Levels in Prostate Cancer Specimens BRD4 protein is upregulated in CRPC patients (Urbanucci et al., *Cell Rep.*, 19:2045-2059 (2017)). NCOR2 was found genomically deleted in a subset of CRPC patients (Robinson et al., *Cell*, 162:454 (2015)) (FIG. 23A), and NCOR2 was more frequently deleted or mutated in metastatic prostate cancers compared to primary lesions (Cancer Genome Atlas Research, *Cell*, 163:1011-1025 (2015)). Intriguingly, meta-analysis showed that DUB3 mRNA level was significantly upregulated in CRPC patient samples compared to normal and primary prostate cancer (Grasso et al., *Nature*, 487:239-243 (2012)) (FIG. 23B). Based upon these genomic data and the finding that NCOR2 represses DUB3 expression in cultured cells (FIG. 15), it was hypothesized that loss of NCOR due to deletions or mutations results in DUB3 upregulation, which in turn causes BRD4 protein deubiquitination and elevation (FIG. 24A). To test this hypothesis, the following was performed to determine the correlation among expression of NCOR2, DUB3 and BRD4 proteins in human prostate cancer specimens. The expression of these three proteins was examined by performing immunohistochemistry (IHC) on a tissue microarray (TMA) containing a cohort of prostate cancer samples (n=53). IHC staining index (SI) was calculated by measuring both percentage of positive staining cells and staining intensity. Representative images of low/no and high staining of NCOR2, DUB3 and BRD4 were obtained (FIG. 24B). A majority of tumors expressed NCOR2 protein at very low level, and NCOR2 expression inversely correlated with the level of DUB3 (Pearson's product-moment correlation co-efficiency r=-0.334, p=0.0146) and BRD4 (Pearson's product-moment correlation co-efficiency r=-0.247, p=0.0747) (FIGS. 24C-24E). In support of this hypothesis, DUB3 expression positively correlated with BRD4 protein level in this cohort (Pearson's product-moment correlation co-efficiency r=0.613, p=1.09e-6) (FIG. 24F). These results demonstrate that decreased expression of NCOR2 correlates with increased expression of DUB3 and BRD4 proteins in prostate cancer patient specimens.

Figure 24G:
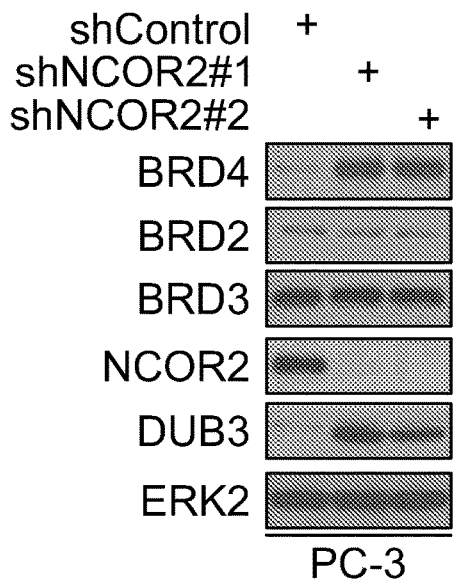
(FIG. 24G, FIG. 24H), PC-3 cells were infected with indicated shRNAs for 48 hours for Western blot (FIG. 24G) and RT-qPCR (FIG. 24H). *P<0.05. n.s., not significant.
Figure 24H:
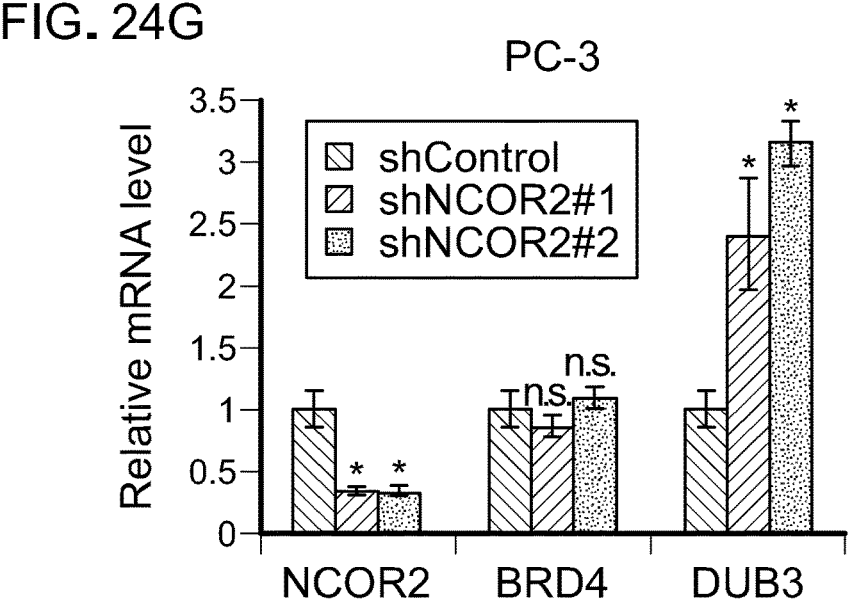
Figure 24I:
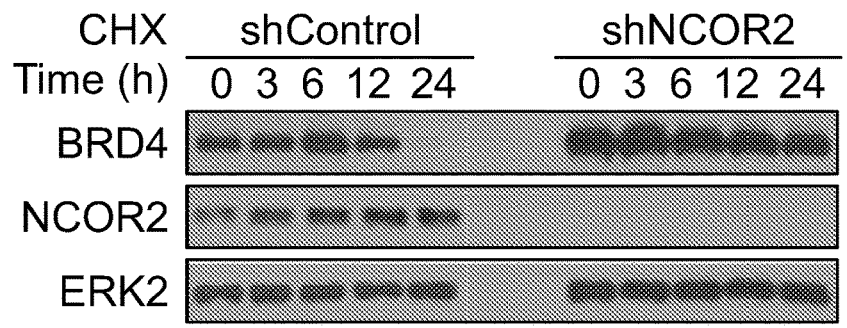
(FIG. 24I, FIG. 24J), PC-3 cells were infected with indicated shRNAs for 48 hours followed by treatment of 50 μg/μL CHX for Western blot. Protein bands were quantified as in FIG. 18E.
Figure 24J:
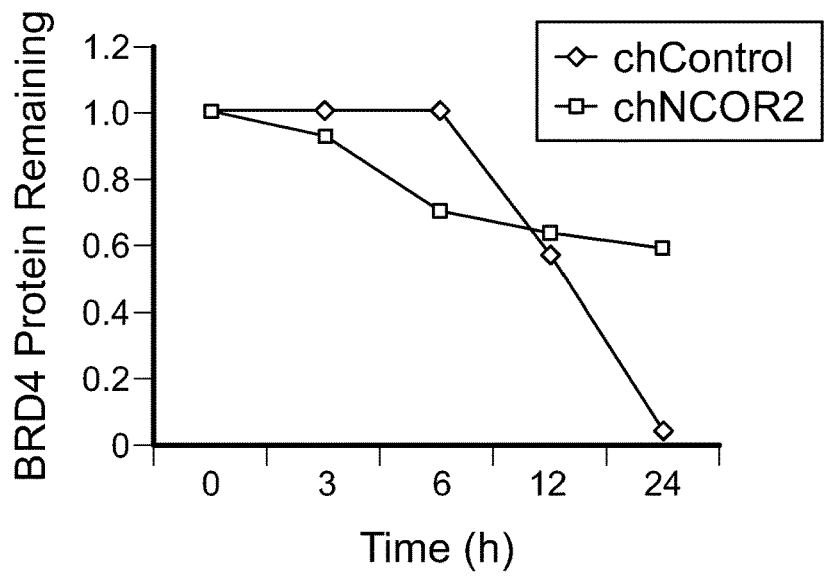
Figure 24K:
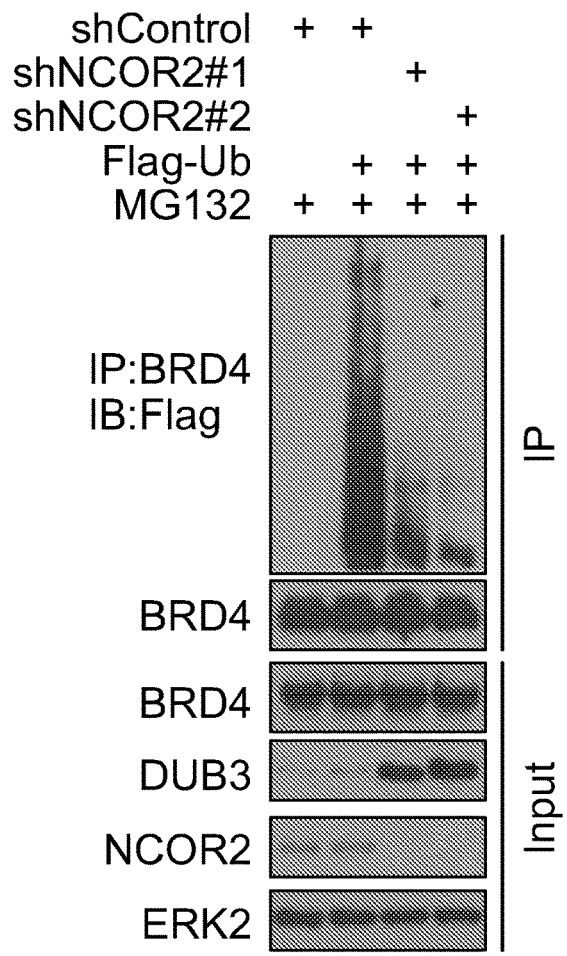
(FIG. 24K), PC-3 cells were infected with indicated shRNAs for 24 hours followed by transfection with indicated plasmids for another 24 hours. Cells were treated with MG132 for 8 hours before immunoprecipitation and Western blot.
Figures 24L, 24M, 24N:
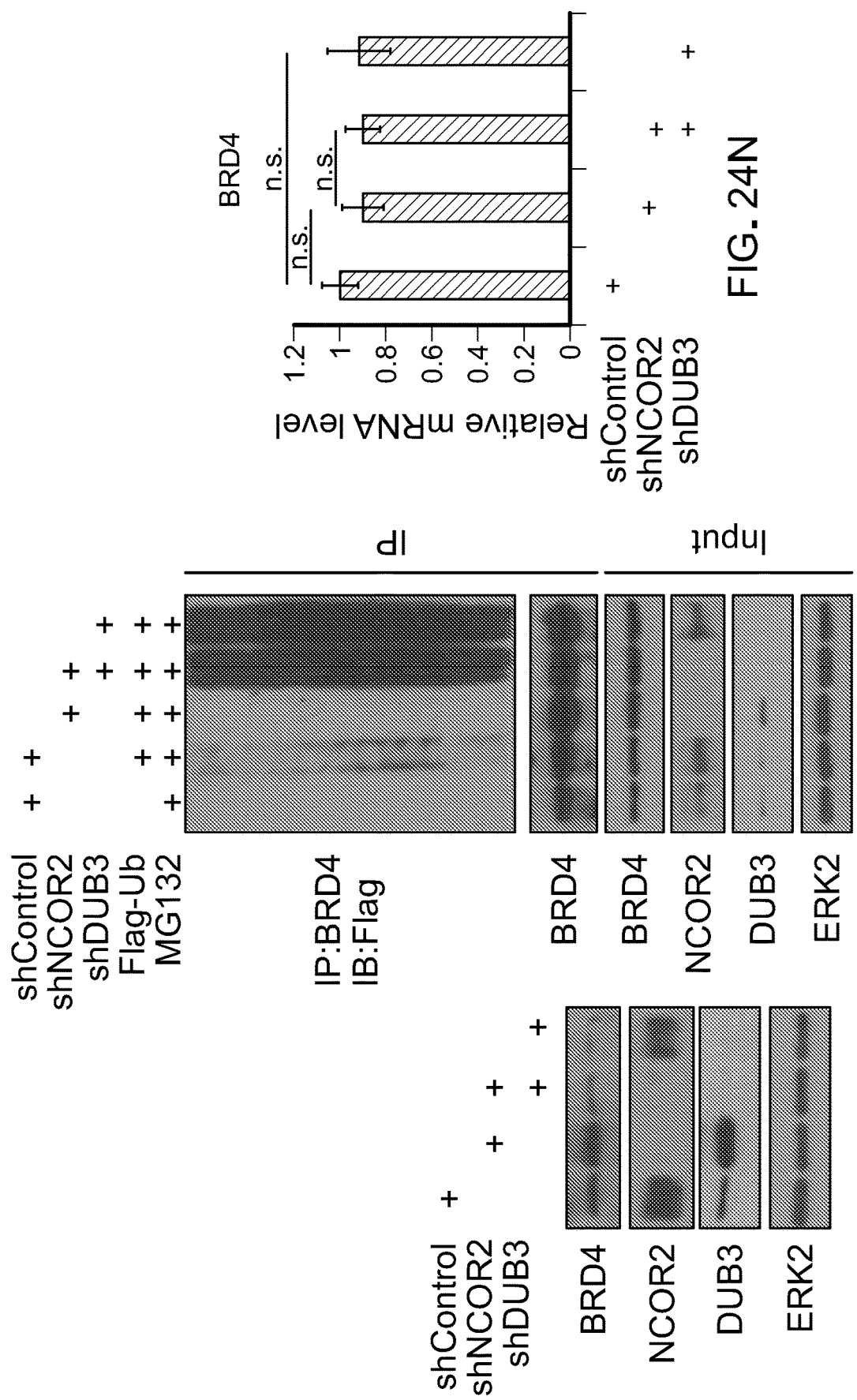
(FIG. 24L), PC-3 cells were infected with indicated shRNAs for 48 hours for Western blot.
(FIG. 24M), PC-3 cells were infected with indicated shRNAs for 24 hours followed by transfection with indicated plasmids for another 24 hours. Cells were treated with MG132 for 8 hours before immunoprecipitation and Western blot.

Cell culture models were used to test this hypothesis further. Knockdown of NCOR2 by two independent shRNAs increased expression of DUB3 and BRD4, but not BRD2 and BRD3 proteins while NCOR2 knockdown only increased mRNA expression of DUB3, but not BRD4 (FIGS. 24G and 24H). Moreover, knockdown of endogenous NCOR2 prolonged BRD4 protein half-life and attenuated BRD4 polyubiquitination (FIGS. 24I-24K). The following was performed to determine whether deletion of NCOR2 affects BRD4 protein level through upregulation of DUB3. Knockdown of DUB3 completely abolished NCOR2 depletion-induced elevation of BRD4 protein and BRD4 protein polyubiquitination, but had no effect on BRD4 mRNA expression (FIGS. 24L-24N and 23C). These results suggest that NCOR2 is an upstream regulator of BRD4 protein, effect of which is mediated through DUB3 (FIG. 24A).

DUB3-Mediated Deubiquitination and Stability of BRD4 is Regulated by CDK4/6

Catalytic activity of DUB3 relies on CDK4/6-mediated phosphorylation, and DUB3-mediated protein deubiquitination is inhibited by CDK4/6 inhibitors (Liu et al., *Nat. Commun.*, 8:13923 (2017)). The following was performed to determine whether CDK4/6 inhibition affects BRD4 stabilization. By knocking down CDK4 or CDK6 alone or in combination in DU145 cells, it was demonstrated that the BRD4 protein level was largely reduced by CDK4 or CDK6 knockdown and the effect was more robust in CDK4 and CDK6 co-knockdown cells (FIG. 25A). Since DU145 cells contain an abnormally small protein translated from an RB messenger RNA that lacks 105 nucleotides encoded by exon 21 (Bookstein et al., *Science*, 247:712-715 (1990)), the effect of CDK4/6 depletion on BRD4 expression appears to be RB-independent. PD0332991 is a selective CDK4/6 inhibitor (Beaver et al., *Clin. Cancer Res.*, 21:4760-4766 (2015); Finn et al., *N. Engl. J. Med.*, 375:1925-1936 (2016); and O'Leary et al., *Nat. Rev. Clin. Oncol.*, 13:417-430 (2016)). Treatment of DU145 cells with PD0332991 decreased BRD4 protein in a time-dependent manner (FIG. 25B), and the effect of PD0332991 was completely impeded by the proteasome inhibitor MG132 (FIG. 25C), demonstrating that CDK4/6 inhibitor accelerates BRD4 degradation.

To investigate whether DUB3 regulation of BRD4 relies on CDK4/6 activity, DU145 cells were treated with PD0332991. PD0332991 treatment completely blocked DUB3-induced upregulation of BRD4 protein (FIG. 25D). Moreover, knockdown of DUB3 largely decreased BRD4 protein level, but little or no further reduction in BRD4 protein expression by co-treatment with PD0332991 (FIG. 25E). Furthermore, PD0332991 treatment also increased BRD4 polyubiquitination, shortened BRD4 protein half-life, and reversed DUB3-mediated deubiquitination of BRD4 in DU145 cells (FIGS. 25F-25H).

Figure 25I:
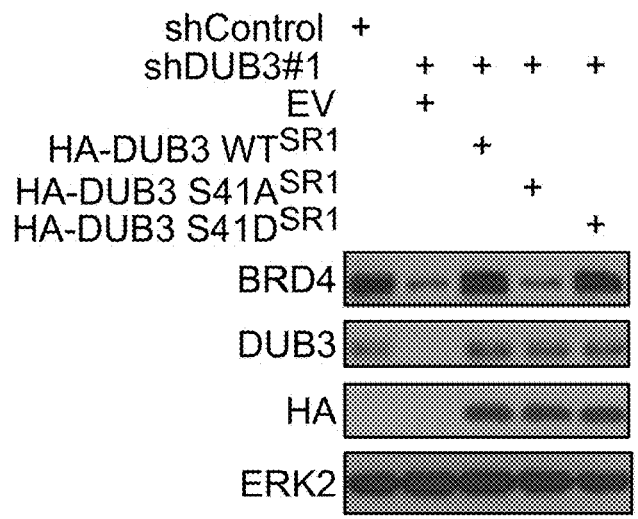
Figure 25J:
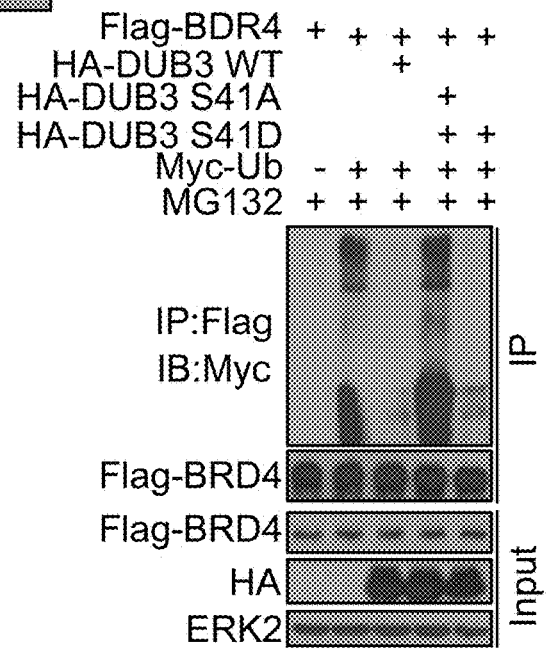
Figure 25K:
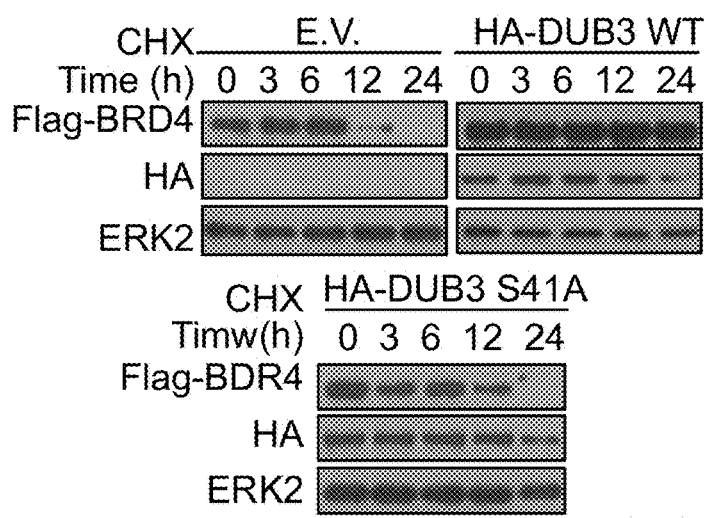
Figure 25L:
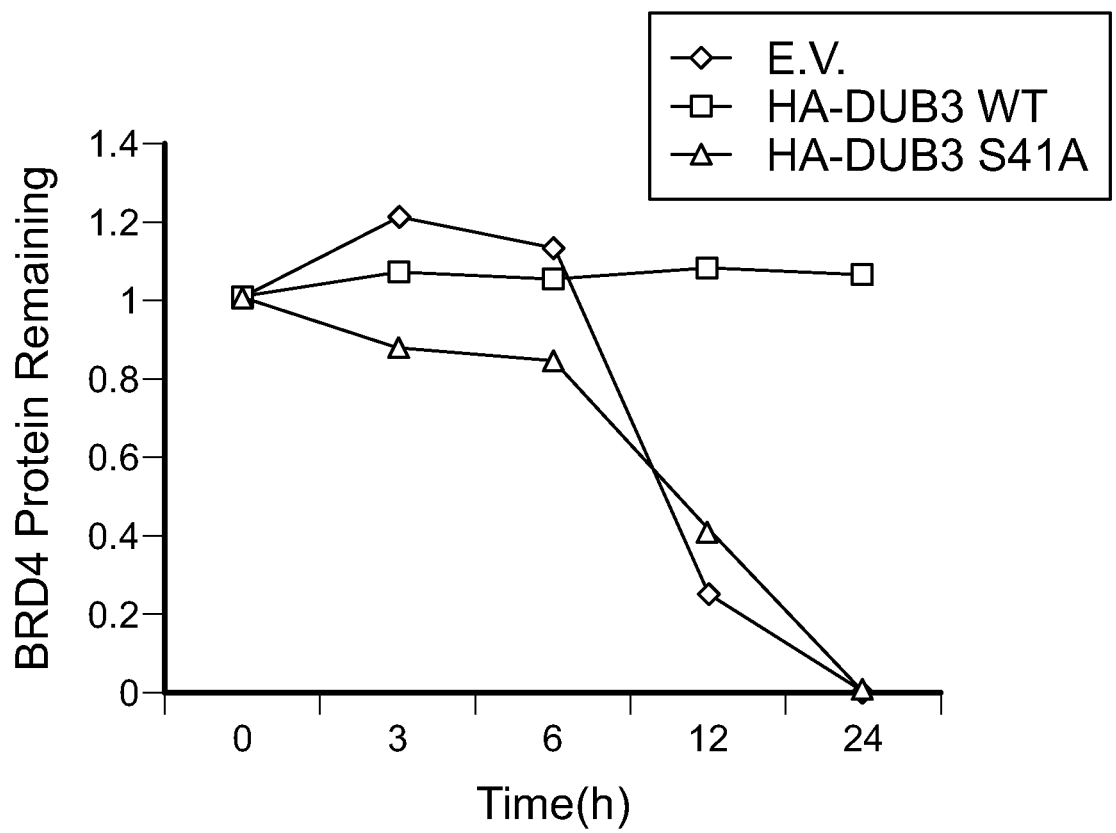
Figure 25M:
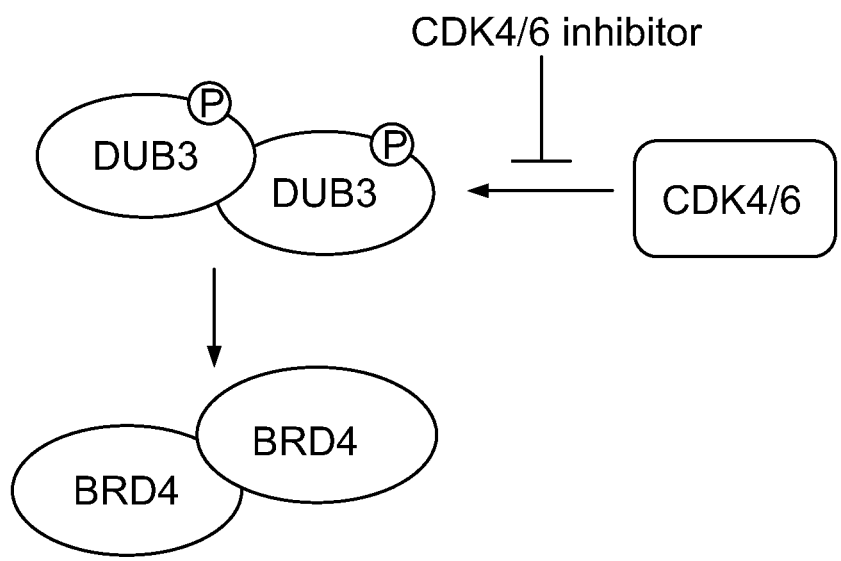
Figure 26A:
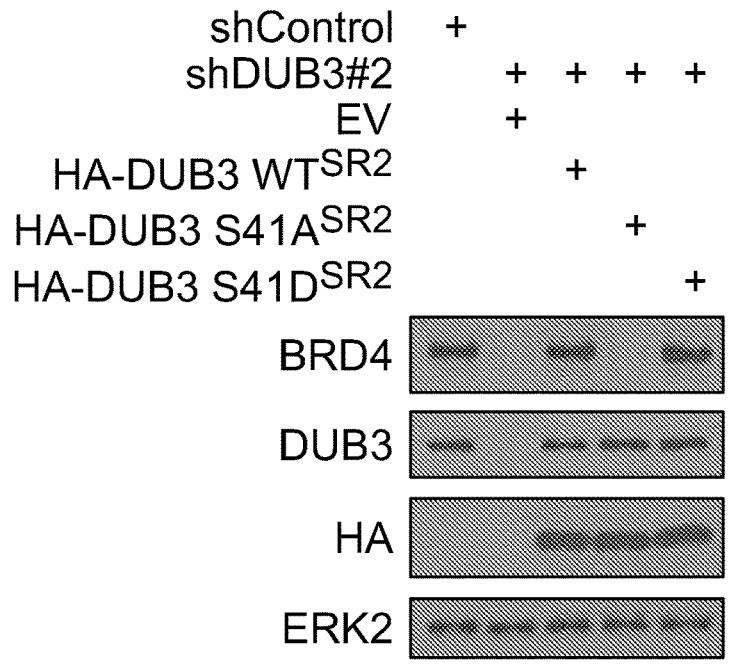
FIGS. 26A-26I. Determination of the role of DUB3-mediated stabilization of BRD4 in BET inhibitor resistance using both loss of function and gain of function approaches.
Figure 26B:
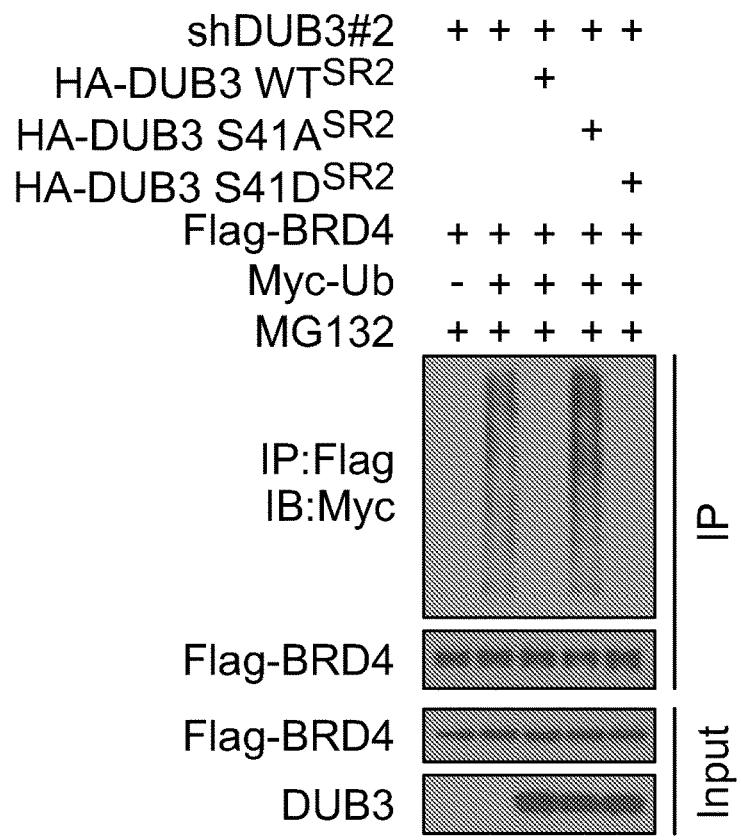

CDK4/6-mediated serine-41 phosphorylation of DUB3 was shown to be involved in the catalytic activity of DUB3 (Liu et al., *Nat. Commun.*, 8:13923 (2017)). Knockdown of endogenous DUB3 by two independent shRNAs largely decreased BRD4 protein, and these effects were reversed by restored expression of DUB3-WT and the phospho-mimicking mutant S41D, but not the phosphorylation-resistant mutant S41A (FIGS. 25I and 26A). Similarly, ectopic or restored expression of DUB3-WT and S41D mutant, but not S41A mutant decreased BRD4 polyubiquitination in PC-3 cells (FIGS. 25J and 26B). Moreover, unlike DUB3-WT, overexpression of the S41A mutant failed to prolong the half-life of BRD4 protein in PC-3 cells (FIGS. 25K and 25L). These results suggest that CDK4/6 phosphorylation of DUB3 is essential for DUB3-mediated deubiquitination and stabilization of BRD4 (FIG. 25M).

Figure 27B:
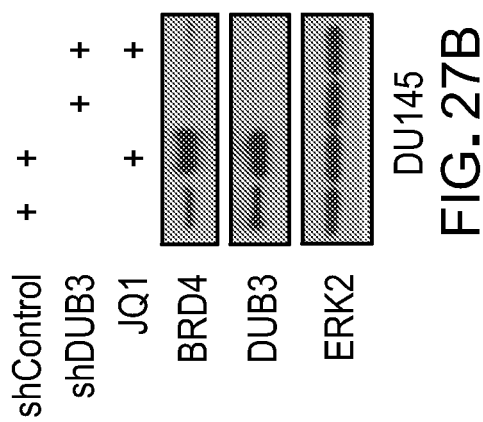
FIGS. 27A-27I. DUB3 inhibition by CDK4/6 inhibitor sensitizes prostate cancer cells to BET-inhibitor in vitro and in vivo.
Figure 27A:
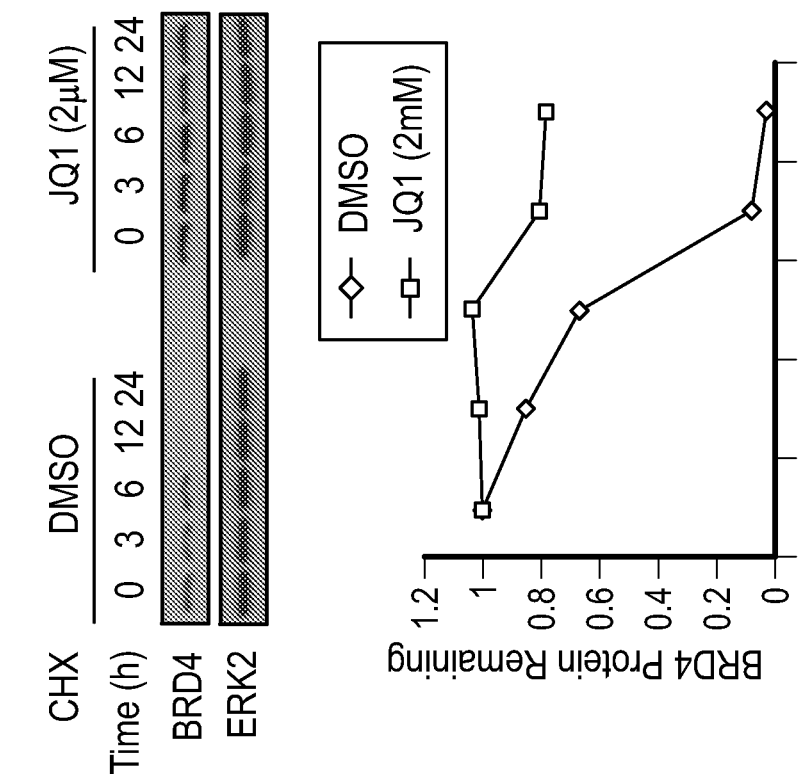
Figure 27C:
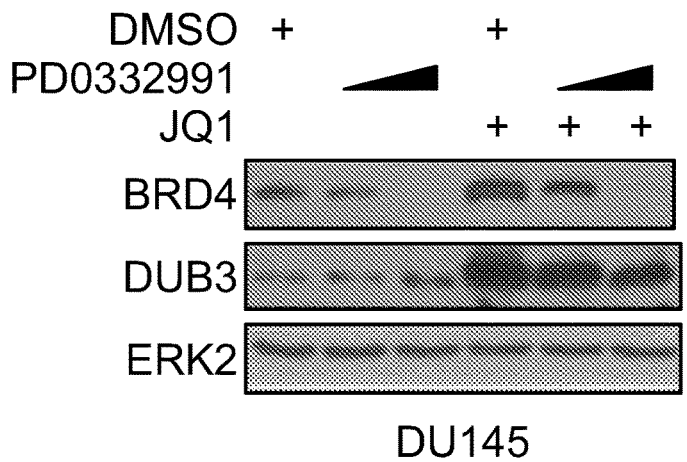
Figure 27D:
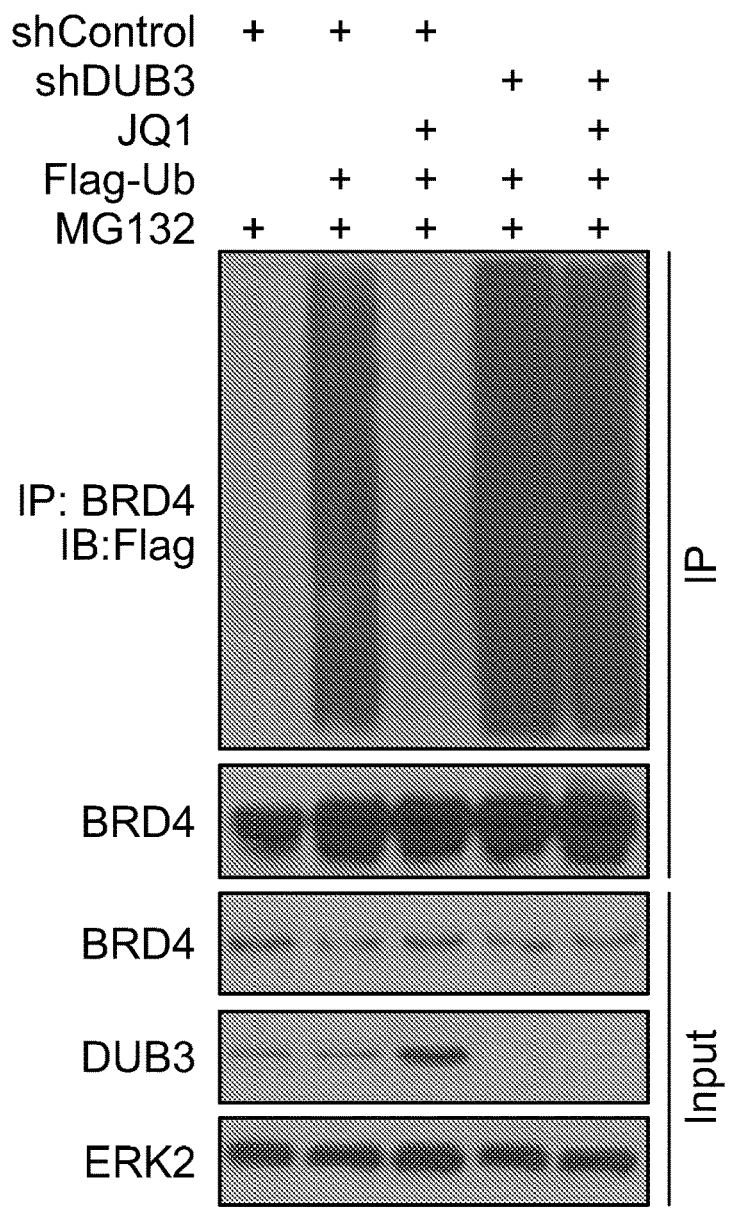
Figure 27E:
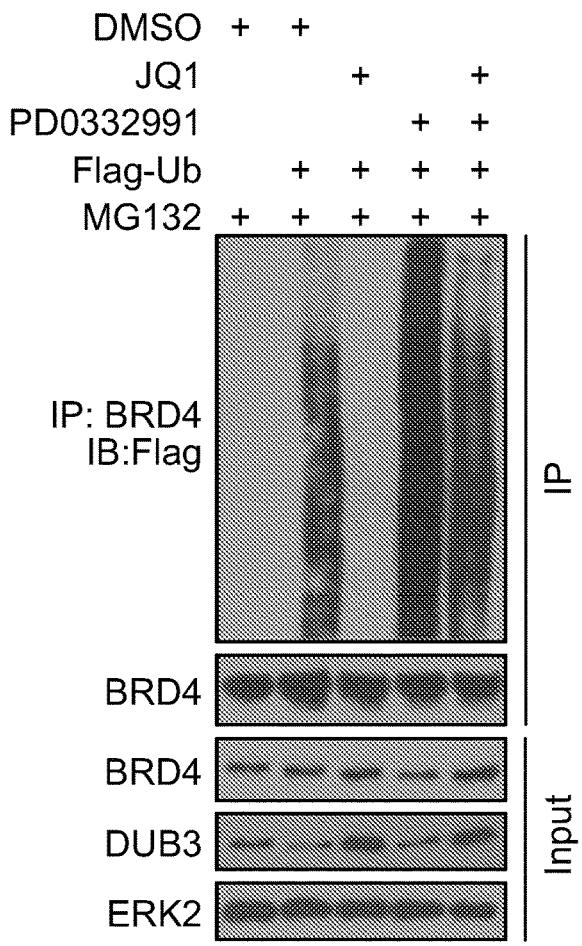

DUB3 Inhibition Sensitizes Prostate Cancer Cells to BET Inhibitor In Vitro and in Mice As described above, JQ1 treatment increased BRD4 expression at the protein, but not mRNA level in prostate cancer cells (FIGS. 17J-17M). JQ1 treatment prolonged BRD4 protein half-life (FIG. 27A). Given that JQ1 induces upregulation of DUB3 at both mRNA and protein levels in different cell types (Borbely et al., *Oncotarget*, 6:33623-33635 (2015)) (FIGS. 17J-17M) and DUB3 binds to BRD4 and promotes its deubiquitination and protein stabilization (FIGS. 18 and 21), the following was performed to determine whether JQ1-induced stabilization of BRD4 is mediated through upregulation of active DUB3. JQ1-induced upregulation of BRD4 protein was almost completely abolished by DUB3 knockdown or inhibition of DUB3 by CDK4/6 inhibitor PD0332991 (FIGS. 27B and 27C). Accordingly, JQ1 treatment markedly inhibited BRD4 polyubiquitination, but this effect was almost completely reversed by DUB3 knockdown or PD0332991 (FIGS. 27D and 27E). These results suggest that BET inhibitor-induced upregulation of DUB3 is involved in BET inhibitor-induced stabilization and elevation of BRD4 proteins.

Figure 26C:
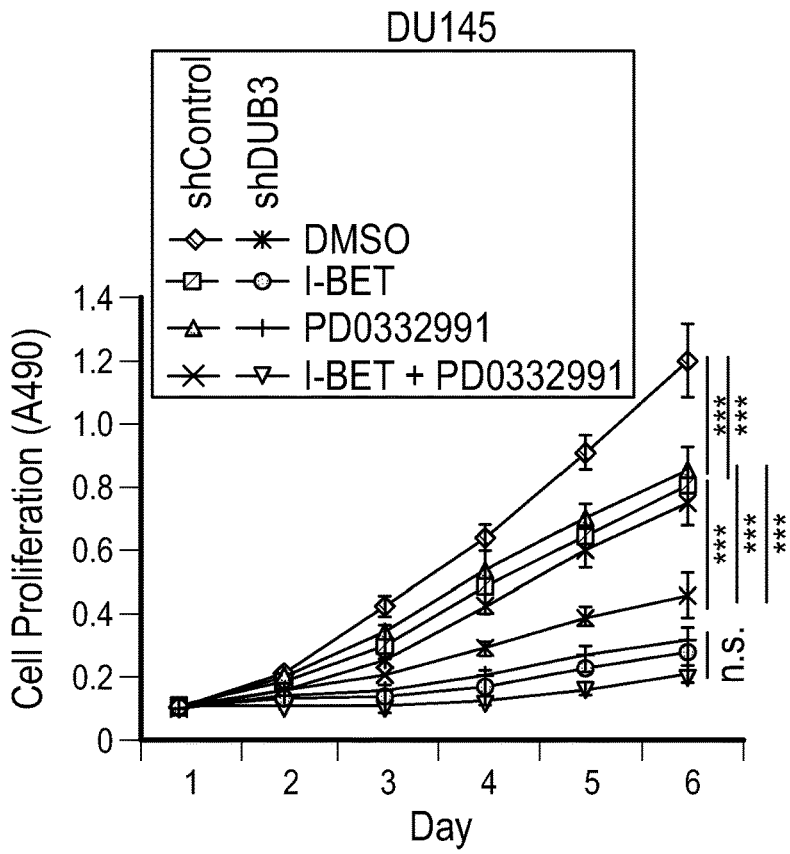
Figure 26D:
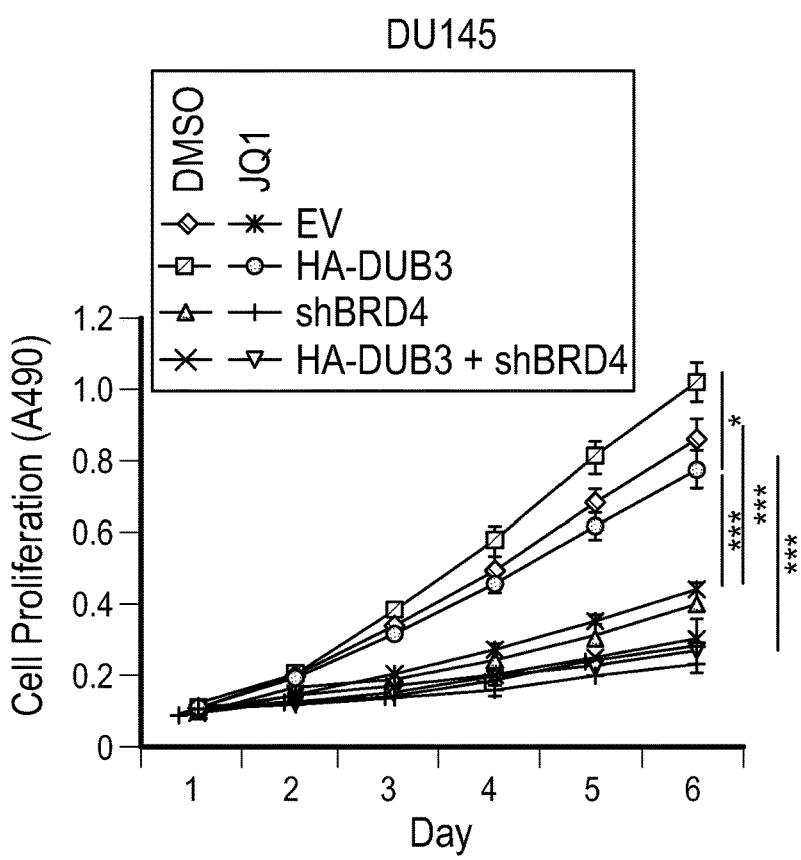
Figure 26E:
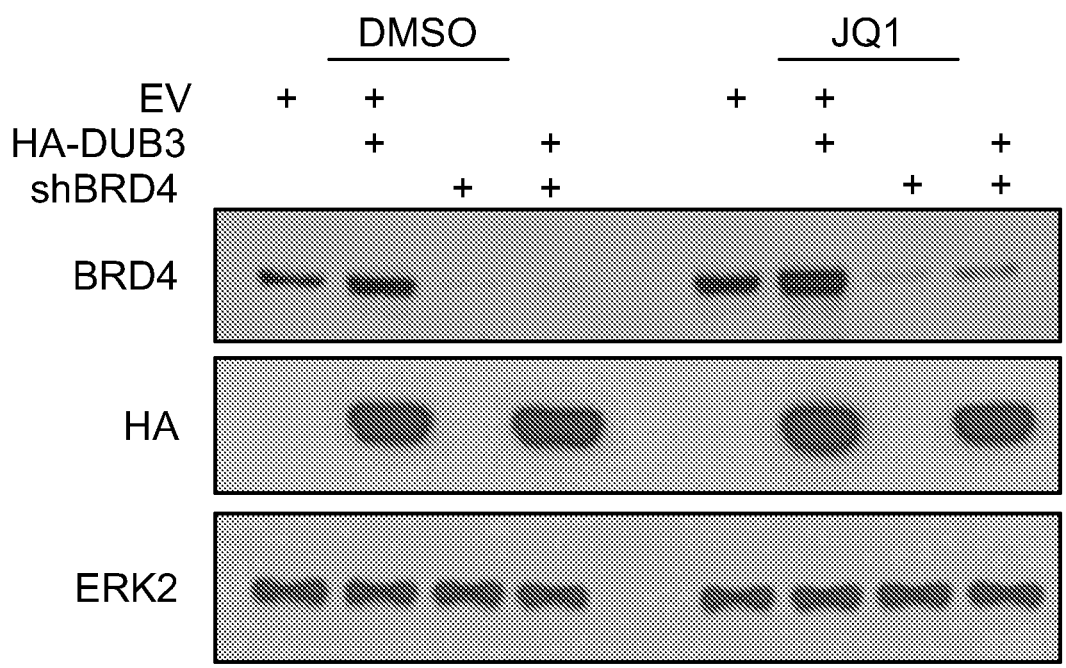
Figure 26F:
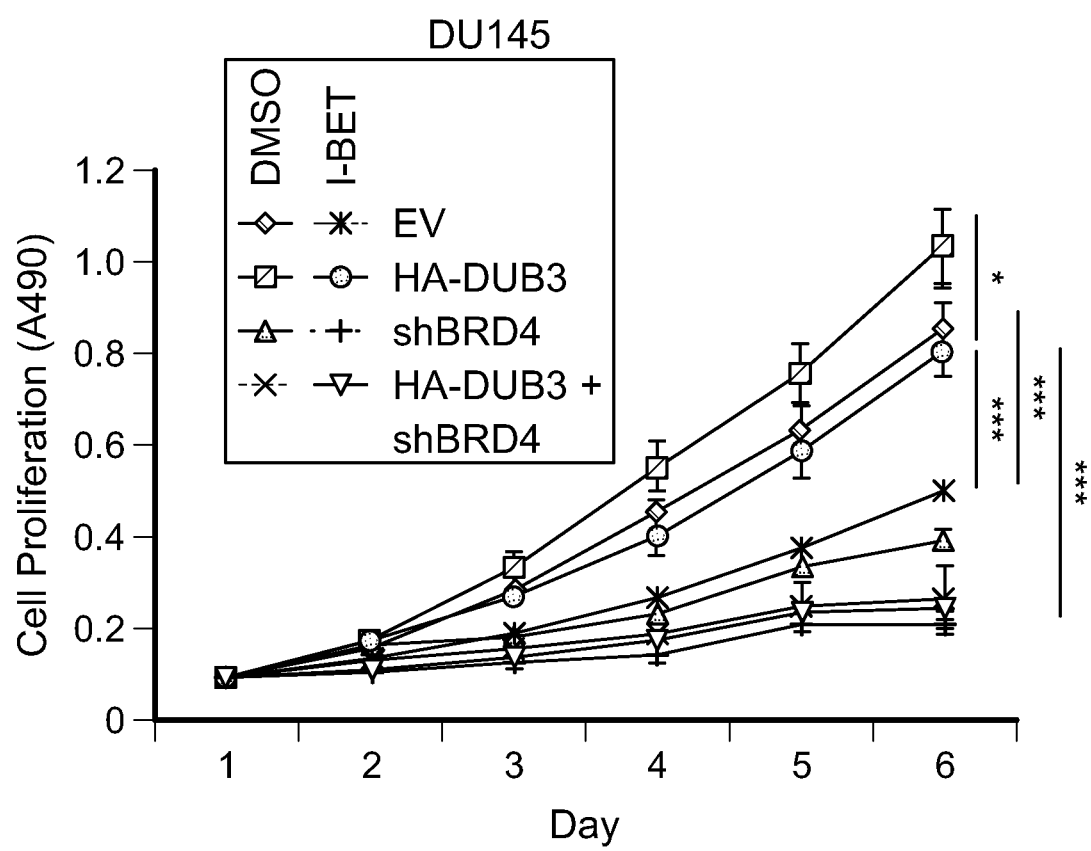
Figure 26G:
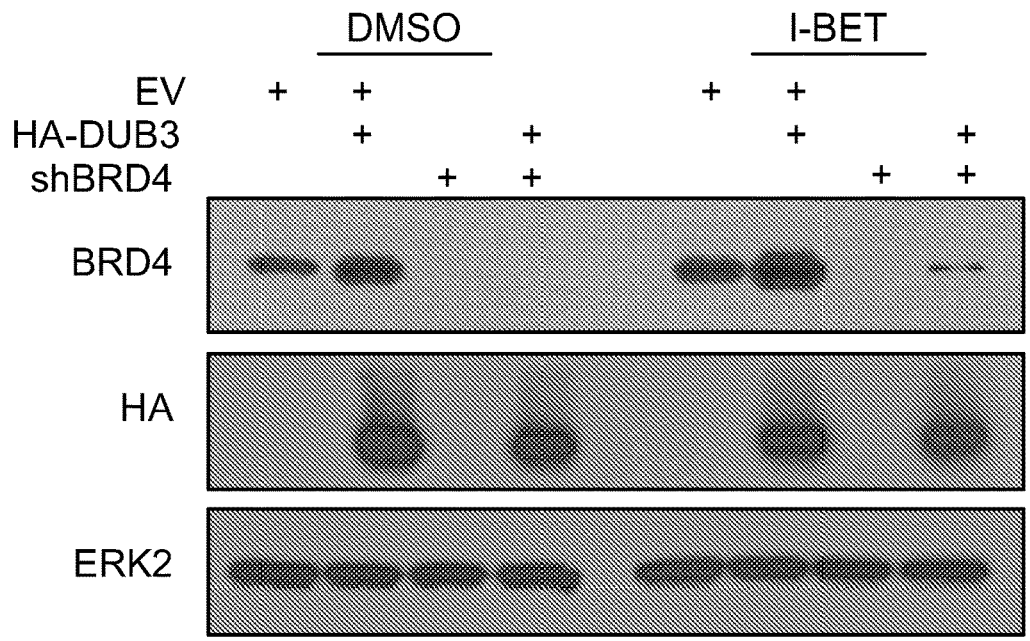
Figure 26H:
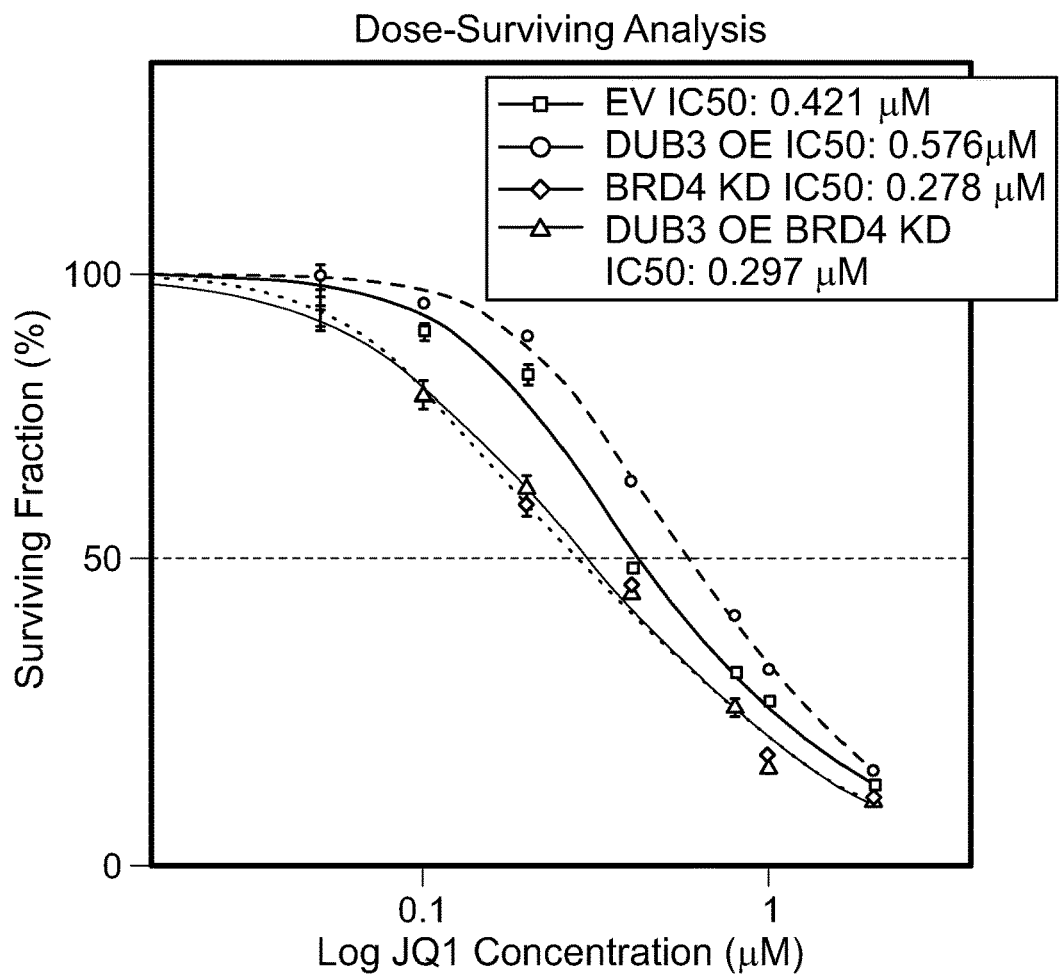
Figure 26I:
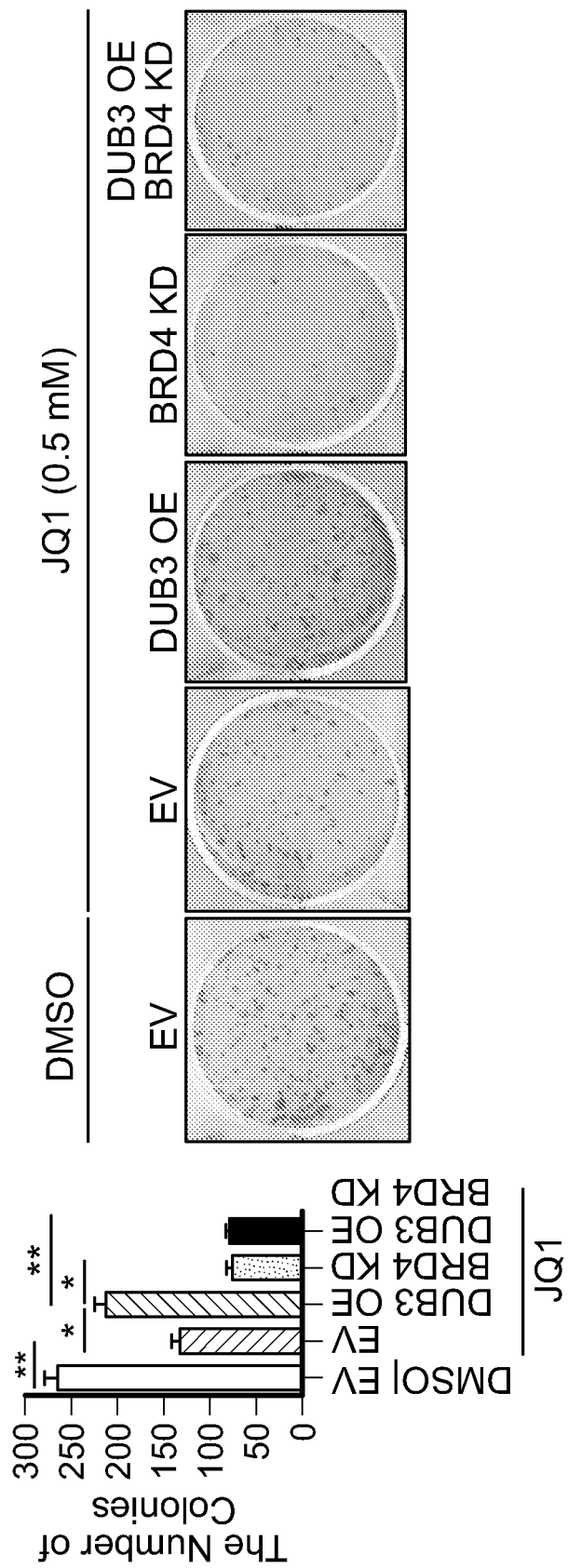
Figure 27F:
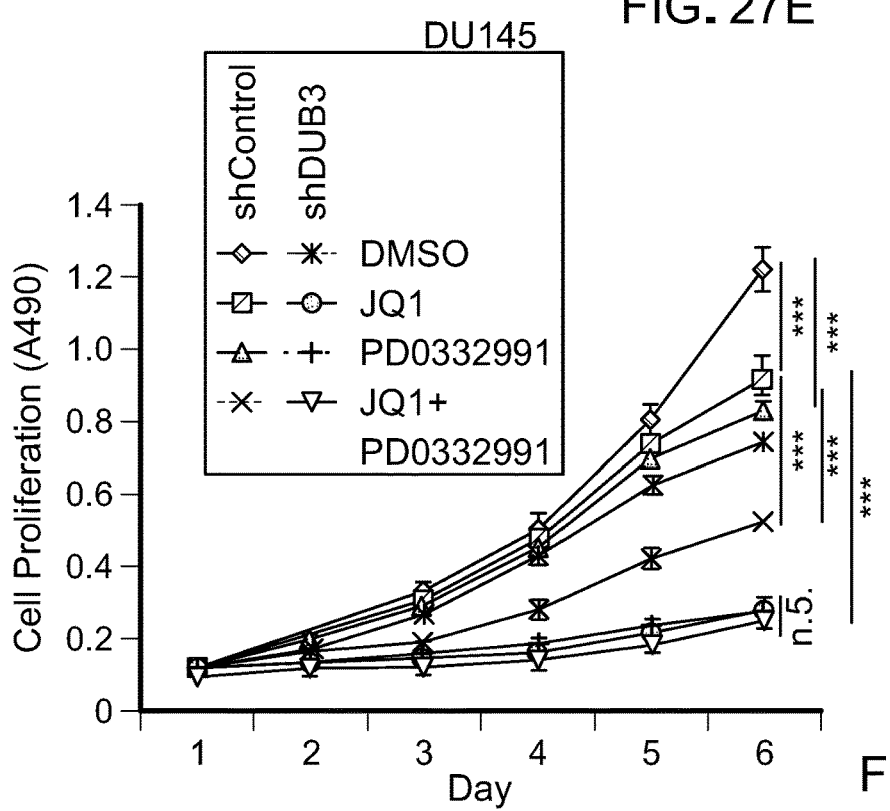
Figure 27G:
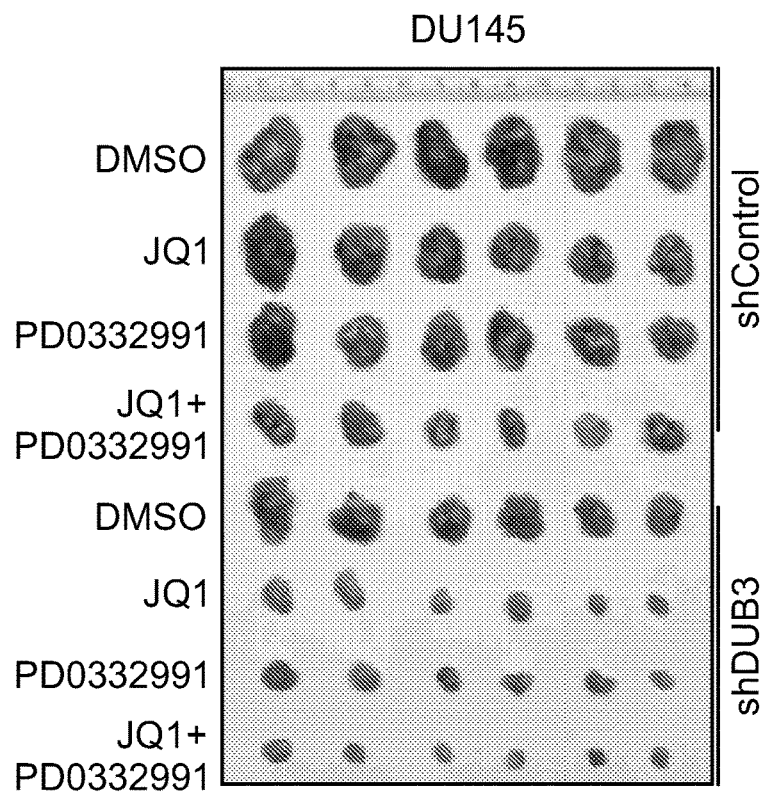
Figure 27H:
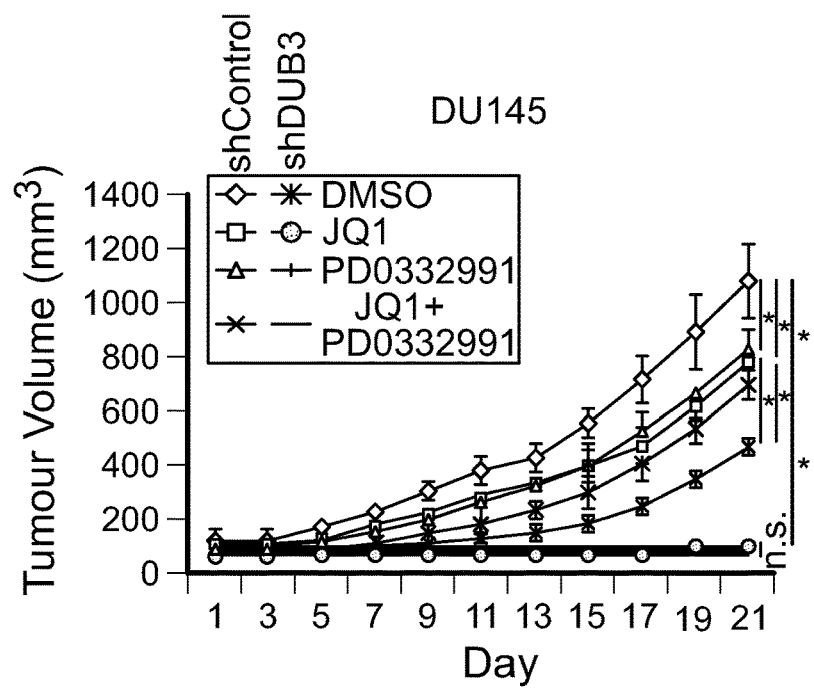
Figure 27I:
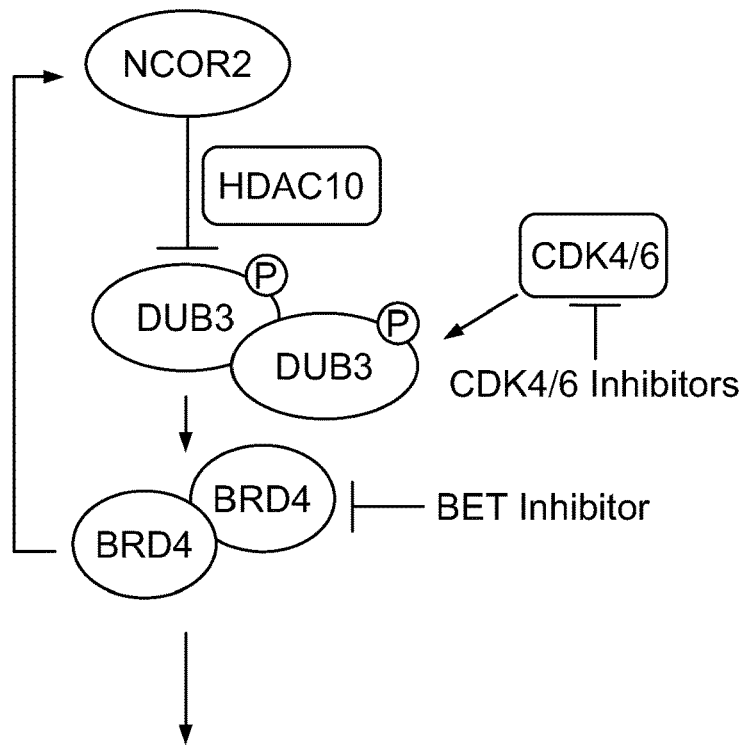

BRD4 stabilization confers resistance to BET inhibitor (Dai et al., *Nat. Med.*, 23:1063-1071 (2017); Janouskova et al., *Nat. Med.*, 23:1046-1054 (2017); and Zhang et al., *Nat. Med.*, 23:1055-1062 (2017)). The following was performed to determine whether DUB3 inhibition sensitizes prostate cancer cells to BET inhibitors. Co-treatment of DUB3-proficient, RB-deficient DU145 cells with JQ1 and PD0332991 resulted in much greater inhibitory effect on cell growth in vitro (FIG. 27F). Similarly, DUB3-knockdown cells were much more sensitive to JQ1 than the control knockdown cells, and little or no additive effect of co-treatment of JQ1 and PD0332991 on cell growth was detected in DUB3-knockdown cells (FIG. 27F). Similar results were obtained when DU145 cells were treated with another BET inhibitor I-BET762 (I-BET) in combination with or without PD0332991 (FIG. 26C). Moreover, DUB3 overexpression experiments demonstrated that overexpression of DUB3 conferred resistance to both JQ1 and I-BET in DU145 cells. These effects were completely abolished by BRD4 knockdown (FIGS. 26D-26G). These results were consistent with the results from colony formation assays that $IC_{50}$ of JQ1 was substantially increased in DUB3 overexpressing cells compared to control cells (FIGS. 26H and 26I). Furthermore, co-treatment with JQ1 and PD0332991 also resulted in much greater inhibition of growth of control DU145 xenograft tumors in mice than each single agent alone, but such effect was recapitulated by JQ1 treatment in combination with DUB3 knockdown (FIGS. 27G and 27H). These results demonstrate that DUB3 is an upstream regulator of BRD4 protein stability and that inhibition of DUB3 by CDK4/6 inhibitor overcomes BET inhibitor-induced elevation of BRD4 protein and BET inhibitor resistance in a RB-independent manner (FIG. 27I).

Figure 28A:
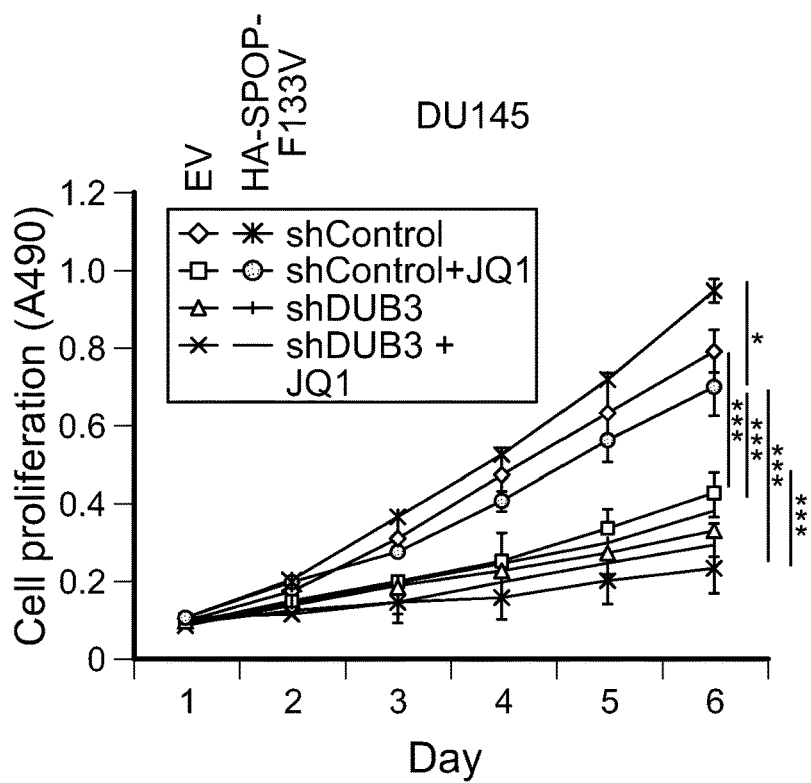
Figure 28C:
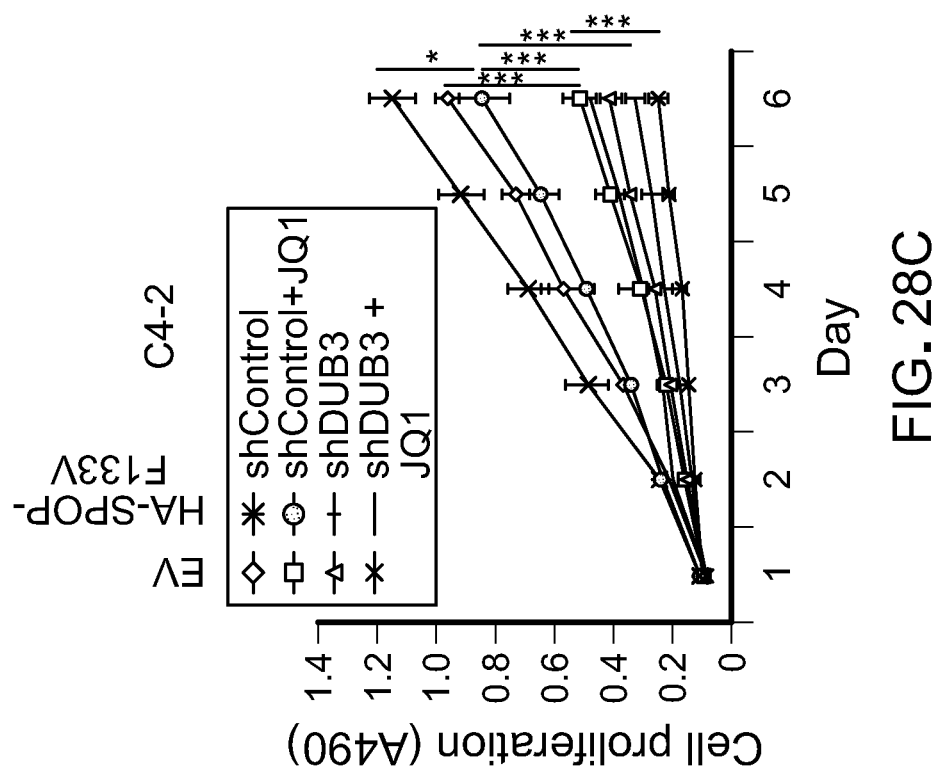
Figure 28B:
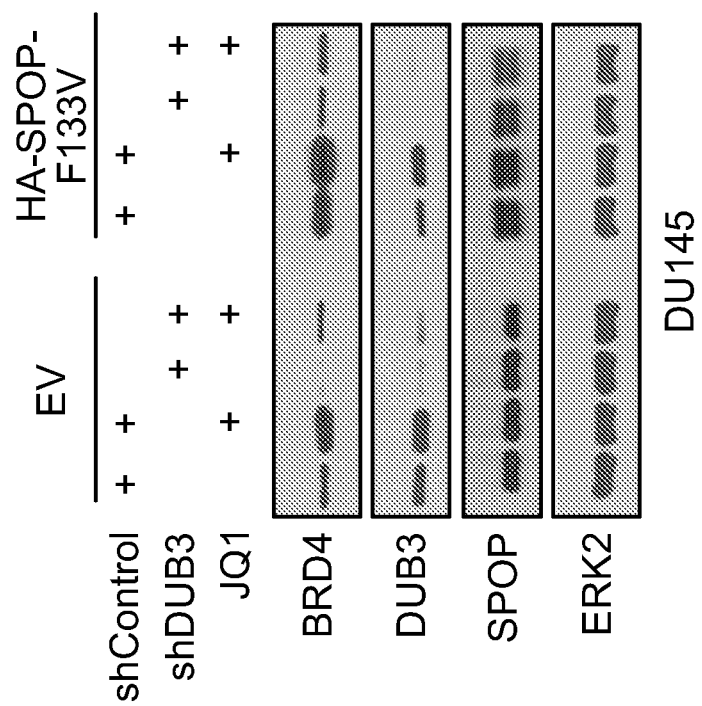
Figure 28H:
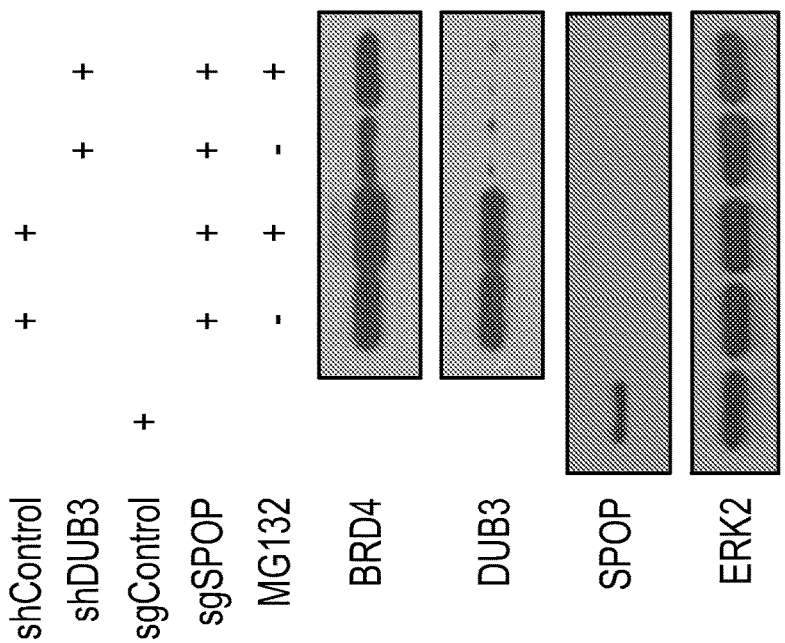

The effect of DUB3 on BRD4 protein degradation and JQ1 sensitivity was examined in SPOP mutated prostate cancer cells. Expression of SPOP F133V, a hot spot mutant of SPOP, largely increased BRD4 levels and caused JQ1 resistance in both DU145 and C4-2 cell lines (FIGS. 28A-28D). Unexpectedly, knockdown of DUB3 not only decreased BRD4 protein level in SPOP F133V-expressing DU145 cells, but also sensitized SPOP-F133V cells to JQ1 treatment (FIGS. 28A-28D), suggesting the presence of a SPOP-independent putative E3 ligase targeting BRD4 protein for degradation. To test this hypothesis, the effect of DUB3 knockdown on BRD4 protein ubiquitination degradation was examined in SPOP F133V-expressing DU145 and SPOP CRISPR knockout PC-3 cells. Knockdown of DUB3 enabled an increase in BRD4 polyubiquitination in F133V-expressing DU145 cells (FIG. 28E). Accordingly, DUB3 knockdown decreased BRD4 protein levels in F133V-expressing cells, and this effect was blocked by MG132 (FIG. 28F). Similar results were observed in SPOP CRISPR knockout PC-3 cells (FIGS. 28G and 28H). These results not only demonstrate that there exists a SPOP-independent undefined E3 ligase for BRD4 degradation, but also demonstrate that inhibition of DUB3 can overcome SPOP mutation-conferred BET inhibitor resistance (FIGS. 28A-28D). Together, these results demonstrate that targeting DUB3 represents a new strategy to overcome BET inhibitor resistance in SPOP-mutated prostate cancer.

Figure 29:
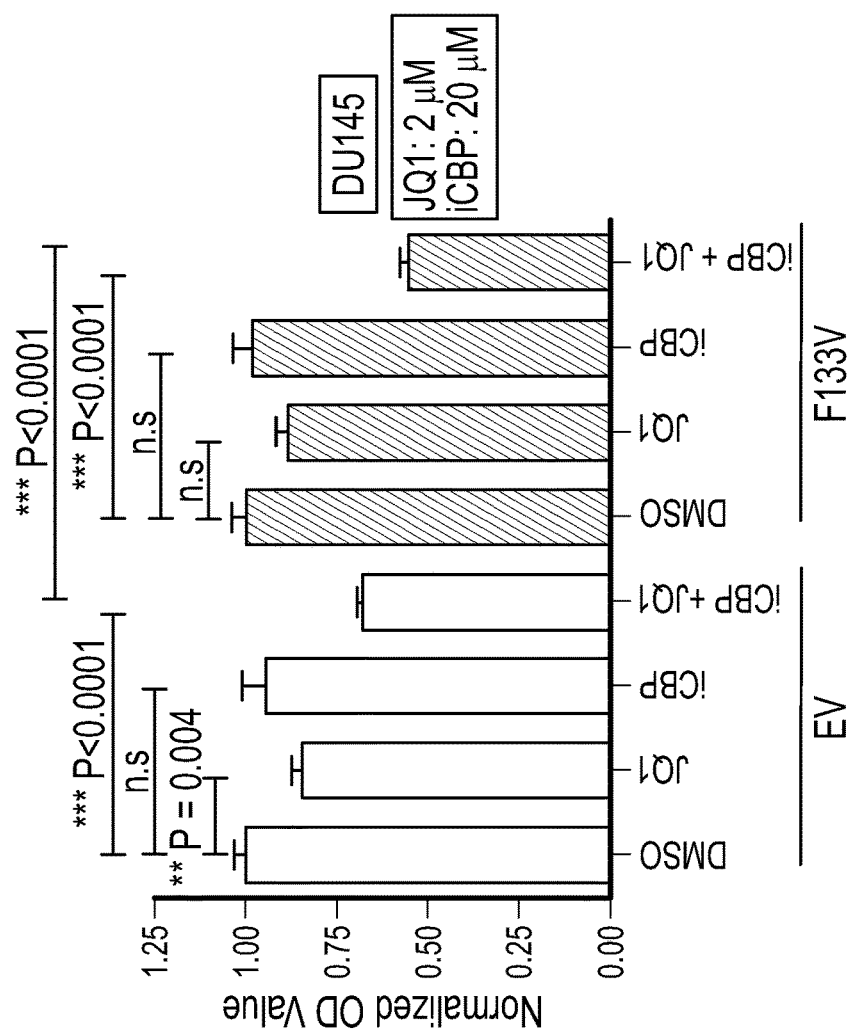
FIG. 29. SPOP mutated prostate cancer cells are very sensitive to the combined treatment of a CBP/p300 inhibitor (CPI-637) and a BET inhibitor (JQ1). DU145 prostate cancer cells were infected with empty vector (EV) or SPOP F133V mutant lentivirus and selected with purimycin for 48 hours, and then cells were treated with vehicle (DMSO), a CBP/p300 inhibitor (CPI-637; iCBP; 20 µM), or a BET inhibitor (JQ1; 2 µM) alone or a combination of CPI-637 and JQ1. After 72 hours, cells were subjected for measurement of cell growth by MTS assay. In each cell type (EV and F133V), the OD value in each group was normalized by the value in the control (vehicle) group.

Example 3—The Combined Use of a CBP/p300 Inhibitor and a BET Inhibitor Effectively Reduces the Number Cancer Cells Having an SPOP Mutation DU145 prostate cancer cells were infected with empty vector (EV) or SPOP F133V mutant lentivirus and selected with purimycin for 48 hours. The cells then were treated with vehicle (DMSO), a CBP/p300 inhibitor (CPI-637; iCBP; 20 µM), or a BET inhibitor (JQ1; 2 µM) alone or a combination of CPI-637 and JQ1. After 72 hours, cells were subjected to measurement of cell growth by an MTS assay. In each cell type (EV and F133V), the OD value in each group was normalized by the value in the control (vehicle) group. SPOP mutated prostate cancer cells were very sensitive to the combined treatment of a CBP/p300 inhibitor (CPI-637) and a BET inhibitor (JQ1) (FIG. 29).

Example 4—Exemplary Embodiments

Embodiment #1. A method for increasing the susceptibility of a cancer to treatment with a BET inhibitor, wherein said method comprises:
  (a) identifying a mammal as having a cancer at least partially resistant to BET inhibitor treatment, and
  (b) administering a CDK inhibitor or a CBP/p300 inhibitor to said mammal, thereby increasing the susceptibility of said cancer to said treatment with said BET inhibitor.

Embodiment #2. The method of Embodiment #1, wherein said mammal is a human.

Embodiment #3. The method of any one of Embodiment #1-2, wherein said cancer is a prostate cancer.

Embodiment #4. The method of any one of Embodiment #1-3, wherein said BET inhibitor is JQ1, I-BET 151 (GSK1210151A), I-BET 762 (GSK525762), OTX-015, TEN-010, CPI-203, CPI-0610, olinone, or RVX-208.

Embodiment #5. The method of any one of Embodiment #1-4, wherein said method comprises administering said CDK inhibitor to said mammal.

Embodiment #6. The method of Embodiment #5, wherein said CDK inhibitor is a CDK4 inhibitor, a CDK6 inhibitor, or a CDK4/6 inhibitor.

Embodiment #7. The method of Embodiment #5, wherein said CDK inhibitor is Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516.

Embodiment #8. The method of any one of Embodiment #1-7, wherein said method comprises administering said CBP/p300 inhibitor to said mammal.

Embodiment #9. The method of Embodiment #8, wherein said CBP/p300 inhibitor is CPI-637, SGC-CBP30, PF-CBP1 HCl, I-CBP 112, or C646.

Embodiment #10. The method of any one of Embodiment #1-9, wherein said method comprises administering an AKT inhibitor to said mammal.

Embodiment #11. The method of Embodiment #10, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

Embodiment #12. A method for increasing the susceptibility of a cancer to treatment with a BET inhibitor, wherein said method comprises administering a CDK inhibitor or a CBP/p300 inhibitor to a mammal identified as having a cancer at least partially resistant to BET inhibitor treatment.

Embodiment #13. The method of Embodiment #12, wherein said mammal is a human.

Embodiment #14. The method of any one of Embodiment #12-13, wherein said cancer is a prostate cancer.

Embodiment #15. The method of any one of Embodiment #12-14, wherein said BET inhibitor is JQ1, I-BET 151 (GSK1210151A), I-BET 762 (GSK525762), OTX-015, TEN-010, CPI-203, CPI-0610, olinone, or RVX-208.

Embodiment #16. The method of any one of Embodiment #12-15, wherein said method comprises administering said CDK inhibitor to said mammal.

Embodiment #17. The method of Embodiment #16, wherein said CDK inhibitor is a CDK4 inhibitor, a CDK6 inhibitor, or a CDK4/6 inhibitor.

Embodiment #18. The method of Embodiment #16, wherein said CDK inhibitor is Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516.

Embodiment #19. The method of any one of Embodiment #12-18, wherein said method comprises administering said CBP/p300 inhibitor to said mammal.

Embodiment #20. The method of Embodiment #19, wherein said CBP/p300 inhibitor is CPI-637, SGC-CBP30, PF-CBP1 HCl, I-CBP 112, or C646.

Embodiment #21. The method of any one of Embodiment #12-20, wherein said method comprises administering an AKT inhibitor to said mammal.

Embodiment #22. The method of Embodiment #21, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

Embodiment #23. A method for treating cancer, wherein said method comprises:
(a) identifying a mammal as having a cancer at least partially resistant to BET inhibitor treatment,
(b) administering a CDK inhibitor or a CBP/p300 inhibitor to said mammal to increase the susceptibility of said cancer to a BET inhibitor, and
(c) administering a BET inhibitor to said mammal.

Embodiment #24. The method of Embodiment #23, wherein said mammal is a human.

Embodiment #25. The method of any one of Embodiment #23-24, wherein said cancer is a prostate cancer.

Embodiment #26. The method of any one of claims 23-25, wherein said BET inhibitor is JQ1, I-BET 151 (GSK1210151A), I-BET 762 (GSK525762), OTX-015, TEN-010, CPI-203, CPI-0610, olinone, or RVX-208.

Embodiment #27. The method of any one of Embodiment #23-26, wherein said method comprises administering said CDK inhibitor to said mammal.

Embodiment #28. The method of Embodiment #27, wherein said CDK inhibitor is a CDK4 inhibitor, a CDK6 inhibitor, or a CDK4/6 inhibitor.

Embodiment #29. The method of Embodiment #27, wherein said CDK inhibitor is Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516.

Embodiment #30. The method of any one of Embodiment #23-29, wherein said method comprises administering said CBP/p300 inhibitor to said mammal.

Embodiment #31. The method of Embodiment #30, wherein said CBP/p300 inhibitor is CPI-637, SGC-CBP30, PF-CBP1 HCl, I-CBP 112, or C646.

Embodiment #32. The method of any one of Embodiment #23-31, wherein said method comprises administering an AKT inhibitor to said mammal.

Embodiment #33. The method of Embodiment #32, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

Embodiment #34. A method for treating cancer, wherein said method comprises:
(a) administering a CDK inhibitor or a CBP/p300 inhibitor to a mammal identified as having a cancer at least partially resistant to BET inhibitor treatment to increase the susceptibility of said cancer to a BET inhibitor, and
(b) administering a BET inhibitor to said mammal to reduce the number of cancer cells within said mammal.

Embodiment #35. The method of Embodiment #34, wherein said mammal is a human.

Embodiment #36. The method of any one of Embodiment #34-35, wherein said cancer is a prostate cancer.

Embodiment #37. The method of any one of Embodiment #34-36, wherein said BET inhibitor is JQ1, I-BET 151 (GSK1210151A), I-BET 762 (GSK525762), OTX-015, TEN-010, CPI-203, CPI-0610, olinone, or RVX-208.

Embodiment #38. The method of any one of Embodiment #34-37, wherein said method comprises administering said CDK inhibitor to said mammal.

Embodiment #39. The method of Embodiment #38, wherein said CDK inhibitor is a CDK4 inhibitor, a CDK6 inhibitor, or a CDK4/6 inhibitor.

Embodiment #40. The method of Embodiment #38, wherein said CDK inhibitor is Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516.

Embodiment #41. The method of any one of Embodiment #34-40, wherein said method comprises administering said CBP/p300 inhibitor to said mammal.
Embodiment #42. The method of Embodiment #41, wherein said CBP/p300 inhibitor is CPI-637, SGC-CBP30, PF-CBP1 HCl, I-CBP 112, or C646.
Embodiment #43. The method of any one of claims 34-42, wherein said method comprises administering an AKT inhibitor to said mammal.
Embodiment #44. The method of Embodiment #43, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.
Embodiment #45. A method for treating cancer, wherein said method comprises administering (a) a CDK inhibitor or a CBP/p300 inhibitor and (b) a BET inhibitor to a mammal identified as having a cancer at least partially resistant to BET inhibitor treatment.
Embodiment #46. The method of Embodiment #45, wherein said mammal is a human.
Embodiment #47. The method of any one of Embodiment #45-46, wherein said cancer is a prostate cancer.
Embodiment #48. The method of any one of Embodiment #45-47, wherein said BET inhibitor is JQ1, I-BET 151 (GSK1210151A), I-BET 762 (GSK525762), OTX-015, TEN-010, CPI-203, CPI-0610, olinone, or RVX-208.
Embodiment #49. The method of any one of Embodiment #45-48, wherein said method comprises administering said CDK inhibitor to said mammal.
Embodiment #50. The method of Embodiment #50, wherein said CDK inhibitor is a CDK4 inhibitor, a CDK6 inhibitor, or a CDK4/6 inhibitor.
Embodiment #51. The method of Embodiment #50, wherein said CDK inhibitor is Palbociclib, Palbociclib HCl, Palbociclib Isethionate, Abemaciclib, Ribociclib, Flavopiridol, AT7519, Flavopiridol HCl, JNJ-7706621, PHA-793887, BMS-265246, Milciclib, R547, P276-00, ON123300, AT7519 HCL, Purvalanol A, or SU9516.
Embodiment #52. The method of any one of Embodiment #45-51, wherein said method comprises administering said CBP/p300 inhibitor to said mammal.
Embodiment #53. The method of Embodiment #52, wherein said CBP/p300 inhibitor is CPI-637, SGC-CBP30, PF-CBP1 HCl, I-CBP 112, or C646.
Embodiment #54. The method of any one of Embodiment #45-53, wherein said method comprises administering an AKT inhibitor to said mammal.
Embodiment #55. The method of Embodiment #54, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer, wherein said method comprises:
   (a) identifying a mammal as having a cancer at least partially resistant to BET inhibitor treatment,
   (b) administering a CBP/p300 inhibitor to said mammal to increase the susceptibility of said cancer to a BET inhibitor, and
   (c) administering a BET inhibitor to said mammal after (i) identifying said mammal as having said cancer at least partially resistant to BET inhibitor treatment and (ii) administering said CBP/p300 inhibitor to said mammal to increase the susceptibility of said cancer to a BET inhibitor.

2. A method for treating cancer, wherein said method comprises:
   (a) administering a CBP/p300 inhibitor to a mammal identified as having a cancer at least partially resistant to BET inhibitor treatment to increase the susceptibility of said cancer to a BET inhibitor, and
   (b) administering a BET inhibitor to said mammal to reduce the number of cancer cells within said mammal, wherein said administering of said BET inhibitor is after (i) said mammal was identified as having said cancer at least partially resistant to BET inhibitor treatment and (ii) administering said CBP/p300 inhibitor to said mammal to increase the susceptibility of said cancer to a BET inhibitor.

3. A method for treating cancer, wherein said method comprises administering (a) a CBP/p300 inhibitor and (b) a BET inhibitor to a mammal after said mammal was identified as having a cancer at least partially resistant to BET inhibitor treatment.

4. The method of claim 1, wherein said method further comprises administering a BET inhibitor to said mammal before (i) and (ii).

5. The method of claim 2, wherein said method further comprises administering a BET inhibitor to said mammal before (i) and (ii).

6. The method of claim 3, wherein said method further comprises administering a BET inhibitor to said mammal before said mammal was identified as having a cancer at least partially resistant to BET inhibitor treatment.

* * * * *